United States Patent
Venkatesan et al.

(10) Patent No.: US 9,174,963 B2
(45) Date of Patent: *Nov. 3, 2015

(54) TRIAZINE COMPOUNDS AS PI3 KINASE AND MTOR INHIBITORS

(71) Applicant: WYETH LLC, New York, NY (US)

(72) Inventors: Aranapakam Mudumbai Venkatesan, Rego Park, NY (US); Zecheng Chen, New City, NY (US); Christoph Martin Dehnhardt, New York, NY (US); Osvaldo Dos Santos, Astoria, NY (US); Efren Guillermo Delos Santos, Nanuet, NY (US); Arie Zask, New York, NY (US); Jeroen Cunera Verheijen, Highland Mills, NY (US); Joshua Aaron Kaplan, Nyack, NY (US); David James Richard, Warwick, NY (US); Semiramis Aryl-Kaloustian, Tarrytown, NY (US); Tarek Suhayl Mansour, New City, NY (US); Ariamala Gopalsamy, Mahwah, NJ (US); Kevin Joseph Curran, Congers, NY (US); Mengxiao Shi, Eastchester, NY (US)

(73) Assignee: Pfizer Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/477,650

(22) Filed: Sep. 4, 2014

(65) Prior Publication Data

US 2015/0011752 A1 Jan. 8, 2015

Related U.S. Application Data

(60) Continuation of application No. 14/259,414, filed on Apr. 23, 2014, now Pat. No. 8,859,542, which is a continuation of application No. 13/950,584, filed on Jul. 25, 2013, now Pat. No. 8,478,421, which is a continuation of application No. 13/718,928, filed on Dec. 18, 2012, now Pat. No. 8,575,159, which is a continuation of application No. 13/490,309, filed on Jun. 6, 2012, now Pat. No. 8,445,486, which is a continuation of application No. 13/218,571, filed on Aug. 26, 2011, now Pat. No. 8,217,036, which is a division of application No. 12/470,521, filed on May 22, 2009, now Pat. No. 8,039,469.

(60) Provisional application No. 61/055,661, filed on May 23, 2008.

(51) Int. Cl.
| A61K 31/5377 | (2006.01) |
| C07D 413/14 | (2006.01) |
| C07D 401/12 | (2006.01) |
| C07D 251/18 | (2006.01) |
| C07D 403/12 | (2006.01) |
| C07D 403/14 | (2006.01) |

(Continued)

(52) U.S. Cl.
CPC .......... *C07D 401/12* (2013.01); *A61K 31/5377* (2013.01); *A61K 45/06* (2013.01); *C07D 251/18* (2013.01); *C07D 401/04* (2013.01); *C07D 401/14* (2013.01); *C07D 403/12* (2013.01); *C07D 403/14* (2013.01); *C07D 405/12* (2013.01); *C07D 405/14* (2013.01); *C07D 407/14* (2013.01); *C07D 409/12* (2013.01); *C07D 413/04* (2013.01); *C07D 413/14* (2013.01); *C07D 451/06* (2013.01); *C07D 453/02* (2013.01); *C07D 491/113* (2013.01); *C07D 498/08* (2013.01)

(58) Field of Classification Search
CPC .......................... A61K 31/5377; C07D 413/14
See application file for complete search history.

(56) References Cited

U.S. PATENT DOCUMENTS 7,071,189 B2   7/2006  Kawashima
8,039,469 B2 * 10/2011  Venkatesan et al. ....... 514/232.2

(Continued)

FOREIGN PATENT DOCUMENTS

| EP | 1 020 462 A1 | 7/2000 |
| EP | 1 020 462 B1 | 2/2004 |
| WO | WO 02/088112 | 11/2002 |

OTHER PUBLICATIONS

Berge et al., Journal of Pharmaceutical Sciences, vol. 66, No. 1, Jan. 1977, pp. 1-19.*

(Continued)

*Primary Examiner* — Rebecca Anderson
(74) *Attorney, Agent, or Firm* — David Rubin

(57) ABSTRACT

Compounds of formula I

I

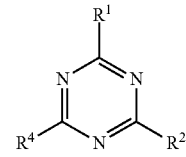

wherein:
$R^1$ is

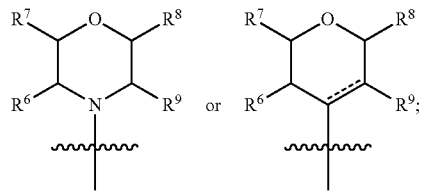

and $R^2$, $R^4$, and $R^{6-9}$ are defined herein, and pharmaceutically acceptable salts and esters thereof. These compounds inhibit PI3 kinase and mTOR, and may be used to treat diseases mediated by PI3 kinase and mTOR, such as a variety of cancers. Methods for making and using the compounds of this invention are disclosed. Various compositions containing the compounds of this invention are also disclosed.

2 Claims, No Drawings

(51) Int. Cl.
*C07D 405/12* (2006.01)
*C07D 405/14* (2006.01)
*C07D 413/04* (2006.01)
*C07D 453/02* (2006.01)
*C07D 491/113* (2006.01)
*C07D 498/08* (2006.01)
*A61K 45/06* (2006.01)
*C07D 401/04* (2006.01)
*C07D 401/14* (2006.01)
*C07D 407/14* (2006.01)
*C07D 409/12* (2006.01)
*C07D 451/06* (2006.01)

(56) References Cited

U.S. PATENT DOCUMENTS 8,575,159 B2 * 11/2013 Venkatesan et al. ....... 514/232.2
8,748,421 B2 * 6/2014 Venkatesan et al. ....... 514/232.2

OTHER PUBLICATIONS

Apr. 8, 2011 Non-Final Office Action issued in connection with U.S. Appl. No. 12/470,525.

* cited by examiner

TRIAZINE COMPOUNDS AS PI3 KINASE AND MTOR INHIBITORS

CROSS-REFERENCE TO RELATED APPLICATIONS

This is a continuation application from U.S. application Ser. No. 14/259,414, filed on Apr. 23, 2014, which is a continuation application from U.S. application Ser. No. 13/950,584, filed on Jul. 25, 2013, and issued on Jun. 10, 2014 as U.S. Pat. No. 8,478,421; which is a continuation application from U.S. application Ser. No. 13/718,928, filed on Dec. 18, 2012, and issued on Nov. 5, 2013 as U.S. Pat. No. 8,575,159; which is a continuation application from U.S. application Ser. No. 13/490,309, filed on Jun. 6, 2012, and issued on May 21, 2013 as U.S. Pat. No. 8,445,486; which is a continuation application from U.S. application Ser. No. 13/218,571, filed on Aug. 26, 2011, and issued on Jul. 10, 2012 as U.S. Pat. No. 8,217,036; which is a divisional application from U.S. application Ser. No. 12/470,521, filed on May 22, 2009, and issued on Oct. 18, 2011 as U.S. Pat. No. 8,039,469; which claims the benefit of U.S. Provisional application Ser. No. 61/055,661, filed on May 23, 2008; the contents of which are hereby incorporated by reference in their entireties.

FIELD OF THE INVENTION

This invention relates to 2,4,6-substituted [1,3,5]triazine compounds in which one substituent is an optionally substituted morpholino, tetrahydropyranyl or dihydropyranyl group, which inhibit PI3 kinase and mTOR, to processes for preparing them, to methods of treatment using them and to pharmaceutical compositions containing them.

BACKGROUND OF THE INVENTION

Phosphatidylinositol (hereinafter abbreviated as "PI") is one of the phospholipids in cell membranes. In recent years it has become clear that PI plays an important role also in intracellular signal transduction. It is well recognized in the art that PI (4,5) bisphosphate (PI(4,5)P2 or PIP2) is degraded into diacylglycerol and inositol(1,4,5)triphosphate by phospholipase C to induce activation of protein kinase C and intracellular calcium mobilization, respectively [M. J. Berridge et al., Nature, 312, 315 (1984); Y. Nishizuka, Science, 225, 1365 (1984)].

Phosphatidylinositol-3 kinase ("PI3K") is an enzyme that phosphorylates the 3-position of the inositol ring of phosphatidylinositol [D. Whitman et al., Nature, 332, 664 (1988)]. Pluralities of PI3K subtypes exist. Three major subtypes of PI3Ks have now been identified on the basis of their in vitro substrate specificity, and these three are designated class I (a & b), class II, and class III [B. Vanhaesebroeck, Trend in Biol. Sci., 22, 267(1997)].

The class Ia PI3K subtype has been most extensively investigated to date. Within the class Ia subtype there are three isoforms (α, β, & δ) that exist as hetero dimers of a catalytic 110-kDa subunit and regulatory subunits of 50-85 kDa. The regulatory subunits contain SH2 domains that bind to phosphorylated tyrosine residues within growth factor receptors or adaptor molecules and thereby localize PI3K to the inner cell membrane. At the inner cell membrane PI3K converts PIP2 to PIP3 (phosphatidylinositol-3,4,5-trisphosphate) that serves to localize the downstream effectors PDK1 and Akt to the inner cell membrane where Akt activation occurs. Activated Akt mediates a diverse array of effects including inhibition of apoptosis, cell cycle progression, response to insulin signaling, and cell proliferation. Class Ia PI3K subtypes also contain Ras binding domains (RBD) that allow association with activated Ras providing another mechanism for PI3K membrane localization. Activated, oncogenic forms of growth factor receptors, Ras, and even PI3K kinase have been shown to aberrantly elevate signaling in the PI3K/Akt/mTOR pathway resulting in cell transformation. As a central component of the PI3K/Akt/mTOR signaling pathway PI3K (particularly the class Ia isoform) has become a major therapeutic target in cancer drug discovery.

Substrates for class I PI3Ks are PI, PI(4)P and PI(4,5)P2, with PI(4,5)P2 being the most favored. Class I PI3Ks are further divided into two groups, class Ia and class Ib, because of their activation mechanism and associated regulatory subunits. The class Ib PI3K is p110γ that is activated by interaction with G protein-coupled receptors. Interaction between p110γ and G protein-coupled receptors is mediated by regulatory subunits of 110, 87, and 84 kDa.

PI and PI(4)P are the known substrates for class II PI3Ks; PI(4,5)P2 is not a substrate for the enzymes of this class. Class II PI3Ks include PI3K C2α, C2β and C2γ isoforms, which contain C2 domains at the C terminus, implying that their activity is regulated by calcium ions.

The substrate for class III PI3Ks is PI only. A mechanism for activation of the class III PI3Ks has not been clarified. Because each subtype has its own mechanism for regulating activity, it is likely that activation mechanism(s) depend on stimuli specific to each respective class of PI3K.

The compound P1103 (3-(4-(4-morpholinyl)pyrido[3',2':4,5]furo[3,2-d]pyrimidin-2-yl)phenol) inhibits PI3Ka and PI3Kg as well as the mTOR enzymes with $IC_{50}$ values of 2, 3, and 50-80 nM respectively. I.P. dosing in mice of this compound in human tumor xenograft models of cancer demonstrated activity against a number of human tumor models, including the glioblastoma (PTEN null U87MG), prostate (PC3), breast (MDA-MB-468 and MDA-MB-435) colon carcinoma (HCT 116); and ovarian carcinoma (SKOV3 and IGROV-1); (Raynaud et al, Pharmacologic Characterization of a Potent Inhibitor of Class I Phosphatidylinositide 3-Kinases, Cancer Res. 2007 67: 5840-5850).

The compound ZSTK474 (2-(2-difluoromethylbenzoimidazol-1-yl)-4,6-dimorpholino-1,3,5-triazine) inhibits PI3Ka and PI3Kg but not the mTOR enzymes with an $IC_{50}$ values of 16, 4.6 and >10,000 nM respectively (Dexin Kong and Takao Yamori, ZSTK474 is an ATP-competitive inhibitor of class I phosphatidylinositol 3 kinase isoforms, Cancer Science, 2007, 98:10 1638-1642). Chronic oral administration of ZSTK474 in mouse human xenograft cancer models, completely inhibited growth which originated from a non-small-cell lung cancer (A549), a prostate cancer (PC-3), and a colon cancer (WiDr) at a dose of 400 mg/kg. (Yaguchi et al, Antitumor Activity of ZSTK474, a New Phosphatidylinositol 3-Kinase Inhibitor, J. Natl. Cancer Inst. 98: 545-556).

The compound NVP-BEZ-235 (2-methyl-2-(4-(3-methyl-2-oxo-8-(quinolin-3-yl)-2,3-dihydro-1H-imidazo[4,5-c]quinolin-1-yl)phenyl)propanenitrile) inhibits both PI3Ka and PI3Kg as well as the mTOR enzymes with $IC_{50}$ values 4, 5, and "nanomolar". Testing in human tumor xenograft models of cancer demonstrated activity against human tumor models of prostate (PC-3) and glioblastoma (U-87) cancer. It entered clinical trials in December of 2006 (Verheijen, J. C. and Zask, A., Phosphatidylinositol 3-kinase (PI3K) inhibitors as anticancer drugs, Drugs Fut. 2007, 32(6): 537-547).

The compound SF-1126 (a prodrug form of LY-294002, which is 2-(4-morpholinyl)-8-phenyl-4H-1-benzopyran-4-one) is "a pan-PI3K inhibitor". It is active in preclinical mouse cancer models of prostate, breast, ovarian, lung, multiple myeloma, and brain cancers. (Verheijen, J. C. and Zask, A., Phosphatidylinositol 3-kinase (PI3K) inhibitors as anticancer drugs, Drugs Fut. 2007, 32(6): 537-547).

Although it seems clear that inhibition of the a isoform is essential for the antitumor activity of PI3K inhibitors, it is not clear whether a more selective inhibitor of a particular PI3K isoform may lead to fewer unwanted biological effects. It has recently been reported that non-PI3Ka class I isoforms (PI3Kβ, δ and γ) have the ability to induce oncogenic transformation of cells, suggesting that nonisoform-specific inhibitors may offer enhanced therapeutic potential over specific inhibitors.

Selectivity versus other related kinases is also an important consideration for the development of PI3K inhibitors. While selective inhibitors may be preferred in order to avoid unwanted side effects, there have been reports that inhibition of multiple targets in the PI3K/Akt pathway (e.g., PI3Ka and mTOR [mammalian target of rapamycin]) may lead to greater efficacy. It is possible that lipid kinase inhibitors may parallel protein kinase inhibitors in that nonselective inhibitors may also be brought forward to the clinic.

Mammalian Target of Rapamycin, mTOR, is a cell-signaling protein that regulates the response of tumor cells to nutrients and growth factors, as well as controlling tumor blood supply through effects on Vascular Endothelial Growth Factor, VEGF. Inhibitors of mTOR starve cancer cells and shrink tumors by inhibiting the effect of mTOR. All mTOR inhibitors bind to the mTOR kinase. This has at least two important effects. First, mTOR is a downstream mediator of the PI3K/Akt pathway. The PI3K/Akt pathway is thought to be over activated in numerous cancers and may account for the widespread response from various cancers to mTOR inhibitors. The over-activation of the upstream pathway would normally cause mTOR kinase to be over activated as well. However, in the presence of mTOR inhibitors, this process is blocked. The blocking effect prevents mTOR from signaling to downstream pathways that control cell growth. Over-activation of the PI3K/Akt kinase pathway is frequently associated with mutations in the PTEN gene, which is common in many cancers and may help predict what tumors will respond to mTOR inhibitors. The second major effect of mTOR inhibition is anti-angiogenesis, via the lowering of VEGF levels.

In lab tests, certain chemotherapy agents were found to be more effective in the presence of mTOR inhibitors. George, J. N., et al., Cancer Research, 61, 1527-1532, 2001. Additional lab results have shown that some rhabdomyosarcoma cells die in the presence of mTOR inhibitors.

There are three mTOR inhibitors, which have progressed into clinical trials. These compounds are Wyeth's Torisel, also known as 42-(3-hydroxy-2-(hydroxymethyl)-rapamycin 2-methylpropanoate, CCI-779 or Temsirolimus; Novartis' Everolimus, also known as 42-O-(2-hydroxyethyl)-rapamycin, or RAD 001; and Ariad's AP23573 also known as 42-(dimethylphopsinoyl)-rapamycin. The FDA has approved Torisel for the treatment of advanced renal cell carcinoma. In addition, Torisel is active in a NOS/SCID xenograft mouse model of acute lymphoblastic leukemia [Teachey et al, Blood, 107(3), 1149-1155, 2006]. On Mar. 30, 2009, the U.S. Food and Drug Administration (FDA) approved Everolimus (AFINITOR™) for the treatment of patients with advanced renal cell carcinoma. AP23573 has been given orphan drug and fast-track status by the FDA for treatment of soft-tissue and bone sarcomas.

The three mTOR inhibitors have non-linear, although reproducible pharmacokinetic profiles. Mean area under the curve (AUC) values for these drugs increase at a less than dose related way. The three compounds are all semi-synthetic derivatives of the natural macrolide antibiotic rapamycin. It would be desirable to find fully synthetic compounds, which inhibit mTOR that are more potent and exhibit improved pharmacokinetic behaviors.

SUMMARY OF THE INVENTION

This invention provides compounds of formula I

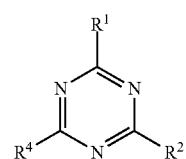

wherein:
$R^1$ is

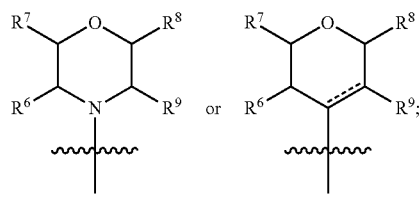

and $R^2$, $R^4$, and $R^6$-9 are defined below, and pharmaceutically acceptable salts and esters thereof. These compounds are useful as inhibitors of mTOR and PI3 kinases.

This invention further provides compositions containing one or more of the aforementioned compounds, which compositions may contain a pharmaceutically acceptable carrier.

The present invention provides methods for making the compounds of the invention, as described below. Methods of using the invention are also provided, for example: a method for inhibiting mTOR, a method for inhibiting a PI3 kinase, and methods for treating various forms of cancer.

DETAILED DESCRIPTION OF THE INVENTION

In one aspect, the present invention provides compounds of formula I

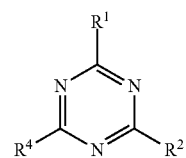

wherein:
R¹ is

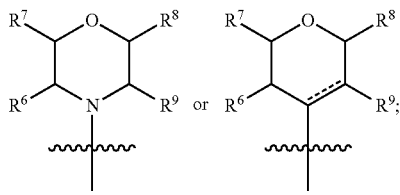

wherein:
R⁶, R⁷, R⁸, R⁹ are each independently selected from the group consisting of a hydrogen atom, and a $C_1$-$C_6$alkyl optionally substituted with $C_2$-$C_6$alkenyl, $C_4$-$C_6$alkadienyl, $C_2$-$C_6$alkynyl or $C_4$-$C_6$alkadiynyl;

or one of R⁶ and R⁷ or R⁸ and R⁹, together with the carbon atoms to which they are attached form an optionally substituted 5-8 membered saturated or unsaturated ring containing 0, 1 or 2 atoms independently selected from O, NH and S;

the dashed line - - - - - represents an optional second bond;

R² is optionally substituted $C_6$-$C_{14}$aryl-NH—COR³, optionally substituted $C_1$-$C_9$heteroaryl-NH—COR³, —CH=CH—$C_6$-$C_{10}$aryl-NH—COR³ or —CH=CH—$C_1$-$C_9$heteroaryl-NH—COR³;

R³ is OR⁵, NR⁵R⁵ or NHR⁵;

R⁵ is independently selected from the group consisting of $C_1$-$C_6$alkyl, $C_3$-$C_6$alkenyl, $C_3$-$C_6$alkynyl, optionally substituted $C_6$-$C_{10}$aryl, $C_1$-$C_6$haloalkyl, optionally substituted $C_1$-$C_9$heteroaryl, $C_1$-$C_6$hydroxylalkyl-, $C_3$-$C_{10}$ saturated or unsaturated mono or bicyclic $C_3$-$C_{10}$cycloalkyl optionally substituted with OH, NR¹¹R¹¹ or 3-7 membered $C_1$-$C_6$heterocyclyl, and 3-10 membered saturated or unsaturated mono or bicyclic $C_1$-$C_9$heterocyclyl, with the proviso that three-membered cycloalkyl and heterocyclyl rings are saturated;

or two R⁵ groups taken together with the nitrogen atom to which they are attached form a 3 to 8 membered ring system optionally substituted with $C_1$-$C_6$alkyl, which ring system is saturated or unsaturated and has, in addition to said nitrogen atom, 0 to 2 heteroatom ring members selected from O, S, S(O), S(O)₂ and NR¹⁰;

R¹⁰ is selected from the group consisting of H, $C_1$-$C_6$alkyl, —SO₂($C_1$-$C_6$alkyl), —COO($C_1$-$C_6$alkyl), —CONH($C_1$-$C_6$alkyl), —CON($C_1$-$C_6$alkyl)₂, —CO($C_1$-$C_6$alkyl), and —SO₂NHR¹¹;

R¹¹ is selected from the group consisting of H, $C_1$-$C_6$alkyl optionally substituted with OH, NR¹¹R¹¹ or a 3-7 membered $C_1$-$C_6$heterocyclyl, —CO($C_1$-$C_6$alkyl), optionally substituted $C_6$-$C_{10}$aryl, and optionally substituted $C_1$-$C_9$heteroaryl;

R⁴ is selected from the group consisting of: a) $C_1$-$C_6$alkyl optionally substituted with: i) 3-10 membered $C_1$-$C_9$heterocyclyl optionally substituted with $C_1$-$C_6$alkyl-, ii) H₂N—, iii) ($C_1$-$C_6$alkyl)NH—, iv) ($C_1$-$C_6$alkyl)₂N—, v) NH(CH₂)ₐN($C_1$-$C_6$alkyl)₂ wherein a is 2, 3 or 4, and vi) CHO, b) $C_3$-$C_6$alkenyl, c) $C_3$-$C_6$alkynyl, d) —O—$C_1$-$C_8$alkyl optionally substituted with —O—$C_1$-$C_8$alkyl, e) —O—$C_3$-$C_8$alkenyl, f) —O—$C_3$-$C_8$alkynyl, g) saturated or unsaturated mono or bicyclic $C_3$-$C_8$cycloalkyl, and h) saturated or unsaturated mono or bicyclic —O—$C_3$-$C_{12}$cycloalkyl, all the above optionally substituted with OH, NR¹¹R¹¹ or a 3-7 membered $C_1$-$C_6$heterocyclyl optionally substituted with $C_1$-$C_6$alkyl-, provided that an OH or NR¹¹R¹¹ is not directly bonded to a carbon atom that is double- or triple-bonded to another carbon atom; i) —CH=CH—$C_6$-$C_{10}$aryl; j) —CH=CH—$C_1$-$C_9$heteroaryl; k) optionally substituted $C_6$-$C_{10}$aryl; l) optionally substituted 5-10 membered $C_1$-$C_9$heteroaryl attached to the triazine moiety via a carbon atom; m) 3-10 membered saturated or unsaturated monocyclic $C_1$-$C_9$heterocyclyl attached to the triazine moiety through a carbon or nitrogen atom and optionally substituted with from 1 to 3 substituents independently selected from: OH, NR¹¹R¹¹, $C_1$-$C_6$alkyl, ($C_1$-$C_6$alkyl)amido-, ($C_1$-$C_6$alkyl)C(O)—, ($C_1$-$C_6$alkoxy)carbonyl-, adamantyl, $C_1$-$C_6$hydroxylalkyl-, ($C_1$-$C_6$alkyl)amido-; or a 3-7 membered $C_1$-$C_6$heterocyclyl, with the proviso that 3 membered heterocyclyl is saturated and attached to the triazine moiety through a nitrogen atom, and 5 membered bicyclic heterocyclyl is saturated; n) optionally substituted —O—$C_6$-$C_{10}$aryl; o) optionally substituted —O—$C_1$-$C_9$heteroaryl; p) —O-(3-12 membered saturated or unsaturated mono or bicyclic)$C_1$-$C_9$heterocyclyl optionally substituted with ($C_1$-$C_6$alkoxy)carbonyl-, H₂NS(O)₂—, or $C_1$-$C_6$alkyl further optionally substituted with OH, NR¹¹R¹¹ or a 3-7 membered $C_1$-$C_6$heterocyclyl, with the proviso that three membered heterocyclyl is saturated; q) —NHC₆-$C_{10}$aryl, r) —NHC₁-$C_9$heteroaryl, s) —NHNH₂, t) —NHNH$C_1$-$C_6$alkyl, u) —NHN($C_1$-$C_6$alkyl)₂, v) —NHOH, w) —COOH, x) —COO—$C_1$-$C_6$alkyl, y) —CONR¹²R¹³, z) —NR¹²R¹³, aa)

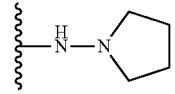

bb)

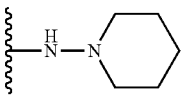

cc)

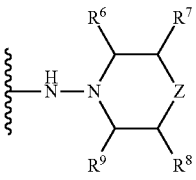

dd)

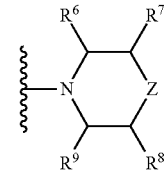

wherein Z is CH₂, O, S(O)ₙ or NR¹⁰ and n is 0, 1 or 2;

ee) halogen, ff) $C_6$-$C_{14}$aryl-S(O)₂—NH—, gg) R¹¹NHC(O)NH—O—, and hh) optionally substituted 5-membered monocyclic $C_1$-$C_4$heteroaryl attached to the triazine moiety via a nitrogen atom;

R¹² and R¹³ are each independently selected from H, optionally mono or disubstituted $C_1$-$C_8$alkyl, optionally substituted $C_3$-$C_8$alkenyl, and optionally substituted $C_3$-$C_8$alkynyl, the optional substituents being selected from $C_1$-$C_6$alkoxy, OH, NR¹¹R¹¹, and 3-7 membered $C_1$-$C_6$heterocyclyl, provided that an OH or NR¹¹R¹¹ is not directly bonded to a carbon atom that is double- or triple-bonded to another carbon atom;

or R¹² and R¹³ taken together with the nitrogen atom to which they are attached form a 3 to 8 membered monocyclic ring system optionally substituted with $C_1$-$C_6$alkyl, which ring system is saturated or unsaturated and has, in addition to said nitrogen atom, 0 to 2 heteroatom ring members selected from O, S(O)$_n$ and NR¹⁰;

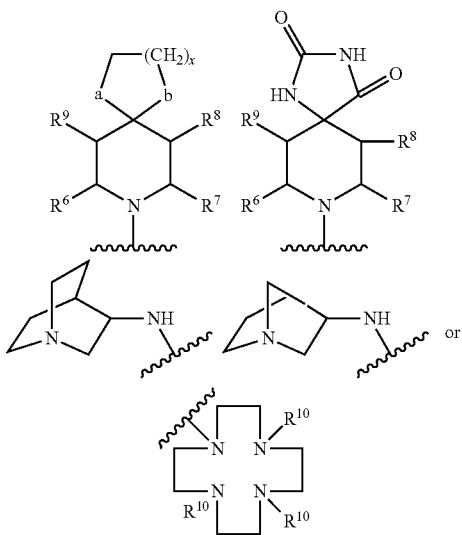

or R¹² and R¹³ taken together with the nitrogen atom to which they are attached form wherein a and b are each independently —CH$_2$—, O, S, or NR¹⁰, and x is 1-3;

$C_1$-$C_9$heteroaryl refers to a 5-10 membered aromatic ring system having one or more rings and 1, 2, 3 or 4 ring members independently selected from O, NR¹⁰, and S(O)$_n$;

$C_1$-$C_9$heterocyclyl refers to a 3-10 membered ring system having one or more rings and 1, 2, 3 or 4 ring members independently selected from O, NR¹⁰, and S(O)$_n$; and optionally substituted aryl and heteroaryl groups are unsubstituted or are substituted with 1 or 2 moieties selected from the group consisting of: a) $C_1$-$C_6$alkyl optionally substituted with OH, NH$_2$, NH($C_1$-$C_6$alkyl), N($C_1$-$C_6$alkyl)$_2$, —NH(CH$_2$)$_w$N($C_1$-$C_6$alkyl)$_2$ wherein w is 2, 3 or 4, or 3-10 membered $C_1$-$C_9$heterocyclyl optionally substituted with from 1 to 3 independently selected $C_1$-$C_6$alkyl-substituents; b) halogen; c) hydroxy; d) NH$_2$; e) NO$_2$; f) SO$_2$NH$_2$; g) COOH; h) COO($C_1$-$C_6$alkyl); i) NHCOO($C_1$-$C_6$alkyl); j) NH($C_1$-$C_6$alkyl); k) N($C_1$-$C_6$alkyl)$_2$; l) C(O)NR$^a$R$^b$, wherein R$^a$ is H or $C_1$-$C_6$alkyl, and R$^b$ is H, $C_1$-$C_6$alkyl, ($C_6$-$C_{14}$aryl) alkyl-, or ($C_1$-$C_9$heteroaryl)alkyl-; m) —Y-Q, wherein Y is: i) O, ii) NH, iii) N($C_1$-$C_6$alkyl), iv) NHSO$_2$, v) SO$_2$NH, vi) NHCONH, vii) NHCON($C_1$-$C_6$alkyl), viii) S(O)$_q$, q is 0, 1 or 2, ix) —C(O)NH—, x) —NHC(O)— xi) —C(O)N(CH$_3$)—, xii) C(O), or xiii) absent, and Q is selected from: i) $C_6$-$C_{10}$aryl, optionally substituted with from 1 to 3 substituents independently selected from: A) $C_1$-$C_6$alkoxy- optionally substituted with 1) H$_2$N—, 2) ($C_1$-$C_6$alkyl)amino-, 3) di($C_1$-$C_6$alkyl)amino-, 4) $C_1$-$C_9$heterocyclyl-optionally substituted by $C_1$-$C_6$alkyl-, or 5) hydroxyl, B) ($C_1$-$C_6$alkoxy) carbonyl-, C) ($C_1$-$C_6$alkoxy)C(O)NH—, D) $C_1$-$C_6$alkyl- optionally substituted with 1) H$_2$N—, 2) ($C_1$-$C_6$alkyl)amino-, or 3) di($C_1$-$C_6$alkyl)amino-, E) ($C_1$-$C_6$alkyl)amino-, F) di($C_1$-$C_6$alkyl)amino-, G) ($C_1$-$C_6$alkyl)amido-optionally substituted with 1) H$_2$N—, 2) ($C_1$-$C_6$alkyl)amino-, or 3) di($C_1$-$C_6$alkyl)amino-, H) ($C_1$-$C_6$alkyl)carboxyamido-, I) $C_1$-$C_9$heterocyclyl- optionally substituted by $C_1$-$C_6$alkyl- or $C_1$-$C_6$hydroxylalkyl-, J) heterocyclyl($C_1$-$C_6$alkyl)- optionally substituted by $C_1$-$C_6$alkyl-, K) halogen, L) hydroxyl, M) $C_1$-$C_6$hydroxylalkyl-, N) perfluoro($C_1$-$C_6$)alkyl-, O) H$_2$N—, P) O$_2$N—, Q) H$_2$NSO$_2$—, R) HO$_2$C—, and S) NC—, ii) 5-10 membered $C_1$-$C_9$heteroaryl, optionally substituted with from 1 to 3 substituents independently selected from: A) $C_1$-$C_6$alkoxy- optionally substituted with 1) H$_2$N—, 2) ($C_1$-$C_6$alkyl)amino-, 3) di($C_1$-$C_6$alkyl)amino-, 4) $C_1$-$C_9$heterocyclyl- optionally substituted by $C_1$-$C_6$alkyl-, or 5) hydroxyl, B) ($C_1$-$C_6$alkoxy)carbonyl-, C) ($C_1$-$C_6$alkoxy)C(O)NH—, D) $C_1$-$C_6$alkyl-optionally substituted with 1) H$_2$N—, 2) ($C_1$-$C_6$alkyl)amino-, or 3) di($C_1$-$C_6$alkyl)amino-, E) ($C_1$-$C_6$alkyl)amino-, F) di($C_1$-$C_6$alkyl)amino-, G) ($C_1$-$C_6$alkyl)amido- optionally substituted with 1) H$_2$N—, 2) ($C_1$-$C_6$alkyl)amino-, or 3) di($C_1$-$C_6$alkyl)amino-, H) ($C_1$-$C_6$alkyl) carboxyamido-, I) $C_1$-$C_9$heterocyclyl- optionally substituted by $C_1$-$C_6$alkyl- or $C_1$-$C_6$hydroxylalkyl-, J) heterocyclyl($C_1$-$C_6$alkyl)- optionally substituted by $C_1$-$C_6$alkyl-, K) halogen, L) hydroxyl, M) $C_1$-$C_6$hydroxylalkyl-, N) perfluoro($C_1$-$C_6$) alkyl-, O) H$_2$N—, P) O$_2$N—, Q) H$_2$NSO$_2$—, R) HO$_2$C—, and S) NC—, iii) 3-10 membered $C_1$-$C_9$heterocyclyl, optionally substituted with from 1 to 3 substituents independently selected from: A) $C_1$-$C_6$alkyl-, B) heterocyclyl($C_1$-$C_6$alkyl)-, C) ($C_6$-$C_{14}$aryl)alkyl-, D) $C_1$-$C_8$acyl-, E) ($C_1$-$C_6$alkoxy)carbonyl-, F) ($C_1$-$C_6$alkyl)carboxyl-, G) halogen, H) $C_1$-$C_6$haloalkyl-, I) hydroxyl, J) $C_1$-$C_6$hydroxyalkyl-, K) H$_2$N—, L) ($C_1$-$C_6$alkyl)amino-, M) di($C_1$-$C_6$alkyl)amino-, N) HO$_2$C—, O) ($C_1$-$C_6$alkoxy)carbonyl-, P) ($C_1$-$C_6$alkyl) carboxyl-, Q) ($C_1$-$C_6$alkyl)amido-, R) H$_2$NC(O)—, S) ($C_1$-$C_6$alkyl)carboxyamido-, T) 5-10 membered $C_1$-$C_9$heteroaryl, U) $C_6$-$C_{14}$ary, V) $C_3$-$C_8$cycloalkyl W) 3-10 membered $C_1$-$C_9$heterocyclyl, X) NC—; and Y) —NO$_2$; iv) $C_3$-$C_{10}$cycloalkyl, v) $C_1$-$C_6$alkyl, vi) $C_2$-$C_6$alkenyl, vii) $C_2$-$C_6$alkynyl, viii) $C_1$-$C_6$hydroxyalkyl-, ix) (CH$_2$)$_v$O($C_1$-$C_6$alkyl), x) (CH$_2$)$_v$NH$_2$, xi) (CH$_2$)$_v$NH($C_1$-$C_6$alkyl), xii) (CH$_2$)$_v$N($C_1$-$C_6$alkyl)$_2$, xiii) O(CH$_2$)$_v$N($C_1$-$C_6$alkyl)$_2$, xiv) (CH$_2$)$_v$$C_6$-$C_{10}$aryl, xv) —CN, xvi) (CH$_2$)$_v$ 5-10 membered $C_1$-$C_9$heteroaryl, xvii) (CH$_2$)$_v$ 3-10 membered $C_1$-$C_9$heterocyclyl, optionally substituted by $C_1$-$C_6$alkyl-, wherein v is 1, 2, 3 or 4, and xviii) $C_1$-$C_6$perfluoroalkyl-; and n) C(O)R$^c$ wherein R$^c$ is: i) H, ii) $C_1$-$C_6$alkyl, or iii) $C_3$-$C_6$cycloalkyl, and pharmaceutically acceptable salts and esters thereof.

In some embodiments of the invention, R¹ and/or R⁴ is

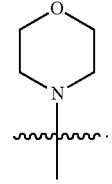

In some embodiments, R¹ and/or R⁴ is

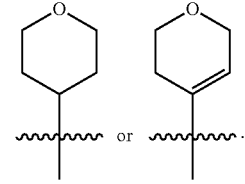

In some embodiments, one of $R^1$ or $R^4$ is

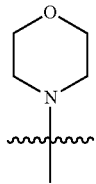

and the other is

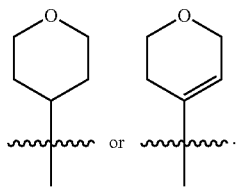

In some embodiments, $R^2$ is optionally substituted $C_6$-$C_{14}$aryl-NH—COR$^3$; in others $R^2$ is optionally substituted phenyl-NH—COR$^3$.

In some embodiments, $R^3$ is NHR$^5$ or OR$^5$. In some embodiments, $R^5$ is optionally substituted $C_6$-$C_{10}$aryl, such as optionally substituted phenyl or $C_1$-$C_9$heteroaryl. In some embodiments, the optionally substituted $C_6$-$C_{10}$aryl or phenyl is substituted with —Y-Q, C(O)NR$^a$R$^b$ or C(O)R$^c$.

In some embodiments, $R^5$ is phenyl substituted with —Y-Q.

The following compounds exemplify illustrative compounds of Formula I:

1-[4-(4,6-dimorpholin-4-yl-1,3,5-triazin-2-yl)phenyl]-3-pyridin-4-ylurea;
1-[4-(4,6-dimorpholin-4-yl-1,3,5-triazin-2-yl)phenyl]-3-pyridin-3-ylurea;
1-[4-(4,6-dimorpholin-4-yl-1,3,5-triazin-2-yl)phenyl]-3-phenylurea;
1-[4-(4,6-dimorpholin-4-yl-1,3,5-triazin-2-yl)phenyl]-3-thiophen-2-ylurea;
1-[4-(4,6-dimorpholin-4-yl-1,3,5-triazin-2-yl)phenyl]-3-(4-methylphenyl)urea;
1-[4-(4,6-dimorpholin-4-yl-1,3,5-triazin-2-yl)phenyl]-3-(4-fluorophenyl)urea;
1-(2,4-dimethoxyphenyl)-3-[4-(4,6-dimorpholin-4-yl-1,3,5-triazin-2-yl)phenyl]-urea;
1-(4-chlorophenyl)-3-[4-(4,6-dimorpholin-4-yl-1,3,5-triazin-2-yl)phenyl]urea;
1-[4-(4,6-dimorpholin-4-yl-1,3,5-triazin-2-yl)phenyl]-3-(4-methoxyphenyl)urea;
(4-chlorophenyl)-3-[4-(4,6-dimorpholin-4-yl-1,3,5-triazin-2-yl)phenyl]urea;
(2,4-difluorophenyl)-3-[4-(4,6-dimorpholin-4-yl-1,3,5-triazin-2-yl)phenyl]urea;
1-[4-(4,6-dimorpholin-4-yl-1,3,5-triazin-2-yl)phenyl]-3-ethylurea;
tert-butyl 3-{[4-(4-{[(4-fluorophenyl)carbamoyl]amino}phenyl)-6-morpholin-4-yl-1,3,5-triazin-2-yl]amino}azetidine-1-carboxylate;
tert-butyl 3-[(4-morpholin-4-yl-6-{4-[(phenylcarbamoyl)amino]phenyl}-1,3,5-triazin-2-yl)amino]azetidine-1-carboxylate;
tert-butyl 3-[(4-morpholin-4-yl-6-{4-[(pyridine-3-ylcarbamoyl)amino]phenyl}-1,3,5-triazin-2-yl)amino]azetidine-1-carboxylate;
tert-butyl 3-{[4-(4-{[(4-methylphenyl)carbamoyl]amino}phenyl)-6-morpholin-4-yl-1,3,5-triazin-2-yl]amino}azetidine-1-carboxylate;
1-{4-[4-(azetidin-3-ylamino)-6-morpholin-4-yl-1,3,5-triazin-2-yl]phenyl}-3-phenylurea;
1-{4-[4-(azetidin-3-ylamino)-6-morpholin-4-yl-1,3,5-triazin-2-yl]phenyl}-3-pyridin-3-ylurea;
1-{4-[4-(azetidin-3-ylamino)-6-morpholin-4-yl-1,3,5-triazin-2-yl]phenyl}-3-(4-fluorophenyl)urea;
1-{4-[4-(azetidin-3-ylamino)-6-morpholin-4-yl-1,3,5-triazin-2-yl]phenyl}-3-(4-methylphenyl)urea;
tert-butyl 3-[(4-morpholin-4-yl-6-{4-[(pyridine-4-ylcarbamoyl)amino]phenyl}-1,3,5-triazin-2-yl)amino]azetidine-1-carboxylate;
1-{4-[4-(azetidin-3-ylamino)-6-morpholin-4-yl-1,3,5-triazin-2-yl]phenyl}-3-pyridin-4-ylurea
1-[2-(dimethylamino)ethyl]-3-{4-[4-(1,4-dioxa-8-azaspiro[4.5]dec-8-yl)-6-morpholin-4-yl-1,3,5-triazin-2-yl]phenyl}urea;
1-[4-(4,6-dimorpholin-4-yl-1,3,5-triazin-2-yl)phenyl]-3-(2-methyl pyridin-4-yl)urea;
1-[4-(4,6-dimorpholin-4-yl-1,3,5-triazin-2-yl)phenyl]-3-[4-(2-hydroxyethyl)phenyl]urea;
1-[4-(4,6-dimorpholin-4-yl-1,3,5-triazin-2-yl)phenyl]-3-[4-(hydroxymethyl)phenyl]urea;
1-[4-(4,6-dimorpholin-4-yl-1,3,5-triazin-2-yl)phenyl]-3-[4-hydroxyphenyl]urea;
1-[4-(4,6-dimorpholin-4-yl-1,3,5-triazin-2-yl)phenyl]-3-[4-(1-hydroxyethyl)phenyl]urea;
1-[4-(4,6-dimorpholin-4-yl-1,3,5-triazin-2-yl)phenyl]-3-[4-(trifluoromethyl)phenyl]urea;
1-[4-(4,6-dimorpholin-4-yl-1,3,5-triazin-2-yl)phenyl]-3-(4-hydroxyphenyl)urea;
1-[4-(4,6-dimorpholin-4-yl-1,3,5-triazin-2-yl)phenyl]-3-[5-(trifluoromethyl)pyridin-2-yl]urea;
1-[4-(4,6-dimorpholin-4-yl-1,3,5-triazin-2-yl)phenyl]-3-{4-[2,2,2-trifluoro-1-hydroxy-1-(trifluoromethyl)ethyl]phenyl}urea;
1-[4-(4,6-dimorpholin-4-yl-1,3,5-triazin-2-yl)phenyl]-3-[3-(1-hydroxyethyl)phenyl]urea;
methyl 4-({[4-(4,6-dimorpholin-4-yl-1,3,5-triazin-2-yl)phenyl]carbamoyl}amino)benzoate;
1-{4-[4-morpholin-4-yl-6-(tetrahydro-2H-pyran-4-yloxy)-1,3,5-triazin-2-yl]phenyl}-3-pyridin-4-ylurea;
1-{4-[4-morpholin-4-yl-6-(tetrahydro-2H-pyran-4-yloxy)-1,3,5-triazin-2-yl]phenyl}-3-phenylurea;
1-{4-[4-morpholin-4-yl-6-(tetrahydro-2H-pyran-4-yloxy)-1,3,5-triazin-2-yl]phenyl}-3-pyridin-3-ylurea;
1-[4-(hydroxymethyl)phenyl]-3-{4-[4-morpholin-4-yl-6-(tetrahydro-2H-pyran-4-yloxy)-1,3,5-triazin-2-yl]phenyl}urea;
1-(2-methyl pyridin-4-yl)-3-{4-[4-morpholin-4-yl-6-(tetrahydro-2H-pyran-4-yloxy)-1,3,5-triazin-2-yl]phenyl}urea;
1-[2-(methylamino)ethyl]-3-{4-[4-morpholin-4-yl-6-(tetrahydro-2H-pyran-4-yloxy)-1,3,5-triazin-2-yl]phenyl}urea;
1-(3-acetylphenyl)-3-{4-[4-morpholin-4-yl-6-(tetra hydro-2H-pyran-4-yloxy)-1,3,5-triazin-2-yl]phenyl}urea;
1-[4-(dimethylamino)phenyl]-3-{4-[4-morpholin-4-yl-6-(tetrahydro-2H-pyran-4-yloxy)-1,3,5-triazin-2-yl]phenyl}urea;
4-[3-{4-(4,6-dimorpholino-1,3,5-triazin-2yl)phenyl}ureido]benzoic acid;
N-(2-(dimethylamino)ethyl)-4-(3-(4-(4,6-dimorpholino-1,3,5-triazin-2-yl)phenyl)ureido)benzamide;
N-(2-(dimethylamino)ethyl)-4-(3-(4-(4,6-dimorpholino-1,3,5-triazin-2-yl)phenyl)ureido)benzamide HCl salt;

1-(4-(4,6-dimorpholino-1,3,5-triazin-2-yl)phenyl)-3-(4-(4-methylpiperazine-1-carbonyl)phenyl)urea;
4-(3-(4-(4,6-dimorpholino-1,3,5-triazin-2-yl)phenyl)ureido)-N-methylbenzamide;
N-(2-(dimethylamino)ethyl)-4-(3-(4-(4,6-dimorpholino-1,3,5-triazin-2-yl)phenyl)ureido)-N-methylbenzamide;
1-(4-(4,6-dimorpholino-1,3,5-triazin-2-yl)phenyl)-3-(4-(4-morpholinopiperidine-1-carbonyl)phenyl)urea;
4-(3-(4-(4,6-dimorpholino-1,3,5-triazin-2-yl)phenyl)ureido)-N-(quinuclidin-3-yl)benzamide;
1-(4-(4,6-dimorpholino-1,3,5-triazin-2-yl)phenyl)-3-(4-(4-(pyrrolidin-1-yl)piperidine-1-carbonyl)phenyl)urea;
1-(4-(1,4'-bipiperidine-1'-carbonyl)phenyl)-3-(4-(4,6-dimorpholino-1,3,5-triazin-2-yl)phenyl)urea;
1-(4-(4-(dimethylamino)piperidine-1-carbonyl)phenyl)-3-(4-(4,6-dimorpholino-1,3,5-triazin-2-yl)phenyl)urea;
1-(4-(4,6-dimorpholino-1,3,5-triazin-2-yl)phenyl)-3-(4-(piperazine-1-carbonyl)phenyl)urea;
1-(4-(4,6-dimorpholino-1,3,5-triazin-2-yl)phenyl)-3-(4-(2-(pyridin-2-yl)acetyl)phenyl)urea;
1-[4-(4,6-dimorpholin-4-yl-1,3,5-triazin-2-yl)phenyl]-3-[4-(1-hydroxyethyl)phenyl]urea;
1-[4-(4,6-dimorpholin-4-yl-1,3,5-triazin-2-yl)phenyl]-3-(2-methylpyridin-4-yl)urea;
1-[4-(4,6-dimorpholin-4-yl-1,3,5-triazin-2-yl)phenyl]-3-[4-(hydroxymethyl)phenyl]urea;
1-[4-(4,6-dimorpholin-4-yl-1,3,5-triazin-2-yl)phenyl]-3-[4-(trifluoromethyl)phenyl]urea;
1-[4-(4,6-dimorpholin-4-yl-1,3,5-triazin-2-yl)phenyl]-3-{4-[2,2,2-trifluoro-1-hydroxy-1-(trifluoromethyl)ethyl]phenyl}urea;
1-[4-(4,6-dimorpholin-4-yl-1,3,5-triazin-2-yl)phenyl]-3-[5-(trifluoromethyl)pyridin-2-yl]urea;
1-[4-(4,6-dimorpholin-4-yl-1,3,5-triazin-2-yl)phenyl]-3-[3-(1-hydroxyethyl)phenyl]urea;
1-(4-{4-[(3S)-3-methylmorpholin-4-yl]-6-morpholin-4-yl-1,3,5-triazin-2-yl}phenyl)-3-pyridin-4-ylurea;
1-[4-(2-hydroxyethyl)phenyl]-3-(4-{4-[(3S)-3-methylmorpholin-4-yl]-6-morpholin-4-yl-1,3,5-triazin-2-yl}phenyl)urea;
1-[4-(2-hydroxymethyl)phenyl]-3-(4-{4-[(3S)-3-methylmorpholin-4-yl]-6-morpholin-4-yl-1,3,5-triazin-2-yl}phenyl)urea;
1-(4-{4-[(3S)-3-methylmorpholin-4-yl]-6-morpholin-4-yl-1,3,5-triazin-2-yl}phenyl)-3-(2-methylpyridin-4-yl)urea;
1-[4-(1-hydroxyethyl)phenyl]-3-(4-{4-[(3S)-3-methylmorpholin-4-yl]-6-morpholin-4-yl-1,3,5-triazin-2-yl}phenyl)urea;
1-[4-(4-isopropoxy-6-morpholin-4-yl-1,3,5-triazin-2-yl)phenyl]-3-pyridin-4-ylurea;
methyl 4-({[4-(4-isopropoxy-6-morpholin-4-yl-1,3,5-triazin-2-yl)phenyl]carbamoyl}-amino)benzoate;
1-[4-(4-isopropoxy-6-morpholin-4-yl-1,3,5-triazin-2-yl)phenyl]-3-{4-[(4-methylpiperazin-1-yl)carbonyl]phenyl}urea;
4-({[4-(4-isopropoxy-6-morpholin-4-yl-1,3,5-triazin-2-yl)phenyl]carbamoyl}amino)-N-(1-methylpiperidin-4-yl)benzamide;
1-[4-(4,6-dimorpholin-4-yl-1,3,5-triazin-2-yl)phenyl]-3-(1-methylpiperidin-4-yl)urea;
1-(4-{4-[(3S)-3-methylmorpholin-4-yl]-6-morpholin-4-yl-1,3,5-triazin-2-yl}phenyl)-3-(1-methylpiperidin-4-yl)urea;
1-{4-[4-(3,6-Dihydro-2H-pyran-4-yl)-6-morpholin-4-yl-[1,3,5]triazin-2-yl]-phenyl}-3-pyridin-4-yl-urea;
1-{4-[4-Morpholin-4-yl-6-(tetrahydro-pyran-4-yl)-[1,3,5]triazin-2-yl]-phenyl}-3-pyridin-4-yl-urea;
3-({4-Morpholin-4-yl-6-[4-(3-pyridin-4-yl-ureido)-phenyl]-[1,3,5]triazin-2-ylamino}-methyl)-azetidine-1-carboxylic acid tert-butyl ester;
1-(4-{4-[(azetidin-3-ylmethyl)-amino]-6-morpholin-4-yl-[1,3,5]triazin-2-yl}-phenyl)-3-pyridin-4-yl-urea;
1-{4-[4-(1,4-dioxa-8-azaspiro[4.5]dec-8-yl)-6-morpholin-4-yl-1,3,5-triazin-2-yl]phenyl}-3-pyridin-4-ylurea;
1-{4-[4-(1,4-dioxa-8-azaspiro[4.5]dec-8-yl)-6-morpholin-4-yl-1,3,5-triazin-2-yl]phenyl}-3-pyridin-3-ylurea;
1-{4-[4-(1,4-dioxa-8-azaspiro[4.5]dec-8-yl)-6-morpholin-4-yl-1,3,5-triazin-2-yl]phenyl}-3-phenylurea;
1-[4-(dimethylamino)phenyl]-3-{4-[4-(1,4-dioxa-8-azaspiro[4.5]dec-8-yl)-6-morpholin-4-yl-1,3,5-triazin-2-yl]phenyl}urea;
1-(4-cyanophenyl)-3-{4-[4-(1,4-dioxa-8-azaspiro[4.5]dec-8-yl)-6-morpholin-4-yl-1,3,5-triazin-2-yl]phenyl}urea;
1-{4-[4-(1,4-dioxa-8-azaspiro[4.5]dec-8-yl)-6-morpholin-4-yl-1,3,5-triazin-2-yl]phenyl}-3-(2-methylpyridin-4-yl)urea;
1-[2-(dimethylamino)ethyl]-3-{4-[4-(1,4-dioxa-8-azaspiro[4.5]dec-8-yl)-6-morpholin-4-yl-1,3,5-triazin-2-yl]phenyl}urea;
1-[4-(4-morpholin-4-yl-6-quinolin-3-yl-1,3,5-triazin-2-yl)phenyl]-3-pyridin-4-ylurea;
1-[4-(4-azetidin-1-yl-6-morpholin-4-yl-1,3,5-triazin-2-yl)phenyl]-3-pyridin-4-ylurea;
methyl 4-({[4-(4-azetidin-1-yl-6-morpholin-4-yl-1,3,5-triazin-2-yl)phenyl]carbamoyl}amino)benzoate;
1-[4-(4-isopropoxy-6-morpholin-4-yl-1,3,5-triazin-2-yl)phenyl]-3-{4-[(4-methylpiperazin-1-yl)carbonyl]phenyl}urea;
4-({[4-(4-isopropoxy-6-morpholin-4-yl-1,3,5-triazin-2-yl)phenyl]carbamoyl}amino)-N-(1-methylpiperidin-4-yl)benzamide;
4-({[4-(4,6-dimorpholin-4-yl-1,3,5-triazin-2-yl)phenyl]carbamoyl}amino)-N-(2-piperidin-1-ylethyl)benzamide;
1-[4-(4,6-dimorpholin-4-yl-1,3,5-triazin-2-yl)phenyl]-3-[4-(morpholin-4-ylcarbonyl)phenyl]urea;
1-[4-(4-methyl-6-morpholin-4-yl-1,3,5-triazin-2-yl)phenyl]-3-pyridin-4-ylurea;
4-({[4-(4-methyl-6-morpholin-4-yl-1,3,5-triazin-2-yl)phenyl]carbamoyl}amino)benzoate;
1-{4-[4-(3,6-dihydro-2H-pyran-4-yl)-6-morpholin-4-yl-1,3,5-triazin-2-yl]phenyl}-3-{4-[(4-methylpiperazin-1-yl)carbonyl]phenyl}urea;
4-({[4-(4-methyl-6-morpholin-4-yl-1,3,5-triazin-2-yl)phenyl]carbamoyl}amino)-N-(1-methylpiperidin-4-yl)benzamide;
N-[2-(dimethylamino)ethyl]-N-methyl-4-({[4-(4-methyl-6-morpholin-4-yl-1,3,5-triazin-2-yl)phenyl]carbamoyl}amino)benzamide;
1-[4-(4-methyl-6-morpholin-4-yl-1,3,5-triazin-2-yl)phenyl]-3-{4-[(4-methylpiperazin-1-yl)carbonyl]phenyl}urea;
1-(4-{[3-(dimethylamino)pyrrolidin-1-yl]carbonyl}phenyl)-3-[4-(4,6-dimorpholin-4-yl-1,3,5-triazin-2-yl)phenyl]urea;
1-[4-({4-[2-(dimethylamino)ethyl]piperazin-1-yl}carbonyl)phenyl]-3-[4-(4,6-dimorpholin-4-yl-1,3,5-triazin-2-yl)phenyl]urea;
1-[4-(4,6-dimorpholin-4-yl-1,3,5-triazin-2-yl)phenyl]-3-{4-[(4-pyrrolidin-1-ylpiperidin-1-yl)carbonyl]phenyl}urea;
4-({[4-(4-butyl-6-morpholin-4-yl-1,3,5-triazin-2-yl)phenyl]carbamoyl}amino)benzoic acid; N-[2-(dimethylamino)ethyl]-4-({[4-(4-isopropoxy-6-morpholin-4-yl-1,3,5-triazin-2-yl)phenyl]carbamoyl}amino)-N-methylbenzamide;

1-[4-(4-butyl-6-morpholin-4-yl-1,3,5-triazin-2-yl)phenyl]-3-pyridin-4-ylurea;

N-[2-(dimethylamino)ethyl]-4-({[4-(4-isopropoxy-6-morpholin-4-yl-1,3,5-triazin-2-yl)phenyl]carbamoyl}amino)benzamide;

4-({[4-(4-butyl-6-morpholin-4-yl-1,3,5-triazin-2-yl)phenyl]carbamoyl}amino)benzoate;

4-({[4-(4-azetidin-1-yl-6-morpholin-4-yl-1,3,5-triazin-2yl)phenyl]carbamoyl}amino)benzoic acid; mp 204° C.;

1-[4-(4-azetidin-1-yl-6-morpholin-4-yl-1,3,5-triazin-2-yl)phenyl]-3-{4-[(4-methylpiperazin-1-yl)carbonyl]phenyl}urea; mp 170° C.;

4-({[4-(4-azetidin-1-yl-6-morpholin-4-yl-1,3,5-triazin-2-yl)phenyl]carbamoyl}amino)-N-[2-(dimethylamino)ethyl]-N-methylbenzamide;

4-({[4-(4-butyl-6-morpholin-4-yl-1,3,5-triazin-2-yl)phenyl]carbamoyl}amino)-N-[2-(dimethylamino)ethyl]-N-methylbenzamide;

1-{4-[4-(1-ethoxyvinyl)-6-morpholin-4-yl-1,3,5-triazin-2-yl]phenyl}-3-pyridin-4-ylurea;

1-{4-[4-(2-methoxyethoxy)-6-morpholin-4-yl-1,3,5-triazin-2-yl]phenyl}-3-pyridin-4-ylurea;

1-[4-(4-acetyl-6-morpholin-4-yl-1,3,5-triazin-2-yl)phenyl]-3-pyridin-4-ylurea;

methyl 4-[({4-[4-(2-methoxyethoxy)-6-morpholin-4-yl-1,3,5-triazin-2-yl]phenyl}carbamoyl)amino]benzoate;

1-{4-[4-(1-hydroxyethyl)-6-morpholin-4-yl-1,3,5-triazin-2-yl]phenyl}-3-pyridin-4-ylurea;

methyl 4-[({4-[4-(3,6-dihydro-2H-pyran-4-yl)-6-morpholin-4-yl-1,3,5-triazin-2-yl]phenyl}carbamoyl)amino]benzoate;

4-[({4-[4-(3,6-dihydro-2H-pyran-4-yl)-6-morpholin-4-yl-1,3,5-triazin-2-yl]phenyl}carbamoyl)amino]benzoic acid;

1-(4-{4-morpholin-4-yl-6-[2-(pyridin-4-ylamino)ethyl]-1,3,5-triazin-2-yl}phenyl)-3-pyridin-4-ylurea;

4-({[4-(4-butyl-6-morpholin-4-yl-1,3,5-triazin-2-yl)phenyl]carbamoyl}amino)-N-[2-(dimethylamino)ethyl]benzamide;

1-[4-(4-butyl-6-morpholin-4-yl-1,3,5-triazin-2-yl)phenyl]-3-{4-[(4-methylpiperazin-1-yl)carbonyl]phenyl}urea;

1-[4-(4-ethyl-6-morpholin-4-yl-1,3,5-triazin-2-yl)phenyl]-3-{4-[(4-methylpiperazin-1-yl)carbonyl]phenyl}urea;

N-[2-(dimethylamino)ethyl]-4-({[4-(4-ethyl-6-morpholin-4-yl-1,3,5-triazin-2-yl)phenyl]carbamoyl}amino)benzamide;

1-(4-{[4-(dimethylamino)piperidin-1-yl]carbonyl}phenyl)-3-[4-(4-ethyl-6-morpholin-4-yl-1,3,5-triazin-2-yl)phenyl]urea;

1-[4-(4-butyl-6-morpholin-4-yl-1,3,5-triazin-2-yl)phenyl]-3-[4-(hydroxymethyl)phenyl]urea;

4-[({4-[4-(3,6-dihydro-2H-pyran-4-yl)-6-morpholin-4-yl-1,3,5-triazin-2-yl]phenyl}carbamoyl)amino]-N-[2-(dimethylamino)ethyl]-N-methylbenzamide;

1-[4-(4-butyl-6-morpholin-4-yl-1,3,5-triazin-2-yl)phenyl]-3-(4-{[4-(dimethylamino)piperidin-1-yl]carbonyl}phenyl)urea;

N-[2-(dimethylamino)ethyl]-4-({[4-(4-ethyl-6-morpholin-4-yl-1,3,5-triazin-2-yl)phenyl]carbamoyl}amino)-N-methylbenzamide;

N-[2-(dimethylamino)ethyl]-4-({[4-(4-methoxy-6-morpholin-4-yl-1,3,5-triazin-2-yl)phenyl]carbamoyl}amino)-N-methylbenzamide;

N-[2-(dimethylamino)ethyl]-4-({[4-(4-methoxy-6-morpholin-4-yl-1,3,5-triazin-2-yl)phenyl]carbamoyl}amino)benzamide;

4-({[4-(4-methoxy-6-morpholin-4-yl-1,3,5-triazin-2-yl)phenyl]carbamoyl}amino)-N-methyl-N-[2-(methylamino)ethyl]benzamide;

1-[4-(4-methoxy-6-morpholin-4-yl-1,3,5-triazin-2-yl)phenyl]-3-{4-[(4-methyl piperazin-1-yl)carbonyl]phenyl}urea;

1-{4-[(3,3-dimethyl piperazin-1-yl)carbonyl]phenyl}-3-[4-(4-methoxy-6-morpholin-4-yl-1,3,5-triazin-2-yl)phenyl]urea;

4-({[4-(4-methoxy-6-morpholin-4-yl-1,3,5-triazin-2-yl)phenyl]carbamoyl}amino)-N-(2-piperidin-1-ylethyl)benzamide;

4-({[4-(4-ethyl-6-morpholin-4-yl-1,3,5-triazin-2-yl)phenyl]carbamoyl}amino)-N-[4-(4-methylpiperazin-1-yl)phenyl]benzamide;

1-[4-(4-butyl-6-morpholin-4-yl-1,3,5-triazin-2-yl)phenyl]-3-[4-({[2-(dimethylamino)ethyl]amino}methyl)phenyl]urea;

4-({[4-(4-butyl-6-morpholin-4-yl-1,3,5-triazin-2-yl)phenyl]carbamoyl}amino)-N-[4-(4-methylpiperazin-1-yl)phenyl]benzamide;

1-[4-(4-butyl-6-morpholin-4-yl-1,3,5-triazin-2-yl)phenyl]-3-{4-[(4-methyl piperazin-1-yl)methyl]phenyl}urea;

1-[4-(4-butyl-6-morpholin-4-yl-1,3,5-triazin-2-yl)phenyl]-3-(4-formylphenyl)urea;

4-({[4-(4,6-dimorpholin-4-yl-1,3,5-triazin-2-yl)phenyl]carbamoyl}amino)-N-(pyridin-2-ylmethyl)benzamide;

1-(4-{4-[2-(1,3-dioxan-2-yl)ethyl]-6-morpholin-4-yl-1,3,5-triazin-2-yl}phenyl)-3-pyridin-4-ylurea;

1-(4-{4-[2,5-bis(hydroxymethyl)pyrrolidin-1-yl]-6-morpholin-4-yl-1,3,5-triazin-2-yl}phenyl)-3-pyridin-4-ylurea;

4-({[4-(4-butyl-6-morpholin-4-yl-1,3,5-triazin-2-yl)phenyl]carbamoyl}amino)-N-{4-[2-(dimethylamino)ethoxy]phenyl}benzamide;

1-{4-[(4-benzylpiperidin-1-yl)carbonyl]phenyl}-3-[4-(4-butyl-6-morpholin-4-yl-1,3,5-triazin-2-yl)phenyl]urea;

4-({[4-(4-ethyl-6-morpholin-4-yl-1,3,5-triazin-2-yl)phenyl]carbamoyl}amino)-N-(1-methylpiperidin-4-yl)benzamide;

4-({[4-(4-butyl-6-morpholin-4-yl-1,3,5-triazin-2-yl)phenyl]carbamoyl}amino)-N-(1-methylpiperidin-4-yl)benzamide;

1-(4-{4-[3-(dimethylamino)propyl]-6-morpholin-4-yl-1,3,5-triazin-2-yl}phenyl)-3-pyridin-4-ylurea;

1-[4-(4-{3-[(1-methyl ethyl)amino]propyl}-6-morpholin-4-yl-1,3,5-triazin-2-yl)phenyl]-3-pyridin-4-ylurea;

1-{4-[4-morpholin-4-yl-6-(3-pyrrolidin-1-ylpropyl)-1,3,5-triazin-2-yl]phenyl}-3-pyridin-4-ylurea;

1-(4-{4-[3-(4-methylpiperazin-1-yl)propyl]-6-morpholin-4-yl-1,3,5-triazin-2-yl}phenyl)-3-pyridin-4-ylurea;

1-{4-[4-(3-{[2-(dimethylamino)ethyl]amino}propyl)-6-morpholin-4-yl-1,3,5-triazin-2-yl]phenyl}-3-pyridin-4-ylurea;

1-{4-[4-(3-hydroxypropyl)-6-morpholin-4-yl-1,3,5-triazin-2-yl]phenyl}-3-pyridin-4-ylurea;

1-{4-[4-morpholin-4-yl-6-(3-oxopropyl)-1,3,5-triazin-2-yl]phenyl}-3-pyridin-4-ylurea;

1-{4-[4-(3,6-dihydro-2H-pyran-4-yl)-6-morpholin-4-yl-1,3,5-triazin-2-yl]phenyl}-3-(4-{[4-(dimethylamino)piperidin-1-yl]carbonyl}phenyl)urea;

4-[({4-[4-(3,6-dihydro-2H-pyran-4-yl)-6-morpholin-4-yl-1,3,5-triazin-2-yl]phenyl}carbamoyl)amino]-N-[2-(dimethylamino)ethyl]benzamide;

1-[4-(4-methylpiperazin-1-yl)phenyl]-3-[4-(4-morpholin-4-yl-6-propyl-1,3,5-triazin-2-yl)phenyl]urea;

1-{4-[2-(dimethylamino)ethoxy]phenyl}-3-[4-(4-ethyl-6-morpholin-4-yl-1,3,5-triazin-2-yl)phenyl]urea;
1-[4-(4-ethyl-6-morpholin-4-yl-1,3,5-triazin-2-yl)phenyl]-3-[4-(4-methyl piperazin-1-yl)phenyl]urea;
1-[4-(4-methylpiperazin-1-yl)phenyl]-3-{4-[4-(2-methylpropyl)-6-morpholin-4-yl-1,3,5-triazin-2-yl]phenyl}urea;
1-{4-[(3,3-dimethylpiperazin-1-yl)carbonyl]phenyl}-3-[4-(4-ethyl-6-morpholin-4-yl-1,3,5-triazin-2-yl)phenyl]urea;
4-({[4-(4-ethyl-6-morpholin-4-yl-1,3,5-triazin-2-yl)phenyl]carbamoyl}amino)-N-(1-methylazetidin-3-yl)benzamide;
methyl 4-[({4-[4-(1-methylethyl)-6-morpholin-4-yl-1,3,5-triazin-2-yl]phenyl}carbamoyl)amino]benzoate
N-[2-(dimethylamino)ethyl]-4-[({4-[4-(1-methylethyl)-6-morpholin-4-yl-1,3,5-triazin-2-yl]phenyl}carbamoyl)amino]benzamide;
N-[2-(dimethylamino)ethyl]-N-methyl-4-[({4-[4-(1-methylethyl)-6-morpholin-4-yl-1,3,5-triazin-2-yl]phenyl}carbamoyl)amino]benzamide;
N-(1-methylazetidin-3-yl)-4-[({4-[4-(1-methylethyl)-6-morpholin-4-yl-1,3,5-triazin-2-yl]phenyl}carbamoyl)amino]benzamide;
1-(4-{[4-(dimethylamino)piperidin-1-yl]carbonyl}phenyl)-3-{4-[4-(1-methylethyl)-6-morpholin-4-yl-1,3,5-triazin-2-yl]phenyl}urea;
4-[({4-[4-(1-methylethyl)-6-morpholin-4-yl-1,3,5-triazin-2-yl]phenyl}carbamoyl)amino]-N-pyridin-4-ylbenzamide;
4-[({4-[4-(1-methylethyl)-6-morpholin-4-yl-1,3,5-triazin-2-yl]phenyl}carbamoyl)amino]-N-pyridin-3-ylbenzamide;
N-cyclobutyl-4-[({4-[4-(1-methylethyl)-6-morpholin-4-yl-1,3,5-triazin-2-yl]phenyl}carbamoyl)amino]benzamide;
1-[4-(4-ethyl-6-morpholin-4-yl-1,3,5-triazin-2-yl)phenyl]-3-{4-[(4-phenylpiperidin-1-yl)carbonyl]phenyl}urea;
4-({[4-(4-ethyl-6-morpholin-4-yl-1,3,5-triazin-2-yl)phenyl]carbamoyl}amino)-N-(pyridin-4-ylmethyl)benzamide;
1-{4-[(4-methylpiperazin-1-yl)carbonyl]phenyl}-3-{4-[4-(2-methylpropyl)-6-morpholin-4-yl-1,3,5-triazin-2-yl]phenyl}urea;
1-(4-{[4-(dimethylamino)piperidin-1-yl]carbonyl}phenyl)-3-{4-[4-(2-methylpropyl)-6-morpholin-4-yl-1,3,5-triazin-2-yl]phenyl}urea;
N-[2-(dimethylamino)ethyl]-N-methyl-4-[({4-[4-(2-methylpropyl)-6-morpholin-4-yl-1,3,5-triazin-2-yl]phenyl}carbamoyl)amino]benzamide;
1-{4-[4-(4-methylphenyl)-6-morpholin-4-yl-1,3,5-triazin-2-yl]phenyl}-3-{4-[(4-methylpiperazin-1-yl)carbonyl]phenyl}urea;
N-[2-(dimethylamino)ethyl]-N-methyl-4-[({4-[4-(4-methylphenyl)-6-morpholin-4-yl-1,3,5-triazin-2-yl]phenyl}carbamoyl)amino]benzamide;
1-{4-[4-(dimethylamino)piperidin-1-yl]phenyl}-3-{4-[4-(4-methylphenyl)-6-morpholin-4-yl-1,3,5-triazin-2-yl]phenyl}urea;
1-{4-[4-(4-methylphenyl)-6-morpholin-4-yl-1,3,5-triazin-2-yl]phenyl}-3-pyridin-4-ylurea;
1-{4-[4-(dimethylamino)piperidin-1-yl]phenyl}-3-[4-(4-ethyl-6-morpholin-4-yl-1,3,5-triazin-2-yl)phenyl]urea;
4-[({4-[4-(4-methyl phenyl)-6-morpholin-4-yl-1,3,5-triazin-2-yl]phenyl}carbamoyl)amino]benzoic acid;
1-{4-[4-(4-methylphenyl)-6-morpholin-4-yl-1,3,5-triazin-2-yl]phenyl}-3-[4-(4-methyl piperazin-1-yl)phenyl]urea;
methyl 4-[({4-[4-(4-methyl phenyl)-6-morpholin-4-yl-1,3,5-triazin-2-yl]phenyl}carbamoyl)amino]benzoate;
1-{4-[4-(dimethylamino)piperidin-1-yl]phenyl}-3-[4-(4-morpholin-4-yl-6-phenyl-1,3,5-triazin-2-yl)phenyl]urea;
1-[4-(4-morpholin-4-yl-6-phenyl-1,3,5-triazin-2-yl)phenyl]-3-pyridin-4-ylurea;
1-(4-{[4-(dimethylamino)piperidin-1-yl]carbonyl}phenyl)-3-{4-[4-morpholin-4-yl-6-(tetrahydro-2H-pyran-4-yl)-1,3,5-triazin-2-yl]phenyl}urea;
1-(4-(4,6-bis((R)-3-methylmorpholino)-1,3,5-triazin-2-yl)phenyl)-3-(pyridin-4-yl)urea;
1-(4-(4,6-bis((R)-3-methylmorpholino)-1,3,5-triazin-2-yl)phenyl)-3-(pyridin-3-yl)urea;
1-(4-(4,6-bis((R)-3-methylmorpholino)-1,3,5-triazin-2-yl)phenyl)-3-(4-(4-methyl piperazin-1-yl)phenyl)urea;
1-(4-(4,6-bis((R)-3-methylmorpholino)-1,3,5-triazin-2-yl)phenyl)-3-(6-(4-methyl piperazin-1-yl)pyridin-3-yl)urea;
1-(4-(4,6-bis((R)-3-methylmorpholino)-1,3,5-triazin-2-yl)phenyl)-3-(4-((dimethylamino)methyl)phenyl)urea;
1-(4-(4,6-bis((R)-3-methylmorpholino)-1,3,5-triazin-2-yl)phenyl)-3-(4-(2-(dimethylamino)ethoxy)phenyl)urea;
1-(4-(4,6-bis((R)-3-methylmorpholino)-1,3,5-triazin-2-yl)phenyl)-3-(4-(2-(pyrrolidin-1-yl)ethoxy)phenyl)urea;
(R)-1-(4-(4-(3-methylmorpholino)-6-(tetrahydro-2H-pyran-4-yl)-1,3,5-triazin-2-yl)phenyl)-3-(pyridin-3-yl)urea;
(R)-1-(4-(4-(3-methylmorpholino)-6-(tetrahydro-2H-pyran-4-yl)-1,3,5-triazin-2-yl)phenyl)-3-(4-(4-methylpiperazin-1-yl)phenyl)urea;
(R)-1-(4-(4-(3-methylmorpholino)-6-(tetrahydro-2H-pyran-4-yl)-1,3,5-triazin-2-yl)phenyl)-3-(4-(piperazin-1-yl)phenyl)urea;
1-(4-(4-((R)-3-methylmorpholino)-6-(tetrahydro-2H-pyran-4-yl)-1,3,5-triazin-2-yl)phenyl)-3-(4-((S)-3-methylpiperazin-1-yl)phenyl)urea;
1-(4-(4-((R)-3-methylmorpholino)-6-(tetrahydro-2H-pyran-4-yl)-1,3,5-triazin-2-yl)phenyl)-3-(4-((R)-3-methylpiperazin-1-yl)phenyl)urea;
1-(4-((3R,5S)-3,5-dimethylpiperazin-1-yl)phenyl)-3-(4-(4-((R)-3-methylmorpholino)-6-(tetrahydro-2H-pyran-4-yl)-1,3,5-triazin-2-yl)phenyl)urea;
(R)-1-(4-(2-(dimethylamino)ethoxy)phenyl)-3-(4-(4-(3-methylmorpholino)-6-(tetrahydro-2H-pyran-4-yl)-1,3,5-triazin-2-yl)phenyl)urea;
(R)-1-(4-(4-ethylpiperazin-1-yl)phenyl)-3-(4-(4-(3-methylmorpholino)-6-(tetrahydro-2H-pyran-4-yl)-1,3,5-triazin-2-yl)phenyl)urea;
(R)-1-(4-(4-isopropylpiperazin-1-yl)phenyl)-3-(4-(4-(3-methylmorpholino)-6-(tetrahydro-2H-pyran-4-yl)-1,3,5-triazin-2-yl)phenyl)urea;
(R)-1-(4-(4-(dimethylamino)piperidin-1-yl)phenyl)-3-(4-(4-(3-methylmorpholino)-6-(tetrahydr-2H-pyran-4-yl)-1,3,5-triazin-2-yl)phenyl)urea;
(R)-1-(4-(4-(3-methylmorpholino)-6-(tetrahydro-2H-pyran-4-yl)-1,3,5-triazin-2-yl)phenyl)-3-(4-(4-methylpiperazine-1-carbonyl)phenyl)urea;
(R)-1-(4-(4-isopropylpiperazine-1-carbonyl)phenyl)-3-(4-(4-(3-methylmorpholino)-6-(tetrahydro-2H-pyran-4-yl)-1,3,5-triazin-2-yl)phenyl)urea;
(R)-1-(4-(4-(3-methylmorpholino)-6-(tetrahydro-2H-pyran-4-yl)-1,3,5-triazin-2-yl)phenyl)-3-(6-(4-methylpiperazin-1-yl)pyridin-3-yl)urea;
1-(4-(4,6-bis((R)-3-methylmorpholino)-1,3,5-triazin-2-yl)phenyl)-3-(4-(4-ethylpiperazin-1-yl)phenyl)urea;
1-(4-(4,6-bis((R)-3-methylmorpholino)-1,3,5-triazin-2-yl)phenyl)-3-(4-(4-isopropylpiperazin-1-yl)phenyl)urea;
1-(4-(4,6-bis((R)-3-methylmorpholino)-1,3,5-triazin-2-yl)phenyl)-3-(4-(4-(dimethylamino)piperidin-1-yl)phenyl)urea;
1-(4-(4,6-bis((R)-3-methylmorpholino)-1,3,5-triazin-2-yl)phenyl)-3-(4-(4-methylpiperazine-1-carbonyl)phenyl)urea;

1-(4-(4,6-bis((R)-3-methylmorpholino)-1,3,5-triazin-2-yl)phenyl)-3-(4-(4-isopropylpiperazine-1-carbonyl)phenyl)urea;

4-(3-(4-(4,6-bis((R)-3-methylmorpholino)-1,3,5-triazin-2-yl)phenyl)ureido)-N,N-dimethylbenzamide;

1-(4-(4,6-bis((R)-3-methylmorpholino)-1,3,5-triazin-2-yl)phenyl)-3-(4-(pyrrolidin-1-ylmethyl)phenyl)urea;

4-({[4-(4-{4-[(methylcarbamoyl)amino]phenyl}-6-morpholin-4-yl-1,3,5-triazin-2-yl)phenyl]carbamoyl}amino)benzamide;

1-{4-[4-(3,5-dimethylmorpholin-4-yl)-6-{4-[(methylcarbamoyl)amino]phenyl}-1,3,5-triazin-2-yl]phenyl}-3-pyridin-3-ylurea;

3-({[4-(4-{4-[(methylcarbamoyl)amino]phenyl}-6-morpholin-4-yl-1,3,5-triazin-2-yl)phenyl]carbamoyl}amino)benzamide;

1-methyl-3-[4-(4-morpholin-4-yl-6-{4-[(pyridin-3-ylcarbamoyl)amino]phenyl}-1,3,5-triazin-2-yl)phenyl]urea;

1-methyl-3-[4-(4-morpholin-4-yl-6-{4-[(pyridin-4-ylcarbamoyl)amino]phenyl}-1,3,5-triazin-2-yl)phenyl]urea;

3-[({4-[4-(3,5-dimethylmorpholin-4-yl)-6-{4-[(methylcarbamoyl)amino]phenyl}-1,3,5-triazin-2-yl]phenyl}carbamoyl)amino]benzamide;

4-[({4-[4-(3,5-dimethylmorpholin-4-yl)-6-{4-[(methylcarbamoyl)amino]phenyl}-1,3,5-triazin-2-yl]phenyl}carbamoyl)amino]benzamide;

1-{4-[4-(3,5-dimethylmorpholin-4-yl)-6-{4-[(methylcarbamoyl)amino]phenyl}-1,3,5-triazin-2-yl]phenyl}-3-pyridin-4-ylurea;

1-[4-(4,6-dimorpholin-4-yl-1,3,5-triazin-2-yl)phenyl]-3-methylurea;

1-(4-{[4-(dimethylamino)piperidin-1-yl]carbonyl}phenyl)-3-{4-[4-morpholin-4-yl-6-(tetrahydro-2H-pyran-4-yl)-1,3,5-triazin-2-yl]phenyl}urea;

1-{4-[(4-methylpiperazin-1-yl)carbonyl]phenyl}-3-(4-{4-morpholin-4-yl-6-[(3S)-tetrahydrofuran-3-yloxy]-1,3,5-triazin-2-yl}phenyl)urea;

1-[4-(4,6-dimorpholin-4-yl-1,3,5-triazin-2-yl)phenyl]-3-pyridazin-4-ylurea;

1-{4-[(4-methylpiperazin-1-yl)carbonyl]phenyl}-3-{4-[4-morpholin-4-yl-6-(oxetan-3-yloxy)-1,3,5-triazin-2-yl]phenyl}urea;

1-(4-{[(3R)-3-(dimethylamino)pyrrolidin-1-yl]carbonyl}phenyl)-3-[4-(4,6-dimorpholin-4-yl-1,3,5-triazin-2-yl)phenyl]urea;

1-(4-{[(3S)-3-(dimethylamino)pyrrolidin-1-yl]carbonyl}phenyl)-3-[4-(4,6-dimorpholin-4-yl-1,3,5-triazin-2-yl)phenyl]urea;

1-[4-(4-isopropyl-6-morpholin-4-yl-1,3,5-triazin-2-yl)phenyl]-3-{4-[(4-methylpiperazin-1-yl)carbonyl]phenyl}urea;

1-{4-[4-(1-methylethyl)-6-morpholin-4-yl-1,3,5-triazin-2-yl]phenyl}-3-(4-pyrimidin-5-ylphenyl)urea;

1-(4-{4-[(2,2-dimethoxyethyl)amino]-6-morpholin-4-yl-1,3,5-triazin-2-yl}phenyl)-3-pyridin-3-ylurea;

1-{4-[4-(1-methylethyl)-6-morpholin-4-yl-1,3,5-triazin-2-yl]phenyl}-3-(4-pyridin-4-ylphenyl)urea;

1-(4-iodophenyl)-3-{4-[4-(1-methylethyl)-6-morpholin-4-yl-1,3,5-triazin-2-yl]phenyl}urea;

1-{4-[4-(1-methylethyl)-6-morpholin-4-yl-1,3,5-triazin-2-yl]phenyl}-3-(4-{[4-(1-methylethyl)piperazin-1-yl]carbonyl}phenyl)urea;

1-[4-(4-azetidin-1-yl-6-morpholin-4-yl-1,3,5-triazin-2-yl)phenyl]-3-(4-{[4-(1-methylethyl)piperazin-1-yl]carbonyl}phenyl)urea;

1-{4-[2-(dimethylamino)pyrimidin-5-yl]phenyl}-3-{4-[4-(1-methylethyl)-6-morpholin-4-yl-1,3,5-triazin-2-yl]phenyl}urea;

tert-butyl 3-[(4-morpholin-4-yl-6-{4-[(pyridin-4-ylcarbamoyl)amino]phenyl}-1,3,5-triazin-2-yl)oxy]azetidine-1-carboxylate;

1-(4-{[4-(dimethylamino)piperidin-1-yl]carbonyl}phenyl)-3-[4-(4,6-dimorpholin-4-yl-1,3,5-triazin-2-yl)phenyl]urea;

1-[4-(4,6-dimorpholin-4-yl-1,3,5-triazin-2-yl)phenyl]-3-(4-nitrophenyl)urea;

1-(4-aminophenyl)-3-[4-(4,6-dimorpholin-4-yl-1,3,5-triazin-2-yl)phenyl]urea;

N-[4-({[4-(4,6-dimorpholin-4-yl-1,3,5-triazin-2-yl)phenyl]carbamoyl}amino)phenyl]-4-methylpiperazine-1-carboxamide;

4-(dimethylamino)-N-[4-({[4-(4,6-dimorpholin-4-yl-1,3,5-triazin-2-yl)phenyl]carbamoyl}amino)phenyl]piperidine-1-carboxamide;

1-[2-(dimethylamino)ethyl]-3-[4-({[4-(4,6-dimorpholin-4-yl-1,3,5-triazin-2-yl)phenyl]carbamoyl}amino)phenyl]-1-methylurea;

1-[4-(4,6-dimorpholin-4-yl-1,3,5-triazin-2-yl)phenyl]-3-(4-{[(2-piperidin-1-ylethyl)carbamoyl]amino}phenyl)urea;

N-[4-({[4-(4,6-dimorpholin-4-yl-1,3,5-triazin-2-yl)phenyl]carbamoyl}amino)phenyl]-4-methyl-1,4-diazepane-1-carboxamide;

N-[4-({[4-(4,6-dimorpholin-4-yl-1,3,5-triazin-2-yl)phenyl]carbamoyl}amino)phenyl]-4-ethylpiperazine-1-carboxamide;

1-{4-[(dimethylcarbamoyl)amino]phenyl}-3-[4-(4,6-dimorpholin-4-yl-1,3,5-triazin-2-yl)phenyl]urea;

1-{4-[4-(3,6-dihydro-2H-pyran-4-yl)-6-morpholin-4-yl-1,3,5-triazin-2-yl]phenyl}-3-(4-{[4-(dimethylamino)piperidin-1-yl]carbonyl}phenyl)urea;

4-[({4-[4-(3,6-dihydro-2H-pyran-4-yl)-6-morpholin-4-yl-1,3,5-triazin-2-yl]phenyl}carbamoyl)amino]-N-[2-(dimethylamino)ethyl]-N-methylbenzamide;

1-{4-[4-(3,6-dihydro-2H-pyran-4-yl)-6-morpholin-4-yl-1,3,5-triazin-2-yl]phenyl}-3-{4-[(4-methylpiperazin-1-yl)carbonyl]phenyl}urea;

4-[({4-[4-(3,6-dihydro-2H-pyran-4-yl)-6-morpholin-4-yl-1,3,5-triazin-2-yl]phenyl}carbamoyl)amino]-N-[2-(dimethylamino)ethyl]benzamide;

1-(4-{[4-(dimethylamino)piperidin-1-yl]carbonyl}phenyl)-3-{4-[4-morpholin-4-yl-6-(tetrahydro-2H-pyran-4-yl)-1,3,5-triazin-2-yl]phenyl}urea;

N-[2-(dimethylamino)ethyl]-4-[({4-[4-morpholin-4-yl-6-(tetrahydro-2H-pyran-4-yl)-1,3,5-triazin-2-yl]phenyl}carbamoyl)amino]benzamide;

4-[({4-[4-morpholin-4-yl-6-(tetrahydro-2H-pyran-4-yl)-1,3,5-triazin-2-yl]phenyl}carbamoyl)amino]-N-(2-pyrrolidin-1-ylethyl)benzamide;

4-[({4-[4-morpholin-4-yl-6-(tetrahydro-2H-pyran-4-yl)-1,3,5-triazin-2-yl]phenyl}carbamoyl)amino]-N-(2-piperidin-1-ylethyl)benzamide;

1-[4-(4,6-dimorpholin-4-yl-1,3,5-triazin-2-yl)phenyl]-3-(4-{[4-(1-methylethyl)piperazin-1-yl]carbonyl}phenyl)urea;

N-[2-(dimethylamino)ethyl]-N-methyl-4-{[(4-{4-morpholin-4-yl-6-[(3S)-tetrahydrofuran-3-yloxy]-1,3,5-triazin-2-yl}phenyl)carbamoyl]amino}benzamide;

4-{[(4-{4-morpholin-4-yl-6-[(3S)-tetrahydrofuran-3-yloxy]-1,3,5-triazin-2-yl}phenyl)carbamoyl]amino}-N-(2-piperidin-1-ylethyl)benzamide;

4-{[(4-{4-morpholin-4-yl-6-[(3S)-tetrahydrofuran-3-yloxy]-1,3,5-triazin-2-yl}phenyl)carbamoyl]amino}-N-(2-pyrrolidin-1-ylethyl)benzamide;

1-(4-{[4-(1-methylethyl)piperazin-1-yl]carbonyl}phenyl)-3-(4-{4-morpholin-4-yl-6-[(3S)-tetrahydrofuran-3-yloxy]-1,3,5-triazin-2-yl}phenyl)urea;

1-(4-{[4-(1-methylethyl)piperazin-1-yl]carbonyl}phenyl)-3-{4-[4-morpholin-4-yl-6-(tetrahydro-2H-pyran-4-yl)-1,3,5-triazin-2-yl]phenyl}urea;

N-[2-(dimethylamino)ethyl]-N-methyl-4-[({4-[4-morpholin-4-yl-6-(tetrahydro-2H-pyran-4-yl)-1,3,5-triazin-2-yl]phenyl}carbamoyl)amino]benzamide;

4-[({4-[4-(2-methylpropyl)-6-morpholin-4-yl-1,3,5-triazin-2-yl]phenyl}carbamoyl)amino]benzoic acid;

1-{4-[4-(4-methylphenyl)-6-morpholin-4-yl-1,3,5-triazin-2-yl]phenyl}-3-[4-(4-methylpiperazin-1-yl)phenyl]urea;

4-[({4-[4-(4-methylphenyl)-6-morpholin-4-yl-1,3,5-triazin-2-yl]phenyl}carbamoyl)amino]benzoic acid;

methyl 4-[({4-[4-(4-methylphenyl)-6-morpholin-4-yl-1,3,5-triazin-2-yl]phenyl}carbamoyl)amino]benzoate;

1-{4-[4-(dimethylamino)piperidin-1-yl]phenyl}-3-[4-(4-ethyl-6-morpholin-4-yl-1,3,5-triazin-2-yl)phenyl]urea;

1-{4-[4-(4-methylphenyl)-6-morpholin-4-yl-1,3,5-triazin-2-yl]phenyl}-3-pyridin-4-ylurea;

1-{4-[4-(dimethylamino)piperidin-1-yl]phenyl}-3-{4-[4-(4-methylphenyl)-6-morpholin-4-yl-1,3,5-triazin-2-yl]phenyl}urea;

N-[2-(dimethylamino)ethyl]-N-methyl-4-[({4-[4-(4-methylphenyl)-6-morpholin-4-yl-1,3,5-triazin-2-yl]phenyl}carbamoyl)amino]benzamide;

1-{4-[4-(4-methylphenyl)-6-morpholin-4-yl-1,3,5-triazin-2-yl]phenyl}-3-{4-[(4-methylpiperazin-1-yl)carbonyl]phenyl}urea;

1-[4-(4-ethyl-6-morpholin-4-yl-1,3,5-triazin-2-yl)phenyl]-3-{4-[(4-pyridin-2-ylpiperazin-1-yl)carbonyl]phenyl}urea;

1-{4-[4-(dimethylamino)piperidin-1-yl]phenyl}-3-[4-(4-morpholin-4-yl-6-phenyl-1,3,5-triazin-2-yl)phenyl]urea;

1-[4-(4-ethyl-6-morpholin-4-yl-1,3,5-triazin-2-yl)phenyl]-3-{4-[(4-methylpiperazin-1-yl)carbonyl]phenyl}urea;

1-[4-(4-morpholin-4-yl-6-phenyl-1,3,5-triazin-2-yl)phenyl]-3-pyridin-4-ylurea;

methyl 4-({[4-(4-morpholin-4-yl-6-phenyl-1,3,5-triazin-2-yl)phenyl]carbamoyl}amino)benzoate;

N-[2-(dimethylamino)ethyl]-N-methyl-4-({[4-(4-morpholin-4-yl-6-phenyl-1,3,5-triazin-2-yl)phenyl]carbamoyl}amino)benzamide;

methyl 4-{[(4-{4,6-bis[(3S)-3-methylmorpholin-4-yl]-1,3,5-triazin-2-yl}phenyl)carbamoyl]amino}benzoate;

4-({[4-(4-morpholin-4-yl-6-phenyl-1,3,5-triazin-2-yl)phenyl]carbamoyl}amino)benzoic acid;

N-[2-(dimethylamino)ethyl]-4-[({4-[4-(4-methylphenyl)-6-morpholin-4-yl-1,3,5-triazin-2-yl]phenyl}carbamoyl)amino]benzamide;

1-{4-[(4-methylpiperazin-1-yl)carbonyl]phenyl}-3-[4-(4-morpholin-4-yl-6-phenyl-1,3,5-triazin-2-yl)phenyl]urea;

1-(4-{[4-(dimethylamino)piperidin-1-yl]carbonyl}phenyl)-3-[4-(4-morpholin-4-yl-6-phenyl-1,3,5-triazin-2-yl)phenyl]urea;

N-[2-(dimethylamino)ethyl]-4-({[4-(4-morpholin-4-yl-6-phenyl-1,3,5-triazin-2-yl)phenyl]carbamoyl}amino)benzamide;

4-{[(4-{4,6-bis[(3S)-3-methylmorpholin-4-yl]-1,3,5-triazin-2-yl}phenyl)carbamoyl]amino}-N-[2-(dimethylamino)ethyl]benzamide;

1-{4-[(4-isopropylpiperazin-1-yl)carbonyl]phenyl}-3-{4-[4-(4-methylphenyl)-6-morpholin-4-yl-1,3,5-triazin-2-yl]phenyl}urea;

4-[({4-[4-(4-methylphenyl)-6-morpholin-4-yl-1,3,5-triazin-2-yl]phenyl}carbamoyl)amino]-N-(2-pyrrolidin-1-ylethyl)benzamide;

4-{[(4-{4,6-bis[(3S)-3-methylmorpholin-4-yl]-1,3,5-triazin-2-yl}phenyl)carbamoyl]amino}benzoic acid;

N-(2-methoxyethyl)-4-[({4-[4-(4-methylphenyl)-6-morpholin-4-yl-1,3,5-triazin-2-yl]phenyl}carbamoyl)amino]benzamide;

N-(2-methoxyethyl)-4-({[4-(4-morpholin-4-yl-6-phenyl-1,3,5-triazin-2-yl)phenyl]carbamoyl}amino)benzamide;

4-({[4-(4-morpholin-4-yl-6-phenyl-1,3,5-triazin-2-yl)phenyl]carbamoyl}amino)-N-(2-pyrrolidin-1-ylethyl)benzamide;

1-{4-[4-(4-methylphenyl)-6-morpholin-4-yl-1,3,5-triazin-2-yl]phenyl}-3-[4-(pyrrolidin-1-ylcarbonyl)phenyl]urea;

N-[3-(dimethylamino)propyl]-4-[({4-[4-(4-methylphenyl)-6-morpholin-4-yl-1,3,5-triazin-2-yl]phenyl}carbamoyl)amino]benzamide;

1-{4-[4-(4-methylphenyl)-6-morpholin-4-yl-1,3,5-triazin-2-yl]phenyl}-3-[4-(piperidin-1-ylcarbonyl)phenyl]urea;

N-[3-(dimethylamino)propyl]-4-({[4-(4-morpholin-4-yl-6-phenyl-1,3,5-triazin-2-yl)phenyl]carbamoyl}amino)benzamide;

1-{4-[4-morpholin-4-yl-6-(2-thienyl)-1,3,5-triazin-2-yl]phenyl}-3-pyridin-4-ylurea;

4-[({4-[4-morpholin-4-yl-6-(2-thienyl)-1,3,5-triazin-2-yl]phenyl}carbamoyl)amino]benzoic acid;

1-{4-[(4-methylpiperazin-1-yl)carbonyl]phenyl}-3-{4-[4-morpholin-4-yl-6-(2-thienyl)-1,3,5-triazin-2-yl]phenyl}urea;

methyl 4-[({4-[4-morpholin-4-yl-6-(2-thienyl)-1,3,5-triazin-2-yl]phenyl}carbamoyl)amino]benzoate;

N-(2-methoxyethyl)-4-[({4-[4-morpholin-4-yl-6-(2-thienyl)-1,3,5-triazin-2-yl]phenyl}carbamoyl)amino]benzamide;

N-[2-(dimethylamino)ethyl]-N-methyl-4-[({4-[4-morpholin-4-yl-6-(2-thienyl)-1,3,5-triazin-2-yl]phenyl}carbamoyl)amino]benzamide;

N-[2-(dimethylamino)ethyl]-4-[({4-[4-morpholin-4-yl-6-(2-thienyl)-1,3,5-triazin-2-yl]phenyl}carbamoyl)amino]benzamide;

4-{[(4-{4,6-bis[(3S)-3-methylmorpholin-4-yl]-1,3,5-triazin-2-yl}phenyl)carbamoyl]amino}-N-[2-(dimethylamino)ethyl]-N-methylbenzamide;

1-(4-{4,6-bis[(3S)-3-methylmorpholin-4-yl]-1,3,5-triazin-2-yl}phenyl)-3-{4-[(4-methylpiperazin-1-yl)carbonyl]phenyl}urea;

1-{4-[4-morpholin-4-yl-6-(1,4-oxazepan-4-yl)-1,3,5-triazin-2-yl]phenyl}-3-pyridin-4-ylurea;

methyl 4-[({4-[4-morpholin-4-yl-6-(1,4-oxazepan-4-yl)-1,3,5-triazin-2-yl]phenyl}carbamoyl)amino]benzoate;

1-(4-{[4-(dimethylamino)piperidin-1-yl]carbonyl}phenyl)-3-{4-[4-morpholin-4-yl-6-(2-thienyl)-1,3,5-triazin-2-yl]phenyl}urea;

4-[({4-[4-morpholin-4-yl-6-(1,4-oxazepan-4-yl)-1,3,5-triazin-2-yl]phenyl}carbamoyl)amino]benzoic acid;

N-[3-(dimethylamino)propyl]-4-[({4-[4-morpholin-4-yl-6-(2-thienyl)-1,3,5-triazin-2-yl]phenyl}carbamoyl)amino]benzamide;

1-(4-{4,6-bis[(3S)-3-methylmorpholin-4-yl]-1,3,5-triazin-2-yl}phenyl)-3-[4-(pyrrolidin-1-ylcarbonyl)phenyl]urea;

N-[2-(dimethylamino)ethyl]-4-[({4-[4-morpholin-4-yl-6-(1,4-oxazepan-4-yl)-1,3,5-triazin-2-yl]phenyl}carbamoyl)amino]benzamide;

1-{4-[(4-methylpiperazin-1-yl)carbonyl]phenyl}-3-{4-[4-morpholin-4-yl-6-(1,4-oxazepan-4-yl)-1,3,5-triazin-2-yl]phenyl}urea;

N-(2-methoxyethyl)-4-[({4-[4-morpholin-4-yl-6-(1,4-oxazepan-4-yl)-1,3,5-triazin-2-yl]phenyl}carbamoyl)amino]benzamide;

1-{4-[(4-ethylpiperazin-1-yl)carbonyl]phenyl}-3-{4-[4-morpholin-4-yl-6-(2-thienyl)-1,3,5-triazin-2-yl]phenyl}urea;

1-{4-[4-(4-methylphenyl)-6-morpholin-4-yl-1,3,5-triazin-2-yl]phenyl}-3-{3-[(4-methylpiperazin-1-yl)carbonyl]phenyl}urea;

3-[({4-[4-(4-methylphenyl)-6-morpholin-4-yl-1,3,5-triazin-2-yl]phenyl}carbamoyl)amino]benzoic acid;

methyl 3-[({4-[4-(4-methylphenyl)-6-morpholin-4-yl-1,3,5-triazin-2-yl]phenyl}carbamoyl)amino]benzoate;

1-(3-{[4-(dimethylamino)piperidin-1-yl]carbonyl}phenyl)-3-{4-[4-(4-methylphenyl)-6-morpholin-4-yl-1,3,5-triazin-2-yl]phenyl}urea;

N-[2-(dimethylamino)ethyl]-N-methyl-3-[({4-[4-(4-methylphenyl)-6-morpholin-4-yl-1,3,5-triazin-2-yl]phenyl}carbamoyl)amino]benzamide;

methyl 3-({[4-(4-ethyl-6-morpholin-4-yl-1,3,5-triazin-2-yl)phenyl]carbamoyl}amino)benzoate;

methyl 3-({[4-(4-morpholin-4-yl-6-thiophen-2-yl-1,3,5-triazin-2-yl)phenyl]carbamoyl}amino)benzoate;

N-[2-(dimethylamino)ethyl]-3-[({4-[4-(4-methylphenyl)-6-morpholin-4-yl-1,3,5-triazin-2-yl]phenyl}carbamoyl)amino]benzamide;

N-[2-(dimethylamino)ethyl]-N-methyl-4-[({4-[4-morpholin-4-yl-6-(1,4-oxazepan-4-yl)-1,3,5-triazin-2-yl]phenyl}carbamoyl)amino]benzamide;

3-({[4-(4-ethyl-6-morpholin-4-yl-1,3,5-triazin-2-yl)phenyl]carbamoyl}amino)benzoic acid;

methyl 3-({[4-(4-morpholin-4-yl-6-phenyl-1,3,5-triazin-2-yl)phenyl]carbamoyl}amino)benzoate;

1-[4-(4-ethyl-6-morpholin-4-yl-1,3,5-triazin-2-yl)phenyl]-3-{3-[(4-pyridin-2-ylpiperazin-1-yl)carbonyl]phenyl}urea;

N-[2-(dimethylamino)ethyl]-3-({[4-(4-ethyl-6-morpholin-4-yl-1,3,5-triazin-2-yl)phenyl]carbamoyl}amino)-N-methylbenzamide;

1-[4-(4-ethyl-6-morpholin-4-yl-1,3,5-triazin-2-yl)phenyl]-3-{3-[(4-methylpiperazin-1-yl)carbonyl]phenyl}urea;

3-({[4-(4-morpholin-4-yl-6-phenyl-1,3,5-triazin-2-yl)phenyl]carbamoyl}amino)benzoic acid;

methyl 4-({[4-(4-morpholin-4-yl-6-piperidin-1-yl-1,3,5-triazin-2-yl)phenyl]carbamoyl}amino)benzoate;

1-[4-(4-morpholin-4-yl-6-piperidin-1-yl-1,3,5-triazin-2-yl)phenyl]-3-pyridin-4-ylurea;

4-({[4-(4-morpholin-4-yl-6-piperidin-1-yl-1,3,5-triazin-2-yl)phenyl]carbamoyl}amino)benzoic acid;

methyl 4-({[4-(4-morpholin-4-yl-6-pyrrolidin-1-yl-1,3,5-triazin-2-yl)phenyl]carbamoyl}amino)benzoate;

1-(4-{[4-(1-methylethyl)piperazin-1-yl]carbonyl}phenyl)-3-[4-(4-morpholin-4-yl-6-piperidin-1-yl-1,3,5-triazin-2-yl)phenyl]urea;

1-{4-[(4-ethylpiperazin-1-yl)carbonyl]phenyl}-3-[4-(4-morpholin-4-yl-6-piperidin-1-yl-1,3,5-triazin-2-yl)phenyl]urea;

1-{4-[(4-methyl piperazin-1-yl)carbonyl]phenyl}-3-[4-(4-morpholin-4-yl-6-piperidin-1-yl-1,3,5-triazin-2-yl)phenyl]urea;

1-(4-{[4-(dimethylamino)piperidin-1-yl]carbonyl}phenyl)-3-[4-(4-morpholin-4-yl-6-piperidin-1-yl-1,3,5-triazin-2-yl)phenyl]urea;

4-({[4-(4-morpholin-4-yl-6-pyrrolidin-1-yl-1,3,5-triazin-2-yl)phenyl]carbamoyl}amino)benzoic acid;

1-[4-(4-morpholin-4-yl-6-pyrrolidin-1-yl-1,3,5-triazin-2-yl)phenyl]-3-pyridin-4-ylurea;

N-[2-(dimethylamino)ethyl]-4-({[4-(4-morpholin-4-yl-6-piperidin-1-yl-1,3,5-triazin-2-yl)phenyl]carbamoyl}amino)benzamide;

1-(4-{[4-(dimethylamino)piperidin-1-yl]carbonyl}phenyl)-3-[4-(4-morpholin-4-yl-6-pyrrolidin-1-yl-1,3,5-triazin-2-yl)phenyl]urea;

1-(4-{[4-(1-methylethyl)piperazin-1-yl]carbonyl}phenyl)-3-[4-(4-morpholin-4-yl-6-pyrrolidin-1-yl-1,3,5-triazin-2-yl)phenyl]urea;

N-[2-(dimethylamino)ethyl]-N-methyl-4-({[4-(4-morpholin-4-yl-6-pyrrolidin-1-yl-1,3,5-triazin-2-yl)phenyl]carbamoyl}amino)benzamide;

N-[2-(dimethylamino)ethyl]-N-methyl-4-({[4-(4-morpholin-4-yl-6-piperidin-1-yl-1,3,5-triazin-2-yl)phenyl]carbamoyl}amino)benzamide;

1-{4-[(4-ethylpiperazin-1-yl)carbonyl]phenyl}-3-[4-(4-morpholin-4-yl-6-pyrrolidin-1-yl-1,3,5-triazin-2-yl)phenyl]urea;

1-{4-[(4-methyl piperazin-1-yl)carbonyl]phenyl}-3-[4-(4-morpholin-4-yl-6-pyrrolidin-1-yl-1,3,5-triazin-2-yl)phenyl]urea;

N-[2-(dimethylamino)ethyl]-4-({[4-(4-morpholin-4-yl-6-pyrrolidin-1-yl-1,3,5-triazin-2-yl)phenyl]carbamoyl}amino)benzamide;

1-(4-{4,6-bis[(3S)-3-methyl morpholin-4-yl]-1,3,5-triazin-2-yl}phenyl)-3-pyridin-4-ylurea;

N-[3-(dimethylamino)propyl]-4-({[4-(4-morpholin-4-yl-6-piperidin-1-yl-1,3,5-triazin-2-yl)phenyl]carbamoyl}amino)benzamide;

N-(2-methoxyethyl)-4-({[4-(4-morpholin-4-yl-6-piperidin-1-yl-1,3,5-triazin-2-yl)phenyl]carbamoyl}amino)benzamide;

1-[4-(4-morpholin-4-yl-6-pyrrolidin-1-yl-1,3,5-triazin-2-yl)phenyl]-3-[4-(pyrrolidin-1-ylcarbonyl)phenyl]urea;

1-(4-{4,6-bis[(3S)-3-methylmorpholin-4-yl]-1,3,5-triazin-2-yl}phenyl)-3-{4-[(4-ethylpiperazin-1-yl)carbonyl]phenyl}urea;

1-(4-{4,6-bis[(3S)-3-methylmorpholin-4-yl]-1,3,5-triazin-2-yl}phenyl)-3-(4-{[4-(1-methylethyl)piperazin-1-yl]carbonyl}phenyl)urea;

methyl 4-{[(4-{4-[(3S)-3-methylmorpholin-4-yl]-6-morpholin-4-yl-1,3,5-triazin-2-yl}phenyl)carbamoyl]amino}benzoate;

1-(4-{4,6-bis[(3S)-3-methylmorpholin-4-yl]-1,3,5-triazin-2-yl}phenyl)-3-(4-{[4-(dimethylamino)piperidin-1-yl]carbonyl}phenyl)urea;

1-(4-{4-[(3S)-3-methylmorpholin-4-yl]-6-morpholin-4-yl-1,3,5-triazin-2-yl}phenyl)-3-{4-[(4-methylpiperazin-1-yl)carbonyl]phenyl}urea;

1-(4-{[4-(1-methylethyl)piperazin-1-yl]carbonyl}phenyl)-3-(4-{4-[(3S)-3-methylmorpholin-4-yl]-6-morpholin-4-yl-1,3,5-triazin-2-yl}phenyl)urea;

4-{[(4-{4-[(3S)-3-methylmorpholin-4-yl]-6-morpholin-4-yl-1,3,5-triazin-2-yl}phenyl)carbamoyl]amino}benzoic acid;

1-{4-[(4-ethylpiperazin-1-yl)carbonyl]phenyl}-3-(4-{4-[(3S)-3-methylmorpholin-4-yl]-6-morpholin-4-yl-1,3,5-triazin-2-yl}phenyl)urea;

N-[3-(dimethylamino)propyl]-4-{[(4-{4-[(3S)-3-methylmorpholin-4-yl]-6-morpholin-4-yl-1,3,5-triazin-2-yl}phenyl)carbamoyl]amino}benzamide;

4-{[(4-{4-[(3S)-3-methylmorpholin-4-yl]-6-morpholin-4-yl-1,3,5-triazin-2-yl}phenyl)carbamoyl]amino}-N-(2-pyrrolidin-1-ylethyl)benzamide;

1-(4-{4-[(3R)-3-methylmorpholin-4-yl]-6-[(3S)-3-methylmorpholin-4-yl]-1,3,5-triazin-2-yl}phenyl)-3-{4-[(4-methylpiperazin-1-yl)carbonyl]phenyl}urea;

1-(4-{4,6-bis[(3S)-3-methylmorpholin-4-yl]-1,3,5-triazin-2-yl}phenyl)-3-(4-{[4-(dipropylamino)piperidin-1-yl]carbonyl}phenyl)urea;

1-{4-[(4-ethylpiperazin-1-yl)carbonyl]phenyl}-3-(4-{4-[(3R)-3-methylmorpholin-4-yl]-6-[(3S)-3-methylmorpholin-4-yl]-1,3,5-triazin-2-yl}phenyl)urea;

4-{[(4-{4-[(3R)-3-methylmorpholin-4-yl]-6-[(3S)-3-methylmorpholin-4-yl]-1,3,5-triazin-2-yl}phenyl)carbamoyl]amino}benzoic acid;

1-{4-[(4-butylpiperazin-1-yl)carbonyl]phenyl}-3-(4-{4-[(3R)-3-methylmorpholin-4-yl]-6-[(3S)-3-methylmorpholin-4-yl]-1,3,5-triazin-2-yl}phenyl)urea;

methyl 4-{[(4-{4-[(3R)-3-methylmorpholin-4-yl]-6-[(3S)-3-methylmorpholin-4-yl]-1,3,5-triazin-2-yl}phenyl)carbamoyl]amino}benzoate;

1-(4-{4,6-bis[(3S)-3-methylmorpholin-4-yl]-1,3,5-triazin-2-yl}phenyl)-3-{4-[(4-butylpiperazin-1-yl)carbonyl]phenyl}urea;

1-(4-{[4-(1-methylethyl)piperazin-1-yl]carbonyl}phenyl)-3-(4-{4-[(3R)-3-methylmorpholin-4-yl]-6-[(3S)-3-methylmorpholin-4-yl]-1,3,5-triazin-2-yl}phenyl)urea;

1-(4-{4,6-bis[(3S)-3-methylmorpholin-4-yl]-1,3,5-triazin-2-yl}phenyl)-3-(4-{[4-(2-methylpropyl)piperazin-1-yl]carbonyl}phenyl)urea;

1-(4-{4,6-bis[(3S)-3-methylmorpholin-4-yl]-1,3,5-triazin-2-yl}phenyl)-3-(4-{[4-(1-methylpropyl)piperazin-1-yl]carbonyl}phenyl)urea;

4-{[(4-{4,6-bis[(3S)-3-methylmorpholin-4-yl]-1,3,5-triazin-2-yl}phenyl)carbamoyl]amino}-N-[2-(4-methylpiperazin-1-yl)ethyl]benzamide;

N-[2-(dimethylamino)ethyl]-4-{[(4-{4-[(3R)-3-methylmorpholin-4-yl]-6-[(3S)-3-methylmorpholin-4-yl]-1,3,5-triazin-2-yl}phenyl)carbamoyl]amino}benzamide;

4-{[(4-{4,6-bis[(3S)-3-methylmorpholin-4-yl]-1,3,5-triazin-2-yl}phenyl)carbamoyl]amino}-N-(2-pyrrolidin-1-ylethyl)benzamide;

1-(4-{4,6-bis[(3S)-3-methylmorpholin-4-yl]-1,3,5-triazin-2-yl}phenyl)-3-{4-[(4-propylpiperidin-1-yl)carbonyl]phenyl}urea;

1-(4-{4,6-bis[(3S)-3-methylmorpholin-4-yl]-1,3,5-triazin-2-yl}phenyl)-3-[4-(piperidin-1-ylcarbonyl)phenyl]urea;

1-(4-{4,6-bis[(3S)-3-methylmorpholin-4-yl]-1,3,5-triazin-2-yl}phenyl)-3-{4-[(4-propylpiperazin-1-yl)carbonyl]phenyl}urea;

4-{[(4-{4,6-bis[(3S)-3-methylmorpholin-4-yl]-1,3,5-triazin-2-yl}phenyl)carbamoyl]amino}-N-(2-methoxyethyl)benzamide;

1-{4-[4-morpholin-4-yl-6-(4-tricyclo[3.3.1.13,7]dec-1-ylpiperazin-1-yl)-1,3,5-triazin-2-yl]phenyl}-3-pyridin-4-ylurea;

methyl 4-{[(4-{4-[4-(dimethylcarbamoyl)piperazin-1-yl]-6-morpholin-4-yl-1,3,5-triazin-2-yl}phenyl)carbamoyl]amino}benzoate;

N,N-dimethyl-4-(4-morpholin-4-yl-6-{4-[(pyridin-4-ylcarbamoyl)amino]phenyl}-1,3,5-triazin-2-yl)piperazine-1-carboxamide;

N,N-dimethyl-4-(4-{4-[({4-[(4-methylpiperazin-1-yl)carbonyl]phenyl}carbamoyl)amino]phenyl}-6-morpholin-4-yl-1,3,5-triazin-2-yl)piperazine-1-carboxamide;

N,N-dimethyl-4-{4-morpholin-4-yl-6-[4-({[4-(pyridazin-4-ylcarbamoyl)phenyl]carbamoyl}amino)phenyl]-1,3,5-triazin-2-yl}piperazine-1-carboxamide;

N,N-dimethyl-4-(4-morpholin-4-yl-6-{4-[({4-[(4-propylpiperidin-1-yl)carbonyl]phenyl}carbamoyl)amino]phenyl}-1,3,5-triazin-2-yl)piperazine-1-carboxamide;

4-{[(4-{4-[4-(dimethylcarbamoyl)piperazin-1-yl]-6-morpholin-4-yl-1,3,5-triazin-2-yl}phenyl)carbamoyl]amino}benzoic acid;

4-(4-{4-[({4-[(2-methoxyethyl)carbamoyl]phenyl}carbamoyl)amino]phenyl}-6-morpholin-4-yl-1,3,5-triazin-2-yl)-N,N-dimethylpiperazine-1-carboxamide;

4-[4-(4-{[(4-{[2-(dimethylamino)ethyl](methyl)carbamoyl}phenyl)carbamoyl]amino}phenyl)-6-morpholin-4-yl-1,3,5-triazin-2-yl]-N,N-dimethylpiperazine-1-carboxamide;

4-(4-{4-[({4-[(4-ethylpiperazin-1-yl)carbonyl]phenyl}carbamoyl)amino]phenyl}-6-morpholin-4-yl-1,3,5-triazin-2-yl)-N,N-dimethylpiperazine-1-carboxamide;

1-(4-{4-[4-(ethylsulfonyl)piperazin-1-yl]-6-morpholin-4-yl-1,3,5-triazin-2-yl}phenyl)-3-pyridin-4-ylurea;

methyl 4-{[(4-{4-[4-(ethylsulfonyl)piperazin-1-yl]-6-morpholin-4-yl-1,3,5-triazin-2-yl}phenyl)carbamoyl]amino}benzoate;

4-{[(4-{4-[4-(ethylsulfonyl)piperazin-1-yl]-6-morpholin-4-yl-1,3,5-triazin-2-yl}phenyl)carbamoyl]amino}benzoic acid;

N-[3-(dimethylamino)propyl]-4-{[(4-{4-[4-(ethylsulfonyl)piperazin-1-yl]-6-morpholin-4-yl-1,3,5-triazin-2-yl}phenyl)carbamoyl]amino}benzamide;

N-[2-(dimethylamino)ethyl]-4-{[(4-{4-[4-(ethylsulfonyl)piperazin-1-yl]-6-morpholin-4-yl-1,3,5-triazin-2-yl}phenyl)carbamoyl]amino}benzamide;

4-{[(4-{4-[4-(1-methylethyl)-1,4-diazepan-1-yl]-6-morpholin-4-yl-1,3,5-triazin-2-yl}phenyl)carbamoyl]amino}benzoic acid;

methyl 4-{[(4-{4-[4-(acetylamino)piperidin-1-yl]-6-morpholin-4-yl-1,3,5-triazin-2-yl}phenyl)carbamoyl]amino}benzoate;

1-(4-{4-[4-(1-methylethyl)-1,4-diazepan-1-yl]-6-morpholin-4-yl-1,3,5-triazin-2-yl}phenyl)-3-{4-[(4-methylpiperazin-1-yl)carbonyl]phenyl}urea;

N-[1-(4-morpholin-4-yl-6-{4-[(pyridin-4-ylcarbamoyl)amino]phenyl}-1,3,5-triazin-2-yl)piperidin-4-yl]acetamide;

4-{[(4-{4-[4-(acetylamino)piperidin-1-yl]-6-morpholin-4-yl-1,3,5-triazin-2-yl}phenyl)carbamoyl]amino}benzoic acid;

N-[2-(dimethylamino)ethyl]-4-{[(4-{4-[4-(1-methylethyl)-1,4-diazepan-1-yl]-6-morpholin-4-yl-1,3,5-triazin-2-yl}phenyl)carbamoyl]amino}benzamide;

N-{1-[(4-{[(4-{4-[4-(1-methylethyl)-1,4-diazepan-1-yl]-6-morpholin-4-yl-1,3,5-triazin-2-yl}phenyl)carbamoyl]amino}phenyl)carbonyl]piperidin-4-yl}acetamide;

1-{4-[(4-ethylpiperazin-1-yl)carbonyl]phenyl}-3-(4-{4-[4-(1-methylethyl)-1,4-diazepan-1-yl]-6-morpholin-4-yl-1,3,5-triazin-2-yl}phenyl)urea;

1-(4-{4-[4-(1-methylethyl)-1,4-diazepan-1-yl]-6-morpholin-4-yl-1,3,5-triazin-2-yl}phenyl)-3-(4-{[4-(1-methylethyl)piperazin-1-yl]carbonyl}phenyl)urea;

1-(4-{4,6-bis[(3S)-3-methylmorpholin-4-yl]-1,3,5-triazin-2-yl}phenyl)-3-(4-{[(3S)-3-methylmorpholin-4-yl]carbonyl}phenyl)urea;

1-{4-[(4-butylpiperazin-1-yl)carbonyl]phenyl}-3-(4-{4-[4-(1-methylethyl)-1,4-diazepan-1-yl]-6-morpholin-4-yl-1,3,5-triazin-2-yl}phenyl)urea;

1-(4-{4-[(4-methylpiperazin-1-yl)amino]-6-morpholin-4-yl-1,3,5-triazin-2-yl}phenyl)-3-phenylurea;

1-(4-{4-[(1-methylpiperidin-4-yl)oxy]-6-morpholin-4-yl-1,3,5-triazin-2-yl}phenyl)-3-pyridin-4-ylurea;

1-{4-[4-morpholin-4-yl-6-(piperidin-4-yloxy)-1,3,5-triazin-2-yl]phenyl}-3-pyridin-4-ylurea;

ethyl 4-[(4-morpholin-4-yl-6-{4-[(pyridin-4-ylcarbamoyl) amino]phenyl}-1,3,5-triazin-2-yl)oxy]piperidine-1-carboxylate;

N-ethyl-4-[(4-morpholin-4-yl-6-{4-[(pyridin-4-ylcarbamoyl)amino]phenyl}-1,3,5-triazin-2-yl)oxy]piperidine-1-carboxamide;

tert-butyl 4-[(4-morpholin-4-yl-6-{4-[(pyridin-4-ylcarbamoyl)amino]phenyl}-1,3,5-triazin-2-yl)oxy]piperidine-1-carboxylate;

4-[(4-morpholin-4-yl-6-{4-[(pyridin-4-ylcarbamoyl)amino] phenyl}-1,3,5-triazin-2-yl)oxy]piperidine-1-sulfonamide;

1-{4-[4-(1,4-dioxa-8-azaspiro[4.5]dec-8-yl)-6-morpholin-4-yl-1,3,5-triazin-2-yl]phenyl}-3-pyridin-4-ylurea;

1-{4-[4-(1,4-dioxa-8-azaspiro[4.5]dec-8-yl)-6-morpholin-4-yl-1,3,5-triazin-2-yl]phenyl}-3-pyridin-3-ylurea;

1-{4-[4-(1,4-dioxa-8-azaspiro[4.5]dec-8-yl)-6-morpholin-4-yl-1,3,5-triazin-2-yl]phenyl}-3-phenylurea;

1-[4-(dimethylamino)phenyl]-3-{4-[4-(1,4-dioxa-8-azaspiro[4.5]dec-8-yl)-6-morpholin-4-yl-1,3,5-triazin-2-yl]phenyl}urea;

1-(4-cyanophenyl)-3-{4-[4-(1,4-dioxa-8-azaspiro[4.5]dec-8-yl)-6-morpholin-4-yl-1,3,5-triazin-2-yl]phenyl}urea;

1-{4-[4-(1,4-dioxa-8-azaspiro[4.5]dec-8-yl)-6-morpholin-4-yl-1,3,5-triazin-2-yl]phenyl}-3-(2-methylpyridin-4-yl) urea;

1-[2-(dimethylamino)ethyl]-3-{4-[4-(1,4-dioxa-8-azaspiro[4.5]dec-8-yl)-6-morpholin-4-yl-1,3,5-triazin-2-yl] phenyl}urea;

1-[4-(4-morpholin-4-yl-6-quinolin-3-yl-1,3,5-triazin-2-yl) phenyl]-3-pyridin-4-ylurea;

1-{4-[4-(2-methoxyethoxy)-6-morpholin-4-yl-1,3,5-triazin-2-yl]phenyl}-3-pyridin-4-ylurea;

methyl 4-[({4-[4-(2-methoxyethoxy)-6-morpholin-4-yl-1,3,5-triazin-2-yl]phenyl}carbamoyl)amino]benzoate;

1-(4-{4-morpholin-4-yl-6-[2-(pyridin-4-ylamino)ethyl]-1,3,5-triazin-2-yl}phenyl)-3-pyridin-4-ylurea;

N-[2-(dimethylamino)ethyl]-4-({[4-(4-methoxy-6-morpholin-4-yl-1,3,5-triazin-2-yl)phenyl]carbamoyl}amino)-N-methylbenzamide;

N-[2-(dimethylamino)ethyl]-4-({[4-(4-methoxy-6-morpholin-4-yl-1,3,5-triazin-2-yl)phenyl]carbamoyl}amino)benzamide;

4-({[4-(4-m ethoxy-6-morpholin-4-yl-1,3,5-triazin-2-yl) phenyl]carbamoyl}amino)-N-methyl-N-[2-(methylamino)ethyl]benzamide;

1-[4-(4-methoxy-6-morpholin-4-yl-1,3,5-triazin-2-yl)phenyl]-3-{4-[(4-methyl piperazin-1-yl)carbonyl] phenyl}urea;

1-{4-[(3,3-dimethyl piperazin-1-yl)carbonyl]phenyl}-3-[4-(4-methoxy-6-morpholin-4-yl-1,3,5-triazin-2-yl)phenyl] urea;

4-({[4-(4-methoxy-6-morpholin-4-yl-1,3,5-triazin-2-yl) phenyl]carbamoyl}amino)-N-(2-piperidin-1-ylethyl)benzamide;

1-(4-{4-[2,5-bis(hydroxymethyl)pyrrolidin-1-yl]-6-morpholin-4-yl-1,3,5-triazin-2-yl}phenyl)-3-pyridin-4-ylurea;

1-(4-{4-[2-(1,3-dioxan-2-yl)ethyl]-6-morpholin-4-yl-1,3,5-triazin-2-yl}phenyl)-3-pyridin-4-ylurea;

1-(4-{4-[3-(dimethylamino)propyl]-6-morpholin-4-yl-1,3,5-triazin-2-yl}phenyl)-3-pyridin-4-ylurea;

1-(4-{4-{3-[(1-methylethyl)amino]propyl}-6-morpholin-4-yl-1,3,5-triazin-2-yl}phenyl]-3-pyridin-4-ylurea;

1-{4-[4-morpholin-4-yl-6-(3-pyrrolidin-1-ylpropyl)-1,3,5-triazin-2-yl]phenyl}-3-pyridin-4-ylurea;

1-(4-{4-[3-(4-methylpiperazin-1-yl)propyl]-6-morpholin-4-yl-1,3,5-triazin-2-yl}phenyl)-3-pyridin-4-ylurea;

1-{4-[4-(3-{[2-(dimethylamino)ethyl]amino}propyl)-6-morpholin-4-yl-1,3,5-triazin-2-yl]phenyl}-3-pyridin-4-ylurea;

1-{4-[4-(3-hydroxypropyl)-6-morpholin-4-yl-1,3,5-triazin-2-yl]phenyl}-3-pyridin-4-ylurea;

1-{4-[4-morpholin-4-yl-6-(3-oxopropyl)-1,3,5-triazin-2-yl] phenyl}-3-pyridin-4-ylurea;

N-(4-morpholin-4-yl-6-{4-[(pyridin-4-ylcarbamoyl)amino] phenyl}-1,3,5-triazin-2-yl)benzenesulfonamide;

N-{4-[4-({[4-(4-methyl piperazin-1-yl)phenyl] carbamoyl}amino)phenyl]-6-morpholin-4-yl-1,3,5-triazin-2-yl}benzenesulfonamide;

N-(4-{4-[({4-[2-(dimethylamino)ethoxy] phenyl}carbamoyl)amino]phenyl}-6-morpholin-4-yl-1,3,5-triazin-2-yl)benzenesulfonamide;

N-(4-{4-[({4-[(4-methylpiperazin-1-yl)carbonyl] phenyl}carbamoyl)amino]phenyl}-6-morpholin-4-yl-1,3,5-triazin-2-yl)benzenesulfonamide;

N-{4-morpholin-4-yl-6-[4-({[4-(piperazin-1-ylcarbonyl) phenyl]carbamoyl}amino)phenyl]-1,3,5-triazin-2-yl}benzenesulfonamide;

N-[4-(4-{[(4-{[4-(dimethylamino)piperidin-1-yl] carbonyl}phenyl)carbamoyl]amino}phenyl)-6-morpholin-4-yl-1,3,5-triazin-2-yl]benzenesulfonamide;

N-[2-(dimethylamino)ethyl]-N-methyl-4-{[(4-{4-morpholin-4-yl-6-[(phenylsulfonyl)amino]-1,3,5-triazin-2-yl}phenyl)carbamoyl]amino}benzamide;

N-[2-(dimethylamino)ethyl]-4-{[(4-{4-morpholin-4-yl-6-[(phenylsulfonyl)amino]-1,3,5-triazin-2-yl}phenyl)carbamoyl]amino}benzamide;

methyl 4-{[(4-{4-morpholin-4-yl-6-[(phenylsulfonyl) amino]-1,3,5-triazin-2-yl}phenyl)carbamoyl] amino}benzoate;

4-{[(4-{4-morpholin-4-yl-6-[(phenylsulfonyl)amino]-1,3,5-triazin-2-yl}phenyl)carbamoyl]amino}benzoic acid;

1-{4-[(4-methylpiperazin-1-yl)carbonyl]phenyl}-3-[4-(6-morpholin-4-yl-4-oxo-4,5-dihydro-1,3,5-triazin-2-yl) phenyl]urea;

1-(4-(2,4-dimethylpiperazine-1-carbonyl)phenyl)-3-(4-(4,6-dimorpholino-1,3,5-triazin-2-yl)phenyl)urea;

1-(4-(4,6-dimorpholino-1,3,5-triazin-2-yl)phenyl)-3-(4-(4-isopropyl-2-methylpiperazine-1-carbonyl)phenyl)urea;

1-(4-(4-cyclobutyl-2-methylpiperazine-1-carbonyl)phenyl)-3-(4-(4,6-dimorpholino-1,3,5-triazin-2-yl)phenyl)urea;

1-(4-(4,6-dimorpholino-1,3,5-triazin-2-yl)phenyl)-3-(4-(4-isopropyl-3-methylpiperazine-1-carbonyl)phenyl)urea;

1-(4-(3,4-dimethylpiperazine-1-carbonyl)phenyl)-3-(4-(4,6-dimorpholino-1,3,5-triazin-2-yl)phenyl)urea;

1-(4-(4-cyclobutyl-3-methylpiperazine-1-carbonyl)phenyl)-3-(4-(4,6-dimorpholino-1,3,5-triazin-2-yl)phenyl)urea;

1-(4-(4-cyclobutylpiperazine-1-carbonyl)phenyl)-3-(4-(4,6-dimorpholino-1,3,5-triazin-2-yl)phenyl)urea;

1-(4-(2,4-dimethylpiperazine-1-carbonyl)phenyl)-3-(4-(4-morpholino-6-(tetrahydro-2H-pyran-4-yl)-1,3,5-triazin-2-yl)phenyl)urea;

1-(4-(4-isopropyl-2-methylpiperazine-1-carbonyl)phenyl)-3-(4-(4-morpholino-6-(tetrahydro-2H-pyran-4-yl)-1,3,5-triazin-2-yl)phenyl)urea;

1-(4-(4-cyclobutyl-2-methylpiperazine-1-carbonyl)phenyl)-3-(4-(4-morpholino-6-(tetrahydro-2H-pyran-4-yl)-1,3,5-triazin-2-yl)phenyl)urea;

1-(4-(4-isopropyl-3-methylpiperazine-1-carbonyl)phenyl)-3-(4-(4-morpholino-6-(tetrahydro-2H-pyran-4-yl)-1,3,5-triazin-2-yl)phenyl)urea;

1-(4-(3,4-dimethylpiperazine-1-carbonyl)phenyl)-3-(4-(4-morpholino-6-(tetrahydro-2H-pyran-4-yl)-1,3,5-triazin-2-yl)phenyl)urea;

1-(4-(4-cyclobutyl-3-methylpiperazine-1-carbonyl)phenyl)-3-(4-(4-morpholino-6-(tetrahydro-2H-pyran-4-yl)-1,3,5-triazin-2-yl)phenyl)urea;

1-(4-(4-cyclobutylpiperazine-1-carbonyl)phenyl)-3-(4-(4-morpholino-6-(tetrahydro-2H-pyran-4-yl)-1,3,5-triazin-2-yl)phenyl)urea;

1-(4-(2-methylpiperazine-1-carbonyl)phenyl)-3-(4-(4-morpholino-6-(tetrahydro-2H-pyran-4-yl)-1,3,5-triazin-2-yl)phenyl)urea;

1-(4-(3-methylpiperazine-1-carbonyl)phenyl)-3-(4-(4-morpholino-6-(tetrahydro-2H-pyran-4-yl)-1,3,5-triazin-2-yl)phenyl)urea;

1-(4-(4,6-dimorpholino-1,3,5-triazin-2-yl)phenyl)-3-(4-(3-methylpiperazine-1-carbonyl)phenyl)urea;

1-(4-(4,6-dimorpholino-1,3,5-triazin-2-yl)phenyl)-3-(4-(2-methylpiperazine-1-carbonyl)phenyl)urea;

1-(4-(3,3-dimethylpiperazine-1-carbonyl)phenyl)-3-(4-(4,6-dimorpholino-1,3,5-triazin-2-yl)phenyl)urea;

1-(4-(3,3-dimethylpiperazine-1-carbonyl)phenyl)-3-(4-(4-morpholino-6-(tetrahydro-2H-pyran-4-yl)-1,3,5-triazin-2-yl)phenyl)urea;

1-(4-(4-morpholino-6-(tetrahydro-2H-pyran-4-yl)-1,3,5-triazin-2-yl)phenyl)-3-(4-(3,3,4-trimethylpiperazine-1-carbonyl)phenyl)urea;

1-(4-(4,6-dimorpholino-1,3,5-triazin-2-yl)phenyl)-3-(4-(3,3,4-trimethylpiperazine-1-carbonyl)phenyl)urea;

1-(4-(2,4-dimethylpiperazine-1-carbonyl)phenyl)-3-(4-(4-morpholino-6-(tetrahydro-2H-pyran-4-yl)-1,3,5-triazin-2-yl)phenyl)urea;

1-(4-(4-(3-methylmorpholino)-6-(tetrahydro-2H-pyran-4-yl)-1,3,5-triazin-2-yl)phenyl)-3-(4-(2-methylpiperazine-1-carbonyl)phenyl)urea;

1-(4-(4-isopropyl-2-methylpiperazine-1-carbonyl)phenyl)-3-(4-(4-(3-methylmorpholino)-6-(tetrahydro-2H-pyran-4-yl)-1,3,5-triazin-2-yl)phenyl)urea;

1-(4-(4-cyclobutyl-2-methylpiperazine-1-carbonyl)phenyl)-3-(4-(4-(3-methylmorpholino)-6-(tetrahydro-2H-pyran-4-yl)-1,3,5-triazin-2-yl)phenyl)urea;

1-(4-(4-isopropyl-3-methylpiperazine-1-carbonyl)phenyl)-3-(4-(4-(3-methylmorpholino)-6-(tetrahydro-2H-pyran-4-yl)-1,3,5-triazin-2-yl)phenyl)urea;

1-(4-(3,4-dimethylpiperazine-1-carbonyl)phenyl)-3-(4-(4-(3-methylmorpholino)-6-(tetrahydro-2H-pyran-4-yl)-1,3,5-triazin-2-yl)phenyl)urea;

1-(4-(4-cyclobutyl-3-methylpiperazine-1-carbonyl)phenyl)-3-(4-(4-(3-methylmorpholino)-6-(tetrahydro-2H-pyran-4-yl)-1,3,5-triazin-2-yl)phenyl)urea;

1-(4-(4-cyclobutylpiperazine-1-carbonyl)phenyl)-3-(4-(4-(3-methylmorpholino)-6-(tetrahydro-2H-pyran-4-yl)-1,3,5-triazin-2-yl)phenyl)urea;

1-(4-(4-(3-methylmorpholino)-6-(tetrahydro-2H-pyran-4-yl)-1,3,5-triazin-2-yl)phenyl)-3-(4-(3,3,4-trimethylpiperazine-1-carbonyl)phenyl)urea;

1-(4-(3,3-dimethylpiperazine-1-carbonyl)phenyl)-3-(4-(4-(3-methylmorpholino)-6-(tetrahydro-2H-pyran-4-yl)-1,3,5-triazin-2-yl)phenyl)urea;

N-(2-(dimethylamino)ethyl)-N-methyl-4-(3-(4-(4-(3-methylmorpholino)-6-(tetrahydro-2H-pyran-4-yl)-1,3,5-triazin-2-yl)phenyl)ureido)benzamide;

N-(2-(dimethylamino)ethyl)-4-(3-(4-(4-(3-methylmorpholino)-6-(tetrahydro-2H-pyran-4-yl)-1,3,5-triazin-2-yl)phenyl)ureido)benzamide;

1-(4-(4-(dimethylamino)piperidine-1-carbonyl)phenyl)-3-(4-(4-(3-methylmorpholino)-6-(tetrahydro-2H-pyran-4-yl)-1,3,5-triazin-2-yl)phenyl)urea;

1-(4-(2,4-dimethylpiperazine-1-carbonyl)phenyl)-3-(4-(4-(2-methylmorpholino)-6-morpholino-1,3,5-triazin-2-yl)phenyl)urea;

1-(4-(2,4-dimethylpiperazine-1-carbonyl)phenyl)-3-(4-(4-(2-methylmorpholino)-6-morpholino-1,3,5-triazin-2-yl)phenyl)urea;

1-(4-(4-isopropyl-2-methyl piperazine-1-carbonyl)phenyl)-3-(4-(4-(2-methylmorpholino)-6-morpholino-1,3,5-triazin-2-yl)phenyl)urea;

1-(4-(4-cyclobutyl-2-methylpiperazine-1-carbonyl)phenyl)-3-(4-(4-(2-methylmorpholino)-6-morpholino-1,3,5-triazin-2-yl)phenyl)urea;

N-(2-(dimethylamino)ethyl)-N-methyl-4-(3-(4-(4-(2-methylmorpholino)-6-morpholino-1,3,5-triazin-2-yl)phenyl)ureido)benzamide;

1-(4-(4-isopropyl-3-methyl piperazine-1-carbonyl)phenyl)-3-(4-(4-(2-methylmorpholino)-6-morpholino-1,3,5-triazin-2-yl)phenyl)urea;

1-(4-(4-(2-methylmorpholino)-6-morpholino-1,3,5-triazin-2-yl)phenyl)-3-(4-(3-methylpiperazine-1-carbonyl)phenyl)urea;

1-(4-(3,4-dimethylpiperazine-1-carbonyl)phenyl)-3-(4-(4-(2-methylmorpholino)-6-morpholino-1,3,5-triazin-2-yl)phenyl)urea;

1-(4-(4-cyclobutyl-3-methylpiperazine-1-carbonyl)phenyl)-3-(4-(4-(2-methylmorpholino)-6-morpholino-1,3,5-triazin-2-yl)phenyl)urea;

1-(4-(3,3-dimethylpiperazine-1-carbonyl)phenyl)-3-(4-(4-(2-methylmorpholino)-6-morpholino-1,3,5-triazin-2-yl)phenyl)urea;

1-(4-(4-(2-methylmorpholino)-6-morpholino-1,3,5-triazin-2-yl)phenyl)-3-(4-(3,3,4-trimethylpiperazine-1-carbonyl)phenyl)urea;

1-(4-(4-cyclobutylpiperazine-1-carbonyl)phenyl)-3-(4-(4-(2-methylmorpholino)-6-morpholino-1,3,5-triazin-2-yl)phenyl)urea;

N-(2-(dimethylamino)ethyl)-4-(3-(4-(4-(2-methylmorpholino)-6-morpholino-1,3,5-triazin-2-yl)phenyl)ureido)benzamide;

1-(4-(4-(dimethylamino)piperidine-1-carbonyl)phenyl)-3-(4-(4-(2-methylmorpholino)-6-morpholino-1,3,5-triazin-2-yl)phenyl)urea;

1-(4-(3-(dimethylamino)pyrrolidine-1-carbonyl)phenyl)-3-(4-(4-(2-methylmorpholino)-6-morpholino-1,3,5-triazin-2-yl)phenyl)urea;

1-(4-(3-(dimethylamino)pyrrolidine-1-carbonyl)phenyl)-3-(4-(4-morpholino-6-(tetrahydro-2H-pyran-4-yl)-1,3,5-triazin-2-yl)phenyl)urea;

1-(4-(3-(dimethylamino)pyrrolidine-1-carbonyl)phenyl)-3-(4-(4-(3-methylmorpholino)-6-(tetra hydro-2H-pyran-4-yl)-1,3,5-triazin-2-yl)phenyl)urea;

1-(4-(4-((2R,5S)-2,5-dimethylpyrrolidin-1-yl)-6-((R)-3-methylmorpholino)-1,3,5-triazin-2-yl)phenyl)-3-(4-(4-methylpiperazin-1-yl)phenyl)urea;

1-(4-(4-(dimethylamino)piperidin-1-yl)phenyl)-3-(4-(4-((2R,5S)-2,5-dimethylpyrrolidin-1-yl)-6-((R)-3-methylmorpholino)-1,3,5-triazin-2-yl)phenyl)urea;

1-(4-(4-((2R,5S)-2,5-dimethylpyrrolidin-1-yl)-6-((R)-3-methylmorpholino)-1,3,5-triazin-2-yl)phenyl)-3-(4-(quinuclidin-4-yl)phenyl)urea;

1-(4-(4-cyclopropylpiperazin-1-yl)phenyl)-3-(4-(4-((2R,5S)-2,5-dimethylpyrrolidin-1-yl)-6-((R)-3-methylmorpholino)-1,3,5-triazin-2-yl)phenyl)urea;

1-(4-(4-(cyclopropylmethyl)piperazin-1-yl)phenyl)-3-(4-(4-((2R,5S)-2,5-dimethylpyrrolidin-1-yl)-6-((R)-3-m ethylmorpholino)-1,3,5-triazin-2-yl)phenyl)urea;

1-(4-(4-((2R,5S)-2,5-dimethylpyrrolidin-1-yl)-6-((R)-3-methylmorpholino)-1,3,5-triazin-2-yl)phenyl)-3-(4-(4-ethylpiperazin-1-yl)phenyl)urea;
1-(4-(4-((2R,5S)-2,5-dimethylpyrrolidin-1-yl)-6-((R)-3-methylmorpholino)-1,3,5-triazin-2-yl)phenyl)-3-(4-(4-isopropylpiperazin-1-yl)phenyl)urea;
1-(4-(4-((2R,5S)-2,5-dimethylpyrrolidin-1-yl)-6-((R)-3-methylmorpholino)-1,3,5-triazin-2-yl)phenyl)-3-(4-(4-methylpiperazine-1-carbonyl)phenyl)urea;
1-(4-(4-((2R,5S)-2,5-dimethylpyrrolidin-1-yl)-6-((R)-3-methylmorpholino)-1,3,5-triazin-2-yl)phenyl)-3-(4-(4-isopropylpiperazine-1-carbonyl)phenyl)urea;
1-(4-(4-(dimethylamino)piperidine-1-carbonyl)phenyl)-3-(4-(4-((2R,5S)-2,5-dimethylpyrrolidin-1-yl)-6-((R)-3-methylmorpholino)-1,3,5-triazin-2-yl)phenyl)urea;
1-(4-(4-((2R,5S)-2,5-dimethylpyrrolidin-1-yl)-6-((R)-3-methylmorpholino)-1,3,5-triazin-2-yl)phenyl)-3-(4-(4-ethylpiperazine-1-carbonyl)phenyl)urea;
1-(4-(4-cyclopropylpiperazine-1-carbonyl)phenyl)-3-(4-(4-((2R,5S)-2,5-dimethylpyrrolidin-1-yl)-6-((R)-3-methylmorpholino)-1,3,5-triazin-2-yl)phenyl)urea;
1-(4-(4-(cyclopropylmethyl)piperazine-1-carbonyl)phenyl)-3-(4-(4-((2R,5S)-2,5-dimethylpyrrolidin-1-yl)-6-((R)-3-methylmorpholino)-1,3,5-triazin-2-yl)phenyl)urea;
1-(4-(4-((2S,5R)-2,5-bis(hydroxymethyl)pyrrolidin-1-yl)-6-((R)-3-methylmorpholino)-1,3,5-triazin-2-yl)phenyl)-3-(4-(4-methyl piperazin-1-yl)phenyl)urea;
1-(4-(4-((2S,5R)-2,5-bis(hydroxymethyl)pyrrolidin-1-yl)-6-((R)-3-methylmorpholino)-1,3,5-triazin-2-yl)phenyl)-3-(4-(4-(dimethylamino)piperidin-1-yl)phenyl)urea;
1-(4-(4-((2S,5R)-2,5-bis(hydroxymethyl)pyrrolidin-1-yl)-6-((R)-3-methylmorpholino)-1,3,5-triazin-2-yl)phenyl)-3-(4-(quinuclidin-4-yl)phenyl)urea;
1-(4-(4-((2S,5R)-2,5-bis(hydroxymethyl)pyrrolidin-1-yl)-6-((R)-3-methylmorpholino)-1,3,5-triazin-2-yl)phenyl)-3-(4-(4-cyclopropylpiperazin-1-yl)phenyl)urea;
1-(4-(4-((2S,5R)-2,5-bis(hydroxymethyl)pyrrolidin-1-yl)-6-((R)-3-methylmorpholino)-1,3,5-triazin-2-yl)phenyl)-3-(4-(4-(cyclopropylmethyl)piperazin-1-yl)phenyl)urea;
1-(4-(4-((2S,5R)-2,5-bis(hydroxymethyl)pyrrolidin-1-yl)-6-((R)-3-methylmorpholino)-1,3,5-triazin-2-yl)phenyl)-3-(4-(4-ethylpiperazin-1-yl)phenyl)urea;
1-(4-(4-((2S,5R)-2,5-bis(hydroxymethyl)pyrrolidin-1-yl)-6-((R)-3-methylmorpholino)-1,3,5-triazin-2-yl)phenyl)-3-(4-(4-isopropylpiperazin-1-yl)phenyl)urea;
1-(4-(4-((2S,5R)-2,5-bis(hydroxymethyl)pyrrolidin-1-yl)-6-((R)-3-methylmorpholino)-1,3,5-triazin-2-yl)phenyl)-3-(4-(4-methylpiperazine-1-carbonyl)phenyl)urea;
1-(4-(4-((2S,5R)-2,5-bis(hydroxymethyl)pyrrolidin-1-yl)-6-((R)-3-methylmorpholino)-1,3,5-triazin-2-yl)phenyl)-3-(4-(4-isopropylpiperazine-1-carbonyl)phenyl)urea;
1-(4-(4-((2S,5R)-2,5-bis(hydroxymethyl)pyrrolidin-1-yl)-6-((R)-3-methylmorpholino)-1,3,5-triazin-2-yl)phenyl)-3-(4-(4-(dimethylamino)piperidine-1-carbonyl)phenyl)urea;
1-(4-(4-((2S,5R)-2,5-bis(hydroxymethyl)pyrrolidin-1-yl)-6-((R)-3-methylmorpholino)-1,3,5-triazin-2-yl)phenyl)-3-(4-(4-ethylpiperazine-1-carbonyl)phenyl)urea;
1-(4-(4-((2S,5R)-2,5-bis(hydroxymethyl)pyrrolidin-1-yl)-6-((R)-3-methylmorpholino)-1,3,5-triazin-2-yl)phenyl)-3-(4-(4-cyclopropylpiperazine-1-carbonyl)phenyl)urea;
1-(4-(4-((2S,5R)-2,5-bis(hydroxymethyl)pyrrolidin-1-yl)-6-((R)-3-methylmorpholino)-1,3,5-triazin-2-yl)phenyl)-3-(4-(4-(cyclopropylmethyl)piperazine-1-carbonyl)phenyl)urea;
1-(4-(4-morpholino-6-(tetrahydrofuran-3-yloxy)-1,3,5-triazin-2-yl)phenyl)-3-(pyridin-4-yl)urea;
1-(4-(4-morpholino-6-(tetrahydrofuran-3-yloxy)-1,3,5-triazin-2-yl)phenyl)-3-(pyridin-3-yl)urea;
1-(4-(4-morpholino-6-(tetrahydrofuran-3-yloxy)-1,3,5-triazin-2-yl)phenyl)-3-(pyridazin-4-yl)urea;
1-(4-(4-morpholino-6-(tetrahydrofuran-3-yloxy)-1,3,5-triazin-2-yl)phenyl)-3-(pyrimidin-5-yl)urea;
4-(3-(4-(4-morpholino-6-(tetrahydrofuran-3-yloxy)-1,3,5-triazin-2-yl)phenyl)ureido)benzamide;
N-(2-(dimethylamino)ethyl)-4-(3-(4-(4-morpholino-6-(tetrahydrofuran-3-yloxy)-1,3,5-triazin-2-yl)phenyl)ureido)benzamide;
N-(2-(dimethylamino)ethyl)-N-methyl-4-(3-(4-(4-morpholino-6-(tetrahydrofuran-3-yloxy)-1,3,5-triazin-2-yl)phenyl)ureido)benzamide;
N-(2-(methylamino)ethyl)-4-(3-(4-(4-morpholino-6-(tetrahydrofuran-3-yloxy)-1,3,5-triazin-2-yl)phenyl)ureido)benzamide;
N-methyl-N-(2-(methylamino)ethyl)-4-(3-(4-(4-morpholino-6-(tetrahydrofuran-3-yloxy)-1,3,5-triazin-2-yl)phenyl)ureido)benzamide;
1-(4-((R)-3-(dimethylamino)pyrrolidine-1-carbonyl)phenyl)-3-(4-(4-morpholino-6-(tetrahydrofuran-3-yloxy)-1,3,5-triazin-2-yl)phenyl)urea;
1-(4-(4-morpholino-6-(tetrahydrofuran-3-yloxy)-1,3,5-triazin-2-yl)phenyl)-3-(4-(piperazine-1-carbonyl)phenyl)urea;
1-(4-(4-methylpiperazine-1-carbonyl)phenyl)-3-(4-(4-morpholino-6-(tetrahydrofuran-3-yloxy)-1,3,5-triazin-2-yl)phenyl)urea;
1-(4-(4-ethylpiperazine-1-carbonyl)phenyl)-3-(4-(4-morpholino-6-(tetrahydrofuran-3-yloxy)-1,3,5-triazin-2-yl)phenyl)urea;
1-(4-(4-isopropylpiperazine-1-carbonyl)phenyl)-3-(4-(4-morpholino-6-(tetrahydrofuran-3-yloxy)-1,3,5-triazin-2-yl)phenyl)urea;
1-(4-(4-((S)-3-methylmorpholino)-6-(tetrahydrofuran-3-yloxy)-1,3,5-triazin-2-yl)phenyl)-3-(pyridin-4-yl)urea;
1-(4-(4-((S)-3-methylmorpholino)-6-(tetrahydrofuran-3-yloxy)-1,3,5-triazin-2-yl)phenyl)-3-(pyridin-3-yl)urea;
1-(4-(4-((S)-3-methylmorpholino)-6-(tetrahydrofuran-3-yloxy)-1,3,5-triazin-2-yl)phenyl)-3-(pyridazin-4-yl)urea;
1-(4-(4-((S)-3-methylmorpholino)-6-(tetrahydrofuran-3-yloxy)-1,3,5-triazin-2-yl)phenyl)-3-(pyrimidin-5-yl)urea;
4-(3-(4-(4-((S)-3-methylmorpholino)-6-(tetrahydrofuran-3-yloxy)-1,3,5-triazin-2-yl)phenyl)ureido)benzamide;
1-(4-(3-(dimethylamino)pyrrolidine-1-carbonyl)phenyl)-3-(4-(4-((S)-3-methylmorpholino)-6-(tetrahydrofuran-3-yloxy)-1,3,5-triazin-2-yl)phenyl)urea;
1-(4-(4-((S)-3-methylmorpholino)-6-(tetrahydrofuran-3-yloxy)-1,3,5-triazin-2-yl)phenyl)-3-(4-(piperazine-1-carbonyl)phenyl)urea;
1-(4-(4-((S)-3-methylmorpholino)-6-(tetrahydrofuran-3-yloxy)-1,3,5-triazin-2-yl)phenyl)-3-(4-(4-methylpiperazine-1-carbonyl)phenyl)urea;
1-(4-(4-ethylpiperazine-1-carbonyl)phenyl)-3-(4-(4-((S)-3-methylmorpholino)-6-(tetrahydrofuran-3-yloxy)-1,3,5-triazin-2-yl)phenyl)urea;
1-(4-(4-isopropylpiperazine-1-carbonyl)phenyl)-3-(4-(4-((S)-3-methylmorpholino)-6-(tetrahydrofuran-3-yloxy)-1,3,5-triazin-2-yl)phenyl)urea;
1-(4-(4-(1,4-diazepan-1-yl)-6-morpholino-1,3,5-triazin-2-yl)phenyl)-3-(pyridin-3-yl)urea;
1-(4-(4-(1,4-diazepan-1-yl)-6-morpholino-1,3,5-triazin-2-yl)phenyl)-3-(pyridazin-4-yl)urea;
1-(4-(4-(1,4-diazepan-1-yl)-6-morpholino-1,3,5-triazin-2-yl)phenyl)-3-(pyrimidin-5-yl)urea;

1-(4-(4-(1,4-diazepan-1-yl)-6-morpholino-1,3,5-triazin-2-yl)phenyl)-3-(pyridin-4-yl)urea;
1-(4-(4-(1,4-diazepan-1-yl)-6-morpholino-1,3,5-triazin-2-yl)phenyl)-3-phenylurea;
1-(4-(4-(1,4-diazepan-1-yl)-6-morpholino-1,3,5-triazin-2-yl)phenyl)-3-(4-chlorophenyl)urea;
1-(4-(4-(1,4-diazepan-1-yl)-6-morpholino-1,3,5-triazin-2-yl)phenyl)-3-(4-fluorophenyl)urea;
methyl4-(3-(4-(4-(1,4-diazepan-1-yl)-6-morpholino-1,3,5-triazin-2yl)phenyl)ureido)benzoate;
4-(3-(4-(4-(1,4-diazepan-1-yl)-6-morpholino-1,3,5-triazin-2-yl)phenyl)ureido)benzoic acid;
4-(3-(4-(4-(1,4-diazepan-1-yl)-6-morpholino-1,3,5-triazin-2-yl)phenyl)ureido)-N-(2-(dimethylamino)ethyl)benzamide;
4-(3-(4-(4-(1,4-diazepan-1-yl)-6-morpholino-1,3,5-triazin-2-yl)phenyl)ureido)-N-(2-(dimethylamino)ethyl)-N-methylbenzamide;
1-(4-(4-(1,4-diazepan-1-yl)-6-morpholino-1,3,5-triazin-2-yl)phenyl)-3-(4-(3-(dimethylamino)pyrrolidine-1-carbonyl)phenyl)urea;
4-(3-(4-(4-(1,4-diazepan-1-yl)-6-morpholino-1,3,5-triazin-2-yl)phenyl)ureido)benzamide;
1-(4-(4-(1,4-diazepan-1-yl)-6-morpholino-1,3,5-triazin-2-yl)phenyl)-3-(4-(piperazine-1-carbonyl)phenyl)urea;
1-(4-(4-(1,4-diazepan-1-yl)-6-morpholino-1,3,5-triazin-2-yl)phenyl)-3-(4-(4-ethylpiperazine-1-carbonyl)phenyl)urea;
1-(4-(4-(1,4-diazepan-1-yl)-6-morpholino-1,3,5-triazin-2-yl)phenyl)-3-(4-(4-isopropylpiperazine-1-carbonyl)phenyl)urea;
1-(4-(4-(1,4-diazepan-1-yl)-6-morpholino-1,3,5-triazin-2-yl)phenyl)-3-(4-(4-(dimethylamino)piperidine-1-carbonyl)phenyl)urea;
1-(4-(4-(dimethylamino)piperidine-1-carbonyl)phenyl)-3-(4-(4-(4-methyl-1,4-diazepan-1-yl)-6-morpholino-1,3,5-triazin-2-yl)phenyl)urea;
1-(4-(4-(4-methyl-1,4-diazepan-1-yl)-6-morpholino-1,3,5-triazin-2-yl)phenyl)-3-(4-(piperazine-1-carbonyl)phenyl)urea;
1-(4-(4-(4-methyl-1,4-diazepan-1-yl)-6-morpholino-1,3,5-triazin-2-yl)phenyl)-3-(4-(4-methylpiperazine-1-carbonyl)phenyl)urea;
1-(4-(4-(4-methyl-1,4-diazepan-1-yl)-6-morpholino-1,3,5-triazin-2-yl)phenyl)-3-(4-(4-ethylpiperazine-1-carbonyl)phenyl)urea;
1-(4-(4-(4-methyl-1,4-diazepan-1-yl)-6-morpholino-1,3,5-triazin-2-yl)phenyl)-3-(4-(4-n-propylpiperazine-1-carbonyl)phenyl)urea;
1-(4-(4-(4-methyl-1,4-diazepan-1-yl)-6-morpholino-1,3,5-triazin-2-yl)phenyl)-3-(4-(4-isopropylpiperazine-1-carbonyl)phenyl)urea;
1-(4-(3-(dimethylamino)pyrrolidine-1-carbonyl)phenyl)-3-(4-(4-(4-methyl-1,4-diazepan-1-yl)-6-morpholino-1,3,5-triazin-2-yl)phenyl)urea;
N-(2-(dimethylamino)ethyl)-4-(3-(4-(4-(4-methyl-1,4-diazepan-1-yl)-6-morpholino-1,3,5-triazin-2-yl)phenyl)ureido)benzamide;
N-(2-(dimethylamino)ethyl)-N-methyl-4-(3-(4-(4-(4-methyl-1,4-diazepan-1-yl)-6-morpholino-1,3,5-triazin-2-yl)phenyl)ureido)benzamide;
1-(4-(4-(4-methyl-1,4-diazepan-1-yl)-6-morpholino-1,3,5-triazin-2-yl)phenyl)-3-phenylurea;
1-(4-chlorophenyl)-3-(4-(4-(4-methyl-1,4-diazepan-1-yl)-6-morpholino-1,3,5-triazin-2-yl)phenyl)urea;
1-(4-fluorophenyl)-3-(4-(4-(4-methyl-1,4-diazepan-1-yl)-6-morpholino-1,3,5-triazin-2-yl)phenyl)urea;
1-(4-(4-(4-methyl-1,4-diazepan-1-yl)-6-morpholino-1,3,5-triazin-2-yl)phenyl)-3-(pyridin-3-yl)urea;
1-(4-(4-(4-methyl-1,4-diazepan-1-yl)-6-morpholino-1,3,5-triazin-2-yl)phenyl)-3-(pyridin-4-yl)urea;
1-(4-(4-(4-methyl-1,4-diazepan-1-yl)-6-morpholino-1,3,5-triazin-2-yl)phenyl)-3-(pyridazin-4-yl)urea;
1-(4-(4-(4-methyl-1,4-diazepan-1-yl)-6-morpholino-1,3,5-triazin-2-yl)phenyl)-3-(pyrimidin-5-yl)urea;
1-(4-(4-(4-ethyl-1,4-diazepan-1-yl)-6-morpholino-1,3,5-triazin-2-yl)phenyl)-3-(4-(piperazine-1-carbonyl)phenyl)urea;
1-(4-(4-(4-ethyl-1,4-diazepan-1-yl)-6-morpholino-1,3,5-triazin-2-yl)phenyl)-3-(4-(4-methylpiperazine-1-carbonyl)phenyl)urea;
1-(4-(4-(4-ethyl-1,4-diazepan-1-yl)-6-morpholino-1,3,5-triazin-2-yl)phenyl)-3-(4-(4-ethylpiperazine-1-carbonyl)phenyl)urea;
1-(4-(4-(4-ethyl-1,4-diazepan-1-yl)-6-morpholino-1,3,5-triazin-2-yl)phenyl)-3-(4-(4-n-propylpiperazine-1-carbonyl)phenyl)urea;
1-(4-(4-(4-ethyl-1,4-diazepan-1-yl)-6-morpholino-1,3,5-triazin-2-yl)phenyl)-3-(4-(4-isopropylpiperazine-1-carbonyl)phenyl)urea;
1-(4-(3-(dimethylamino)pyrrolidine-1-carbonyl)phenyl)-3-(4-(4-(4-ethyl-1,4-diazepan-1-yl)-6-morpholino-1,3,5-triazin-2-yl)phenyl)urea;
N-(2-(dimethylamino)ethyl)-4-(3-(4-(4-(4-ethyl-1,4-diazepan-1-yl)-6-morpholino-1,3,5-triazin-2-yl)phenyl)ureido)benzamide;
N-(2-(dimethylamino)ethyl)-N-methyl-4-(3-(4-(4-(4-ethyl-1,4-diazepan-1-yl)-6-morpholino-1,3,5-triazin-2-yl)phenyl)ureido)benzamide;
1-(4-(4-(4-ethyl-1,4-diazepan-1-yl)-6-morpholino-1,3,5-triazin-2-yl)phenyl)-3-phenylurea;
1-(4-chlorophenyl)-3-(4-(4-(4-ethyl-1,4-diazepan-1-yl)-6-morpholino-1,3,5-triazin-2-yl)phenyl)urea;
1-(4-fluorophenyl)-3-(4-(4-(4-ethyl-1,4-diazepan-1-yl)-6-morpholino-1,3,5-triazin-2-yl)phenyl)urea;
1-(4-(4-(4-ethyl-1,4-diazepan-1-yl)-6-morpholino-1,3,5-triazin-2-yl)phenyl)-3-(pyridin-3-yl)urea;
1-(4-(4-(4-ethyl-1,4-diazepan-1-yl)-6-morpholino-1,3,5-triazin-2-yl)phenyl)-3-(pyridin-4-yl)urea;
1-(4-(4-(4-ethyl-1,4-diazepan-1-yl)-6-morpholino-1,3,5-triazin-2-yl)phenyl)-3-(pyridazin-4-yl)urea;
1-(4-(4-(4-ethyl-1,4-diazepan-1-yl)-6-morpholino-1,3,5-triazin-2-yl)phenyl)-3-(pyrimidin-5-yl)urea;
1-(4-(4-(4-propyl-1,4-diazepan-1-yl)-6-morpholino-1,3,5-triazin-2-yl)phenyl)-3-(4-(piperazine-1-carbonyl)phenyl)urea;
1-(4-(4-(4-propyl-1,4-diazepan-1-yl)-6-morpholino-1,3,5-triazin-2-yl)phenyl)-3-(4-(4-methylpiperazine-1-carbonyl)phenyl)urea;
1-(4-(4-(4-propyl-1,4-diazepan-1-yl)-6-morpholino-1,3,5-triazin-2-yl)phenyl)-3-(4-(4-ethylpiperazine-1-carbonyl)phenyl)urea;
1-(4-(4-(4-propyl-1,4-diazepan-1-yl)-6-morpholino-1,3,5-triazin-2-yl)phenyl)-3-(4-(4-n-propylpiperazine-1-carbonyl)phenyl)urea;
1-(4-(4-(4-propyl-1,4-diazepan-1-yl)-6-morpholino-1,3,5-triazin-2-yl)phenyl)-3-(4-(4-isopropylpiperazine-1-carbonyl)phenyl)urea;
1-(4-(3-(dimethylamino)pyrrolidine-1-carbonyl)phenyl)-3-(4-(4-(4-propyl-1,4-diazepan-1-yl)-6-morpholino-1,3,5-triazin-2-yl)phenyl)urea;
N-(2-(dimethylamino)ethyl)-4-(3-(4-(4-(4-propyl-1,4-diazepan-1-yl)-6-morpholino-1,3,5-triazin-2-yl)phenyl)ureido)benzamide;

N-(2-(dimethylamino)ethyl)-N-methyl-4-(3-(4-(4-(4-propyl-1,4-diazepan-1-yl)-6-morpholino-1,3,5-triazin-2-yl)phenyl)ureido)benzamide;

1-(4-(4-(4-propyl-1,4-diazepan-1-yl)-6-morpholino-1,3,5-triazin-2-yl)phenyl)-3-phenylurea;

1-(4-chlorophenyl)-3-(4-(4-(4-propyl-1,4-diazepan-1-yl)-6-morpholino-1,3,5-triazin-2-yl)phenyl)urea;

1-(4-fluorophenyl)-3-(4-(4-(4-propyl-1,4-diazepan-1-yl)-6-morpholino-1,3,5-triazin-2-yl)phenyl)urea;

1-(4-(4-(4-propyl-1,4-diazepan-1-yl)-6-morpholino-1,3,5-triazin-2-yl)phenyl)-3-(pyridin-3-yl)urea;

1-(4-(4-(4-propyl-1,4-diazepan-1-yl)-6-morpholino-1,3,5-triazin-2-yl)phenyl)-3-(pyridin-4-yl)urea;

1-(4-(4-(4-propyl-1,4-diazepan-1-yl)-6-morpholino-1,3,5-triazin-2-yl)phenyl)-3-(pyridazin-4-yl)urea;

1-(4-(4-(4-propyl-1,4-diazepan-1-yl)-6-morpholino-1,3,5-triazin-2-yl)phenyl)-3-(pyrimidin-5-yl)urea;

1-(4-(4-(4-isopropyl-1,4-diazepan-1-yl)-6-morpholino-1,3,5-triazin-2-yl)phenyl)-3-(pyridin-3-yl)urea;

1-(4-(4-(4-isopropyl-1,4-diazepan-1-yl)-6-morpholino-1,3,5-triazin-2-yl)phenyl)-3-(pyridin-4-yl)urea;

1-(4-(4-(4-isopropyl-1,4-diazepan-1-yl)-6-morpholino-1,3,5-triazin-2-yl)phenyl)-3-(pyridazin-4-yl)urea;

1-(4-(4-(4-isopropyl-1,4-diazepan-1-yl)-6-morpholino-1,3,5-triazin-2-yl)phenyl)-3-(pyrimidin-5-yl)urea;

1-(4-(4-(4-acetyl-1,4-diazepan-1-yl)-6-morpholino-1,3,5-triazin-2-yl)phenyl)-3-(pyridin-3-yl)urea;

1-(4-(4-(4-acetyl-1,4-diazepan-1-yl)-6-morpholino-1,3,5-triazin-2-yl)phenyl)-3-(pyridin-4-yl)urea;

1-(4-(4-(4-acetyl-1,4-diazepan-1-yl)-6-morpholino-1,3,5-triazin-2-yl)phenyl)-3-(pyridazin-4-yl)urea;

1-(4-(4-(4-acetyl-1,4-diazepan-1-yl)-6-morpholino-1,3,5-triazin-2-yl)phenyl)-3-(pyrimidin-5-yl)urea;

1-(4-(4-(4-acetyl-1,4-diazepan-1-yl)-6-morpholino-1,3,5-triazin-2-yl)phenyl)-3-phenylurea;

1-(4-(4-(4-acetyl-1,4-diazepan-1-yl)-6-morpholino-1,3,5-triazin-2-yl)phenyl)-3-(4-chlorophenyl)urea;

1-(4-(4-(4-acetyl-1,4-diazepan-1-yl)-6-morpholino-1,3,5-triazin-2-yl)phenyl)-3-(4-fluorophenyl)urea;

Methyl-4-(3-(4-(4-(4-acetyl-1,4-diazepan-1-yl)-6-morpholino-1,3,5-triazin-2-yl)phenyl)ureido)benzoate;

4-(3-(4-(4-(4-acetyl-1,4-diazepan-1-yl)-6-morpholino-1,3,5-triazin-2-yl)phenyl)ureido)benzoic acid;

4-(3-(4-(4-(4-acetyl-1,4-diazepan-1-yl)-6-morpholino-1,3,5-triazin-2-yl)phenyl)ureido)-N-(2-(dimethylamino)ethyl)benzamide;

4-(3-(4-(4-(4-acetyl-1,4-diazepan-1-yl)-6-morpholino-1,3,5-triazin-2-yl)phenyl)ureido)-N-(2-(dimethylamino)ethyl)-N-methylbenzamide;

1-(4-(4-(4-acetyl-1,4-diazepan-1-yl)-6-morpholino-1,3,5-triazin-2-yl)phenyl)-3-(4-(3-(dimethylamino)pyrrolidine-1-carbonyl)phenyl)urea;

4-(3-(4-(4-(4-acetyl-1,4-diazepan-1-yl)-6-morpholino-1,3,5-triazin-2-yl)phenyl)ureido)benzamide;

1-(4-(4-(4-acetyl-1,4-diazepan-1-yl)-6-morpholino-1,3,5-triazin-2-yl)phenyl)-3-(4-(4-methylpiperazine-1-carbonyl)phenyl)urea;

1-(4-(4-(4-acetyl-1,4-diazepan-1-yl)-6-morpholino-1,3,5-triazin-2-yl)phenyl)-3-(4-(4-ethylpiperazine-1-carbonyl)phenyl)urea;

1-(4-(4-(4-acetyl-1,4-diazepan-1-yl)-6-morpholino-1,3,5-triazin-2-yl)phenyl)-3-(4-(4-n-propylpiperazine-1-carbonyl)phenyl)urea;

1-(4-(4-(4-acetyl-1,4-diazepan-1-yl)-6-morpholino-1,3,5-triazin-2-yl)phenyl)-3-(4-(4-isopropylpiperazine-1-carbonyl)phenyl)urea;

1-(4-(4-(4-acetyl-1,4-diazepan-1-yl)-6-morpholino-1,3,5-triazin-2-yl)phenyl)-3-(4-(piperazine-1-carbonyl)phenyl)urea;

1-(4-(4-(4-acetyl-1,4-diazepan-1-yl)-6-morpholino-1,3,5-triazin-2-yl)phenyl)-3-(4-(4-(dimethylamino)piperidine-1-carbonyl)phenyl)urea;

1-(4-(4-(dimethylamino)piperidine-1-carbonyl)phenyl)-3-(4-(4-(4-isobutyryl-1,4-diazepan-1-yl)-6-morpholino-1,3,5-triazin-2-yl)phenyl)urea;

1-(4-(4-(4-isobutyryl-1,4-diazepan-1-yl)-6-morpholino-1,3,5-triazin-2-yl)phenyl)-3-(4-(piperazine-1-carbonyl)phenyl)urea;

1-(4-(4-(4-isobutyryl-1,4-diazepan-1-yl)-6-morpholino-1,3,5-triazin-2-yl)phenyl)-3-(4-(4-methylpiperazine-1-carbonyl)phenyl)urea;

1-(4-(4-ethylpiperazine-1-carbonyl)phenyl)-3-(4-(4-(4-isobutyryl-1,4-diazepan-1-yl)-6-morpholino-1,3,5-triazin-2-yl)phenyl)urea;

1-(4-(4-(4-isobutyryl-1,4-diazepan-1-yl)-6-morpholino-1,3,5-triazin-2-yl)phenyl)-3-(4-(4-isopropylpiperazine-1-carbonyl)phenyl)urea;

1-(4-(3-(dimethylamino)pyrrolidine-1-carbonyl)phenyl)-3-(4-(4-(4-isobutyryl-1,4-diazepan-1-yl)-6-morpholino-1,3,5-triazin-2-yl)phenyl)urea;

1-(4-(4-(4-isobutyryl-1,4-diazepan-1-yl)-6-morpholino-1,3,5-triazin-2-yl)phenyl)-3-phenylurea;

1-(4-chlorophenyl)-3-(4-(4-(4-isobutyryl-1,4-diazepan-1-yl)-6-morpholino-1,3,5-triazin-2-yl)phenyl)urea;

1-(4-fluorophenyl)-3-(4-(4-(4-isobutyryl-1,4-diazepan-1-yl)-6-morpholino-1,3,5-triazin-2-yl)phenyl)urea;

1-(4-(4-(4-isobutyryl-1,4-diazepan-1-yl)-6-morpholino-1,3,5-triazin-2-yl)phenyl)-3-(pyridin-4-yl)urea;

1-(4-(4-(4-isobutyryl-1,4-diazepan-1-yl)-6-morpholino-1,3,5-triazin-2-yl)phenyl)-3-(pyridazin-4-yl)urea;

1-(4-(4-(4-isobutyryl-1,4-diazepan-1-yl)-6-morpholino-1,3,5-triazin-2-yl)phenyl)-3-(pyridin-3-yl)urea;

1-(4-(4-(4-isobutyryl-1,4-diazepan-1-yl)-6-morpholino-1,3,5-triazin-2-yl)phenyl)-3-(pyrimidin-5-yl)urea;

tert-butyl 4-(4-(4-(3-(4-(methoxycarbonyl)phenyl)ureido)phenyl)-6-morpholino-1,3,5-triazin-2-yl)-1,4-diazepane-1-carboxylate;

methyl4-(3-(4-(4-(1,4-diazepan-1-yl)-6-morpholino-1,3,5-triazin-2-yl)phenyl) ureido)benzoate;

1-(4-(4-(1,4-diazepan-1-yl)-6-morpholino-1,3,5-triazin-2-yl)phenyl)-3-phenylurea;

1-(4-(4-(1,4-diazepan-1-yl)-6-morpholino-1,3,5-triazin-2-yl)phenyl)-3-(4-chlorophenyl)urea;

1-(4-(4-(1,4-diazepan-1-yl)-6-morpholino-1,3,5-triazin-2-yl)phenyl)-3-(4-fluorophenyl)urea;

1-(4-(4-(1,4-diazepan-1-yl)-6-morpholino-1,3,5-triazin-2-yl)phenyl)-3-(pyridin-3-yl)urea;

1-(4-(4-(1,4-diazepan-1-yl)-6-morpholino-1,3,5-triazin-2-yl)phenyl)-3-(pyridin-4-yl)urea;

1-(4-(4-(1,4-diazepan-1-yl)-6-morpholino-1,3,5-triazin-2-yl)phenyl)-3-(pyridazin-4-yl)urea;

1-(4-(4-(1,4-diazepan-1-yl)-6-morpholino-1,3,5-triazin-2-yl)phenyl)-3-(pyrimidin-5-yl)urea;

N-methyl-4-(4-morpholino-6-(4-(3-phenylureido)phenyl)-1,3,5-triazin-2-yl)-1,4-diazepane-1-carboxamide (M+H) 532.2;

4-(4-(4-(3-(4-chlorophenyl)ureido)phenyl)-6-morpholino-1,3,5-triazin-2-yl)-N-methyl-1,4-diazepane-1-carboxamide;

4-(4-(4-(3-(4-fluorophenyl)ureido)phenyl)-6-morpholino-1,3,5-triazin-2-yl)-N-methyl-1,4-diazepane-1-carboxamide;

4-(4-(4-(3-(4-(2-(dimethylamino)ethylcarbamoyl)phenyl) ureido)phenyl)-6-morpholino-1,3,5-triazin-2-yl)-N-methyl-1,4-diazepane-1-carboxamide;
4-(4-(4-(3-(4-((2-(dimethylamino)ethyl)(methyl)carbamoyl)phenyl)ureido)phenyl)-6-morpholino-1,3,5-triazin-2-yl)-N-methyl-1,4-diazepane-1-carboxamide;
4-(4-(4-(3-(4-carbamoylphenyl)ureido)phenyl)-6-morpholino-1,3,5-triazin-2-yl)-N-methyl-1,4-diazepane-1-carboxamide;
4-(4-(4-(3-(4-(3-(dimethylamino)pyrrolidine-1-carbonyl) phenyl)ureido)phenyl)-6-morpholino-1,3,5-triazin-2-yl)-N-methyl-1,4-diazepane-1-carboxamide;
N-methyl-4-(4-morpholino-6-(4-(3-(4-(piperazine-1-carbonyl)phenyl)ureido)phenyl)-1,3,5-triazin-2-yl)-1,4-diazepane-1-carboxamide;
N-methyl-4-(4-(4-(3-(4-(4-methylpiperazine-1-carbonyl) phenyl)ureido)phenyl)-6-morpholino-1,3,5-triazin-2-yl)-1,4-diazepane-1-carboxamide;
4-(4-(4-(3-(4-(4-ethylpiperazine-1-carbonyl)phenyl)ureido) phenyl)-6-morpholino-1,3,5-triazin-2-yl)-N-methyl-1,4-diazepane-1-carboxamide;
4-(4-(4-(3-(4-(4-isopropylpiperazine-1-carbonyl)phenyl) ureido)phenyl)-6-morpholino-1,3,5-triazin-2-yl)-N-methyl-1,4-diazepane-1-carboxamide;
4-(4-(4-(3-(4-(4-(dimethylamino)piperidine-1-carbonyl) phenyl)ureido)phenyl)-6-morpholino-1,3,5-triazin-2-yl)-N-methyl-1,4-diazepane-1-carboxamide;
4-(4-(4-(3-(4-(4-(dimethylamino)piperidine-1-carbonyl) phenyl)ureido)phenyl)-6-morpholino-1,3,5-triazin-2-yl)-N-isopropyl-1,4-diazepane-1-carboxamide;
N-isopropyl-4-(4-(4-(3-(4-(4-isopropylpiperazine-1-carbonyl)phenyl)ureido)phenyl)-6-morpholino-1,3,5-triazin-2-yl)-1,4-diazepane-1-carboxamide;
4-(4-(4-(3-(4-(4-ethylpiperazine-1-carbonyl)phenyl)ureido) phenyl)-6-morpholino-1,3,5-triazin-2-yl)-N-isopropyl-1,4-diazepane-1-carboxamide;
N-isopropyl-4-(4-(4-(3-(4-(4-methylpiperazine-1-carbonyl) phenyl)ureido)phenyl)-6-morpholino-1,3,5-triazin-2-yl)-1,4-diazepane-1-carboxamide;
N-isopropyl-4-(4-morpholino-6-(4-(3-(4-(piperazine-1-carbonyl)phenyl)ureido)phenyl)-1,3,5-triazin-2-yl)-1,4-diazepane-1-carboxamide;
N-isopropyl-4-(4-morpholino-6-(4-(3-pyridin-4-ylureido) phenyl)-1,3,5-triazin-2-yl)-1,4-diazepane-1-carboxamide;
N-isopropyl-4-(4-morpholino-6-(4-(3-pyridazin-4-ylureido) phenyl)-1,3,5-triazin-2-yl)-1,4-diazepane-1-carboxamide;
N-isopropyl-4-(4-morpholino-6-(4-(3-pyrimidin-5-ylureido)phenyl)-1,3,5-triazin-2-yl)-1,4-diazepane-1-carboxamide;
N-isopropyl-4-(4-morpholino-6-(4-(3-pyridin-3-ylureido) phenyl)-1,3,5-triazin-2-yl)-1,4-diazepane-1-carboxamide;
1-(4-(4-morpholino-6-(1H-pyrazol-1-yl)-1,3,5-triazin-2-yl) phenyl)-3-(pyridin-3-yl)urea;
1-(4-(4-morpholino-6-(1H-pyrazol-1-yl)-1,3,5-triazin-2-yl) phenyl)-3-(pyridin-4-yl)urea;
1-(4-(4-morpholino-6-(1H-pyrazol-1-yl)-1,3,5-triazin-2-yl) phenyl)-3-(pyridazin-4-yl)urea;
1-(4-(4-morpholino-6-(1H-pyrazol-1-yl)-1,3,5-triazin-2-yl) phenyl)-3-(pyrimidin-5-yl)urea;
1-(4-(4-morpholino-6-(1H-pyrazol-1-yl)-1,3,5-triazin-2-yl) phenyl)-3-phenylurea;
1-(4-chlorophenyl)-3-(4-(4-morpholino-6-(1H-pyrazol-1-yl)-1,3,5-triazin-2-yl)phenyl)urea;
1-(4-fluorophenyl)-3-(4-(4-morpholino-6-(1H-pyrazol-1-yl)-1,3,5-triazin-2-yl)phenyl)urea;
1-(4-(4-(2-methyl-1H-imidazol-1-yl)-6-morpholino-1,3,5-triazin-2-yl)phenyl)-3-phenylurea;
1-(4-chlorophenyl)-3-(4-(4-(2-methyl-1H-imidazol-1-yl)-6-morpholino-1,3,5-triazin-2-yl)phenyl)urea;
1-(4-fluorophenyl)-3-(4-(4-(2-methyl-1H-imidazol-1-yl)-6-morpholino-1,3,5-triazin-2-yl)phenyl)urea;
1-(4-(4-(2-methyl-1H-imidazol-1-yl)-6-morpholino-1,3,5-triazin-2-yl)phenyl)-3-(pyridin-4-yl)urea;
1-(4-(4-(2-methyl-1H-imidazol-1-yl)-6-morpholino-1,3,5-triazin-2-yl)phenyl)-3-(pyridazin-4-yl)urea;
1-(4-(4-(2-methyl-1H-imidazol-1-yl)-6-morpholino-1,3,5-triazin-2-yl)phenyl)-3-(pyrimidin-5-yl)urea;
1-(4-acetylphenyl)-3-(4-(4,6-bis((R)-3-methylmorpholino)-1,3,5-triazin-2-yl)phenyl)urea;
1-(4-(4,6-bis((R)-3-methylmorpholino)-1,3,5-triazin-2-yl) phenyl)-3-(4-(piperazin-1-yl)phenyl)urea;
1-(4-(4,6-bis((R)-3-methylmorpholino)-1,3,5-triazin-2-yl) phenyl)-3-(4-(2-(dimethylamino)acetyl)phenyl)urea;
1-(4-(4,6-bis((R)-3-methylmorpholino)-1,3,5-triazin-2-yl) phenyl)-3-(4-(2-morpholinoacetyl)phenyl)urea;
1-(4-(4,6-bis((R)-3-methylmorpholino)-1,3,5-triazin-2-yl) phenyl)-3-(4-(2-hydroxyacetyl)phenyl)urea;
1-(4-(4,6-bis((R)-3-methylmorpholino)-1,3,5-triazin-2-yl) phenyl)-3-(4-(methoxymethyl)phenyl)urea;
1-(4-(4,6-bis((R)-3-methylmorpholino)-1,3,5-triazin-2-yl) phenyl)-3-(4-(2-methoxyethyl)phenyl)urea;
1-(4-(4,6-bis((R)-3-methylmorpholino)-1,3,5-triazin-2-yl) phenyl)-3-(4-(1-hydroxyethyl)phenyl)urea;
1-(4-(4,6-bis((R)-3-methylmorpholino)-1,3,5-triazin-2-yl) phenyl)-3-(4-(2-hydroxypropan-2-yl)phenyl)urea;
1-(4-(4,6-bis((R)-3-methylmorpholino)-1,3,5-triazin-2-yl) phenyl)-3-(4-(2-hydroxypropyl)phenyl)urea;
1-(4-(4,6-bis((R)-3-methylmorpholino)-1,3,5-triazin-2-yl) phenyl)-3-(4-(2-hydroxy-2-methylpropyl)phenyl)urea;
1-(4-(4,6-bis((R)-3-methylmorpholino)-1,3,5-triazin-2-yl) phenyl)-3-(4-(4-(dimethylamino)piperidine-1-carbonyl) phenyl)urea;
1-(4-(4,6-bis((R)-3-methylmorpholino)-1,3,5-triazin-2-yl) phenyl)-3-(4-cyanophenyl)urea;
4-(3-(4-(4,6-bis((R)-3-methylmorpholino)-1,3,5-triazin-2-yl)phenyl)ureido)-N-methylbenzamide;
4-(3-(4-(4,6-bis((R)-3-methylmorpholino)-1,3,5-triazin-2-yl)phenyl)ureido)-N,N-dimethylbenzamide;
4-(3-(4-(4,6-bis((R)-3-methylmorpholino)-1,3,5-triazin-2-yl)phenyl)ureido)benzamide;
1-(4-(4,6-bis((R)-3-methylmorpholino)-1,3,5-triazin-2-yl) phenyl)-3-(6-(4-methylpiperazine-1-carbonyl)pyridin-3-yl)urea;
(R)-1-(4-((dimethylamino)methyl)phenyl)-3-(4-(4-(3-methylmorpholino)-6-(tetrahydro-2H-pyran-4-yl)-1,3,5-triazin-2-yl)phenyl)urea;
(R)-1-(4-(4-(3-methylmorpholino)-6-(tetrahydro-2H-pyran-4-yl)-1,3,5-triazin-2-yl)phenyl)-3-(pyridin-4-yl)urea;
(R)-1-(4-acetylphenyl)-3-(4-(4-(3-methylmorpholino)-6-(tetrahydro-2H-pyran-4-yl)-1,3,5-triazin-2-yl)phenyl) urea;
(R)-1-(4-(2-(dimethylamino)acetyl)phenyl)-3-(4-(4-(3-methylmorpholino)-6-(tetrahydro-2H-pyran-4-yl)-1,3,5-triazin-2-yl)phenyl)urea;
(R)-1-(4-(4-(3-methylmorpholino)-6-(tetrahydro-2H-pyran-4-yl)-1,3,5-triazin-2-yl)phenyl)-3-(4-(2-morpholinoacetyl)phenyl)urea;
(R)-1-(4-(2-hydroxyacetyl)phenyl)-3-(4-(4-(3-methylmorpholino)-6-(tetrahydro-2H-pyran-4-yl)-1,3,5-triazin-2-yl) phenyl)urea;

(R)-1-(4-(methoxymethyl)phenyl)-3-(4-(4-(3-methylmorpholino)-6-(tetrahydro-2H-pyran-4-yl)-1,3,5-triazin-2-yl)phenyl)urea;

(R)-1-(4-(2-methoxyethyl)phenyl)-3-(4-(4-(3-methylmorpholino)-6-(tetrahydro-2H-pyran-4-yl)-1,3,5-triazin-2-yl)phenyl)urea;

1-(4-(1-hydroxyethyl)phenyl)-3-(4-(4-((R)-3-methylmorpholino)-6-(tetra hydro-2H-pyran-4-yl)-1,3,5-triazin-2-yl)phenyl)urea;

(R)-1-(4-(2-hydroxypropan-2-yl)phenyl)-3-(4-(4-(3-methylmorpholino)-6-(tetra hydro-2H-pyran-4-yl)-1,3,5-triazin-2-yl)phenyl)urea;

1-(4-(2-hydroxypropyl)phenyl)-3-(4-(4-((R)-3-methylmorpholino)-6-(tetrahydro-2H-pyran-4-yl)-1,3,5-triazin-2-yl)phenyl)urea;

(R)-1-(4-(2-hydroxy-2-methylpropyl)phenyl)-3-(4-(4-(3-methylmorpholino)-6-(tetra hydro-2H-pyran-4-yl)-1,3,5-triazin-2-yl)phenyl)urea;

(R)-1-(4-(4-(dimethylamino)piperidine-1-carbonyl)phenyl)-3-(4-(4-(3-methylmorpholino)-6-(tetrahydro-2H-pyran-4-yl)-1,3,5-triazin-2-yl)phenyl)urea;

(R)-1-(4-cyanophenyl)-3-(4-(4-(3-methylmorpholino)-6-(tetrahydro-2H-pyran-4-yl)-1,3,5-triazin-2-yl)phenyl)urea;

(R)—N-methyl-4-(3-(4-(4-(3-methylmorpholino)-6-(tetrahydro-2H-pyran-4-yl)-1,3,5-triazin-2-yl)phenyl)ureido)benzamide;

(R)—N,N-dimethyl-4-(3-(4-(4-(3-methylmorpholino)-6-(tetra hydro-2H-pyran-4-yl)-1,3,5-triazin-2-yl)phenyl)ureido)benzamide;

(R)-4-(3-(4-(4-(3-methylmorpholino)-6-(tetrahydro-2H-pyran-4-yl)-1,3,5-triazin-2-yl)phenyl)ureido)benzamide;

(R)-1-(4-(4-(3-methylmorpholino)-6-(tetrahydro-2H-pyran-4-yl)-1,3,5-triazin-2-yl)phenyl)-3-(6-(4-methylpiperazine-1-carbonyl)pyridin-3-yl)urea;

1-(4-(4-(3-methyl-1H-pyrazol-1-yl)-6-morpholino-1,3,5-triazin-2-yl)phenyl)-3-(pyrimidin-5-yl)urea;

1-(4-(4-(3-methyl-1H-pyrazol-1-yl)-6-morpholino-1,3,5-triazin-2-yl)phenyl)-3-(pyridin-3-yl)urea;

1-(4-(4-(3-methyl-1H-pyrazol-1-yl)-6-morpholino-1,3,5-triazin-2-yl)phenyl)-3-(pyridin-4-yl)urea;

1-(4-(4-(3-methyl-1H-pyrazol-1-yl)-6-morpholino-1,3,5-triazin-2-yl)phenyl)-3-(pyridazin-4-yl)urea;

1-(4-(4-(3-methyl-1H-pyrazol-1-yl)-6-morpholino-1,3,5-triazin-2-yl)phenyl)-3-phenylurea;

1-(4-chlorophenyl)-3-(4-(4-(3-methyl-1H-pyrazol-1-yl)-6-morpholino-1,3,5-triazin-2-yl)phenyl)urea;

1-(4-fluorophenyl)-3-(4-(4-(3-methyl-1H-pyrazol-1-yl)-6-morpholino-1,3,5-triazin-2-yl)phenyl)urea;

methyl 4-(3-(4-(4-(3-methyl-1H-pyrazol-1-yl)-6-morpholino-1,3,5-triazin-2-yl)phenyl)ureido)benzoate;

4-(3-(4-(4-(3-methyl-1H-pyrazol-1-yl)-6-morpholino-1,3,5-triazin-2-yl)phenyl)ureido)benzoic acid;

4-(3-(4-(4-(3-methyl-1H-pyrazol-1-yl)-6-morpholino-1,3,5-triazin-2-yl)phenyl)ureido)benzamide;

1-(4-(3-(dimethylamino)pyrrolidine-1-carbonyl)phenyl)-3-(4-(4-(3-methyl-1H-pyrazol-1-yl)-6-morpholino-1,3,5-triazin-2-yl)phenyl)urea;

1-(4-(4-(3-methyl-1H-pyrazol-1-yl)-6-morpholino-1,3,5-triazin-2-yl)phenyl)-3-(4-(piperazine-1-carbonyl)phenyl)urea;

1-(4-(4-(3-methyl-1H-pyrazol-1-yl)-6-morpholino-1,3,5-triazin-2-yl)phenyl)-3-(4-(4-methylpiperazine-1-carbonyl)phenyl)urea;

1-(4-(4-ethylpiperazine-1-carbonyl)phenyl)-3-(4-(4-(3-methyl-1H-pyrazol-1-yl)-6-morpholino-1,3,5-triazin-2-yl)phenyl)urea;

1-(4-(4-isopropylpiperazine-1-carbonyl)phenyl)-3-(4-(4-(3-methyl-1H-pyrazol-1-yl)-6-morpholino-1,3,5-triazin-2-yl)phenyl)urea;

1-(4-(4-(dimethylamino)piperidine-1-carbonyl)phenyl)-3-(4-(4-(3-methyl-1H-pyrazol-1-yl)-6-morpholino-1,3,5-triazin-2-yl)phenyl)urea;

1-{4-[(4-butylpiperazin-1-yl)carbonyl]phenyl}-3-(4-{4-[(1-methylethyl)-1,4-diazepan-1-yl]-6-morpholin-4-yl-1,3,5-triazin-2-yl}phenyl)urea;

1-(4-{4-[(1-methylethyl)-1,4-diazepan-1-yl]-6-morpholin-4-yl-1,3,5-triazin-2-yl}phenyl)-3-(4-{[4-(1-methylethyl)piperazin-1-yl]carbonyl}phenyl)urea;

1-{4-[(4-ethylpiperazin-1-yl)carbonyl]phenyl}-3-(4-{4-[(1-methylethyl)-1,4-diazepan-1-yl]-6-morpholin-4-yl-1,3,5-triazin-2-yl}phenyl)urea;

1-{4-[(4-methylpiperazin-1-yl)carbonyl]phenyl}-3-{4-[4-morpholin-4-yl-6-(tetrahydro-2H-pyran-4-yl)-1,3,5-triazin-2-yl]phenyl}urea;

1-(4-{[(3R)-3-(dimethylamino)pyrrolidin-1-yl]carbonyl}phenyl)-3-[4-(4,6-dimorpholin-4-yl-1,3,5-triazin-2-yl)phenyl]urea;

1-(4-{[(3S)-3-(dimethylamino)pyrrolidin-1-yl]carbonyl}phenyl)-3-[4-(4,6-dimorpholin-4-yl-1,3,5-triazin-2-yl)phenyl]urea;

1-(4-{[4-(1-methylethyl)piperazin-1-yl]carbonyl}phenyl)-3-{4-[4-morpholin-4-yl-6-(tetrahydro-2H-pyran-4-yl)-1,3,5-triazin-2-yl]phenyl}urea;

N-[2-(dimethylamino)ethyl]-N-methyl-4-[({4-[4-morpholin-4-yl-6-(tetrahydro-2H-pyran-4-yl)-1,3,5-triazin-2-yl]phenyl}carbamoyl)amino]benzamide;

1-{4-[4-(azetidin-3-yloxy)-6-morpholin-4-yl-1,3,5-triazin-2-yl]phenyl}-3-pyridin-4-ylurea;

N-(1-methylethyl)-3-[(4-[4-morpholin-4-yl-6-{4-[(pyridin-4-ylcarbamoyl)amino]phenyl}-1,3,5-triazin-2-yl)oxy]azetidine-1-carboxamide;

N-{1-[(4-{[(4-{4,6-bis[(3S)-3-methylmorpholin-4-yl]-1,3,5-triazin-2-yl}phenyl)carbamoyl]amino}phenyl)carbonyl]piperidin-4-yl}acetamide;

1-(4-{4,6-bis[(3S)-3-methylmorpholin-4-yl]-1,3,5-triazin-2-yl}phenyl)-3-(4-{[4-(1-methylethyl)-1,4-diazepan-1-yl]carbonyl}phenyl)urea;

1-(4-{4,6-bis[(3S)-3-methylmorpholin-4-yl]-1,3,5-triazin-2-yl}phenyl)-3-[4-(3-oxa-8-azabicyclo[3.2.1]oct-8-ylcarbonyl)phenyl]urea;

1-(4-{4,6-bis[(3S)-3-methylmorpholin-4-yl]-1,3,5-triazin-2-yl}phenyl)-3-{4-[(4-cyanopiperidin-1-yl)carbonyl]phenyl}urea;

1-(4-{4,6-bis[(3S)-3-methylmorpholin-4-yl]-1,3,5-triazin-2-yl}phenyl)-3-(4-{[(3S)-3-(dimethylamino)pyrrolidin-1-yl]carbonyl}phenyl)urea;

1-(4-{4,6-bis[(3S)-3-methylmorpholin-4-yl]-1,3,5-triazin-2-yl}phenyl)-3-(4-{[(3R)-3-(dimethylamino)pyrrolidin-1-yl]carbonyl}phenyl)urea;

1-(4-{[(3S)-3-(dimethylamino)pyrrolidin-1-yl]carbonyl}phenyl)-3-(4-{4-(morpholin-4-yl)-6-[4-(propan-2-yl)-1,4-diazepan-1-yl]-1,3,5-triazin-2-yl}phenyl)urea;

1-(4-{[(3R)-3-(dimethylamino)pyrrolidin-1-yl]carbonyl}phenyl)-3-(4-{4-(morpholin-4-yl)-6-[4-(propan-2-yl)-1,4-diazepan-1-yl]-1,3,5-triazin-2-yl}phenyl)urea;

1-{4-[4,6-di(morpholin-4-yl)-1,3,5-triazin-2-yl]phenyl}-3-{4-[(2-methylpiperazin-1-yl)carbonyl]phenyl}urea;

1-(4-{4-(morpholin-4-yl)-6-[4-(propan-2-yl)-1,4-diazepan-1-yl]-1,3,5-triazin-2-yl}phenyl)-3-[4-(piperazin-1-ylcarbonyl)phenyl]urea;

1-(4-{[(3R)-3-(dimethylamino)pyrrolidin-1-yl]
carbonyl}phenyl)-3-(4-{4-(morpholin-4-yl)-6-[4-(propan-2-yl)-1,4-diazepan-1-yl]-1,3,5-triazin-2-yl}phenyl)
urea;

1-{4-[4,6-di(morpholin-4-yl)-1,3,5-triazin-2-yl]phenyl}-3-
{4-[(3,3,4-trimethylpiperazin-1-yl)carbonyl]phenyl}urea;

1-{4-[4,6-di(morpholin-4-yl)-1,3,5-triazin-2-yl]phenyl}-3-
(4-{[(3R)-3-methylpiperazin-1-yl]carbonyl}phenyl)urea;

1-(4-{[(3R)-3,4-dimethylpiperazin-1-yl]carbonyl}phenyl)-
3-{4-[4,6-di(morpholin-4-yl)-1,3,5-triazin-2-yl]
phenyl}urea;

1-(4-{[(3R)-4-cyclobutyl-3-methylpiperazin-1-yl]
carbonyl}phenyl)-3-{4-[4,6-di(morpholin-4-yl)-1,3,5-triazin-2-yl]phenyl}urea;

1-{4-[4,6-di(morpholin-4-yl)-1,3,5-triazin-2-yl]phenyl}-3-
(4-{[(3R)-3-methyl-4-(propan-2-yl)piperazin-1-yl]
carbonyl}phenyl)urea;

1-{4-[4,6-di(morpholin-4-yl)-1,3,5-triazin-2-yl]phenyl}-3-
(4-{[(3S)-3-methylpiperazin-1-yl]carbonyl}phenyl)urea;

N-[2-(dimethylamino)ethyl]-N-methyl-4-{[(4-{4-[(3S)-3-
methylmorpholin-4-yl]-6-[4-(propan-2-yl)-1,4-diazepan-1-yl]-1,3,5-triazin-2-yl}phenyl)carbamoyl]
amino}benzamide;

1-(4-{4-[(3S)-3-methylmorpholin-4-yl]-6-[4-(propan-2-yl)-1,4-diazepan-1-yl]-1,3,5-triazin-2-yl}phenyl)-3-{4-[(4-methylpiperazin-1-yl)carbonyl]phenyl}urea;

1-(4-{[(3S)-3-(dimethylamino)pyrrolidin-1-yl]
carbonyl}phenyl)-3-(4-{4-[(3S)-3-methylmorpholin-4-yl]-6-[4-(propan-2-yl)-1,4-diazepan-1-yl]-1,3,5-triazin-2-yl}phenyl)urea;

N-[3-(dimethylamino)propyl]-4-{[(4-{4-(morpholin-4-yl)-6-[4-(propan-2-yl)-1,4-diazepan-1-yl]-1,3,5-triazin-2-yl}phenyl)carbamoyl]amino}benzamide;

N-[2-(dimethylamino)ethyl]-N-methyl-4-{[(4-{4-(morpholin-4-yl)-6-[4-(propan-2-yl)-1,4-diazepan-1-yl]-1,3,5-triazin-2-yl}phenyl)carbamoyl]amino}benzamide;

1-[4-(morpholin-4-ylcarbonyl)phenyl]-3-(4-{4-(morpholin-4-yl)-6-[4-(propan-2-yl)-1,4-diazepan-1-yl]-1,3,5-triazin-2-yl}phenyl)urea;

N-(2-methoxyethyl)-4-{[(4-{4-(morpholin-4-yl)-6-[4-(propan-2-yl)-1,4-diazepan-1-yl]-1,3,5-triazin-2-yl}phenyl)carbamoyl]amino}benzamide;

1-[4-(1,4-diazepan-1-ylcarbonyl)phenyl]-3-(4-{4-(morpholin-4-yl)-6-[4-(propan-2-yl)-1,4-diazepan-1-yl]-1,3,5-triazin-2-yl}phenyl)urea;

1-(4-{4-(morpholin-4-yl)-6-[4-(propan-2-yl)-1,4-diazepan-1-yl]-1,3,5-triazin-2-yl}phenyl)-3-(4-{[4-(propan-2-yl)-1,4-diazepan-1-yl]carbonyl}phenyl)urea;

1-(4-{[(3S)-4-cyclobutyl-3-methylpiperazin-1-yl]
carbonyl}phenyl)-3-{4-[4,6-di(morpholin-4-yl)-1,3,5-triazin-2-yl]phenyl}urea;

1-(4-{[(3S)-3,4-dimethylpiperazin-1-yl]carbonyl}phenyl)-
3-{4-[4,6-di(morpholin-4-yl)-1,3,5-triazin-2-yl]
phenyl}urea;

1-{4-[4-(morpholin-4-yl)-6-(tetrahydro-2H-pyran-4-yl)-1,3,5-triazin-2-yl]phenyl}-3-{4-[(3,3,4-trimethylpiperazin-1-yl)carbonyl]phenyl}urea;

1-(4-{[(3S)-3,4-dimethylpiperazin-1-yl]carbonyl}phenyl)-
3-{4-[4-(morpholin-4-yl)-6-(tetrahydro-2H-pyran-4-yl)-1,3,5-triazin-2-yl]phenyl}urea;

1-(4-{[(3S)-3-methylpiperazin-1-yl]carbonyl}phenyl)-3-{4-[4-(morpholin-4-yl)-6-(tetrahydro-2H-pyran-4-yl)-1,3,5-triazin-2-yl]phenyl}urea;

1-(4-{[(3R)-3-(dimethylamino)pyrrolidin-1-yl]
carbonyl}phenyl)-3-{4-[4-morpholin-4-yl-6-(tetrahydro-2H-pyran-4-yl)-1,3,5-triazin-2-yl]phenyl}urea; and 1-(4-{[(3S)-3-(dimethylamino)pyrrolidin-1-yl]
carbonyl}phenyl)-3-{4-[4-morpholin-4-yl-6-(tetrahydro-2H-pyran-4-yl)-1,3,5-triazin-2-yl]phenyl}urea.

The invention also includes pharmaceutical compositions comprising a compound of formula I and a pharmaceutically acceptable carrier. The invention includes a compound of formula I when provided as a pharmaceutically acceptable prodrug, hydrated salt, such as pharmaceutically acceptable salt, or mixtures thereof.

In other aspects, the invention provides that the pharmaceutically acceptable carrier suitable for oral administration and the composition comprises an oral dosage form.

In other aspects, the invention provides a composition comprising a compound of Formula I, a second compound selected from the group consisting of a topoisomerase I inhibitor, a MEK 1/2 inhibitor, a HSP90 inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, docetaxel, paclitaxel, leucovorin, levamisole, irinotecan, estramustine, etoposide, nitrogen mustards, BCNU, carmustine, lomustine, vinblastine, vincristine, vinorelbine, cisplatin, carboplatin, oxaliplatin, imatinib mesylate, Avastin (bevacizumab), hexamethylmelamine, topotecan, tyrosine kinase inhibitors, tyrphostins, herbimycin A, genistein, erbstatin, hydroxyzine, glatiramer acetate, interferon beta-1a, interferon beta-1b, natalizumab and lavendustin A; and a pharmaceutically acceptable carrier.

In other aspects, the second compound is Avastin.

In other aspects, the invention provides a method of treating a PI3K-related disorder, comprising administering to a mammal in need thereof a compound of Formula I in an amount effective to treat a PI3K-related disorder.

In other aspects, the PI3K-related disorder is selected from restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, and cancer.

In other aspects, the PI3K-related disorder is cancer.

In other aspects, the cancer is selected from the group consisting of leukemia, skin cancer, bladder cancer, breast cancer, uterus cancer, ovary cancer, prostate cancer, lung cancer, colon cancer, pancreas cancer, renal cancer, gastric cancer, and brain cancer.

In other aspects, the invention provides a method of treating an mTOR-related disorder, comprising administering to a mammal in need thereof a compound of Formula I in an amount effective to treat an mTOR-related disorder.

In other aspects, the mTOR-related disorder is selected from restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, and cancer.

In other aspects, the mTOR-related disorder is cancer.

In other aspects, the cancer is selected from the group consisting of leukemia, skin cancer, bladder cancer, breast cancer, uterus cancer, ovary cancer, prostate cancer, lung cancer, colon cancer, pancreas cancer, renal cancer, gastric cancer, and brain cancer.

In other aspects, the invention provides a method of treating a hSMG-1-related disorder, comprising administering to a mammal in need thereof a compound of Formula I in an amount effective to treat a hSMG-1-related disorder.

In other aspects, the hSMG-1-related disorder is selected from restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, and cancer.

In other aspects, the hSMG-1-related disorder is cancer.

In other aspects, the cancer is selected from the group consisting of leukemia, skin cancer, bladder cancer, breast cancer, uterus cancer, ovary cancer, prostate cancer, lung cancer, colon cancer, pancreas cancer, renal cancer, gastric cancer, and brain cancer.

In other aspects, the invention provides a method of treating advanced renal cell carcinoma, comprising administering to a mammal in need thereof a compound of Formula I in an amount effective to treat advanced renal cell carcinoma.

In other aspects, the invention provides a method of treating acute lymphoblastic leukemia, comprising administering to a mammal in need thereof a compound of Formula I in an amount effective to treat acute lymphoblastic leukemia.

In other aspects, the invention provides a method of treating acute malignant melanoma, comprising administering to a mammal in need thereof a compound of Formula I in an amount effective to treat malignant melanoma.

In other aspects, the invention provides a method of treating soft-tissue or bone sarcoma, comprising administering to a mammal in need thereof a compound of Formula I in an amount effective to treat soft-tissue or bone sarcoma.

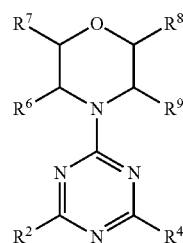

In other aspects, the invention provides a method of treating a cancer selected from the group consisting of leukemia, skin cancer, bladder cancer, breast cancer, uterus cancer, ovary cancer, prostate cancer, lung cancer, colon cancer, pancreas cancer, renal cancer, gastric cancer, and brain cancer comprising administering to a mammal in need thereof a composition comprising a compound of Formula I; a second compound selected from the group consisting of a topoisomerase I inhibitor, a MEK 1/2 inhibitor, a HSP90 inhibitor, procarbazine, dacarbazine, gemcitabine, capecitabine, methotrexate, taxol, taxotere, mercaptopurine, thioguanine, hydroxyurea, cytarabine, cyclophosphamide, ifosfamide, nitrosoureas, cisplatin, carboplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epirubicin, 5-fluorouracil, docetaxel, paclitaxel, leucovorin, levamisole, irinotecan, estramustine, etoposide, nitrogen mustards, BCNU, carmustine, lomustine, vinblastine, vincristine, vinorelbine, cisplatin, carboplatin, oxaliplatin, imatinib mesylate, Avastin (bevacizumab), hexamethylmelamine, topotecan, tyrosine kinase inhibitors, tyrphostins, herbimycin A, genistein, erbstatin, and lavendustin A; and a pharmaceutically acceptable carrier. in an amount effective to treat the cancer.

In other aspects, the invention provides a method of inhibiting mTOR in a subject, comprising administering to a subject in need thereof a compound of Formula I in an amount effective to inhibit mTOR.

In other aspects, the invention provides a method of inhibiting PI3K in a subject, comprising administering to a subject in need thereof a compound of Formula I in an amount effective to inhibit PI3K.

In other aspects, the invention provides a method of inhibiting hSMG-1 in a subject, comprising administering to a subject in need thereof a compound of Formula I in an amount effective to inhibit hSMG-1.

In other aspects, the invention provides a method of inhibiting mTOR, PI3K, and hSMG-1 together in a subject, comprising administering to a subject in need thereof a compound of Formula I in an amount effective to inhibit mTOR, PI3K, and hSMG-1.

In another aspect, the invention provides a method of synthesizing compounds of the Formula I, which are:

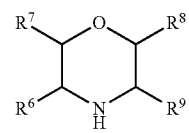

said method comprising reacting 2,4,6-trichloro[1,3,5]triazine with to form the intermediate dichlorotriazine compound The method of synthesizing compounds of the Formula I further comprising reacting the intermediate dichlorotriazine compound with

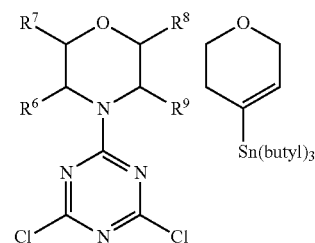

to form the intermediate compound

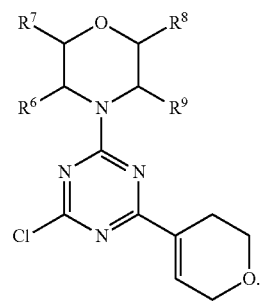

The method of synthesizing compounds of the Formula I further comprising reacting the intermediate dichlorotriazine compound with

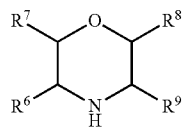

to form the intermediate compound

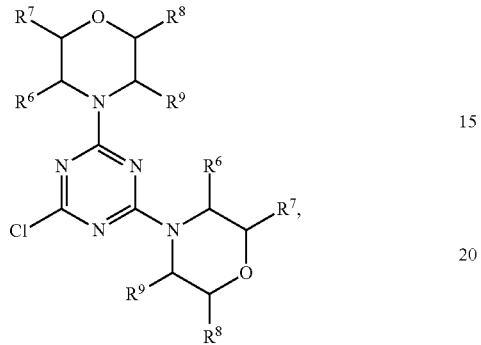

wherein each $R^6$, $R^7$, $R^8$ and $R^9$ is independently selected and defined according to formula I.

The method of synthesizing compounds of the Formula I wherein the reacting moiety is

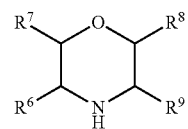

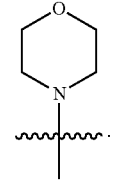

Procedures used to synthesize the compounds of the present invention are described in Schemes 1-12 and are illustrated in the examples. Reasonable variations of the described procedures are intended to be within the scope of the present invention:

Scheme 1

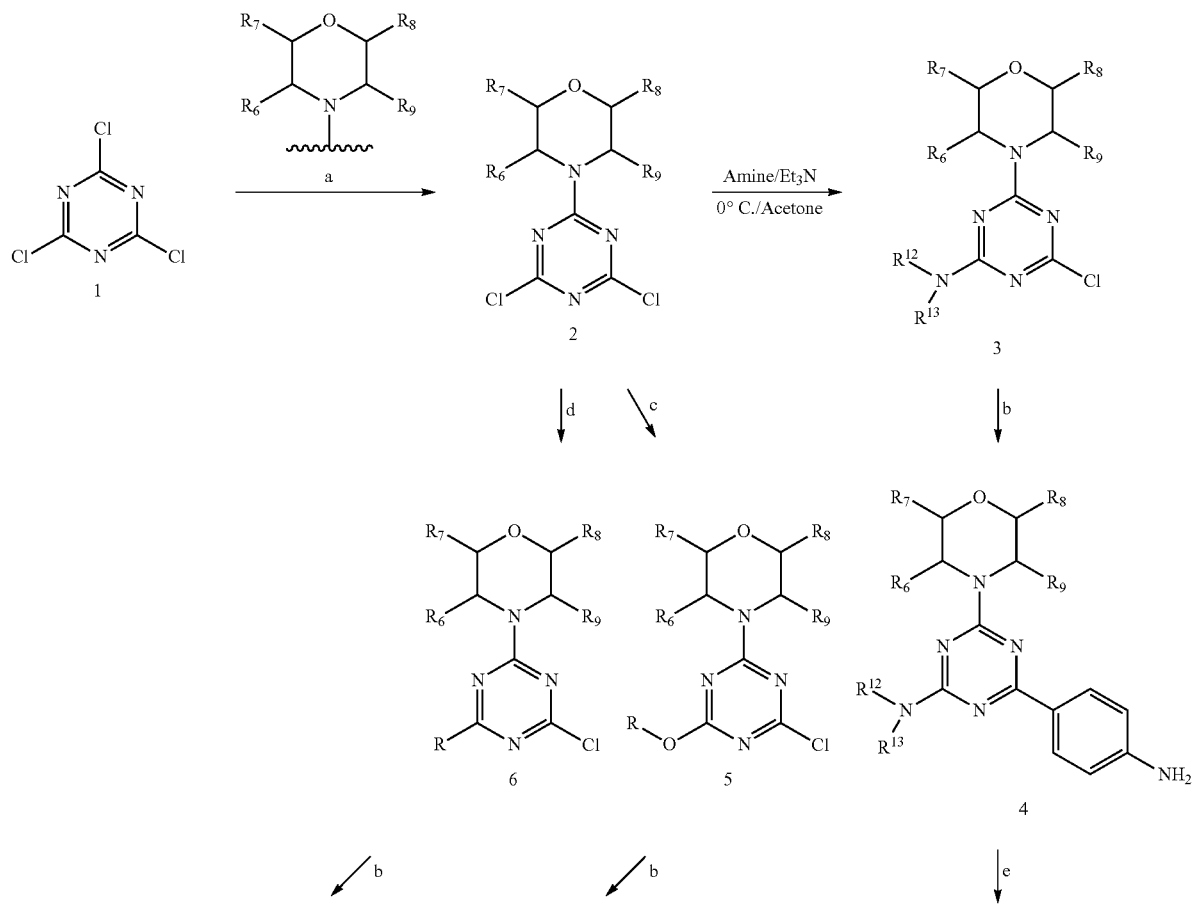

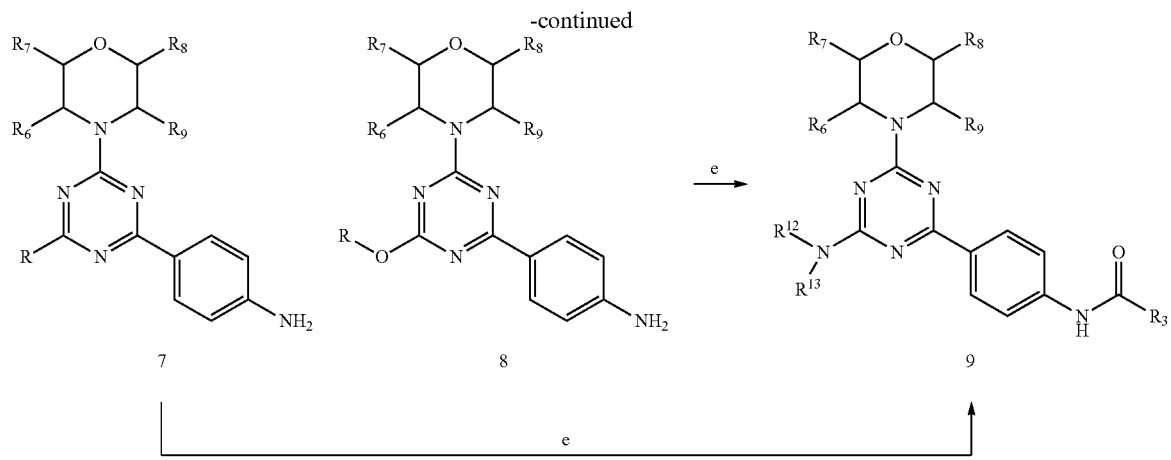

R = Alkyl, Alkene, Alkyne
Aryl, Heteroaryl, Cycloalkyl, Cycloalkyl with one or two heteroatoms selcted from O, S(O)$_n$, N—R$_{10}$,
(a) Acetone/H$_2$O, Et$_3$N/-10° C.; (b) 4-aminophenyl boronic acid/(Ph$_3$)$_4$P(Pd)/Na$_2$CO$_3$/DME/Reflux or m Wave
(c) Corresponding alcohol/n-BuLi or NaH/THF/RT or Reflux; (d) When R = alky RMgBr/Pd (0)/THF;
when R = Alkene or cycloalkyl or cycloalkyl with one or two heteroatoms the transformation is via vinyl stanane/Pd(0)/
Organic solvent/Reflux (Stille coupling); When R = aryl or heteroaryl the transformation is via Aryl bornate/(Ph$_3$)$_4$P(Pd)/
Na$_2$CO$_3$/DME/Reflux or m Wave (Suzuki coupling); (e) When R$_3$ is —OR$_5$, DCM/ClCOOR$_5$/Et$_3$N/
0° C.-RT; When R$_5$ is NHR$_5$, DMAP/DCM/R$_5$NCO or (COCl$_2$)$_3$/Et$_3$N/R$_5$NH$_2$ Compounds of the present inventions were prepared by a multi-step sequence as depicted in Scheme 1. One chlorine atom at a time was selectively replaced at different temperatures. The commercially available cyanuric acid chloride 1 was reacted with morpholine or substituted morpholine derivatives at −10° C. to give the mono morpholine derivative 2. This pivotal intermediate 2 can be reacted with different nucleophiles. In this present invention, intermediates 2 were reacted with different amines and alcohols to give 3 and 5 respectively. The third chlorine atom in intermediates 3 and 5 was replaced with 4-aminoaryl and aminoheteroaryl boronic acid in the presence of (Ph$_3$)$_4$P(Pd)/Na$_2$CO$_3$/DME/Reflux or microwave condition to yield 4 and 8 respectively. The amino group was converted to the urea derivatives by different two procedures depending upon the availability of the starting material. Some of the examples reported here were transformed into the urea derivative by reacting 4 or 8 with an appropriately substituted isocyanate derivative. Many of the urea derivatives reported here were prepared by reacting intermediates 4 or 8 with triphosgene/Et$_3$N and an appropriately substituted primary amine derivative. The corresponding carbamate derivatives were prepared by reacting intermediates 4 or 8 with an appropriately substituted chloroformate reagents. The intermediates 2 were also used to prepare derivatives of 6, where in R is a alkyl, alkene, alkyne, aryl or heteroaryl. Reacting 6 with the appropriately substituted alkyl introduced alkyl or cycloalkyl groups in intermediate 6 or cycloalkyl magnesium bromide or the corresponding appropriately substituted organo-zinc reagent. Alkenes can be introduced in compound 6 by a Pd catalyzed appropriately substituted vinyl tin derivatives. Similarly, aryl or heteroaryl substituents can be introduced either by reacting 6 with the corresponding boronic acid (Suzuki coupling) or aryl or heteroaryl magnesium bromide. Alkynes can be introduced by reacting compound 6 with an appropriately substitute alkyne and Pd(0). The alkyne and the alkene introduced can also be functionally converted into other derivatives such as alkyl, alcohol and amine moieties. Detailed procedures are described in the experimental section for each derivative prepared.

Scheme 2

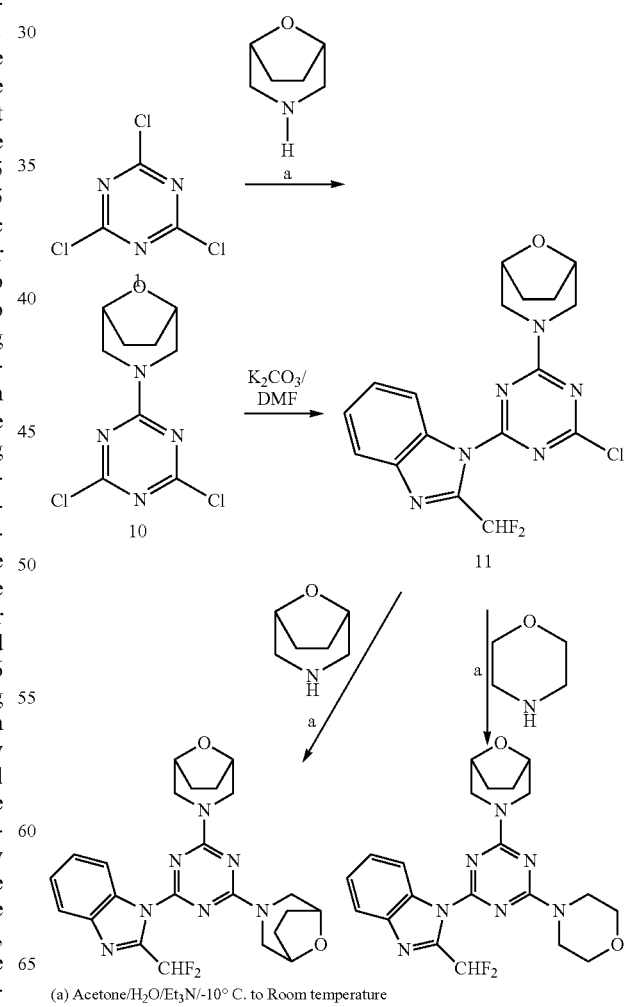

(a) Acetone/H$_2$O/Et$_3$N/-10° C. to Room temperature

Certain compounds of the invention were prepared by the methods outlined in Scheme 2.
Scheme 3
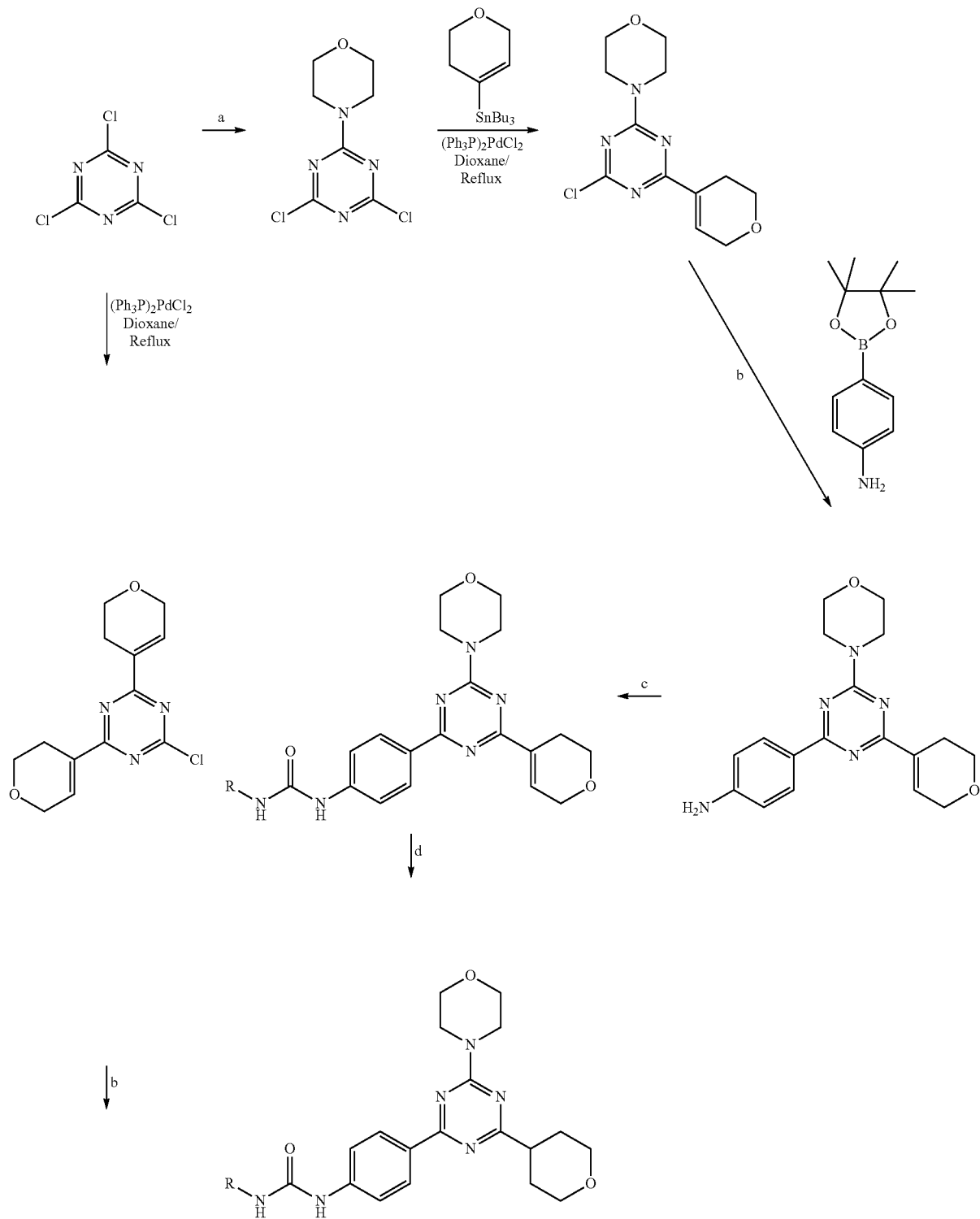

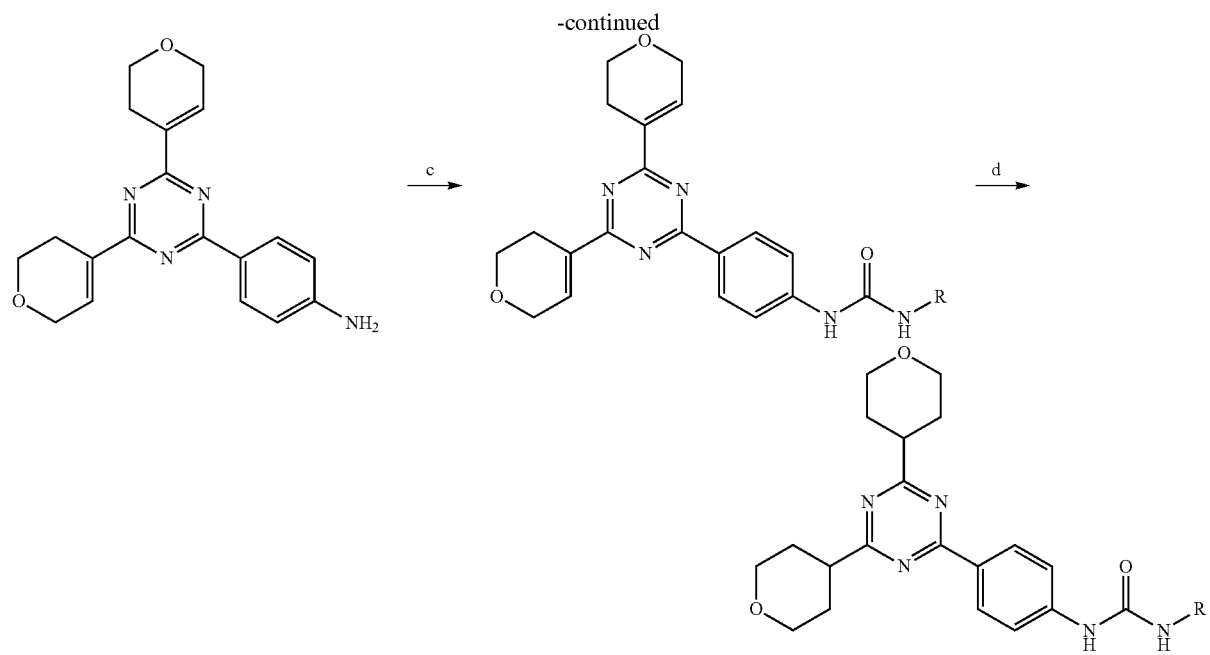

(a) 1 Eq. of morpholine/Et₃N/Acetone/Water/-20° C.; (b) (Ph₃P)₄Pd, DME, Na₂CO₃, Reflux; (c) RNCO, CH₂Cl₂, RT or (COCl)₃, RNH₂, Et₃N, CHCl₃; (d) H₂/Pd (0)

Compounds of the invention were also prepared according to the method illustrated in Scheme 3.

Scheme 4

The benzene-1,4-diamine intermediates were prepared from 4-fluoronitrobenzene and

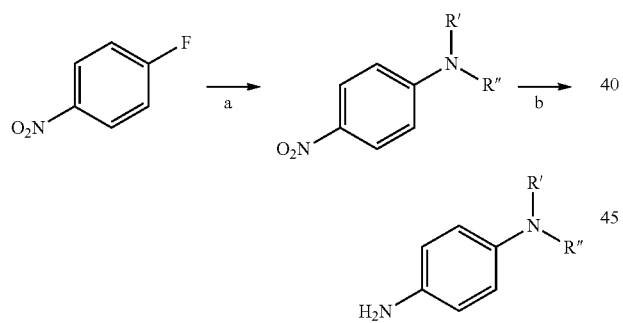

(a) NHR'R"/toluene; (b) H₂/palladium on carbon, ethyl acetate, methanol.
NOTE:
If either R' or R" = H or contain a a nucleophilic amine, that amine was converted to its Boc derivative. Deprotection was accomplished following the final step of urea formation.

the appropriate amine as shown in Scheme 4.

Scheme 5

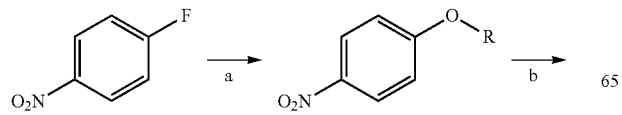

-continued (a) ROH/NaH/toluene; (b) H₂/palladium on carbon, ethyl acetate, methanol.
NOTE:
If R contains a nucleophilic amine, that amine was converted to its Boc derivative. Deprotection was accomplished following the final step of urea formation.

The 4-(alkoxy)aniline intermediates were prepared from 4-fluoronitrobenzene and the appropriate alcohol as shown in Scheme 5.

Scheme 6

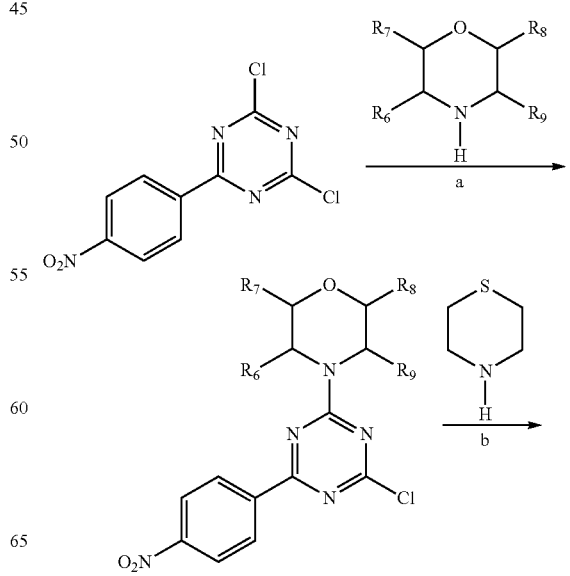

51
-continued
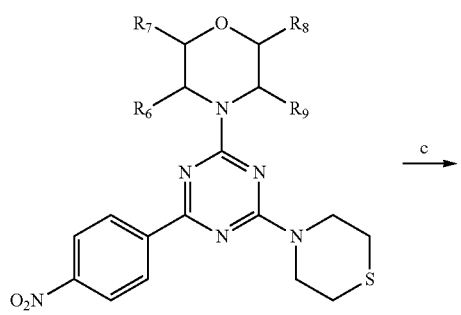
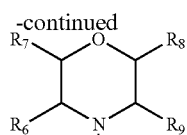
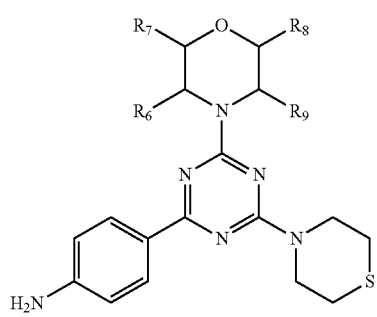
52
-continued
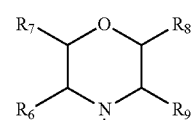
(a) Na$_2$CO$_3$, acetone, water; (b) NaHCO$_3$, acetone, water
(c) SnCl$_2$, pyridine, DMF; (d) triphosgene, Et$_3$N, CH$_2$Cl$_2$, then RNH$_2$
(e) oxone, acetonitrile, water.
The thiomorpholine and bis morpholine compounds were prepared from 2,4-dichloro-6-(4-nitrophenyl)-1,3,5-triazine and the appropriate morpholine and thiomorpholine reagents as shown in Scheme 6.
Scheme 7
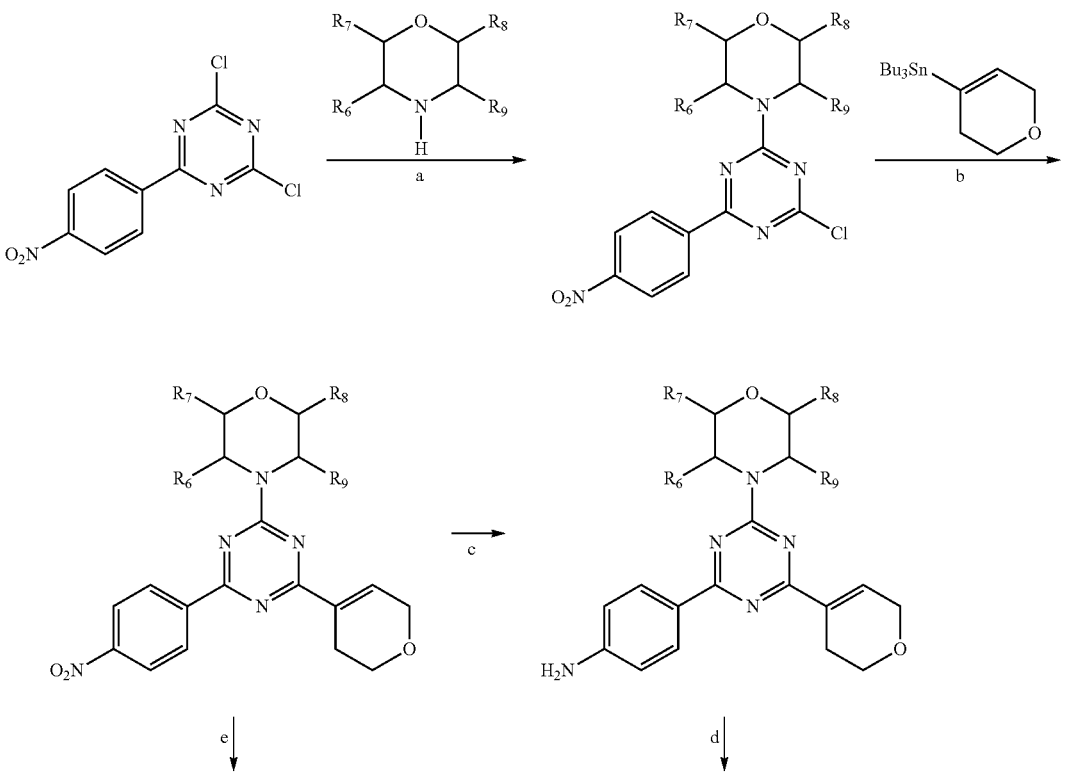

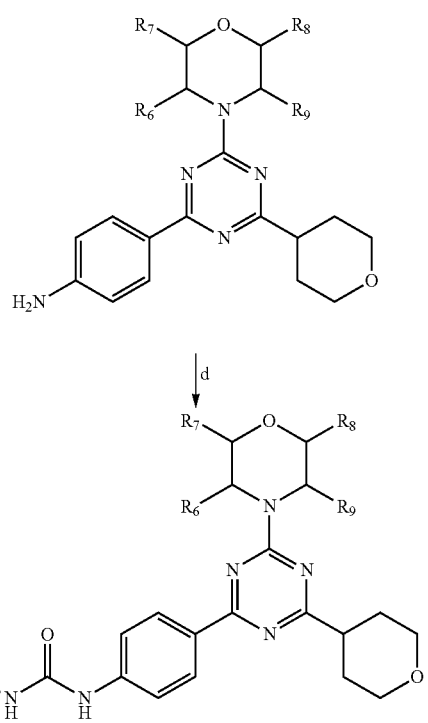

(a) Na$_2$CO$_3$, acetone, water; (b) Pd(PPh$_3$)$_4$, toluene
(c) Fe, acetic acid, ethyl acetate, water
(d) triphosgene, Et$_3$N, CH$_2$Cl$_2$, then RNH$_2$
(e) H$_2$/Pd—C, ethyl acetate, methylene chloride, methanol.

The dihydropyran and tetrahydropyran compounds were prepared from 2,4-dichloro-6-(4-nitrophenyl)-1,3,5-triazine, tributyl(3,6-dihydro-2H-pyran-4-yl)stannane, and the appropriate morpholine as shown in Scheme 7.

The (4-aminophenyl)(piperazin-1-yl)methanone intermediates were prepared from 4-nitrobenzoyl chloride and the appropriate amine as shown in Scheme 8.

Scheme 8

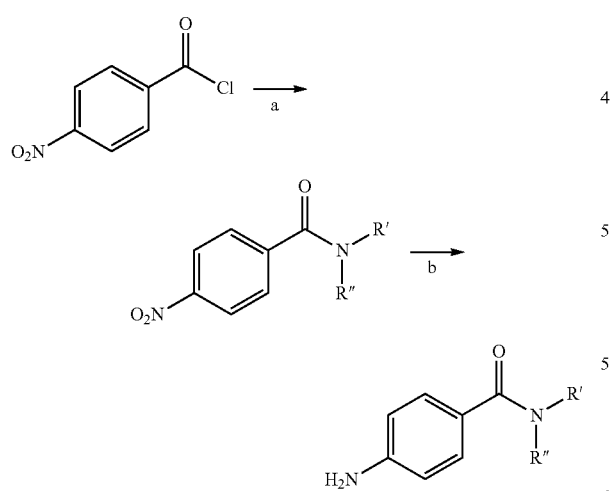

(a) NHR'R", Et$_3$N, CH$_2$Cl$_2$
(b) H$_2$/palladium on carbon, ethyl acetate, methanol.
NOTE:
If R$_1$ or R$_2$ contain a nucleophilic amine, that amine was converted to its Boc derivative. Deprotection was accomplished following the final step of urea formation.

Scheme 9

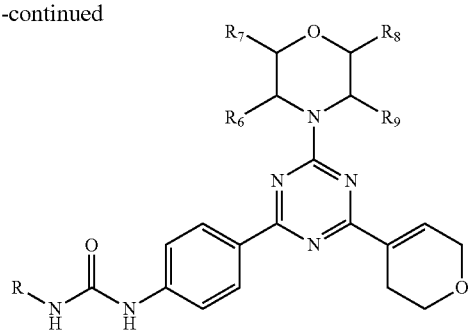

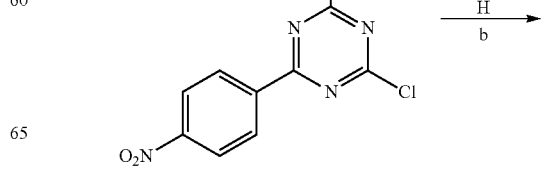

55
-continued

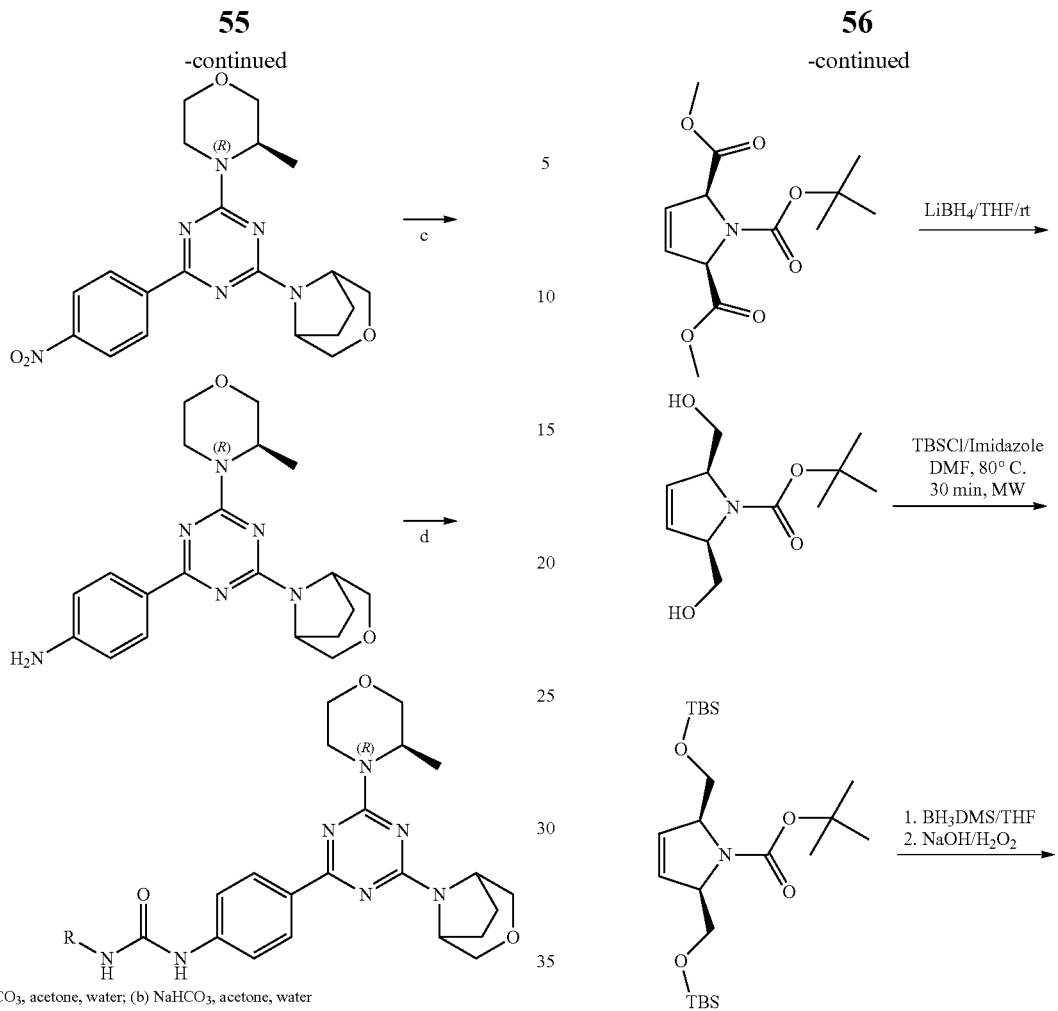

(a) Na$_2$CO$_3$, acetone, water; (b) NaHCO$_3$, acetone, water
(c) H$_2$—Pd—C, ethyl acetate, methylene chloride, methanol
(d) triphosgene, Et$_3$N, CH$_2$Cl$_2$, then RNH$_2$.

The 1-(4-(4-(3-oxa-8-azabicyclo[3.2.1]octan-8-yl)-6-((R)-3-methylmorpholino)-1,3,5-triazin-2-yl)phenyl)-3-urea compounds were prepared from 2,4-dichloro-6-(4-nitrophenyl)-1,3,5-triazine, (R)-3-methylmorpholine, 3-oxa-8-azabicyclo[3.2.1]octane-hydrochloride, and the appropriate amine as shown in Scheme 9.

56
-continued

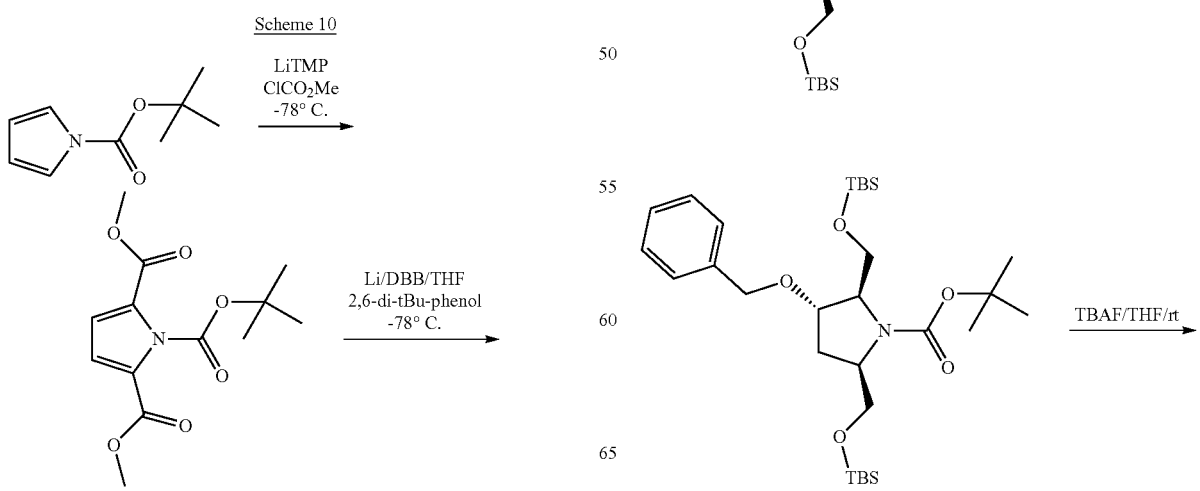

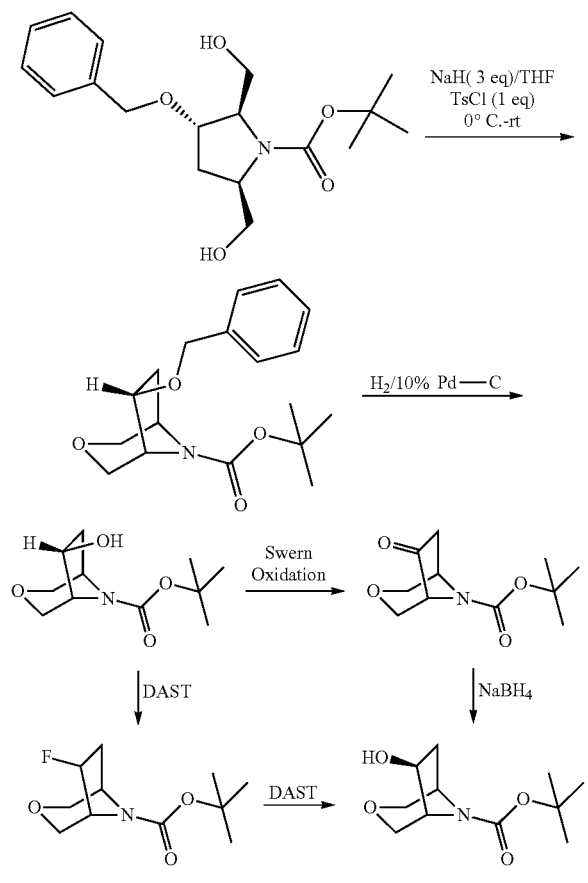

The preparation of both the (6S') and (6R') isomers of tert-butyl 6-hydroxy-3-oxa-8-azabicyclo[3.2.1]octane-8-carboxylate from tert-butyl 1H-pyrrole-1-carboxylate is shown in Scheme 10.

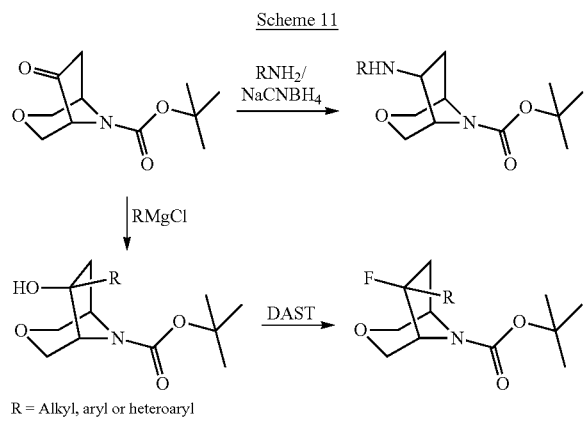

R = Alkyl, aryl or heteroaryl

The (6S')-tert-butyl 6-amino-3-oxa-8-azabicyclo[3.2.1]octane-8-carboxylate and (6R')-tert-butyl 6-fluoro-6-(alkyl, aryl, or heteroaryl)-3-oxa-8-azabicyclo[3.2.1]octane-8-carboxylate compounds could be prepared from tert-butyl 6-oxo-3-oxa-8-azabicyclo[3.2.1]octane-8-carboxylate (Scheme 10) and the appropriate amine or Grignard reagent as shown in Scheme 11.

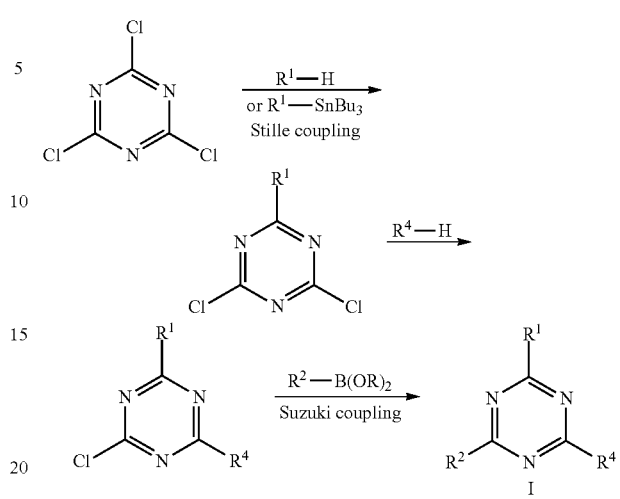

Compounds of formula I can be prepared from cyanuric chloride as shown in Scheme 12.

DEFINITIONS

The following definitions are used in connection with the compounds of the present invention unless the context indicates otherwise. In general, the number of carbon atoms present in a given group is designated "$C_x$-$C_y$", where x and y are the lower and upper limits, respectively. For example, a group designated as "$C_1$-$C_6$" contains from 1 to 6 carbon atoms. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are arrived at by naming from left to right the terminal portion of the functionality followed by the adjacent functionality toward the point of attachment. For example, the substituent "arylalkyloxycabonyl" refers to the group ($C_6$-$C_{14}$aryl)-($C_1$-$C_6$alkyl)-O—C(O)—. Terms not defined herein have the meaning commonly attributed to them by those skilled in the art.

"Acyl-" refers to a group having a straight, branched, or cyclic configuration or a combination thereof, attached to the parent structure through a carbonyl functionality. Such groups may be saturated or unsaturated, aliphatic or aromatic, and carbocyclic or heterocyclic. Examples of a $C_1$-$C_8$acyl-group include acetyl-, benzoyl-, nicotinoyl-, propionyl-, isobutyryl-, oxalyl-, and the like. Lower-acyl refers to acyl groups containing one to four carbons. An acyl group can be unsubstituted or substituted with one or more of the following groups: halogen, $H_2N$—, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_6$alkyl)carboxyamido-, HC(O)NH—, $H_2$NC(O)—, ($C_1$-$C_6$alkyl)NHC(O)—, di($C_1$-$C_6$alkyl)NC(O)—, —CN, hydroxyl, $C_1$-$C_6$alkoxy-, $C_1$-$C_6$alkyl-, $HO_2C$—, ($C_1$-$C_6$alkoxy)carbonyl-, ($C_1$-$C_6$alkyl)C(O)—, $C_6$-$C_{14}$aryl-, $C_1$-$C_9$heteroaryl-, or $C_3$-$C_8$cycloalkyl-.

"Alkyl" refers to a hydrocarbon chain that may be a straight chain or branched chain, containing the indicated number of carbon atoms, for example, a $C_1$-$C_{12}$alkyl group may have from 1 to 12 (inclusive) carbon atoms in it. Examples of $C_1$-$C_6$alkyl groups include, but are not limited to, methyl, ethyl, propyl, butyl, pentyl, hexyl, isopropyl, isobutyl, sec-butyl, tert-butyl, isopentyl, neopentyl, and isohexyl. Examples of $C_1$-$C_8$alkyl groups include, but are not limited to, methyl, propyl, pentyl, hexyl, heptyl, 3-methylhex-1-yl, 2,3-dimethylpent-2-yl, 3-ethylpent-1-yl, octyl, 2-methylhept-2-yl, 2,3-dimethylhex-1-yl, and 2,3,3-trimethylpent-1-yl. An alkyl group can be unsubstituted or substituted with one or more groups, including: halogen, —$NH_2$, ($C_1$-$C_6$alkyl)N—, ($C_1$-$C_6$alkyl)($C_1$-$C_6$alkyl)N—, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —C(O)O($C_1$-$C_6$alkyl), —C(O)($C_1$-$C_6$alkyl), $C_6$-$C_{14}$aryl, $C_1$-$C_9$heteroaryl, $C_3$-$C_8$cycloalkyl, $C_1$-$C_6$haloalkyl-, $C_1$-$C_6$aminoalkyl-, —OC(O)($C_1$-$C_6$alkyl), $C_1$-$C_6$carboxyamidoalkyl-, and —$NO_2$.

"Alkadienyl" refer to a straight or branched chain unsaturated hydrocarbon containing at least two double bonds, and either may exist in the E or Z conformation. Examples of a $C_4$-$C_6$alkadienyl group include, but are not limited to, buta-1,3-dienyl, buta-2,3-dienyl, isoprenyl, penta-1,3-dienyl, and penta-2,4-dien-2-yl.

"Alkadiynyl" refer to a straight or branched chain unsaturated hydrocarbon containing at least two triple bonds. Examples of a $C_4$-$C_6$alkadiynyl group include, but are not limited to, buta-1,3-diynyl, buta-2,3-diynyl, penta-1,3-diynyl, and penta-2,4-diynyl.

"Alkenyl" refer to a straight or branched chain unsaturated hydrocarbon containing at least one double bond, and may exist in the E or Z conformation. Examples of a $C_2$-$C_8$alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, 1-octene, 2-octene, 3-octene, and 4-octene. Examples of a $C_2$-$C_6$alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, and isohexene. Examples of a $C_3$-$C_8$alkenyl group include, but are not limited to, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, 1-octene, 2-octene, 3-octene, and 4-octene. Examples of a $C_3$-$C_6$alkenyl group include, but are not limited to, prop-2-enyl, but-3-enyl, but-2-enyl, 2-methylallyl, pent-4-enyl, and hex-5-enyl. An alkenyl group can be unsubstituted or substituted with one or more groups, including: halogen, —$NH_2$, ($C_1$-$C_6$alkyl)N—, ($C_1$-$C_6$alkyl)($C_1$-$C_6$alkyl)N—, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —C(O)O($C_1$-$C_6$alkyl), —C(O)($C_1$-$C_6$alkyl), $C_6$-$C_{14}$aryl, $C_1$-$C_9$heteroaryl, and $C_3$-$C_8$cycloalkyl.

"Alkynyl" refers to a straight or branched chain unsaturated hydrocarbon containing at least one triple bond. Examples of a $C_2$-$C_6$alkynyl group include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne, and isohexyne. Examples of a $C_3$-$C_6$alkynyl group include, but are not limited to, prop-2-ynyl, but-3-ynyl, but-2-ynyl, pent-4-ynyl, and hex-5-ynyl. Examples of a $C_3$-$C_8$alkynyl group include, but are not limited to, prop-2-ynyl, but-3-ynyl, but-2-ynyl, pent-4-ynyl, hex-5-ynyl, hept-3-ynyl, 2-methylhex-3-ynyl, oct-4-ynyl, and 2-methylhept-3-ynyl. An alkynyl group can be unsubstituted or substituted with one or more groups, including: halogen, —$NH_2$, ($C_1$-$C_6$alkyl)N—, ($C_1$-$C_6$alkyl)($C_1$-$C_6$alkyl)N—, —N($C_1$-$C_3$alkyl)C(O)($C_1$-$C_6$alkyl), —NHC(O)($C_1$-$C_6$alkyl), —NHC(O)H, —C(O)$NH2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —C(O)O($C_1$-$C_6$alkyl), —C(O)($C_1$-$C_6$alkyl), $C_6$-$C_{14}$aryl, $C_1$-$C_9$heteroaryl, and $C_3$-$C_8$cycloalkyl.

"Alkoxy-" refers to the group R—O— where R is an alkyl group, as defined above. Exemplary $C_1$-$C_6$alkoxy- groups include but are not limited to methoxy, ethoxy, n-propoxy, 1-propoxy, n-butoxy and t-butoxy. An alkoxy group can be unsubstituted or substituted with one or more of the following groups: halogen, hydroxyl, $C_1$-$C_6$alkoxy-, $H_2N$—, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_6$alkyl)carboxyamido-, HC(O)NH—, $H_2$NC(O)—, ($C_1$-$C_6$alkyl)NHC(O)—, di($C_1$-$C_6$alkyl)NC(O)—, NC—, $C_1$-$C_6$alkoxy-, $HO_2C$—, ($C_1$-$C_6$alkoxy)carbonyl-, ($C_1$-$C_6$alkyl)C(O)—, $C_6$-$C_{14}$aryl-, $C_1$-$C_9$heteroaryl-, $C_3$-$C_8$cycloalkyl-, $C_1$-$C_6$haloalkyl-, amino($C_1$-$C_6$alkyl)-, ($C_1$-$C_6$alkyl)carboxyl-, $C_1$-$C_6$carboxyamidoalkyl-, or $O_2N$—.

"(Alkoxy)carbonyl-" refers to the group alkyl-O—C(O)—. Exemplary ($C_1$-$C_6$alkoxy)carbonyl- groups include but are not limited to methoxy, ethoxy, n-propoxy, 1-propoxy, n-butoxy and t-butoxy. An (alkoxy)carbonyl group can be unsubstituted or substituted with one or more of the following groups: halogen, hydroxyl, $H_2N$—, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_6$alkyl)carboxyamido-, HC(O)NH—, $H_2$NC(O)—, ($C_1$-$C_6$alkyl)NHC(O)—, di($C_1$-$C_6$alkyl)NC(O)—, NC—, $C_1$-$C_6$alkoxy-, $HO_2C$—, ($C_1$-$C_6$alkoxy)carbonyl-, ($C_1$-$C_6$alkyl)C(O)—, $C_6$-$C_{14}$aryl-, $C_1$-$C_9$heteroaryl-, $C_3$-$C_8$cycloalkyl-, $C_1$-$C_6$haloalkyl-, amino($C_1$-$C_6$alkyl)-($C_1$-$C_6$alkyl)carboxyl-, $C_1$-$C_6$carboxyamidoalkyl-, or $O_2N$—.

"(Alkyl)amido-" refers to a —C(O)NH— group in which the nitrogen atom of said group is attached to a $C_1$-$C_6$alkyl group, as defined above. Representative examples of a ($C_1$-$C_6$alkyl)amido- group include, but are not limited to, —C(O)$NHCH_3$, —C(O)$NHCH_2CH_3$, C(O)$NHCH_2CH_2CH_3$, —C(O)$NHCH_2CH_2CH_2CH_3$, —C(O)$NHCH_2CH_2CH_2CH_2CH_3$, —C(O)$NHCH(CH_3)_2$, —C(O)$NHCH_2CH(CH_3)_2$, —C(O)$NHCH(CH_3)CH_2CH_3$, —C(O)NH—C($CH_3)_3$ and —C(O)$NHCH_2C(CH_3)_3$.

"(Alkyl)amino-" refers to an —NH group, the nitrogen atom of said group being attached to a alkyl group, as defined above. Representative examples of an ($C_1$-$C_6$alkyl)amino- group include, but are not limited to $CH_3NH$—, $CH_3CH_2NH$—, $CH_3CH_2CH_2NH$—, $CH_3CH_2CH_2CH_2NH$—, ($CH_3)_2CHNH$—, ($CH_3)_2CHCH_2NH$—, $CH_3CH_2CH(CH_3)NH$— and ($CH_3)_3CNH$—. An (alkyl)amino group can be unsubstituted or substituted with one or more of the following groups: halogen, $H_2N$—, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_6$alkyl)carboxyamido-, HC(O)NH—, $H_2$NC(O)—, ($C_1$-$C_6$alkyl)NHC(O)—, di($C_1$-$C_6$alkyl)NC(O)—, NC—, hydroxyl, $C_1$-$C_6$alkoxy-, $C_1$-$C_6$alkyl-, $HO_2C$—, ($C_1$-$C_6$alkoxy)carbonyl-, ($C_1$-$C_6$alkyl)C(O)—, $C_6$-$C_{14}$aryl-, $C_1$-$C_9$heteroaryl-, $C_3$-$C_8$cycloalkyl-, $C_1$-$C_6$haloalkyl-, amino($C_1$-$C_6$alkyl)-, ($C_1$-$C_6$alkyl)carboxyl-, $C_1$-$C_6$carboxyamidoalkyl-, or $O_2N$—.

"Aminoalkyl-" refers to an alkyl group, as defined above, wherein one or more of the alkyl group's hydrogen atoms has been replaced with —$NH_2$; one or both H of the $NH_2$ may be replaced by a substituent.

"Alkylcarboxyl-" refers to an alkyl group, defined above that is attached to the parent structure through the oxygen atom of a carboxyl (C(O)—O—) functionality. Examples of ($C_1$-$C_6$alkyl)carboxyl- include acetoxy, propionoxy, propylcarboxyl, and isopentylcarboxyl.

"(Alkyl)carboxyamido-" refers to a —NHC(O)— group in which the carbonyl carbon atom of said group is attached to a $C_1$-$C_6$alkyl group, as defined above. Representative examples of a ($C_1$-$C_6$alkyl)carboxyamido- group include, but are not limited to, —NHC(O)$CH_3$, —NHC(O)$CH_2CH_3$, —NHC(O)$CH_2CH_2CH_3$, —NHC(O)$CH_2CH_2CH_2CH_3$, —NHC(O)$CH_2CH_2CH_2CH_2CH_3$, —NHC(O)CH($CH_3$)$_2$, —NHC(O)$CH_2CH(CH_3)_2$, —NHC(O)CH($CH_3$)$CH_2CH_3$, —NHC(O)—C($CH_3$)$_3$ and —NHC(O)$CH_2$C($CH_3$)$_3$.

"Alkylene", "alkenylene", and "alkynylene" refers to alkyl, alkenyl and alkynyl groups, as defined above, having two points of attachment within a chemical structure. Examples of $C_1$-$C_6$alkylene include ethylene, propylene, and dimethylpropylene. Likewise, examples of $C_2$-$C_6$alkenylene include ethenylene and propenylene. Examples of $C_2$-$C_6$alkynylene include ethynylene and propynylene.

Aryl refers to an aromatic hydrocarbon group. Examples of a $C_6$-$C_{14}$aryl group include, but are not limited to, phenyl, α-naphthyl, β-naphthyl, biphenyl, anthryl, tetrahydronaphthyl, fluorenyl, indanyl, biphenylenyl, and acenanaphthyl. Examples of a $C_6$-$C_{10}$aryl group include, but are not limited to, phenyl, α-naphthyl, β-naphthyl, biphenyl, and tetrahydronaphthyl. An aryl group can be unsubstituted or substituted with one or more groups, including: $C_1$-$C_6$alkyl, halo, haloalkyl-, hydroxyl, hydroxyl($C_1$-$C_6$alkyl)-, —$NH_2$, aminoalkyl-, dialkylamino-, —COOH, —C(O)O—($C_1$-$C_6$alkyl), —OC(O)($C_1$-$C_6$alkyl), N-alkylamido-, —C(O)$NH_2$, ($C_1$-$C_6$alkyl)amido-, or —$NO_2$.

"(Aryl)alkyl" refers to an alkyl group, as defined above, wherein one or more of the alkyl group's hydrogen atoms has been replaced with an aryl group as defined above. ($C_6$-$C_{14}$Aryl)alkyl- moieties include benzyl, benzhydryl, 1-phenylethyl, 2-phenylethyl, 3-phenylpropyl, 2-phenylpropyl, 1-naphthylmethyl, 2-naphthylmethyl and the like. An (aryl)alkyl group can be unsubstituted or substituted with one or more of the following groups: halogen, $H_2$N—, hydroxyl, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_6$alkyl)carboxyamido-, HC(O)NH—, $H_2$NC(O)—, ($C_1$-$C_6$alkyl)NHC(O)—, di($C_1$-$C_6$alkyl)NC(O)—, NC—, hydroxyl, $C_1$-$C_6$alkoxy-, $C_1$-$C_6$alkyl-, $HO_2$C—, ($C_1$-$C_6$alkoxy)carbonyl-, ($C_1$-$C_6$alkyl)C(O)—, $C_6$-$C_{14}$aryl-, $C_1$-$C_9$heteroaryl-, $C_3$-$C_8$cycloalkyl-, $C_1$-$C_6$haloalkyl-, amino($C_1$-$C_6$alkyl)-, ($C_1$-$C_6$alkyl)carboxyl-, $C_1$-$C_6$carboxyamidoalkyl-, or $O_2$N—.

"(Aryl)amino" refers to a radical of formula (aryl)-NH—, wherein aryl is as defined above. "(Aryl)oxy" refers to the group Ar—O— where Ar is an aryl group, as defined above.

"Cycloalkyl" refers to a non-aromatic, saturated, monocyclic, bicyclic or polycyclic hydrocarbon ring system. Representative examples of a $C_3$-$C_{12}$cycloalkyl include, but are not limited to, cyclopropyl, cyclopentyl, cycloheptyl, cyclooctyl, decahydronaphthalen-1-yl, octahydro-1H-inden-2-yl, decahydro-1H-benzo[7]annulen-2-yl, and dodecahydros-indacen-4-yl. Representative examples of a $C_3$-$C_{10}$cycloalkyl include, but are not limited to, cyclopropyl, cyclobutyl, cyclopentyl, cyclohexyl, cycloheptyl, cyclooctyl, decahydronaphthalen-1-yl, and octahydro-1H-inden-2-yl. Representative examples of a $C_3$-$C_8$cycloalkyl include, but are not limited to, cyclopropyl, cyclobutyl, cyclopentyl, cyclohexyl, cycloheptyl, cyclooctyl, and octahydropentalen-2-yl. A cycloalkyl can be unsubstituted or substituted with one or more groups, including: halogen, —$NH_2$, ($C_1$-$C_6$alkyl)N—, ($C_1$-$C_6$alkyl)($C_1$-$C_6$alkyl)N—, —N($C_1$-$C_3$alkyl)C(O)($C_1$-$C_6$alkyl), —NHC(O)($C_1$-$C_6$alkyl), —NHC(O)H, —C(O)$NH_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —C(O)O($C_1$-$C_6$alkyl), —C(O)($C_1$-$C_6$alkyl), $C_6$-$C_{14}$aryl, $C_1$-$C_9$heteroaryl, $C_3$-$C_8$cycloalkyl, $C_1$-$C_6$haloalkyl-, $C_1$-$C_6$aminoalkyl-, —OC(O)($C_1$-$C_6$alkyl), $C_1$-$C_6$carboxyamidoalkyl-, and —$NO_2$. Additionally, each of any two hydrogen atoms on the same carbon atom of the carbocyclic ring can be replaced by an oxygen atom to form an oxo (=O) substituent.

"Cycloalkenyl" refers to a non-aromatic, unsaturated, monocyclic, bicyclic or polycyclic hydrocarbon ring system containing at least one double bond connecting two ring carbon atoms. Representative examples of a $C_5$-$C_8$cycloalkenyl include, but are not limited to, cyclopentenyl, cyclohexenyl, 4,4a-octalin-3-yl, and cyclooctenyl. A cycloalkenyl can be unsubstituted or substituted with one or more groups, including: halogen, —$NH_2$, ($C_1$-$C_6$alkyl)N—, ($C_1$-$C_6$alkyl)($C_1$-$C_6$alkyl)N—, —N($C_1$-$C_3$alkyl)C(O)($C_1$-$C_6$alkyl), —NHC(O)($C_1$-$C_6$alkyl), —NHC(O)H, —C(O)$NH_2$, C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —C(O)O($C_1$-$C_6$alkyl), —C(O)($C_1$-$C_6$alkyl), $C_6$-$C_{14}$aryl, $C_1$-$C_9$heteroaryl, and $C_3$-$C_8$cycloalkyl. Additionally, each of any two hydrogen atoms on the same carbon atom of the carbocyclic ring can be replaced by an oxygen atom to form an oxo (=O) substituent.

"Di(alkyl)amino-" refers to a nitrogen atom attached to two alkyl groups, as defined above. Each alkyl group can be independently selected. Representative examples of an di($C_1$-$C_6$alkyl)amino- group include, but are not limited to, —N($CH_3$)$_2$, —N($CH_2CH_3$)($CH_3$), —N($CH_2CH_3$)$_2$, —N($CH_2CH_2CH_3$)$_2$, —N($CH_2CH_2CH_2CH_3$)$_2$, —N(CH($CH_3$)$_2$)$_2$, —N(CH($CH_3$)$_2$)($CH_3$), —N($CH_2$CH($CH_3$)$_2$)$_2$, —NH(CH($CH_3$)$CH_2CH_3$)$_2$, —N(C($CH_3$)$_3$)$_2$, —N(C($CH_3$)$_3$)($CH_3$), and —N($CH_3$)($CH_2CH_3$). The two alkyl groups on the nitrogen atom, when taken together with the nitrogen to which they are attached, can form a 3- to 7-membered nitrogen containing heterocycle wherein up to two of the carbon atoms of the heterocycle can be replaced with —N(H)—, —N($C_1$-$C_6$alkyl)-, —N($C_3$-$C_8$cycloalkyl)-, —N($C_6$-$C_{14}$aryl)-, —N($C_1$-$C_9$heteroaryl)-, —N(amino($C_1$-$C_6$alkyl))-, —N($C_6$-$C_{14}$arylamino)-, —O—, —S—, —S(O)—, or —S(O)$_2$—.

"Halo" or "halogen" refers to —F, —Cl, —Br and —I.

"$C_1$-$C_6$Haloalkyl-" refers to a $C_1$-$C_6$alkyl group, as defined above, wherein one or more of the $C_1$-$C_6$alkyl group's hydrogen atoms has been replaced with —F, —Cl, —Br, or —I. Each substitution can be independently selected from —F, —Cl, —Br, or —I. Representative examples of an $C_1$-$C_6$haloalkyl- group include, but are not limited to, —$CH_2$F, —$CCl_3$, —$CF_3$, $CH_2CF_3$, —$CH_2$Cl, —$CH_2CH_2$Br, —$CH_2CH_2$I, —$CH_2CH_2CH_2$F, —$CH_2CH_2CH_2$Cl, —$CH_2CH_2CH_2CH_2$Br, —$CH_2CH_2CH_2CH_2$I, —$CH_2CH_2CH_2CH_2CH_2$Br, —$CH_2CH_2CH_2CH_2CH_2$I, —$CH_2$CH(Br)$CH_3$, —$CH_2$CH(Cl)$CH_2CH_3$, —CH(F)$CH_2CH_3$ and —C($CH_3$)$_2$($CH_2$Cl).

"Heteroaryl" refers to a monocyclic, bicyclic, or polycyclic aromatic ring system containing at least one ring atom selected from the heteroatoms oxygen, sulfur and nitrogen. Examples of $C_1$-$C_9$heteroaryl groups include furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic $C_1$-$C_9$hetroaryl groups include those where a phenyl, pyridine, pyrimidine or pyridazine ring is fused to a 5 or 6-membered monocyclic heteroaryl ring having one or two nitrogen atoms in the ring, one nitrogen atom together with either one oxygen or one sulfur atom in the ring, or one O or S ring atom. Examples of monocyclic $C_1$-$C_4$heteroaryl groups include 2H-tetrazole, 3H-1,2,4-triazole, furan, thiophene, oxazole, thiazole, isoxazole, isothiazole, imidazole, and pyrrole. A heteroaryl group can be unsubstituted or substituted with one or more groups, including: $C_1$-$C_6$alkyl, halo, haloalkyl-, hydroxyl, hydroxyl($C_1$-$C_6$alkyl)-, —NH$_2$, aminoalkyl-, dialkylamino-, —COOH, —C(O)O—($C_1$-$C_6$alkyl), —OC(O)($C_1$-$C_6$alkyl), N-alkylamido-, —C(O)NH$_2$, ($C_1$-$C_6$alkyl)amido-, or —NO$_2$.

"(Heteroaryl)alkyl-" refers to an alkyl group, as defined above, wherein one or more of the alkyl group's hydrogen atoms has been replaced with a heteroaryl- group as defined above. Examples of ($C_1$-$C_9$heteroaryl)alkyl- moieties include 2-pyridylmethyl, 2-thiophenylethyl, 3-pyridylpropyl, 2-quinolinylmethyl, 2-indolylmethyl, and the like. A (heteroaryl)alkyl group can be unsubstituted or substituted with one or more of the following groups: halogen, H$_2$N—, hydroxyl, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_6$alkyl)carboxyamido-, HC(O)NH—, H$_2$NC(O)—, ($C_1$-$C_6$alkyl)NHC(O)—, di($C_1$-$C_6$alkyl)NC(O)—, NC—, hydroxyl, $C_1$-$C_6$alkoxy-, $C_1$-$C_6$alkyl-, HO$_2$C—, ($C_1$-$C_6$alkoxy)carbonyl-, ($C_1$-$C_6$alkyl)C(O)—, $C_6$-$C_{14}$aryl-, $C_1$-$C_9$heteroaryl-, $C_3$-$C_8$cycloalkyl-, $C_1$-$C_6$haloalkyl-, amino($C_1$-$C_6$alkyl)-, ($C_1$-$C_6$alkyl)carboxyl-, $C_1$-$C_6$carboxyamidoalkyl-, or O$_2$N—.

The term "heteroatom" refers to a sulfur, nitrogen, or oxygen atom.

"Heterocycle" or "heterocyclyl" refers to monocyclic, bicyclic and polycyclic groups in which at least one ring atom is a heteroatom. A heterocycle may be saturated or partially saturated. Exemplary $C_1$-$C_9$heterocyclyl- groups include but are not limited to aziridine, oxirane, oxirene, thiirane, pyrroline, pyrrolidine, dihydrofuran, tetrahydrofuran, dihydrothiophene, tetrahydrothiophene, dithiolane, piperidine, 1,2,3,6-tetrahydropyridine-1-yl, tetrahydropyran, pyran, thiane, thiine, piperazine, oxazine, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 2-methyl-2,5-diazabicyclo[2.2.1]heptane-5-yl, 1,3,3-trimethyl-6-azabicyclo[3.2.1]oct-6-yl, 3-hydroxy-8-azabicyclo[3.2.1]octan-8-yl-, 7-methyl-3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 4-methyl-3,4-dihydro-2H-1,4-benzoxazin-7-yl, thiazine, dithiane, and dioxane. The contemplated heterocycle rings or ring systems have a minimum of 3 members. Therefore, for example, $C_1$heterocyclyl- radicals would include but are not limited to oxaziranyl, diaziridinyl, and diazirinyl, $C_2$heterocyclyl- radicals include but are not limited to aziridinyl, oxiranyl, and diazetidinyl, $C_9$heterocyclyl- radicals include but are not limited to azecanyl, tetrahydroquinolinyl, and perhydroisoquinolinyl. A heterocyclyl group can be unsubstituted or substituted with one or more groups, including: $C_1$-$C_6$alkyl, halo, haloalkyl-, hydroxyl, hydroxyl($C_1$-$C_6$alkyl)-, —NH$_2$, aminoalkyl-, dialkylamino-, —COOH, —C(O)O—($C_1$-$C_6$alkyl), —OC(O)($C_1$-$C_6$alkyl), N-alkylamido-, —C(O)NH$_2$, ($C_1$-$C_6$alkyl)amido-, or —NO$_2$.

"Heterocyclyl(alkyl)-" refers to an alkyl group, as defined above, wherein one or more of the alkyl group's hydrogen atoms has been replaced with a heterocycle group as defined above. Heterocyclyl($C_1$-$C_6$alkyl)- moieties include 2-pyridylmethyl, 1-piperazinylethyl, 4-morpholinylpropyl, 6-piperazinylhexyl, and the like. A heterocyclyl(alkyl) group can be unsubstituted or substituted with one or more of the following groups: halogen, H$_2$N—, ($C_1$-$C_6$alkyl)amino-, di($C_1$-$C_6$alkyl)amino-, ($C_1$-$C_6$alkyl)C(O)N($C_1$-$C_3$alkyl)-, ($C_1$-$C_6$alkyl)carboxyamido-, HC(O)NH—, H$_2$NC(O)—, ($C_1$-$C_6$alkyl)NHC(O)—, di($C_1$-$C_6$alkyl)NC(O)—, NC—, hydroxyl, $C_1$-$C_6$alkoxy-, $C_1$-$C_6$alkyl-, HO$_2$C—, ($C_1$-$C_6$alkoxy)carbonyl-, ($C_1$-$C_6$alkyl)C(O)—, 4- to 7-membered monocyclic heterocycle, $C_6$-$C_{14}$aryl-, $C_1$-$C_9$heteroaryl-, or $C_3$-$C_8$cycloalkyl-.

"Hydroxylalkyl-" refers to a alkyl group, as defined above, wherein one or more of the alkyl group's hydrogen atoms has been replaced with hydroxyl groups. Examples of $C_1$-$C_6$hydroxylalkyl- moieties include, for example, —CH$_2$OH, —CH$_2$CH$_2$OH, —CH$_2$CH$_2$CH$_2$OH, —CH$_2$CH(OH)CH$_2$OH, —CH$_2$CH(OH)CH$_3$, —CH(CH$_3$)CH$_2$OH and higher homologs.

"Monocyclic heterocyclyl" refers to monocyclic groups in which at least one ring atom is a heteroatom. A heterocycle may be saturated or partially saturated. Exemplary monocyclic $C_1$-$C_9$heterocyclyl- groups include but are not limited to aziridine, oxirane, oxirene, thiirane, pyrroline, pyrrolidine, dihydrofuran, tetrahydrofuran, dihydrothiophene, tetrahydrothiophene, dithiolane, piperidine, 1,2,3,6-tetrahydropyridine-1-yl, tetrahydropyran, pyran, thiane, thiine, piperazine, oxazine, 5,6-dihydro-4H-1,3-oxazin-2-yl, 4-methyl-3,4-dihydro-2H-1,4-benzoxazin-7-yl, thiazine, dithiane, and dioxane. The contemplated heterocycle ring systems have a minimum of 3 members. Therefore, for example, $C_1$heterocyclyl- radicals would include but are not limited to oxaziranyl, diaziridinyl, and diazirinyl, $C_2$heterocyclyl- radicals include but are not limited to aziridinyl, oxiranyl, and diazetidinyl, $C_9$heterocyclyl- radicals include but are not limited to azecanyl. A heterocyclyl group can be unsubstituted or substituted with one or more groups, including: $C_1$-$C_6$alkyl, halo, haloalkyl-, hydroxyl, hydroxyl($C_1$-$C_6$alkyl)-, —NH$_2$, aminoalkyl-, dialkylamino-, —COOH, —C(O)O—($C_1$-$C_6$alkyl), —OC(O)($C_1$-$C_6$alkyl), N-alkylamido-, —C(O)NH$_2$, ($C_1$-$C_6$alkyl)amido-, or —NO$_2$.

"Perfluoroalkyl-" refers to alkyl group, defined above, having two or more fluorine atoms. Examples of a $C_1$-$C_6$perfluoroalkyl- group include CF$_3$, CH$_2$CF$_3$, CF$_2$CF$_3$ and CH(CF$_3$)$_2$.

A "subject" is a mammal, e.g., a human, mouse, rat, guinea pig, dog, cat, horse, cow, pig, or non-human primate, such as a monkey, chimpanzee, baboon or gorilla.

The term "optionally substituted" as used herein means that at least one hydrogen atom of the optionally substituted group has been substituted with halogen, —NH$_2$, —NH($C_1$-$C_6$alkyl), —N($C_1$-$C_6$alkyl)($C_1$-$C_6$alkyl), —N($C_1$-$C_3$alkyl)C(O)($C_1$-$C_6$alkyl), —NHC(O)($C_1$-$C_6$alkyl), —NHC(O)H, —C(O)NH$_2$, —C(O)NH($C_1$-$C_6$alkyl), —C(O)N($C_1$-$C_6$alkyl)($C_1$-$C_6$alkyl), —CN, hydroxyl, $C_1$-$C_6$alkoxy, $C_1$-$C_6$alkyl, —C(O)OH, —C(O)O($C_1$-$C_6$alkyl), —C(O)($C_1$-$C_6$alkyl), $C_6$-$C_{14}$aryl, $C_1$-$C_9$heteroaryl, or $C_3$-$C_8$cycloalkyl.

Representative "pharmaceutically acceptable salts" include but are not limited to, e.g., water-soluble and water-insoluble salts, such as the acetate, aluminum, amsonate (4,4-diaminostilbene-2,2-disulfonate), benzathine (N,N'-dibenzylethylenediamine), benzenesulfonate, benzoate, bicarbonate, bismuth, bisulfate, bitartrate, borate, bromide, butyrate, calcium, calcium edetate, camsylate (camphorsulfonate), carbonate, chloride, choline, citrate, clavulariate, diethanolamine, dihydrochloride, diphosphate, edetate, edisylate (camphorsulfonate), esylate (ethanesulfonate), ethylenediamine, fumarate, gluceptate (glucoheptonate), gluconate, glucuronate, glutamate, hexafluorophosphate, hexylresorcinate, hydrabamine (N,N'-bis(dehydroabietyl) ethylenediamine), hydrobromide, hydrochloride, hydroxynaphthoate, 1-hydroxy-2-naphthoate, 3-hydroxy-2-naphthoate, iodide, isothionate (2-hydroxyethanesulfonate), lactate, lactobionate, laurate, lauryl sulfate, lithium, magnesium, malate, maleate, mandelate, meglumine (1-deoxy-1-(methylamino)-D-glucitol), mesylate, methyl bromide, methylnitrate, methylsulfate, mucate, napsylate, nitrate, N-methylglucamine ammonium salt, oleate, oxalate, palmitate, pamoate (4,4'-methylenebis-3-hydroxy-2-naphthoate, or embonate), pantothenate, phosphate, picrate, polygalacturonate, potassium, propionate, p-toluenesulfonate, salicylate, sodium, stearate, subacetate, succinate, sulfate, sulfosalicylate, suramate, tannate, tartrate, teoclate (8-chloro-3,7-dihydro-1,3-dimethyl-1H-purine-2,6-dione), triethiodide, tromethamine (2-amino-2-(hydroxymethyl)-1,3-propanediol), valerate, and zinc salts.

An "effective amount" when used in connection with a compound of this invention is an amount effective for inhibiting mTOR or PI3K in a subject.

Some compounds within the present invention possess one or more chiral centers, and the present invention includes each separate enantiomer of such compounds as well as mixtures of the enantiomers. Where multiple chiral centers exist in compounds of the present invention, the invention includes each combination as well as mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The compounds of the present invention exhibit an mTOR inhibitory activity and therefore, can be utilized in order to inhibit abnormal cell growth in which mTOR plays a role. Thus, the compounds of the present invention are effective in the treatment of disorders with which abnormal cell growth actions of mTOR are associated, such as restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, cancer, etc. In particular, the compounds of the present invention possess excellent cancer cell growth inhibiting effects and are effective in treating cancers, preferably all types of solid cancers and malignant lymphomas, and especially, leukemia, skin cancer, bladder cancer, breast cancer, uterus cancer, ovary cancer, prostate cancer, lung cancer, colon cancer, pancreas cancer, renal cancer, gastric cancer, brain tumor, advanced renal cell carcinoma, acute lymphoblastic leukemia, malignant melanoma, soft-tissue or bone sarcoma, etc.

The compounds of the present invention exhibit a PI3 kinase inhibitory activity and, therefore, can be utilized in order to inhibit abnormal cell growth in which PI3 kinases play a role. Thus, the compounds of the present invention are effective in the treatment of disorders with which abnormal cell growth actions of PI3 kinases are associated, such as restenosis, atherosclerosis, bone disorders, arthritis, diabetic retinopathy, psoriasis, benign prostatic hypertrophy, atherosclerosis, inflammation, angiogenesis, immunological disorders, pancreatitis, kidney disease, cancer, etc. In particular, the compounds of the present invention possess excellent cancer cell growth inhibiting effects and are effective in treating cancers, preferably all types of solid cancers and malignant lymphomas, and especially, leukemia, skin cancer, bladder cancer, breast cancer, uterus cancer, ovary cancer, prostate cancer, lung cancer, colon cancer, pancreas cancer, renal cancer, gastric cancer, brain tumor, advanced renal cell carcinoma, acute lymphoblastic leukemia, malignant melanoma, soft-tissue or bone sarcoma, etc.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjutants and excipients employing standard and conventional techniques.

The pharmaceutical compositions of this invention include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington: The Science and Practice of Pharmacy*, 20th Edition. Baltimore, Md.: Lippincott Williams & Wilkins, 2000.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that one skilled in the art would adjust the unit dosage form accordingly to reflect the relative level of activity. The decision as to the particular dosage to be employed (and the number of times to be administered per day is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.01 mg/kg to 10 mg/kg body weight. For parenteral administration, the dose may be in the range of 0.1 mg/kg to 1 mg/kg body weight for intravenous administration. For oral administration, the dose may be in the range about 0.1 mg/kg to 5 mg/kg body weight. The active ingredient will preferably be administered in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The amount of the compound of the present invention or a pharmaceutically acceptable salt thereof that is effective for inhibiting mTOR or PI3K in a subject. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The effective dosage amounts described herein refer to total amounts administered; that is, if more than one compound of the present invention or a pharmaceutically acceptable salt thereof is administered, the effective dosage amounts correspond to the total amount administered.

In one embodiment, the compound of the present invention or a pharmaceutically acceptable salt thereof is administered concurrently with another therapeutic agent.

In one embodiment, a composition comprising an effective amount of a compound of the present invention or a pharmaceutically acceptable salt thereof and an effective amount of another therapeutic agent within the same composition can be administered.

Effective amounts of the other therapeutic agents are well known to those skilled in the art. However, it is well within the skilled artisan's purview to determine the other therapeutic agent's optimal effective amount range. The compound of the present invention or a pharmaceutically acceptable salt thereof and the other therapeutic agent can act additively or, in one embodiment, synergistically. In one embodiment, of the invention, where another therapeutic agent is administered to an animal, the effective amount of the compound of the present invention or a pharmaceutically acceptable salt thereof is less than its effective amount would be where the other therapeutic agent is not administered. In this case, without being bound by theory, it is believed that the compound of the present invention or a pharmaceutically acceptable salt thereof and the other therapeutic agent act synergistically.

Methods useful for making the compounds of Formula I are set forth in the Examples below and generalized in Schemes 1-3:

Scheme 1:

One of skill in the art will recognize that Schemes 1-3 can be adapted to produce the other compounds of Formula I and pharmaceutically acceptable salts of compounds of Formula I according to the present invention.

The following abbreviations are used herein and have the indicated definitions: ACN is acetonitrile, AcOH is acetic acid, ATP is adenosine triphosphate, CHAPS is 3[(3-cholamidopropyl)dimethylammonio]-propanesulfonic acid, DEAD is diethyl azodicarboxylate, DIAD is diisopropyl azodicarboxylate, DMAP is dimethylaminopyridine, DMF is N,N-dimethylformamide, DMF-DMA is dimethylformamide dimethyl acetal, DMSO is dimethylsulfoxide. Dowtherm™ is a eutectic mixture of biphenyl ($C_{12}H_{10}$) and diphenyl oxide ($C_{12}H_{10}O$). Dowtherm™ is a registered trademark of Dow Corning Corporation. DPBS is Dulbecco's Phosphate Buffered Saline Formulation, EDTA is ethylenediaminetetraacetic acid, ESI stands for Electrospray Ionization, EtOAc is ethyl acetate, EtOH is ethanol, HEPES is 4-(2-hydroxyethyl)-1-piperazineethanesulfonic acid, GMF is Glass, Hunig's Base is diisopropylethylamine, HPLC is high pressure liquid chromatography, LPS is lipopolysaccharide, MeCN is acetonitrile, MeOH is methanol, MS is mass spectrometry, $NEt_3$ is triethylamine, NMR is nuclear magnetic resonance, PBS is phosphate-buffered saline (pH 7.4), RPMI 1640 is a buffer (Sigma-Aldrich Corp., St. Louis, Mo., USA), SDS is dodecyl sulfate (sodium salt), SRB is Sulforhodamine B, TBSCl is tert-butyldimethylsilyl chloride, TCA is tricholoroacetic acid, TFA is trifluoroacetic acid, THF is tetrahydrofuran, TLC is thin-layer chromatography, and TRIS is tris(hydroxymethyl)aminomethane.

Methods

The following methods outline the synthesis of the compounds of Formula I. The following examples are presented to illustrate certain embodiments of the present invention, but should not be construed as limiting the scope of this invention.

Example 1

Preparation of 1-[4-(4,6-dimorpholin-4-yl-1,3,5-triazin-2-yl)phenyl]-3-pyridin-4-ylurea Step 1: Preparation of 2-chloro-4,6-di-morpholin-4-yl-[1,3,5]triazine To a stirred solution of cyanuric chloride (18.4 g, 10 mmol) in acetone (100 ml) and crushed ice (500 g), a mixture of triethylamine (30.0 g, excess) and morpholine (17.4 g, 20 mmol) was added at −10° C. After the addition, reaction mixture was stirred at room temperature and for 1 hour and diluted with 50 ml water. Separated white solid was filtered and washed with water. The white solid was dried and filtered. The crude product was found to be pure and taken to next step without purification. Yield: 25 g, 87%; (M+H) 286.7

Step 2: Preparation of 4-(4,6-dimorpholin-4-yl-1,3,5-triazin-2-yl)aniline

A mixture of 2-chloro-4,6-di-morpholin-4-yl-[1,3,5]triazine (1.4 g, 4.9 mmoles), a catalytic amount of tetrakis(triphenylphosphine)palladium(0) (70 mg, 0.061 mmoles), sodium carbonate solution 2 M (3 mL), 4-aminophenylboronic acid pinacol ester (1.6 g, 7.3 mmoles) and DME (100 mL) was refluxed for 24 hours. The solvent was evaporated, and the residue was dissolved in methylene chloride and filtered through Celite™. The filtrate was washed with water (200 mL) and the organic layer was dried with magnesium sulfate. This was filtered and the solvent was evaporated. The residue was purified by Silica gel column chromatography and eluted with Ethyl acetate/hexanes (1:1) to give 1.40 g, (83% yield) of 4-(4,6-dimorpholin-4-yl-1,3,5-triazin-2-yl)aniline as an amorphous solid. (M+H) 343.

Step 3: Preparation of 1-[4-(4,6-dimorpholin-4-yl-1,3,5-triazin-2-yl)phenyl]-3-pyridin-4-ylurea To a mixture of 4-(4,6-dimorpholin-4-yl-1,3,5-triazin-2-yl)aniline (0.20 g 0.40 mmoles) in methylene chloride (80 mL) at 0° C. was added triphosgene (0.25 mg, 0.84 mmoles) and triethylamine (3 mL). The mixture was stirred for 20 minutes at 0° C. and 4-amino pyridine (0.10 g 0.83 mmoles) was added to the reaction mixture and stirred for another 2 hours at room temperature. The solvent was evaporated and the residue was submitted to the HPLC using acetonitrile/ TFA as mobile phase to give 98.2 mg (36% yield) of 1-[4-(4,6-dimophorlin-4-yl-1,3,5-triazin-2-yl)phenyl]-3-pyridin-4-ylurea. (M+H)=463.3.

Procedure a for Preparation of Ureas Using Aryl Isocyanates:

To a stirred mixture of 4-(4,6-dimorpholin-4-yl-1,3,5-triazin-2-yl)aniline (140 mg, 0.40 mmoles) and a catalytic amount of dimethylaminopyridine (DMAP) in methylene chloride 100 (mL), was added a small excess of aryl isocyanate (0.61 mmoles). The mixture was stirred at room temperature for 48 hours. The reaction mixture was concentrated to half of its original volume and the separated precipitate was collected by filtration and washed with methanol (15 ml) and then with diethyl ether. In some cases the crude product obtained was purified by Silica gel column chromatography by eluting it with appropriate solvents, depending upon the polarity of the products.

The following compounds were prepared according to Procedure A:

Example 2

Preparation of 1-[4-(4,6-dimorpholin-4-yl-1,3,5-triazin-2-yl)phenyl]-3-pyridin-3-ylurea Starting from 4-(4,6-dimorpholin-4-yl-1,3,5-triazin-2-yl) aniline (0.08 g 0.23 mmoles) and 3-pyridyl isocyanate (30 mg, 0.25 mmoles) the title compound was isolated as a white solid. The product was purified by Silica gel column chromatography by eluting it with 10% MeOH: ethyl acetate. Yield; 60 mg (56%); (M+H)=463.5.

Example 3

Preparation of 1-[4-(4,6-dimorpholin-4-yl-1,3,5-triazin-2-yl)phenyl]-3-phenylurea Starting from 4-(4,6-dimorpholin-4-yl-1,3,5-triazin-2-yl) aniline (140 mg, 0.40 mmoles) and phenyl isocyanate (72 mg, 0.61 mmoles), the title compound was isolated as a white solid. The product was purified by Silica gel column chromatography by eluting it with ethyl acetate. Yield: 0.128 g (68%) (M+H)=462.3

Example 4

Preparation of 1-[4-(4,6-dimorpholin-4-yl-1,3,5-triazin-2-yl)phenyl]-3-thiophen-2-ylurea Starting from 4-(4,6-dimorpholin-4-yl-1,3,5-triazin-2-yl) aniline (60 mg, 0.17 mmoles) and 2-thienyl isocyanate (18 mg, 0.14 mmoles), the title compound was isolated as a grey solid after Silica gel column chromatography by eluting with 5% ethyl acetate: methanol. Yield: 12 mg (14%); (M+H) =470.

Example 5

Preparation of 1-[4-(4,6-dimorpholin-4-yl-1,3,5-triazin-2-yl)phenyl]-3-(4-methylphenyl)urea Starting from 4-(4,6-dimorpholin-4-yl-1,3,5-triazin-2-yl) aniline (0.140 g 0.40 mmoles) and 4-methylphenyl isocyanate (74 mg, 0.56 mmoles), the title compound was isolated as a white solid. Yield; 65 mg (33%) (M+H)=476.4

Example 6

Preparation of 1-[4-(4,6-dimorpholin-4-yl-1,3,5-triazin-2-yl)phenyl]-3-(4-fluorophenyl)urea Starting from 4-(4,6-dimorpholin-4-yl-1,3,5-triazin-2-yl) aniline (0.140 g 0.40 mmoles) and 4-fluorophenyl isocyanate (83 mg, 0.61 mmole), 65 mg (33% yield) of the title product was isolated as white solid. (M+H)=480.3

Example 7

Preparation of 1-(2,4-dimethoxyphenyl)-3-[4-(4,6-dimorpholin-4-yl-1,3,5-triazin-2-yl)phenyl]-urea Starting from 4-(4,6-dimorpholin-4-yl-1,3,5-triazin-2-yl) aniline (0.140 g 0.40 mmoles) and 2,4-dimethoxyphenyl isocyanate (131 mg, 0.73 mmoles), the title compound was isolated as a white solid. Yield; 76 mg (36%); (M+H)=522.4

Example 8

Preparation of 1-(4-chlorophenyl)-3-[4-(4,6-dimorpholin-4-yl-1,3,5-triazin-2-yl)phenyl]-urea Starting from 4-(4,6-dimorpholin-4-yl-1,3,5-triazin-2-yl) aniline (0.140 g 0.40 mmoles) and 4-chlorophenyl isocyanate (94 mg, 0.61 mmoles), the title compound was isolated as a white solid. Yield; 60 mg (30%); (M+H)=496.3

Example 9

Preparation 1-[4-(4,6-dimorpholin-4-yl-1,3,5-triazin-2-yl)phenyl]-3-(4-methoxyphenyl)urea Starting from 4-(4,6-dimorpholin-4-yl-1,3,5-triazin-2-yl) aniline (0.140 g 0.40 mmoles) and 4-methoxyphenyl isocyanate (91 mg, 0.63 mmoles) the title compound was isolated as a white solid. Yield; 48 mg (24%); (M+H)=492.3

Example 10

Preparation of (4-chlorophenyl)-3-[4-(4,6-dimorpholin-4-yl-1,3,5-triazin-2-yl)phenyl]urea Starting from 4-(4,6-dimorpholin-4-yl-1,3,5-triazin-2-yl) aniline (0.140 g 0.40 mmoles) and 4-chlorophenyl isocyanate (94 mg, 0.61 mmoles) the title compound was isolated as a white solid. Yield; 60 mg (30%); (M+H)=496.3

Example 11

Preparation of (2,4-difluorophenyl)-3-[4-(4,6-dimorpholin-4-yl-1,3,5-triazin-2-yl)phenyl]urea Starting from 4-(4,6-dimorpholin-4-yl-1,3,5-triazin-2-yl) aniline (0.105 g 0.30 mmoles) and 2,4-difluorophenyl isocyanate (71 mg, 0.45 mmoles) the title compound was isolated as a white solid. Yield; 40 mg (27%); (M+H)=498.6

Example 12

Preparation of 1-[4-(4,6-dimorpholin-4-yl-1,3,5-triazin-2-yl)phenyl]-3-ethylurea Starting from 4-(4,6-dimorpholin-4-yl-1,3,5-triazin-2-yl) aniline (0.130 g 0.38 mmoles) and ethyl isocyanate (260 mg, 10 fold excess) the title compound was isolated as a white solid. Yield; 38 mg (25%); (M+H)=414.4

Example 13

Preparation of tert-butyl 3-{[4-(4-{[(4-fluorophenyl) carbamoyl]-amino}phenyl)-6-morpholin-4-yl-1,3,5-triazin-2-yl]amino}azetidine-1-carboxylate Step 1: Preparation of 2,4-dichloro-6-morpholin-4-yl-[1,3,5]triazine To a stirred solution of cyanuric chloride (18.4 g, 10 mmol) in acetone (100 ml) and crushed ice (500 g), a mixture of triethylamine (30.0 g, excess) and morpholine (8.7 g, 10 mmol) was added at −10° C. After the addition, reaction mixture was stirred at room temperature and for 1 hour and diluted with 50 ml water. Separated white solid was filtered and washed with water. The white solid was dried and filtered. The crude product was found to be pure and taken to next step with out purification. Yield: 18 g, 76%; (M+H) 236.4

Step 2: Preparation of tert-butyl 3-(4-chloro-6-morpholine-1,3,5-triazin-2-2-ylamino)azetidine-1-carboxylate To a stirred solution of 2,4-dichloro-6-morpholin-4-yl-[1, 3,5]triazine (2.35 g, 10 mmol) in acetone (50 ml) and crushed ice, a mixture of triethylamine and 1-boc-3-(amino)azetidine (1.72 g) was added slowly. The reaction mixture was stirred at room temperature for 6 hours and the separated solid was filtered. The product was dried and taken to next step with out purification. Yield: 3.0 g (81%); (M+H) 373

Step 3: Preparation of tert-butyl-3-4-(4-(4-aminophenyl)-6-morpholine-1,3,5-triazin-2-ylamino)azetidine-1-carboxylate A mixture of tert-butyl 3-(4-chloro-6-morpholine-1,3,5-triazin-2-2-ylamino)azetidine-1-carboxylate (1.1 g, 3.0 mmoles), tetrakis(triphenylphosphine)palladium (0) in catalytic amount (70 mg, 0061 mmoles), sodium carbonate solution 2 M (3 mL), 4-aminophenylboronic acid pinacol ester (0.97 g, 4.5 mmoles), DME (100 mL) was refluxed for 24 hours. The solvent was evaporated and the residue was dissolved in methylene chloride and filtered though Celite™. The organic layer was washed with water (200 mL) and dried over magnesium sulfate. It was filtered and the solvent was evaporated. The residue was chromatographed on silica gel column using Ethyl acetate/hexanes (1:1) as an eluent, to give 0.86 g, (68% yield) of tert-butyl-3-4-(4-(4-aminophenyl)-6-morpholine-1,3,5-triazin-2-ylamino)azetidine-1-carboxylate. (M+H) 428

Step 4: Preparation of tert-butyl 3-{[4-(4-{[(4-fluorophenyl)carbamoyl]amino}phenyl)-6-morpholin-4-yl-1,3,5-triazin-2-yl]amino}azetidine-1-carboxylate A mixture of tert-butyl 3-{[4-(4-aminophenyl)-6-morpholin-4-yl-1,3,5-triazin-2-yl]amino}azetidine-1-carboxylate (100 mg, 0.23 mmol), 4-fluorophenylisocyanate (63 mg, 0.46 mmol) and DMAP (5 mg) was stirred at room temperature for a period of 24 hours. At the end, reaction mixture was concentrated and purified by Gilson HPLC, using ACN/water and TFA. White solid; Yield 40 mg (30%); (M+H) 565.6

Example 14

Preparation of tert-butyl 3-[(4-morpholin-4-yl-6-{4-[(phenylcarbamoyl)amino]phenyl}-1,3,5-triazin-2-yl)amino]azetidine-1-carboxylate The titled compound was prepared by starting from tert-butyl 3-{[4-(4-aminophenyl)-6-morpholin-4-yl-1,3,5-triazin-2-yl]amino}azetidine-1-carboxylate (140 mg, 0.32 mmol)phenylisocyanate (58 mg, 0.49 mmol) and DMAP (5 mg) was stirred at room temperature for a period of 24 hours. At the end, reaction mixture was concentrated and purified by Gilson HPLC, using ACN/water and TFA. White solid; Yield 40 mg (31%); (M+H) 547.6

Example 15

Preparation of tert-butyl 3-[(4-morpholin-4-yl-6-{4-[(pyridine-3-ylcarbamoyl)amino]phenyl}-1,3,5-triazin-2-yl)amino]azetidine-1-carboxylate The titled compound was prepared by starting from tert-butyl 3-{[4-(4-aminophenyl)-6-morpholin-4-yl-1,3,5-triazin-2-yl]amino}azetidine-1-carboxylate (140 mg, 0.32 mmol) 3-pyridylisocyanate (70 mg, 0.58 mmol) and DMAP (5 mg) was stirred at room temperature for a period of 24 hours. At the end, reaction mixture was concentrated and purified by Gilson HPLC, using ACN/water and TFA. White solid; Yield 40 mg (23%); (M+H) 548.7.

Example 16

Preparation of tert-butyl 3-{[4-(4-{[(4-methylphenyl) carbamoyl]amino}phenyl)-6-morpholin-4-yl-1,3,5-triazin-2-yl]amino}azetidine-1-carboxylate The titled compound was prepared by starting from tert-butyl 3-{[4-(4-aminophenyl)-6-morpholin-4-yl-1,3,5-triazin-2-yl]amino}azetidine-1-carboxylate (130 mg, 0.27 mmol) 4-tolyl isocyanate (40 mg, 0.30 mmol) and DMAP (5 mg) was stirred at room temperature for a period of 24 hours.

At the end, reaction mixture was concentrated and purified by Gilson HPLC, using ACN/water and TFA. White solid; Yield 85 mg (47%); (M+H) 561.6.

Example 17

Preparation of 1-{4-[4-(azetidin-3-ylamino)-6-morpholin-4-yl-1,3,5-triazin-2-yl]phenyl}-3-phenylurea To a stirred solution of tert-butyl 3-[(4-morpholin-4-yl-6-{4-[(phenylcarbamoyl)amino]phenyl}-1,3,5-triazin-2-yl)amino]azetidine-1-carboxylate
30 mg (0.055 mmoles) in DCM, (20 ml) TFA (1.5 ml) was added at room temperature and stirred for 24 hours. At the end, reaction mixture was concentrated and purified by Gilson HPLC, using ACN/water and TFA. Yield: 20 (83%); (M+H) 447.

Example 18

Preparation of 1-{4-[4-(azetidin-3-ylamino)-6-morpholin-4-yl-1,3,5-triazin-2-yl]phenyl}-3-pyridin-3-ylurea To a stirred solution of tert-butyl 3-[(4-morpholin-4-yl-6-{4-[(pyridin-3-ylcarbamoyl)amino]phenyl}-1,3,5-triazin-2-yl)amino]azetidine-1-carboxylate
30 mg (0.055 mmoles) in DCM, (20 ml) TFA (1.5 ml) was added at room temperature and stirred for 24 hours. At the end, reaction mixture was concentrated and purified by Gilson HPLC, using ACN/water and TFA. Yield: 21 (83%); (M+H) 448.5.

Example 19

Preparation of 1-{4-[4-(azetidin-3-ylamino)-6-morpholin-4-yl-1,3,5-triazin-2-yl]phenyl}-3-(4-fluorophenyl)urea To a stirred solution of tert-butyl 3-[(4-morpholin-4-yl-6-{4-[(4-fluoro-phenylcarbamoyl)amino]phenyl}-1,3,5-triazin-2-yl)amino]azetidine-1-carboxylate
30 mg (0.053 mmoles) in DCM, (20 ml) TFA (1.5 ml) was added at room temperature and stirred for 24 hours. At the end, reaction mixture was concentrated and purified by Gilson HPLC, using ACN/water and TFA. Yield: 20 (83%); (M+H) 465.5.

Example 20

Preparation of 1-{4-[4-(azetidin-3-ylamino)-6-morpholin-4-yl-1,3,5-triazin-2-yl]phenyl}-3-(4-methylphenyl)urea To a stirred solution of tert-butyl 3-[(4-morpholin-4-yl-6-{4-[(4-methyl-phenylcarbamoyl)amino]phenyl}-1,3,5-triazin-2-yl)amino]azetidine-1-carboxylate
130 mg (0.23 mmoles) in DCM, (20 ml) TFA (1.5 ml) was added at room temperature and stirred for 24 hours. At the end, reaction mixture was concentrated and purified by Gilson HPLC, using ACN/water and TFA. Yield: 40 (37%); (M+H) 461.5.

Example 21

Preparation of tert-butyl 3-[(4-morpholin-4-yl-6-{4-[(pyridine-4-ylcarbamoyl)amino]phenyl}-1,3,5-triazin-2-yl)amino]azetidine-1-carboxylate To a stirred solution of tert-butyl 3-{[4-(4-aminophenyl)-6-morpholin-4-yl-1,3,5-triazin-2-yl]amino}azetidine-1-carboxylate (200 mg, 0.47 mmol) in DCM (100 ml) at 0° C., triphosgene (300 mg) and triethylamine (3 ml) was added slowly. The reaction mixture was stirred for 15 minutes and 4-aminopyridine (200 mg. 2.1 mmol) was added. The reaction mixture was stirred at room temperature for 24 hours and concentrated. It was quenched with cold water and the separated solid was filtered and washed with water. It was dried and purified by Gilson HPLC. Yield 100 mg (40%); (M+H) 548.6

Example 22

Preparation of 1-{4-[4-(azetidin-3-ylamino)-6-morpholin-4-yl-1,3,5-triazin-2-yl]phenyl}-3-pyridin-4-ylurea To a stirred solution of tert-butyl 3-[(4-morpholin-4-yl-6-{4-[(pyridine-4-ylcarbamoyl)amino]phenyl}-1,3,5-triazin-2-yl)amino]azetidine-1-carboxylate
40 mg (0.073 mmoles) in DCM, (20 ml) TFA (1.5 ml) was added at room temperature and stirred for 24 hours. At the end, reaction mixture was concentrated and purified by Gilson HPLC, using ACN/water and TFA. Yield: 26 (81%); (M+H) 448.5.

Example 23

Preparation of 1-{4-[4-morpholin-4-yl-6-(8-oxa-3-azabicyclo[3.2.1]oct-3-yl)-1,3,5-triazin-2-yl]phenyl}-3-phenylurea Step 1: Preparation of 3-(4-chloro-6-morpholin-4-yl-1,3,5-triazin-2-yl)-8-oxa-3-azabicyclo[3.2.1]octane To a stirred acetone/crushed ice suspension of 2,4-dichloro-6-morpholin-4-yl-[1,3,5]triazine (1.5 g, 6.5 mmol), 8-oxa-3-azabicyclo[3.2.1]octane (980 mg, 6.5 mmol) and triethylamine (3 ml) was added and stirred at room temperature for 6 hours. At the end, the separated solid was filtered and washed with water. The crude product was found to be pure enough for further transformations. Yield: 2.0 g (99%); mp. 118; (M+H) 313.1

Step 2: Preparation of 4-[4-morpholin-4-yl-6-(8-oxa-3-azabicyclo[3.2.1]oct-3-yl)-1,3,5-triazin-2-yl]aniline A mixture of 3-(4-chloro-6-morpholin-4-yl-1,3,5-triazin-2-yl)-8-oxa-3-azabicyclo[3.2.1]octane (2.0 g, 6.4 mmol), tet rakis(triphenylphosphine)palladium (0) in catalytic amount (100 mg), sodium carbonate solution 2 M (5 mL), 4-aminophenylboronic acid pinacol ester (1.5 g, 6.43 mmoles), DME (200 mL) was refluxed for 24 hours. The solvent was evaporated and the residue was dissolved in methylene chloride and filtered though Celite™. The organic layer was washed with water (200 mL) and dried over magnesium sulfate. It was filtered and the solvent was evaporated. The residue was chromatographed on silica gel column using Ethyl acetate/hexanes (1:1) as an eluent, to give 1.4 g, (59% yield) of the titled product. mp. 154; (M+H) 369.4.

Step 3: Preparation of 1-{4-[4-morpholin-4-yl-6-(8-oxa-3-azabicyclo[3.2.1]oct-3-yl)-1,3,5-triazin-2-yl]phenyl}-3-phenylurea The titled compound was prepared by starting from 4-[4-morpholin-4-yl-6-(8-oxa-3-azabicyclo[3.2.1]oct-3-yl)-1,3,5-triazin-2-yl]aniline (120 mg, 0.32 mmol)phenylisocyanate (80 mg, 0.67 mmol) and DMAP (5 mg) was stirred at room temperature for a period of 24 hours. At the end, reaction mixture was concentrated and purified by Gilson HPLC, using ACN/water and TFA. White solid; mp: 242; Yield 35 mg (28%); (M+H) 488.56

Example 24

Preparation of 1-(4-fluorophenyl)-3-{4-[4-morpholin-4-yl-6-(8-oxa-3-azabicyclo[3.2.1]oct-3-yl)-1,3,5-triazin-2-yl]phenyl}urea The titled compound was prepared by starting from 4-[4-morpholin-4-yl-6-(8-oxa-3-azabicyclo[3.2.1]oct-3-yl)-1,3,5-triazin-2-yl]aniline (100 mg, 0.27 mmol) 4-fluoro phenylisocyanate (50 mg, 0.36 mmol) and DMAP (5 mg) was stirred at room temperature for a period of 24 hours. At the end, reaction mixture was concentrated and purified by Gilson HPLC, using ACN/water and TFA. White solid; mp: 248; Yield 86 mg (86%); (M+H) 506.4

Example 25

Preparation of 1-(4-methylphenyl)-3-{4-[4-morpholin-4-yl-6-(8-oxa-3-azabicyclo[3.2.1]oct-3-yl)-1,3,5-triazin-2-yl]phenyl}urea The titled compound was prepared by starting from 4-[4-morpholin-4-yl-6-(8-oxa-3-azabicyclo[3.2.1]oct-3-yl)-1,3,5-triazin-2-yl]aniline (100 mg, 0.27 mmol) 4-tolylisocyanate (60 mg, 0.45 mmol) and DMAP (5 mg) was stirred at room temperature for a period of 24 hours. At the end, reaction mixture was concentrated and purified by Gilson HPLC, using ACN/water and TFA. White solid; mp: 228; Yield 80 mg (80%); (M+H) 502.4

Following the procedure as outlined in example 25, compounds described in examples 26 to 32 were prepared.

Example 26

1-[4-(4,6-di-8-oxa-3-azabicyclo[3.2.1]oct-3-yl-1,3,5-triazin-2-yl)phenyl]-3-methylurea (M+H) 452.53

Example 27

2-hydroxyethyl[4-(4,6-di-8-oxa-3-azabicyclo[3.2.1]oct-3-yl-1,3,5-triazin-2-yl)phenyl]carbamate (M+H) 483.54

Example 28

1-[4-(4,6-di-8-oxa-3-azabicyclo[3.2.1]oct-3-yl-1,3,5-triazin-2-yl)phenyl]-3-[4-(4-methylpiperazin-1-yl)phenyl]urea (M+H) 612.8

Example 29

1-[4-(4,6-di-8-oxa-3-azabicyclo[3.2.1]oct-3-yl-1,3,5-triazin-2-yl)phenyl]-3-ethylurea (M+H) 466.56

Example 30

1-cyclopropyl-3-[4-(4,6-di-8-oxa-3-azabicyclo[3.2.1]oct-3-yl-1,3,5-triazin-2-yl)phenyl]urea (M+H) 478.55

Example 31

1-[4-(4,6-di-8-oxa-3-azabicyclo[3.2.1]oct-3-yl-1,3,5-triazin-2-yl)phenyl]-3-pyridin-4-ylurea (M+H) 515

Example 32

1-[4-(4,6-di-8-oxa-3-azabicyclo[3.2.1]oct-3-yl-1,3,5-triazin-2-yl)phenyl]-3-[4-(hydroxymethyl)phenyl]urea (M+H) 544.6

Example 33

Preparation of 4-[4-morpholin-4-yl-6-(3-oxa-8-azabicyclo[3.2.1]oct-8-yl)-1,3,5-triazin-2-yl]aniline Step 1: Synthesis of 4-(4,6-dichloro-1,3,5-triazin-2-yl)morpholine To a solution of cyanuric chloride (2.5 g, 13.5 mmol) in $CH_2Cl_2$ (150 mL) was added dropwise morpholine (1.14 g, 13.5 mmol) at −78° C., followed by addition of Et3N (3.0 mL, 21.5 mmol). The resulting reaction mixture was stirred at −78° C. for 20 min, and then diluted with $CH_2Cl_2$. The organic phase was washed with water and brine, and dried over $MgSO_4$. The solvent was removed in vacuum to give the title compound as white crystalline solid (3.027 g, 95% yield). MS (ESI) m/z 235.1.

Step 2: Synthesis of 8-(4-chloro-6-morpholino-1,3,5-triazin-2-yl)-3-oxa-8-azabicyclo[3,2,1]octane To a solution of 4-(4,6-dichloro-1,3,5-triazin-2-yl)morpholine (2.34 g, 10 mmol) in $CH_2Cl_2$ (100 mL) were added 3-oxa-8-azabicyclo[3,2,1]octane hydrochloride (1.645 g, 11 mmol) and Et3N (4.2 mL, 30 mmol). The mixture was stirred at room temperature over night. The reaction mixture was washed with water and brine, and dried over $MgSO_4$. The solvent was removed in vacuum to give the title compound as white solid (3.0 g, 96% yield). MS (ESI) m/z 312.1.

Step 3: Synthesis of 4-[4-morpholin-4-yl-6-(3-oxa-8-azabicyclo[3.2.1]oct-8-yl)-1,3,5-triazin-2-yl]aniline To a 10 mL vial were added 8-(4-chloro-6-morpholino-1,3,5-triazin-2-yl)-3-oxa-8-azabicyclo[3,2,1]octane (311 mg, 1.0 mmol), 4-aminophenylboronic acid pinacol ester (328 mg, 1.5 mmol), Pd(PPh3)4 (58 mg, 5 mol %), 1,2-dimethoxyethane (DME, 2.5 mL) and 2M Na2CO3 aqueous solution (1.5 mL). The resulting mixture was heated at 130° C. for 30 min in microwave oven. The reaction mixture was cooled to room temperature. The aqueous phase was extracted with EtOAc, and the combined organic phases were dried over (MgSO$_4$). The solvent was removed under reduced pressure and the residue was subjected to HPLC separation to give the title compound as off-white solid (280 mg, 76% yield). MS (ESI) m/z 369.2.

Example 34

Preparation of 1-{4-[4-morpholin-4-yl-6-(3-oxa-8-azabicyclo[3.2.1]oct-8-yl)-1,3,5-triazin-2-yl]phenyl}-3-pyridin-4-ylurea To a solution of 4-[4-morpholin-4-yl-6-(3-oxa-8-azabicyclo[3.2.1]oct-8-yl)-1,3,5-triazin-2-yl]aniline (22 mg, 0.06 mmol) in CHCl3 (1 mL) were added Et3N (25 mL, 0.18 mmol) and triphosgene (18 mg, 0.06 mmol). The mixture was stirred at room temperature for 15 min and 4-aminopyridine (17 mg, 0.18 mmol) was added. The mixture was stirred at room temperature overnight. The solvent was removed, and the residue was subjected to HPLC separation to give the title compound as off-white solid (1TFA salt, 8.8 mg, 24% yield). MS (ESI) m/z 489.2.

Example 35

Preparation of 4-[({4-[4-morpholin-4-yl-6-(3-oxa-8-azabicyclo[3.2.1]oct-8-yl)-1,3,5-triazin-2-yl]phenyl}carbamoyl)amino]benzamide Following the procedure described in example 34, reaction of 4-[4-morpholin-4-yl-6-(3-oxa-8-azabicyclo[3.2.1]oct-8-yl)-1,3,5-triazin-2-yl]aniline (22 mg, 0.06 mmol) (22 mg, 0.06 mmol, triphosgene (18 mg, 0.06 mmol) and 4-aminobenzamide (25 mg, 0.18 mmol) gave the title compound as off-white solid (10.6 mg, 33% yield). MS (ESI) m/z 531.2.

Example 36

Preparation of 1-{4-[4-morpholin-4-yl-6-(3-oxa-8-azabicyclo[3.2.1]oct-8-yl)-1,3,5-triazin-2-yl]phenyl}-3-pyridin-3-ylurea Following the procedure described in example 34, reaction of 4-[4-morpholin-4-yl-6-(3-oxa-8-azabicyclo[3.2.1]oct-8-yl)-1,3,5-triazin-2-yl]aniline (22 mg, 0.06 mmol) (22 mg, 0.06 mmol, triphosgene (18 mg, 0.06 mmol) and 3-aminopyridine (17 mg, 0.18 mmol) gave the title compound as off-white solid (1TFA salt, 14.8 mg, 41% yield). MS (ESI) m/z 489.5.

Example 37

Preparation of 1-(4-fluorophenyl)-3-{4-[4-morpholin-4-yl-6-(3-oxa-8-azabicyclo[3.2.1]oct-8-yl)-1,3,5-triazin-2-yl]phenyl}urea Following the procedure described in example 34, reaction of 4-[4-morpholin-4-yl-6-(3-oxa-8-azabicyclo[3.2.1]oct-8-yl)-1,3,5-triazin-2-yl]aniline (22 mg, 0.06 mmol) (22 mg, 0.06 mmol, triphosgene (18 mg, 0.06 mmol) and 4-fluoroaniline (20 mg, 0.18 mmol) gave the title compound as off-white solid (14.8 mg, 49% yield). MS (ESI) m/z 506.5.

Example 38

Preparation of 1-[4-(hydroxymethyl)phenyl]-3-{4-[4-morpholin-4-yl-6-(3-oxa-8-azabicyclo[3.2.1]oct-8-yl)-1,3,5-triazin-2-yl]phenyl}urea Following the procedure described in example 34, reaction of 4-[4-morpholin-4-yl-6-(3-oxa-8-azabicyclo[3.2.1]oct-8-yl)-1,3,5-triazin-2-yl]aniline (22 mg, 0.06 mmol) (22 mg, 0.06 mmol, triphosgene (18 mg, 0.06 mmol) and 4-aminobenzyl alcohol (22 mg, 0.18 mmol) gave the title compound as off-white solid (9.6 mg, 31% yield). MS (ESI) m/z 518.5.

Example 39

Preparation of 1-[4-(2-hydroxyethyl)phenyl]-3-{4-[4-morpholin-4-yl-6-(3-oxa-8-azabicyclo[3.2.1]oct-8-yl)-1,3,5-triazin-2-yl]phenyl}urea Following the procedure described in example 34, reaction of 4-[4-morpholin-4-yl-6-(3-oxa-8-azabicyclo[3.2.1]oct-8-yl)-1,3,5-triazin-2-yl]aniline (22 mg, 0.06 mmol) (22 mg, 0.06 mmol, triphosgene (18 mg, 0.06 mmol) and 4-aminophenethyl alcohol (24 mg, 0.18 mmol) gave the title compound as off-white solid (10.6 mg, 33% yield). MS (ESI) m/z 532.5.

Example 40

Preparation of 2-(diethylamino)ethyl 4-[({4-[4-morpholin-4-yl-6-(3-oxa-8-azabicyclo[3.2.1]oct-8-yl)-1,3,5-triazin-2-yl]phenyl}carbamoyl)amino]benzoate Following the procedure described in example 34, reaction of 4-[4-morpholin-4-yl-6-(3-oxa-8-azabicyclo[3.2.1]oct-8-yl)-1,3,5-triazin-2-yl]aniline (22 mg, 0.06 mmol) (22 mg, 0.06 mmol, triphosgene (18 mg, 0.06 mmol) and procaine hydrochloride (50 mg, 0.18 mmol) gave the title compound as off-white solid (1TFA salt, 14.6 mg, 33% yield). MS (ESI) m/z 613.6.

Example 41

Preparation of 1-(4-methylphenyl)-3-{4-[4-morpholin-4-yl-6-(3-oxa-8-azabicyclo[3.2.1]oct-8-yl)-1,3,5-triazin-2-yl]phenyl}urea Following the procedure described in example 34, reaction of 4-[4-morpholin-4-yl-6-(3-oxa-8-azabicyclo[3.2.1]oct-8-yl)-1,3,5-triazin-2-yl]aniline (22 mg, 0.06 mmol) (22 mg, 0.06 mmol, triphosgene (18 mg, 0.06 mmol) and p-toluidine (20 mg, 0.18 mmol) gave the title compound as off-white solid (9.2 mg, 31% yield). MS (ESI) m/z 502.5.

Example 42

Preparation of 1-(4-cyanophenyl)-3-{4-[4-morpholin-4-yl-6-(3-oxa-8-azabicyclo[3.2.1]oct-8-yl)-1,3,5-triazin-2-yl]phenyl}urea Following the procedure described in example 34, reaction of 4-[4-morpholin-4-yl-6-(3-oxa-8-azabicyclo[3.2.1]oct-8-yl)-1,3,5-triazin-2-yl]aniline (22 mg, 0.06 mmol) (22 mg, 0.06 mmol, triphosgene (18 mg, 0.06 mmol) and 4-aminobezonitrile (21 mg, 0.18 mmol) gave the title compound as off-white solid (14.3 mg, 46% yield). MS (ESI) m/z 513.5.

Example 43

Preparation of 1-[4-(4-methylpiperazin-1-yl)phenyl]-3-{4-[4-morpholin-4-yl-6-(3-oxa-8-azabicyclo[3.2.1]oct-8-yl)-1,3,5-triazin-2-yl]phenyl}urea Following the procedure described in example 34, reaction of 4-[4-morpholin-4-yl-6-(3-oxa-8-azabicyclo[3.2.1]oct-8-yl)-1,3,5-triazin-2-yl]aniline (22 mg, 0.06 mmol) (22 mg, 0.06 mmol, triphosgene (18 mg, 0.06 mmol) and 4-(4-methylpiperazin-1-yl)aniline (54 mg, 0.18 mmol) gave the title compound as off-white solid (2TFA salt, 3.2 mg, 7% yield). MS (ESI) m/z 586.6.

Example 44

Preparation of 1-isopropyl-3-{4-[4-morpholin-4-yl-6-(3-oxa-8-azabicyclo[3.2.1]oct-8-yl)-1,3,5-triazin-2-yl]phenyl}urea Following the procedure described in example 34, reaction of 4-[4-morpholin-4-yl-6-(3-oxa-8-azabicyclo[3.2.1]oct-8-yl)-1,3,5-triazin-2-yl]aniline (22 mg, 0.06 mmol) (22 mg, 0.06 mmol, triphosgene (18 mg, 0.06 mmol) and isopropylamine (11 mg, 0.18 mmol) gave the title compound as off-white solid (13.6 mg, 50% yield). MS (ESI) m/z 454.5.

Example 45

Preparation of 1-(2-hydroxyethyl)-3-{4-[4-morpholin-4-yl-6-(3-oxa-8-azabicyclo[3.2.1]oct-8-yl)-1,3,5-triazin-2-yl]phenyl}urea Following the procedure described in example 34, reaction of 4-[4-morpholin-4-yl-6-(3-oxa-8-azabicyclo[3.2.1]oct-8-yl)-1,3,5-triazin-2-yl]aniline (22 mg, 0.06 mmol) (22 mg, 0.06 mmol, triphosgene (18 mg, 0.06 mmol) and ethanolamine (11 mg, 0.18 mmol) gave the title compound as off-white solid (14.4 mg, 53% yield). MS (ESI) m/z 456.5.

Example 46

Preparation of 1-[2-(dimethylamino)ethyl]-3-{4-[4-(1,4-dioxa-8-azaspiro[4.5]dec-8-yl)-6-morpholin-4-yl-1,3,5-triazin-2-yl]phenyl}urea

MS (ES+) 513.62 (M+H)+

Example 47

Preparation of 1-{4-[4-morpholin-4-yl-6-(8-oxa-3-azabicyclo[3.2.1]oct-3-yl)-1,3,5-triazin-2-yl]phenyl}-3-pyridin-3-ylurea MS (ESI) m/z 489.3.

Example 48

Preparation of 1-{4-[4-morpholin-4-yl-6-(8-oxa-3-azabicyclo[3.2.1]oct-3-yl)-1,3,5-triazin-2-yl]phenyl}-3-pyridin-4-ylurea mp 258° C.; MS (ESI) m/z 489.3.

Following the procedure as outlined in example 1, step 3 the following compounds were prepared.

Example 49

1-[4-(4,6-dimorpholin-4-yl-1,3,5-triazin-2-yl)phenyl]-3-(2-methylpyridin-4-yl)urea MS (ESI) m/z 477.3.

Example 50

1-[4-(4,6-dimorpholin-4-yl-1,3,5-triazin-2-yl)phenyl]-3-[4-(2-hydroxyethyl)phenyl]urea MS (ESI) m/z 506.4.

Example 51

1-[4-(4,6-dimorpholin-4-yl-1,3,5-triazin-2-yl)phenyl]-3-[4-(hydroxymethyl)phenyl]urea Example 52

1-[4-(4,6-dimorpholin-4-yl-1,3,5-triazin-2-yl)phenyl]-3-[4-(1-hydroxyethyl)phenyl]urea MS (ESI) m/z 506.4.

Example 53

1-[4-(4,6-dimorpholin-4-yl-1,3,5-triazin-2-yl)phenyl]-3-[4-(trifluoromethyl)phenyl]urea MS (ESI) m/z 530.2.

Example 54

1-[4-(4,6-dimorpholin-4-yl-1,3,5-triazin-2-yl)phenyl]-3-(4-hydroxyphenyl)urea

MS (ESI) m/z 478.2.

Example 55

1-[4-(4,6-dimorpholin-4-yl-1,3,5-triazin-2-yl)phenyl]-3-[5-(trifluoromethyl)pyridin-2-yl]urea MS (ESI) m/z 530.5.

Example 56

1-[4-(4,6-dimorpholin-4-yl-1,3,5-triazin-2-yl)phenyl]-3-{4-[2,2,2-trifluoro-1-hydroxy-1-(trifluoromethyl)ethyl]phenyl}urea MS (ESI) m/z 621.54.

Example 57

1-[4-(4,6-dimorpholin-4-yl-1,3,5-triazin-2-yl)phenyl]-3-[3-(1-hydroxyethyl)phenyl]urea MS (ESI) m/z 506.3.

Example 58 methyl 4-({[4-(4,6-dimorpholin-4-yl-1,3,5-triazin-2-yl)phenyl]carbamoyl}amino)benzoate MS (ESI) m/z 520.3.

Example 59

Preparation of 1-{4-[4-morpholin-4-yl-6-(tetrahydro-2H-pyran-4-yloxy)-1,3,5-triazin-2-yl]phenyl}-3-pyridin-4-ylurea Step 1: To a stirred solution of NaH (50% 460 mg) in dry THF tetrahydro-2H-pyran-4-ol (1.02 g, 10 mmol) was slowly added at room temperature. The reaction mixture was stirred at room temperature for 30 min and 2,4-dichloro-6-morpholin-4-yl-[1,3,5]triazine (2.35 g, 10 mmol) in THF (50 ml) was slowly added. The reaction mixture was stirred at room temperature for 48 hours and slowly quenched with ice-cold water. It was extracted with $CHCl_3$; washed well with water and dried over anhydrous $MgSO_4$. It was filtered and concentrated and 2-chloro-4-morpholin-4-yl-6-(tetrahydro-2H-pyran-4-yloxy)-1,3,5-triazine was purified by silica gel column chromatography by eluting it with 40% ethyl acetate:hexane. Yield: 1.5 g, 50%; White solid; mp 91° C.; MS (ESI) m/z 301.52

Step 2: 4-[4-morpholin-4-yl-6-(tetrahydro-2H-pyran-4-yloxy)-1,3,5-triazin-2-yl]aniline was prepared by the procedure as described in example 1, step 2. Starting from 2-chloro-4-morpholin-4-yl-6-(tetrahydro-2H-pyran-4-yloxy)-1,3,5-triazine (1.5 g, 4.9 mmol) 980 mg (56% yield) of the product was isolated after purification using Silica gel column chromatography by eluting it with ethyl acetate. Mp. 188° C.; MS (ESI) m/z 358.2.

Step 3: 1-{4-[4-morpholin-4-yl-6-(tetrahydro-2H-pyran-4-yloxy)-1,3,5-triazin-2-yl]phenyl}-3-pyridin-4-ylurea was prepared by the procedure as described in example 1, step 3. Starting from 4-[4-morpholin-4-yl-6-(tetrahydro-2H-pyran-4-yloxy)-1,3,5-triazin-2-yl]aniline (212 mg. 0.59 mmol) 190 mg (Yield, 67%) of the final product was isolated as a white solid. mp 238° C.; MS (ESI) m/z 478.3.

Example 60

Preparation of 1-{4-[4-morpholin-4-yl-6-(tetrahydro-2H-pyran-4-yloxy)-1,3,5-triazin-2-yl]phenyl}-3-phenylurea 1-{4-[4-morpholin-4-yl-6-(tetrahydro-2H-pyran-4-yloxy)-1,3,5-triazin-2-yl]phenyl}-3-phenylurea was prepared by reacting the 4-[4-morpholin-4-yl-6-(tetrahydro-2H-pyran-4-yloxy)-1,3,5-triazin-2-yl]aniline and the corresponding phenylisocyanate. Product was purified by Gilson, HPLC. MS (ESI) m/z 476.5.

Example 61

Preparation of 1-{4-[4-morpholin-4-yl-6-(tetrahydro-2H-pyran-4-yloxy)-1,3,5-triazin-2-yl]phenyl}-3-pyridin-3-ylurea 1-{4-[4-morpholin-4-yl-6-(tetrahydro-2H-pyran-4-yloxy)-1,3,5-triazin-2-yl]phenyl}-3-pyridin-3-ylurea was prepared by reacting the 4-[4-morpholin-4-yl-6-(tetrahydro-2H-pyran-4-yloxy)-1,3,5-triazin-2-yl]aniline and the corresponding 3-pyridylisocyanate. Product was purified by Gilson, HPLC. MS (ESI) m/z 477.53.

Example 62

Preparation of 1-[4-(hydroxymethyl)phenyl]-3-{4-[4-morpholin-4-yl-6-(tetrahydro-2H-pyran-4-yloxy)-1,3,5-triazin-2-yl]phenyl}urea 1-[4-(hydroxymethyl)phenyl]-3-{4-[4-morpholin-4-yl-6-(tetrahydro-2H-pyran-4-yloxy)-1,3,5-triazin-2-yl]phenyl}urea was prepared by the triphosgene procedure as described in example 1, step 3. Product was purified by Gilson. MS (ESI) m/z 506.6.

Example 63

Preparation of 1-(2-methylpyridin-4-yl)-3-{4-[4-morpholin-4-yl-6-(tetrahydro-2H-pyran-4-yloxy)-1,3,5-triazin-2-yl]phenyl}urea 1-(2-methylpyridin-4-yl)-3-{4-[4-morpholin-4-yl-6-(tetrahydro-2H-pyran-4-yloxy)-1,3,5-triazin-2-yl]phenyl}urea was prepared by the triphosgene procedure as described in example 1, step 3. Product was purified by Gilson, HPLC. MS (ESI) m/z 491.5.

Example 64

Preparation of 1-[2-(methylamino)ethyl]-3-{4-[4-morpholin-4-yl-6-(tetrahydro-2H-pyran-4-yloxy)-1,3,5-triazin-2-yl]phenyl}urea 1-[2-(methylamino)ethyl]-3-{4-[4-morpholin-4-yl-6-(tetrahydro-2H-pyran-4-yloxy)-1,3,5-triazin-2-yl]phenyl}urea was prepared by the triphosgene procedure as described in example 1, step 3. Product was purified by Gilson, HPLC. MS (ESI) m/z 457.54.

Example 65

Preparation of 1-(3-acetylphenyl)-3-{4-[4-morpholin-4-yl-6-(tetrahydro-2H-pyran-4-yloxy)-1,3,5-triazin-2-yl]phenyl}urea 1-(3-acetylphenyl)-3-{4-[4-morpholin-4-yl-6-(tetrahydro-2H-pyran-4-yloxy)-1,3,5-triazin-2-yl]phenyl}urea was prepared by reacting the 4-[4-morpholin-4-yl-6-(tetrahydro-2H-pyran-4-yloxy)-1,3,5-triazin-2-yl]aniline and the corresponding 3-acetylisocyanate. Product was purified by Gilson, HPLC. MS (ESI) m/z 518.58.

Example 66

Preparation of 1-[4-(dimethylamino)phenyl]-3-{4-[4-morpholin-4-yl-6-(tetrahydro-2H-pyran-4-yloxy)-1,3,5-triazin-2-yl]phenyl}urea 1-[4-(dimethylamino)phenyl]-3-{4-[4-morpholin-4-yl-6-(tetrahydro-2H-pyran-4-yloxy)-1,3,5-triazin-2-yl]phenyl}urea was prepared by reacting the 4-[4-morpholin-4-yl-6-(tetrahydro-2H-pyran-4-yloxy)-1,3,5-triazin-2-yl]aniline and the corresponding 4-(N,N-dimethylamino) phenylisocyanate. Product was purified by Gilson, HPLC. MS (ESI) m/z 519.61.

Example 67

Preparation of 4-[3-{4-(4,6-dimorpholino-1,3,5-triazin-2yl)phenyl}ureido]benzoic acid To a stirred mixture of methyl 4-(3-(4-(4,6-dimorpholino-1,3,5-triazin-2-yl)phenyl)ureido)benzoate (1.4 g, 2.69 mmol), THF (10 mL), MeOH (5 mL) and H2O (2.5 mL) was added LiOH.H2O (339 mg, 8.07 mmol) then heated under reflux for 8 hrs. Concentrated and added H2O (5 mL) then acidified with 2N HCl. The solid was filtered washed with H2O and dried to give the product as a tan solid (1.3 g, 96% yield); MS (ESI) m/z=506.3

Example 68

Preparation of N-(2-(dimethylamino)ethyl)-4-(3-(4-(4,6-dimorpholino-1,3,5-triazin-2-yl)phenyl)ureido) benzamide To a stirred solution of 4-[3-{4-(4,6-dimorpholino-1,3,5-triazin-2yl)phenyl}ureido]benzoic acid (150 mg; 0.297 mmol), Hunig's base (303 µL, 1.782 mmol), HBTU (563 mg, 1.485 mmol) in 2 mL of NMP was stirred for 1 hr. at room temperature and added N',N'-dimethylethane-1,2-diamine (130 µL, 1.188 mmol) then stirred overnight. Added $CH_2Cl_2$ (40 mL) and washed with sat. NaHCO3 and H2O. Concentrated and purified by silica gel chromatography $CH_2Cl_2$:MeOH:7N NH3 in MeOH (10:1:0.22) to give the product as a white solid (98 mg, 57% yield); MS (ESI) m/z=576.4.

Example 68

Preparation N-(2-(dimethylamino)ethyl)-4-(3-(4-(4,6-dimorpholino-1,3,5-triazin-2-yl)phenyl)ureido) benzamide as an HCl salt To the N-(2-(dimethylamino)ethyl)-4-(3-(4-(4,6-dimorpholino-1,3,5-triazin-2-yl)phenyl)ureido)benzamide (72 mg, 0.125 mmol) and MeOH (1 mL) was added 4N HCl in dioxane (1 mL) and stirred for 3 hrs. The solid was filtered and washed with ether to give the product as a white solid (73 mg, yield=95%); MS (ESI) m/z=576.4.

Example 69

Preparation of 1-(4-(4,6-dimorpholino-1,3,5-triazin-2-yl)phenyl)-3-(4-(4-methylpiperazine-1-carbonyl) phenyl)urea hydrochloride To a stirred solution of 4-(3-(4-(4,6-dimorpholino-1,3,5-triazin-2yl)phenyl)ureido)benzoic acid (150 mg; 0.297 mmol), Hunig's base (303 µL, 1.782 mmol), HBTU (563 mg, 1.485 mmol) in 2 mL of NMP was reacted according to example 68 with 1-methylpiperazine (132 µL, 1.188 mmol) to give 1-(4-(4,6-dimorpholino-1,3,5-triazin-2-yl)phenyl)-3-(4-(4-methylpiperazine-1-carbonyl)phenyl)urea as a white solid (95 mg, 54% yield); MS (ESI) m/z=588.4.

To a 1-(4-(4,6-dimorpholino-1,3,5-triazin-2-yl)phenyl)-3-(4-(4-methylpiperazine-1-carbonyl)phenyl)urea (70 mg, 0.119 mmol) and MeOH (1 mL) was added 4N HCl in Dioxane (1 mL), stirred for 3 hrs. The solid was filtered and washed with ether to give the product as a white solid (74 mg, yield=100%).

Example 70

Preparation of 4-(3-(4-(4,6-dimorpholino-1,3,5-triazin-2-yl)phenyl)ureido)-N-methylbenzamide To the stirred solution of 4-(3-(4-(4,6-dimorpholino-1,3,5-triazin-2yl)phenyl)ureido)benzoic acid (150 mg; 0.297 mmol), Hunig's base (303 µL, 1.782 mmol), HBTU (563 mg, 1.485 mmol) in 2 mL of NMP was reacted according to example 68 with methylamine (594 µL, 2M solution. in THF) to give the product as a white solid (118 mg, 77% yield); MS (ESI) m/z=519.3.

Example 71

Preparation of N-(2-(dimethylamino)ethyl)-4-(3-(4-(4,6-dimorpholino-1,3,5-triazin-2-yl)phenyl)ureido)-N-methylbenzamide hydrochloride To the stirred solution of 4-(3-(4-(4,6-dimorpholino-1,3,5-triazin-2yl)phenyl)ureido)benzoic acid (150 mg; 0.297 mmol), Hunig's base (303 µL, 1.782 mmol), HBTU (563 mg, 1.485 mmol) in 2 mL of NMP was reacted according to example 68 with N1,N1,N2-trimethylethane-1,2-diamine (154 µL, 1.188 mmol) to give N-(2-(dimethylamino)ethyl)-4-(3-(4-(4,6-dimorpholino-1,3,5-triazin-2-yl)phenyl)ureido)-N-methylbenzamide as a white solid (88 mg, 50% yield); MS (ESI) m/z=590.2.

To the N-(2-(dimethylamino)ethyl)-4-(3-(4-(4,6-dimorpholino-1,3,5-triazin-2-yl)phenyl)ureido)-N-methylbenzamide (55 mg, 0.127 mmol) and MeOH (1 mL) was added 4N HCl in Dioxane (1 mL) and stirred for 3 hrs. The solid was filtered and washed with ether to give the product as a white solid (70 mg, yield=88%).

Example 72

Preparation of 1-(4-(4,6-dimorpholino-1,3,5-triazin-2-yl)phenyl)-3-(4-(4-morpholinopiperidine-1-carbonyl)phenyl)urea To the stirred solution of 4-(3-(4-(4,6-dimorpholino-1,3,5-triazin-2yl)phenyl)ureido)benzoic acid (50 mg; 0.099 mmol), Hunig's base (103 µL, 0.594 mmol), HBTU (188 mg, 0.495 mmol) in 1 mL of NMP was reacted according to example 68 with 4-(piperidin-4-yl)morpholine (67 mg, 0.396 mmol). Evaporated the solvent and purified by HPLC to give the product (40.1 mg, 62% yield); MS (ESI) m/z=658.7

Example 73

Preparation of 4-(3-(4-(4,6-dimorpholino-1,3,5-triazin-2-yl)phenyl)ureido)-N-(quinuclidin-3-yl)benzamide To the solution of 4-(3-(4-(4,6-dimorpholino-1,3,5-triazin-2yl)phenyl)ureido)benzoic acid (50 mg; 0.099 mmol), Hunig's base (103 µL, 0.594 mmol), HBTU (188 mg, 0.495 mmol) in 2 mL of NMP was reacted according to according to example 68 with quinuclidin-3-amine (79 mg, 0.396 mmol). Evaporated the solvent and purified by HPLC to give the product (24.3 mg, 40% yield); MS (ESI) m/z=614.7

Example 74

Preparation of 1-(4-(4,6-dimorpholino-1,3,5-triazin-2-yl)phenyl)-3-(4-(4-(pyrrolidin-1-yl)piperidine-1-carbonyl)phenyl)urea To the solution of 4-(3-(4-(4,6-dimorpholino-1,3,5-triazin-2yl)phenyl)ureido)benzoic acid (50 mg; 0.099 mmol), Hunig's base (103 µL, 0.594 mmol), HBTU (188 mg, 0.495 mmol) in 2 mL of NMP was reacted according to example 68 with 4-[1-pyrrolidinyl]piperidine (61 mg, 0.396 mmol). Evaporated the solvent and purified by HPLC to give the product as a white solid (37 mg, 58% yield); MS (ESI) m/z=642.7

Example 75

Preparation of 1-(4-(1,4'-bipiperidine-1'-carbonyl)phenyl)-3-(4-(4,6-dimorpholino-1,3,5-triazin-2-yl)phenyl)urea To the solution of 4-(3-(4-(4,6-dimorpholino-1,3,5-triazin-2yl)phenyl)ureido)benzoic acid (50 mg; 0.099 mmol), Hunig's base (103 µL, 0.594 mmol), HBTU (188 mg, 0.495 mmol) in 2 mL of NMP was reacted according to example 68 with 1,4'-bipiperidine (67 mg, 0.396 mmol). Evaporated the solvent and purified by HPLC to give the product as a white solid (39 mg, 60% yield); MS (ESI) m/z=656.8.

Example 76

Preparation of 1-(4-(4-(dimethylamino)piperidine-1-carbonyl)phenyl)-3-(4-(4,6-dimorpholino-1,3,5-triazin-2-yl)phenyl)urea To the solution of 4-(3-(4-(4,6-dimorpholino-1,3,5-triazin-2yl)phenyl)ureido)benzoic acid (50 mg; 0.099 mmol), Hunig's base (103 µL, 0.594 mmol), HBTU (188 mg, 0.495 mmol) in 2 mL of NMP was reacted according to example 68 with N,N-dimethylpiperidin-4-amine (51 mg, 0.396 mmol). Evaporated the solvent and purified by HPLC to give the product (30.6 mg, 52% yield); MS (ESI) m/z=616.7

Example 77

Preparation of 1-(4-(4,6-dimorpholino-1,3,5-triazin-2-yl)phenyl)-3-(4-(piperazine-1-carbonyl)phenyl)urea To the solution of 4-(3-(4-(4,6-dimorpholino-1,3,5-triazin-2yl)phenyl)ureido)benzoic acid (50 mg; 0.099 mmol), Hunig's base (103 µL, 0.594 mmol), HBTU (188 mg, 0.495 mmol) in 2 mL of NMP was reacted according to example 68 with piperazine (34 mg, 0.396 mmol). Evaporated the solvent and purified by HPLC to give the product (17.2 mg, 30% yield); MS (ESI) m/z=573.6

Example 78

Preparation of 1-(4-(4,6-dimorpholino-1,3,5-triazin-2-yl)phenyl)-3-(4-(2-(pyridin-2-yl)acetyl)phenyl)urea To the solution of 4-(3-(4-(4,6-dimorpholino-1,3,5-triazin-2yl)phenyl)ureido)benzoic acid (50 mg; 0.099 mmol), Hunig's base (103 µL, 0.594 mmol), HBTU (188 mg, 0.495 mmol) in 2 mL of NMP was reacted according to example 68 with pyridin-2-ylmethanamine (43 mg, 0.396 mmol). Evaporated the solvent and purified by HPLC to give the product (9 mg, 15% yield); MS (ESI) m/z=596.6.

Preparation of 3-(4,6-dichloro-1,3,5-triazin-2-yl)-8-oxa-3-azabicyclo[3.2.1]octane To a solution of cyanuric chloride (2.00 g, 10.85 mmoles) in acetone (20 mL) and water (10 mL) at 0° C. was added a solution of 8-oxa-3-azabicyclo[3.2.1]octane hydrochloride (1.46 g, 9.76 mmoles) in saturated aqueous NaHCO3 (25 mL) and acetone (25 mL) via addition funnel over 15 minutes. The reaction was stirred at 0° C. for 2 hours, then filtered to collect a white precipitate. The precipitate was washed with water (25 mL) and dried. The crude product was purified by column chromatography (30:70 ethyl acetate in hexanes) to provide 3-(4,6-dichloro-1,3,5-triazin-2-yl)-8-oxa-3-azabicyclo [3.2.1]octane (1.55 g) as a white solid.

Procedure to prepare 3-(4-chloro-6-(substituted amino)-1,3,5-triazin-2-yl)-8-oxa-3-azabicyclo[3.2.1] octane To a solution of 3-(4,6-dichloro-1,3,5-triazin-2-yl)-8-oxa-3-azabicyclo[3.2.1]octane (0.085 g, 0.33 mmoles) and Na2CO3 (0.041 g, 0.39 mmoles) in acetone (1 mL) and water (1 mL) was added the desired amine (0.36 mmoles). The solution was heated to 55° C. and stirred for 2 hours then concentrated to provide crude amino-triazine, which was used directly without purification.

Following this procedure, the following compounds were prepared.

3-(4-chloro-6-(piperidin-1-yl)-1,3,5-triazin-2-yl)-8-oxa-3-azabicyclo[3.2.1]octane (310.3, M+H)

3-(4-chloro-6-(pyrrolidin-1-yl)-1,3,5-triazin-2-yl)-8-oxa-3-azabicyclo[3.2.1]octane (296.3, M+H)

t-butyl 2-(4-(8-oxa-3-azabicyclo[3.2.1]octan-3-yl)-6-chloro-1,3,5-triazin-2-ylamino)ethylcarbamate (385.3, M+H)

2-(4-(8-oxa-3-azabicyclo[3.2.1]octan-3-yl)-6-chloro-1,3,5-triazin-2-ylamino)ethanol (286.3, M+H)

4-(8-oxa-3-azabicyclo[3.2.1]octan-3-yl)-6-chloro-N-phenyl-1,3,5-triazin-2-amine (318.3, M+H)

4-(8-oxa-3-azabicyclo[3.2.1]octan-3-yl)-6-chloro-N-cyclohexyl-1,3,5-triazin-2-amine (324.3, M+H)

t-butyl 3-(4-(8-oxa-3-azabicyclo[3.2.1]octan-3-yl)-6-chloro-1,3,5-triazin-2-ylamino)azetidine-1-carboxylate (397.3, M+H)

Method to prepare 4-(4-(8-oxa-3-azabicyclo[3.2.1]octan-3-yl)-6-(substituted amino)-1,3,5-triazin-2-yl)aniline A suspension of bis-amino triazine chloride (0.33 mmoles) in toluene (2 mL), ethanol (2 mL), and 2M aqueous Na2CO3 (0.700 mL) in a microwave vial was sparged with N2 for 5 minutes. Pd(PPh3)4 (0.021 mgs, 0.018 mmoles) and 4-aminophenylboronic acid pinacol ester (0.094 mgs, 0.43 mmoles) were added and the vial was sealed and heated to 110° C. for 1 hour. The mixture was cooled and filtered through Celite™. The filter cake was washed with ethyl acetate and the filtrate was washed with brine, dried, and concentrated. The crude material was purified by HPLC (Waters system, 5-70% CH3CN in H2O w/0.05% NH4OH) to provide the aryl-substituted triazine compounds. Following this procedure, the following compounds were prepared.

4-(4-(8-oxa-3-azabicyclo[3.2.1]octan-3-yl)-6-(piperidin-1-yl)-1,3,5-triazin-2-yl)aniline (367.4, M+H)

4-(4-(8-oxa-3-azabicyclo[3.2.1]octan-3-yl)-6-(pyrrolidin-1-yl)-1,3,5-triazin-2-yl)aniline (353.3, M+H)

2-(4-(4-aminophenyl)-6-(8-oxa-3-azabicyclo[3.2.1]octan-3-yl)-1,3,5-triazin-2-ylamino)ethanol (343.3, M+H)

4-(4-aminophenyl)-6-(8-oxa-3-azabicyclo[3.2.1]octan-3-yl)-N-phenyl-1,3,5-triazin-2-amine (375.3, M+H)

4-(4-aminophenyl)-6-(8-oxa-3-azabicyclo[3.2.1]octan-3-yl)-N-cyclohexyl-1,3,5-triazin-2-amine (381.4, M+H)

t-butyl 3-(4-(4-aminophenyl)-6-(8-oxa-3-azabicyclo[3.2.1]octan-3-yl)-1,3,5-triazin-2-ylamino)azetidine-1-carboxylate; (454.4, M+H)

Procedure to prepare 1-(4-(4-(8-oxa-3-azabicyclo[3.2.1]octan-3-yl)-6-(substituted amino)-1,3,5-triazin-2-yl)phenyl)-3-(pyridin-4-yl)urea A solution of triphosgene (0.034 mgs, 0.114 mmoles) in CH$_2$Cl$_2$ (1 mL) was prepared. A solution of the desired triazine aniline derivative (0.23 mmoles) in CH$_2$Cl$_2$ (1 mL) and triethylamine (0.095 mL, 0.68 mmoles) was added and the reaction was allowed to stir at room temperature for 15 minutes. A solution of 4-aminopyridine (0.043 mgs, 0.46 mmoles) in THF (1 mL) was then added and the solution was stirred at room temperature for 3 hours, then concentrated and purified by HPLC (Waters system, 5-70% CH3CN in H2O w/0.05% NH4OH) to provide the 1-(4-(4-(8-oxa-3-azabicyclo[3.2.1]octan-3-yl)-6-(substituted amino)-1,3,5-triazin-2-yl)phenyl)-3-(pyridin-4-yl)urea derivatives. The following compounds were prepared by this procedure:

Example 79

Preparation of 1-(4-(4-(8-oxa-3-azabicyclo[3.2.1]octan-3-yl)-6-(piperidin-1-yl)-1,3,5-triazin-2-yl)phenyl)-3-(pyridin-4-yl)urea 487.2, M+H.

Example 80

Preparation of 1-(4-(4-(8-oxa-3-azabicyclo[3.2.1]octan-3-yl)-6-(pyrrolidin-1-yl)-1,3,5-triazin-2-yl)phenyl)-3-(pyridin-4-yl)urea 474.2, M+H.

Example 81

Preparation of 1-[4-(4,6-dimorpholin-4-yl-1,3,5-triazin-2-yl)phenyl]-3-[4-(1-hydroxyethyl)phenyl]urea To a stirred mixture of 4-(4,6-dimorpholin-4-yl-1,3,5-triazin-2-yl)aniline (0.140, 0.40 mmoles) in methylene chloride at 0° C. was added triphosgene (0.25, 0.84 mmoles) and Et3N (3 mL). The reaction mixture was stirred for 20 minutes at 0° C. Then 1-(4-aminophenyl)ethanol (0.10 g, 0.73 mmoles) was added to the mixture. The reaction mixture was stirred for about 16 hours at room temperature. The solvent was removed. The residue was dissolved in DMSO and place at HPLC using acetonitrile buffer TFA to give 48 mg (24%) of [4-(4,6-dimorpholin-4-yl-1,3,5-triazin-2-yl)phenyl]-3-[4-(1-hydroxyethyl)phenyl]urea. M+H 506.4.

Example 82

Preparation of 1-[4-(4,6-dimorpholin-4-yl-1,3,5-triazin-2-yl)phenyl]-3-(2-methylpyridin-4-yl)urea Starting from 4-(4,6-dimorpholin-4-yl-1,3,5-triazin-2-yl)aniline (0.140, 0.40 mmoles) and 2-methyl-4-aminopyridine (80 mg, 0.73 mmol) and following the procedure as outlined in Example 81, 1-[4-(4,6-dimorpholin-4-yl-1,3,5-triazin-2-yl)phenyl]-3-(2-methylpyridin-4-yl)urea was isolated by HPLC purification. Yield: 60 mg, 27%; MS (ESI) m/z=477.3.

Example 83

Preparation of 1-[4-(4,6-dimorpholin-4-yl-1,3,5-triazin-2-yl)phenyl]-3-[4-(hydroxymethyl)phenyl]urea Starting from 4-(4,6-dimorpholin-4-yl-1,3,5-triazin-2-yl)aniline (0.140, 0.40 mmoles) and 4-aminophenylmethanol (100 mg, 0.81 mmol) and following the procedure described in example 81, 1-[4-(4,6-dimorpholin-4-yl-1,3,5-triazin-2- yl)phenyl]-3-[4-(hydroxymethyl)-phenyl]urea was isolated by HPLC purification. Yield: 58 mg, 26%; MS (ESI) m/z=492.3.

Example 84

Preparation of 1-[4-(4,6-dimorpholin-4-yl-1,3,5-triazin-2-yl)phenyl]-3-[4-hydroxyphenyl]urea Starting from 4-(4,6-dimorpholin-4-yl-1,3,5-triazin-2-yl)aniline (0.140, 0.40 mmoles) and 4-aminophenol (89 mg, 0.81 mmol) and following the procedure as outlined in example 81, 1-[4-(4,6-dimorpholin-4-yl-1,3,5-triazin-2-yl)phenyl]-3-[4-hydroxyphenyl]urea was isolated by HPLC purification. Yield: 62 mg, 16%; MS (ESI) m/z=478.2.

Example 85

Preparation of 1-[4-(4,6-dimorpholin-4-yl-1,3,5-triazin-2-yl)phenyl]-3-[4-(trifluoromethyl)phenyl]urea Starting from 4-(4,6-dimorpholin-4-yl-1,3,5-triazin-2-yl)aniline (0.140, 0.40 mmoles) and 4-trifluoromethylaniline (100 mg, 0.62 mmol) and following the procedure as outlined in example 81, 1-[4-(4,6-dimorpholin-4-yl-1,3,5-triazin-2-yl)phenyl]-3-[4-(trifluoromethyl)phenyl]urea was isolated by HPLC purification. Yield: 25 mg, 13%; MS (ESI) m/z=430.2.

Example 86

Preparation of 1-[4-(4,6-dimorpholin-4-yl-1,3,5-triazin-2-yl)phenyl]-3-{4-[2,2,2-trifluoro-1-hydroxy-1-(trifluoromethyl)ethyl]phenyl}urea Starting from 4-(4,6-dimorpholin-4-yl-1,3,5-triazin-2-yl)aniline (0.140, 0.40 mmoles) and 4-trifluoromethylaniline (140 mg, 0.40 mmol) and following the procedure as outlined in example 81, 1-[4-(4,6-dimorpholin-4-yl-1,3,5-triazin-2-yl)phenyl]-3-{4-[2,2,2-trifluoro-1-hydroxy-1-(trifluoromethyl)ethyl]phenyl}urea was isolated by HPLC purification. Yield: 40 mg, 16%; MS (ESI) m/z=628.3.

Example 87

Preparation of 1-[4-(4,6-dimorpholin-4-yl-1,3,5-triazin-2-yl)phenyl]-3-[5-(trifluoromethyl)pyridin-2-yl]urea Starting from 4-(4,6-dimorpholin-4-yl-1,3,5-triazin-2-yl)aniline (0.160, 0.47 mmoles) and 2-amino-5-trifluorophenylpyridine (100 mg, 0.61 mmol) and following the procedure as outlined in example 81, 1-[4-(4,6-dimorpholin-4-yl-1,3,5-triazin-2-yl)phenyl]-3-[5-(trifluoromethyl)pyridin-2-yl]urea was isolated by HPLC purification. Yield: 10 mg, 4.1%; MS (ESI) m/z=531.3.

Example 88

Preparation of 1-[4-(4,6-dimorpholin-4-yl-1,3,5-triazin-2-yl)phenyl]-3-[3-(1-hydroxyethyl)phenyl]urea Starting from 4-(4,6-dimorpholin-4-yl-1,3,5-triazin-2-yl)aniline (0.160, 0.47 mmoles) and 1-(3-aminophenyl)ethanol (100 mg, 0.73 mmoles) and following the procedure as outlined in example 81, 1-[4-(4,6-dimorpholin-4-yl-1,3,5-triazin-2-yl)phenyl]-3-[3-(1-hydroxyethyl)phenyl]urea was isolated by HPLC purification. Yield: 10 mg, 4.1%; MS (ESI) m/z=531.3.

Example 89

Preparation of 1-(4-{4-[(3S)-3-methylmorpholin-4-yl]-6-morpholin-4-yl-1,3,5-triazin-2-yl}phenyl)-3-pyridin-4-ylurea Step 1: Preparation of 2-chloro-4-[(3S)-3-methylmorpholin-4-yl]-6-morpholin-4-yl-1,3,5-triazine To a stirred solution of dichoromonomorpholino derivative of 1,3,5-triazine (2.0 g, 8.5 mmoles) in methylene chloride 200 mL, was added 3S-3-methylmorpholine (0.85 g, 8.5 mmoles) combined with two equivalents of triethylamine 1.7 mL dropwise manner. After the addition reaction mixture was stirred at room temperature for 3 hours and quenched with water. The aqueous layer was washed well with water; dried over anhydrous MgSO$_4$ and filtered. The solvent was evaporated and the residue obtained was triturated with diethyl ether/hexane (1:1) and filtered. The solid was used without further purification. (1.0 g, 40% yield). M+H 357.3.

Step 2: Preparation of 4-{4-[(3S)-3-methylmorpholin-4-yl]-6-morpholin-4-yl-1,3,5-triazin-2-yl}aniline A mixture of 2-chloro-4-[(3S)-3-methylmorpholin-4-yl]-6-morpholin-4-yl-1,3,5-triazine (1.26, 4.2 mmol), sodium carbonate solution (2M, 2 mL), tetrakis palladium triphenylphosphine 70 mg (catalytic amount) and 4-aminophenyl boronic pinacol ester (1.37 g, 6.3 mmoles) in DME (100 mL) was heated to reflux for 24 hours. The solvent was evaporated, the residue was re-dissolved in methylene chloride and filtered through Celite™. The solvent was evaporated and the residue was chromatographed on silica gel eluting with first 26/4 hexanes/ethyl acetate then increased to 1/1 hexanes ethyl acetate to give 1.0 of 4-{4-[(3S)-3-methylmorpholin-4-yl]-6-morpholin-4-yl-1,3,5-triazin-2-yl}aniline (71% yield); M+H 357.2.

Step 3: Preparation of 1-(4-{4-[(3S)-3-methylmorpholin-4-yl]-6-morpholin-4-yl-1,3,5-triazin-2-yl}phenyl)-3-pyridin-4-ylurea Starting from 4-{4-[(3S)-3-methylmorpholin-4-yl]-6-morpholin-4-yl-1,3,5-triazin-2-yl}aniline (0.160, 0.44 mmoles) and 4-aminopyridine (100 mg, 1.06 mmoles) and following the procedure as outlined in example 81, 1-(4-{4-[(3S)-3-methylmorpholin-4-yl]-6-morpholin-4-yl-1,3,5-triazin-2-yl}phenyl)-3-pyridin-4-ylurea was isolated by HPLC purification. Yield: 125 mg, 60%; MS (ESI) m/z 477.3.

Example 90

Preparation of 1-[4-(2-hydroxyethyl)phenyl]-3-(4-{4-[(3S)-3-methylmorpholin-4-yl]-6-morpholin-4-yl-1,3,5-triazin-2-yl}phenyl)urea Starting from 4-{4-[(3S)-3-methylmorpholin-4-yl]-6-morpholin-4-yl-1,3,5-triazin-2-yl}aniline (0.160, 0.44 mmoles) and 4-(1-hydroxyethyl)aniline (137 mg, 1 mmole) and following the procedure described in example 81, 1-[4-(2-hydroxyethyl)phenyl]-3-(4-{4-[(3S)-3-methylmorpholin- 4-yl]-6-morpholin-4-yl-1,3,5-triazin-2-yl}phenyl)urea was isolated by HPLC purification. Yield: 125 mg, 60%; MS (ESI) m/z 519.6

Example 91

Preparation of 1-[4-(2-hydroxymethyl)phenyl]-3-(4-{4-[(3S)-3-methylmorpholin-4-yl]-6-morpholin-4-yl-1,3,5-triazin-2-yl}phenyl)urea Starting from 4-{4-[(3S)-3-methylmorpholin-4-yl]-6-morpholin-4-yl-1,3,5-triazin-2-yl}aniline (0.160, 0.44 mmoles) and 4-aminophenylmethanol (0.10 g, 0.81 mmoles) and following the procedure as outlined in example 81, 1-[4-(2-hydroxymethyl)phenyl]-3-(4-{4-[(3S)-3-methylmorpholin-4-yl]-6-morpholin-4-yl-1,3,5-triazin-2-yl}phenyl)urea was isolated by HPLC purification. Yield: 55 mg, 16%; MS (ESI) m/z 506.3.

Example 92

Preparation of 1-(4-{4-[(3S)-3-methylmorpholin-4-yl]-6-morpholin-4-yl-1,3,5-triazin-2-yl}phenyl)-3-(2-methylpyridin-4-yl)urea Starting from 4-{4-[(3S)-3-methylmorpholin-4-yl]-6-morpholin-4-yl-1,3,5-triazin-2-yl}aniline (0.160, 0.44 mmoles) and 2-methyl-4-aminopyridine (0.10 g, 0.92 mmoles) and following the procedure as outlined in example 81, 1-(4-{4-[(3S)-3-methylmorpholin-4-yl]-6-morpholin-4-yl-1,3,5-triazin-2-yl}phenyl)-3-(2-methylpyridin-4-yl)urea was isolated by HPLC purification. Yield: 75 mg, 36%; MS (ESI) m/z 491.3.

Example 93

Preparation of 1-[4-(1-hydroxyethyl)phenyl]-3-(4-{4-[(3S)-3-methylmorpholin-4-yl]-6-morpholin-4-yl-1,3,5-triazin-2-yl}phenyl)urea Starting from 4-{4-[(3S)-3-methylmorpholin-4-yl]-6-morpholin-4-yl-1,3,5-triazin-2-yl}aniline (0.160, 0.44 mmoles) and 1-(4-aminophenyl)ethanol (126 mg, 0.92 mmoles) and following the procedure as outlined in example 81, 1-[4-(1-hydroxyethyl)phenyl]-3-(4-{4-[(3S)-3-methylmorpholin-4-yl]-6-morpholin-4-yl-1,3,5-triazin-2-yl}phenyl)urea was isolated by HPLC purification. MS (ESI) m/z 519.6.

Example 94

Preparation of 1-[4-(4-isopropoxy-6-morpholin-4-yl-1,3,5-triazin-2-yl)phenyl]-3-pyridin-4-ylurea Step 1: To a stirred solution of isopropanol (250 mg, 4.1 mmol) in dry THF (50 ml) at −78° C., n-butyllithium (2.6 ml, 1.6 mol solution) was slowly added. The reaction mixture was stirred for 30 minutes and a solution of 2,4-dichloro-6-morpholin-4-yl-[1,3,5]triazine (1.00 g, 4.25 mmol) in THF was added to the solution. The reaction mixture was stirred at room temperature for 24 hours and quenched with water and extracted with DCM. The crude product obtained was taken to next step without purification.

Step 2: A mixture of (crude) 4-(chloro-6-isopropoxyl-1,2,3-triazin-2yl)morpholine of (2.91 g, 11.27 mmol) 4-aminophenylboronic acid pinacol ester (3.59 g, 16.4 mmoles), tetrakis palladium triphenylphosphine (120 mg catalytic amount) and sodium carbonate solution (2M, 2 mL) was refluxed in DME (100 mL) for 24 hours. The solvent was removed and the residue was re-dissolved in methylene chloride and filtered through Celite™. The solvent was evaporated and the residue was chromatographed on silica gel eluting with first 26:4 hexane:ethyl acetate then increased to 1/1 hexanes ethyl acetate to give 0.65 g (yield 18%) of 4-(4-isopropoxy-6-morpholino-1,3,5-triazin-2-yl)aniline. M+H 316.3.

Step 3: Starting from 4-(4-isopropoxy-6-morpholino-1,3,5-triazin-2-yl)aniline (0.140, 0.44 mmoles) and 4-aminopyridine (100 mg, 1.06 mmoles) and following the procedure as outlined in example 81, 1-[4-(4-(4-isopropoxy-6-morpholin-4-yl-1,3,5-triazin-2-yl)phenyl]-3-pyridin-4-ylurea was isolated by HPLC purification. Yield: 15 mg, 7.8%; MS (ESI) m/z=436.3.

Example 95

Preparation of methyl 4-({[4-(4-isopropoxy-6-morpholin-4-yl-1,3,5-triazin-2-yl)phenyl]carbamoyl}amino)benzoate A mixture of 4-(4-isopropoxy-6-morpholino-1,3,5-triazin-2-yl)aniline (1.3 g, 4.1 mmol), triethylamine (2 ml) and 4-carbomethoxy-phenylisocyanate (1451 mg, 8.2 mmol) was stirred for 48 hours and quenched with water and washed well. The organic layer was dried and filtered. It was concentrated and purified by column chromatography by eluting it initially with 10% ethyl acetate: hexane and latter with 40% ethyl acetate:hexane. White solid; 600 mg, 30%; MS (ESI) m/z 492.5.

Example 96

Preparation of 1-[4-(4-isopropoxy-6-morpholin-4-yl-1,3,5-triazin-2-yl)phenyl]-3-{4-[(4-methylpiperazin-1-yl)carbonyl]phenyl}urea Starting from methyl 4-({[4-(4-isopropoxy-6-morpholin-4-yl-1,3,5-triazin-2-yl)phenyl]carbamoyl}amino)benzoic acid (160 mg, 0.33 mmol) and 4-methylpiperazine following the procedure as outlined in Experimental 71, 80 mg (44% Yield) of the titled compound was isolated as white solid. MS (ESI) m/z 281.2.

Example 97

Preparation of 4-({[4-(4-isopropoxy-6-morpholin-4-yl-1,3,5-triazin-2-yl)phenyl]carbamoyl}amino)-N-(1-methylpiperidin-4-yl)benzamide Starting from methyl 4-({[4-(4-isopropoxy-6-morpholin-4-yl-1,3,5-triazin-2-yl)phenyl]carbamoyl}amino)benzoic acid (200 mg, 0.42 mmol) and 4-amino-1-methylpiperidine following the procedure as outlined in Experimental 71, 65 mg (27% Yield) of the titled compound was isolated as white solid. MS (ESI) m/z 574.68.

Example 98

Preparation of 1-[4-(4,6-dimorpholin-4-yl-1,3,5-triazin-2-yl)phenyl]-3-(1-methylpiperidin-4-yl)urea Starting from 4-(4,6-dimorpholin-4-yl-1,3,5-triazin-2-yl)aniline (140 mg 0.40 mmoles) and 4-amino-1-methylpiperidine (70 mg, 0.62 mmol) and following the procedure as outlined in example 1, step 3, 20 mg (10% Yield) of the final compound was isolated as a solid. MS (ESI) m/z=483.4

Example 99

Preparation of 1-(4-{4-[(3S)-3-methylmorpholin-4-yl]-6-morpholin-4-yl-1,3,5-triazin-2-yl}phenyl)-3-(1-methylpiperidin-4-yl)urea Starting from 4-{4-[(3S)-3-methylmorpholin-4-yl]-6-morpholin-4-yl-1,3,5-triazin-2-yl}aniline (0.140, 0.39 mmoles) and 4-amino-1-methylpiperidine (70 mg, 0.62 mmol) and following the procedure as outlined in example 81, the titled product was prepared and purified by HPLC.
Yield: 120 mg, 40%; 497.4.

Example 100

Preparation of 1-{4-[4-(3,6-Dihydro-2H-pyran-4-yl)-6-morpholin-4-yl-[1,3,5]triazin-2-yl]-phenyl}-3-pyridin-4-yl-urea Step 1: Preparation of 2-Chloro-4-(3,6-dihydro-2H-pyran-4-yl)-6-morpholin-4-yl-[1,3,5]triazine In a three necked flask under nitrogen equipped was dissolved 2,4-dichloro-6-morpholin-4-yl-[1,3,5]triazine (610 mg, 2.6 mmol), tributyldihydropyranylstanane (1.45 g, 3.89 mmol, 1.5 eq), and $(Ph_3P)_2PdCl_2$ (150 mg, 0.21 mmol, 0.1 eq) in anhydrous dioxan (5 ml). The reaction mixture was heated under stirring to 90° C. for 16 hrs. For purification silica gel (10 g) was added to the mixture and the solvent was removed to let the product adsorbed on the silica gel. The silica gel plug was placed on a column and the mixture was flash chromatographed with hexane:ethyl acetate (10:1) to give after removal solvent the product as off white solid (345 mg=47% yield); MS (ESI) m/z 281.

Step 2: Preparation of 4-[4-(3,6-Dihydro-2H-pyran-4-yl)-6-morpholin-4-yl-[1,3,5]triazin-2-yl]-phenylamine To a microwave processing tube was added dimethoxyethane (4 mL), aqueous $Na_2CO_3$ (2 molar) (1 mL, 2 mmol, 2 eq), $(Ph_3P)_4Pd$ (101 mg, 0.088 mmol), 4-anilinoboronic acid or ester (581 mg, 2.65 mmol, 1.5 eq) and the 2-chloro-4-(3,6-dihydro-2H-pyran-4-yl)-6-morpholin-4-yl-[1,3,5]triazine (500 mg, 1.76 mmol) and the vessel was sealed. The mixture was heated to 140° C. for 60 minutes. The solvents were distilled and the crude compound was purified by silica gel chromatography using $CH_2Cl_2$/ethyl acetate (10:1) and later $CH_2Cl_2$/MeOH/NH3 (20:1:0.1) to give the product as a off-white solid (520 mg, 87% yield); MS (ESI) m/z 340.2

Step 3: Preparation of 1-{4-[4-(3,6-Dihydro-2H-pyran-4-yl)-6-morpholin-4-yl-[1,3,5]triazin-2-yl]-phenyl}-3-pyridin-4-yl-urea To a stirred solution of triphosgene (140 mg, 0.47 mmol) in $CH_2Cl_2$ (6 mL) was added 4-[4-(3,6-dihydro-2H-pyran-4-yl)-6-morpholin-4-yl-[1,3,5]triazin-2-yl]-phenylamine (200 mg, 0.59 mmol) at 25° C. The reaction mixture was stirred for 15 min and 4-aminopyridine (166 mg, 1.77 mmol) and $NEt_3$ (814 µL, 5.89 mmol) were added and the reaction mixture was stirred for additional 1 hr. The solvents were distilled and the crude mixture was purified by semi-prep-HPLC (TFA-method) to give 1-{4-[4-(3,6-dihydro-2H-pyran-4-yl)-6-morpholin-4-yl-[1,3,5]triazin-2-yl]-phenyl}-3-pyridin-4-yl-urea (75 mg, 22% yield); MS (ESI) m/z 460

Example 101

Preparation of 1-{4-[4-Morpholin-4-yl-6-(tetrahydro-pyran-4-yl)-[1,3,5]triazin-2-yl]-phenyl}-3-pyridin-4-yl-urea 1-{4-[4-(3,6-dihydro-2H-pyran-4-yl)-6-morpholin-4-yl-[1,3,5]triazin-2-yl]-phenyl}-3-pyridin-4-yl-urea (130 mg, 0.28 mmol) and Pd—C (10%, wet) (113 mg) were suspended in methanol/THF/$CH_2Cl_2$ (4:1:1) (30 mL) and hydrogenated (at 1 atm pressure) for 3 h. After completion, the catalyst was removed by filtration over Celite™ and the solvents were removed in vacuo to obtain the crude product, which was purified by semi-prep-HPLC (TFA-method), to give (32 mg=20% yield) of 1-{4-[4-Morpholin-4-yl-6-(tetrahydro-pyran-4-yl)-[1,3,5]triazin-2-yl]-phenyl}-3-pyridin-4-yl-urea; MS (ESI) m/z 462.

Example 102

Preparation of 1-{4-[4-(8-methyl-8-aza-bicyclo[3.2.1]oct-3-yloxy)-6-morpholin-4-yl-[1,3,5]triazin-2-yl]-phenyl}-3-pyridin-4-yl-urea Step 1: Preparation of 3-(4-Chloro-6-morpholin-4-yl-[1,3,5]triazin-2-yloxy)-8-methyl-8-aza-bicyclo[3.2.1]octane In a three neck flask equipped with stirring bar under $N_2$ atmosphere tropine (1 g, 4.24 mmol) was suspended in (anhydrous) THF (15 mL). The mixture was cooled to −78° C. and BuLi (2M in THF) (5.53 ml, 1.2 eq) was added dropwise and the mixture was allowed to warm to 25° C. over 30 minutes. To the reaction mixture 2,4,-dichloro-6-morpholin-4-yl-[1,3,5]triazine (996 mg, 4.24, mmole) was added and allowed to stir overnight. For work up, ether (100 mL) was added. The organic layer was washed with water (20 mL) and brine (20 mL) and dried over $MgSO_4$. filtered and the solvents were removed to obtain a colorless oil. Further purification by flash-chromatography using $CH_2Cl_2$/MeOH/NH3 (15:1:0.1) gave the product as white solid (600 mg, 42% yield); MS (ESI) m/z 340

Step 2: Preparation of 4-[4-(8-Methyl-8-aza-bicyclo[3.2.1]oct-3-yloxy)-6-morpholin-4-yl-[1,3,5]triazin-2-yl]-phenylamine To a microwave processing tube was added dimethoxyethane (4 mL), aqueous Na2CO3 (2 molar) (1 mL, 2 mmol, 2 eq), (Ph3P)4Pd (85 mg, 0.074 mmol), 4-(4,4,5,5-tetramethyl-[1,3,2]dioxaborolan-2-yl)-phenylamine (482 mg, 2.21 mmol, 1.5 eq) and the 3-(4-chloro-6-morpholin-4-yl-[1,3,5]triazin-2-yloxy)-8-methyl-8-aza-bicyclo[3.2.1]octane (500 mg, 1.47 mmol) and the vessel was sealed. The mixture was heated to 140° C. for 60 minutes. The solvents were distilled and the crude compound was purified by silica gel chromatography using $CH_2Cl_2$/ethyl acetate (10:1) and later with $CH_2Cl_2$/MeOH/NH3 (10:1:0.1) to give the product as an off-white solid (300 mg, 51% yield); MS (ESI) m/z 369.

Step 3: Preparation of 1-{4-[4-(8-methyl-8-aza-bicyclo[3.2.1]oct-3-yloxy)-6-morpholin-4-yl-[1,3,5]triazin-2-yl]-phenyl}-3-pyridin-4-yl-urea To a stirred solution of triphosgene (60 mg, 0.20 mmol) in $CH_2Cl_2$ (3 mL) was added 4-[4-(8-Methyl-8-aza-bicyclo

[3.2.1]oct-3-yloxy)-6-morpholin-4-yl-[1,3,5]triazin-2-yl]-phenylamine (100 mg, 0.25 mmol) at 25° C. The reaction mixture was stirred for 15 min and 4-aminopyridine (70 mg, 0.75 mmol) and NEt₃ (346 µL, 2.5 mmol) were added and the reaction mixture was stirred for additional 1 hr. The solvents were removed and the crude mixture was purified by semi-prep-HPLC (NH3-method) to give 1-{4-[4-(8-methyl-8-aza-bicyclo[3.2.1]oct-3-yloxy)-6-morpholin-4-yl-[1,3,5]triazin-2-yl]-phenyl}-3-pyridin-4-yl-urea (28 mg, 22% yield); MS (ESI) m/z 517.

Example 103

Preparation of 4-(3-{4-[4-(8-Methyl-8-aza-bicyclo [3.2.1]oct-3-yloxy)-6-morpholin-4-yl-[1,3,5]triazin-2-yl]-phenyl}-ureido)-benzamide To a stirred solution of triphosgene (120 mg, 0.40 mmol) in CH₂Cl₂ (3 mL) was added 4-[4-(8-Methyl-8-aza-bicyclo [3.2.1]oct-3-yloxy)-6-morpholin-4-yl-[1,3,5]triazin-2-yl]-phenylamine (200 mg, 0.5 mmol) at 25° C. The reaction mixture was stirred for 15 min and 4-aminobenzamide (204 mg, 1.5 mmol) and NEt₃ (692 µL, 5 mmol) were added and the reaction mixture was stirred for additional 1 hr. The solvents were removed and the crude mixture was purified by semi-prep-HPLC (NH3-method) to give 4-(3-{4-[4-(8-Methyl-8-aza-bicyclo[3.2.1]oct-3-yloxy)-6-morpholin-4-yl-[1,3,5]triazin-2-yl]-phenyl}-ureido)-benzamide (42 mg, 15% yield) MS (ESI) m/z 559.

Example 104

Preparation of 3-({4-Morpholin-4-yl-6-[4-(3-pyridin-4-yl-ureido)-phenyl]-[1,3,5]triazin-2-ylamino}-methyl)-azetidine-1-carboxylic acid tert-butyl ester Step 1: Preparation of 3-[(4-Chloro-6-morpholin-4-yl-[1,3,5]triazin-2-ylamino)-methyl]-azetidine-1-carboxylic acid tert-butyl ester To a solution of the 3-aminomethyl-azetidine-1-carboxylic acid tert-butyl ester HCl salt (945 mg, 4.24 mmol) and NEt₃ (856 mg, 8.48 mmol) in THF (10 mL) at 0° C. was added a suspension of 2,4-dichloro-6-morpholin-4-yl-[1,3,5]triazine (996 mg, 4.24 mmol) at 0° C. The reaction mixture was stirred for another 1 hr at 0° C. and allowed to warm to 20° C. and stirred for 1-4 hrs to drive the reaction to completion. Silica gel (20 g) was added to the reaction mixture and the solvent was removed so that product was adsorbed on the silica gel. The silica gel plug was placed on top of a column to purify by flash chromatography using CH₂Cl₂/MeOH/NH3 (20:1:01) eluent. After unifying the product fraction, and evaporation of solvent, (750 mg, 46% yield) product was obtained as yellow solid; MS (ESI) m/z 385

Step 2: Preparation of 3-{[4-(4-Amino-phenyl)-6-morpholin-4-yl-[1,3,5]triazin-2-ylamino]-methyl}-azetidine-1-carboxylic acid tert-butyl ester To a microwave processing tube was added dimethoxyethane (15 mL), aqueous Na2CO3 (2 molar) (4 mL, 8 mmol, 2 eq), (Ph3P)4Pd (317 mg, 0.55 mmol), 4-(4,4,5,5-tetramethyl-[1,3,2]dioxaborolan-2-yl)-phenylamine (1.81 g, 8.30 mmol, 1.5 eq) and 3-[(4-Chloro-6-morpholin-4-yl-[1,3,5]triazin-2-ylamino)-azetidine-1-carboxylic acid tert-butyl ester (1.3 g, 5.53 mmol) and the vessel was sealed. The mixture was heated to 140° C. for 60 minutes. The solvents were removed and the crude compound was purified by silica gel chromatography using CH₂Cl₂/Ethyl acetate (10:1) and later CH₂Cl₂/MeOH/NH3 (15:1:0.1) to give the product as a off-white solid (1.3 g, 53% yield).

MS (ESI) m/z=442

Step 3: Preparation of 3-({4-Morpholin-4-yl-6-[4-(3-pyridin-4-yl-ureido)-phenyl]-[1,3,5]triazin-2-ylamino}-methyl)-azetidine-1-carboxylic acid tert-butyl ester To a stirred solution of triphosgene (269 mg, 0.90 mmol) in CH₂Cl₂ (5 mL) was added 3-{[4-(4-Amino-phenyl)-6-morpholin-4-yl-[1,3,5]triazin-2-ylamino]-methyl}-azetidine-1-carboxylic acid tert-butyl ester (500 mg, 1.13 mmol) at 25° C. The reaction mixture was stirred for 15 min and 4-aminopyridine (319 mg, 3.39 mmol) and NEt₃ (1.56 mL, 11.3 mmol) were added and the reaction mixture was stirred for additional 1 hr. The solvents were removed on a rotary evaporator and the crude mixture was purified by semi-prep-HPLC (TFA-method) to give 3-({4-Morpholin-4-yl-6-[4-(3-pyridin-4-yl-ureido)-phenyl]-[1,3,5]triazin-2-ylamino}-methyl)-azetidine-1-carboxylic acid tert-butyl ester (150 mg, 16% yield); MS (ESI) m/z 562.

Example 105

Preparation of 1-(4-{4-[(azetidin-3-ylmethyl)-amino]-6-morpholin-4-yl-[1,3,5]triazin-2-yl}-phenyl)-3-pyridin-4-yl-urea 3-({4-Morpholin-4-yl-6-[4-(3-pyridin-4-yl-ureido)-phenyl]-[1,3,5]triazin-2-ylamino}-methyl)-azetidine-1-carboxylic acid tert-butyl ester (100 mg, 0.18 mmol) was dissolved CH₂Cl₂ (1 mL) and TFA (1 mL) was added. It was stirred for 16 hrs at 25° C. and then the solvents were removed under reduced pressure and the residue was treated with acetonitrile/MeOH (1:1) (2 mL) to obtain a white solid, which was collected by filtration to obtain the product as bis-TFA salt (59 mg, 46% yield). MS (ESI) m/z 462.

Example 106

Preparation of Tert-butyl 4-(4-(8-oxa-3-azabicyclo [3.2.1]octan-3-yl)-6-(4-(3-pyridin-4-ylureido)phenyl)-1,3,5-triazin-2-yl)piperazine-1-carboxylate Tert-butyl 4-(4,6-dichloro-1,3,5-triazin-2-yl)piperazine-1-carboxylate was prepared according to Löwik, D. W. P. M. and Lowe, C. R. Eur. J. Org. Chem. 2001, 2825-2839.

Step 1: Preparation of tert-butyl 4-(4-(8-oxa-3-azabicyclo[3.2.1]octan-3-yl)-6-chloro-1,3,5-triazin-2-yl) piperazine-1-carboxylate To a solution of 8-oxa-3-azabicyclo[3.2.1]octane hydrochloride (0.49 g, 3.3 mmol) in water (18 mL) was added a suspension of tert-butyl 4-(4,6-dichloro-1,3,5-triazin-2-yl) piperazine-1-carboxylate (1.0 g, 3.0 mmol) in acetone (about 10 mL). The suspension was stirred magnetically while solid sodium carbonate (0.70 g, 6.6 mmol) was added in a single portion. The mixture was stirred for two hours while heating in a 70-75° C. in an oil bath. After allowing the mixture to cool to room temperature, the title compound was removed by filtration, washed with water, and dried under vacuum.

MS (ES+) 411.0, 412.3 (M+H)+

Step 2: Preparation of tert-butyl 4-(4-(4-aminophenyl)-6-(8-oxa-3-azabicyclo[3.2.1]octan-3-yl)-1,3,5-triazin-2-yl)piperazine-1-carboxylate A suspension of tert-butyl 4-(4-(8-oxa-3-azabicyclo[3.2.1]octan-3-yl)-6-chloro-1,3,5-triazin-2-yl)piperazine-1-carboxylate (1.0 g, 2.4 mmol), 4-aminophenylboronic acid, pinacol ester (0.69 g, 3.2 mmol), and tetrakis(triphenylphosphine)palladium (0.28 g, 0.24 mmol) in aqueous 2 M sodium carbonate solution (3 mL) and 1:1 ethanol/toluene (12 mL) was irradiated in the microwave at 120° C. for 1 hour. After cooling, the biphasic mixture was extracted thrice with ethyl acetate. The extracts were washed with saturated aqueous sodium chloride solution, dried over anhydrous magnesium sulfate, filtered, and concentrated to dryness under reduced pressure to give the title compound.
MS (ES+) 468.1 (M+H)+

Step 3: Preparation of tert-butyl 4-(4-(8-oxa-3-azabicyclo[3.2.1]octan-3-yl)-6-(4-(3-pyridin-4-ylureido)phenyl)-1,3,5-triazin-2-yl)piperazine-1-carboxylate Crude tert-butyl 4-(4-(4-aminophenyl)-6-(8-oxa-3-azabicyclo[3.2.1]octan-3-yl)-1,3,5-triazin-2-yl)piperazine-1-carboxylate (approx. 1.4 mmol) was dissolved in tetrahydrofuran (20 mL) and then treated sequentially with triphosgene (0.30 g, 1.0 mmol) and triethylamine (2 mL). After 5 minutes, the mixture was treated with a solution of 4-aminopyridine (0.53 g, 5.6 mmol) in tetrahydrofuran. The mixture was concentrated under reduced pressure to give crude tert-butyl 4-(4-(8-oxa-3-azabicyclo[3.2.1]octan-3-yl)-6-(4-(3-pyridin-4-ylureido)phenyl)-1,3,5-triazin-2-yl)piperazine-1-carboxylate, a sample of which was purified by reversed phase HPLC to give a pure title compound.
MS (ES+) 588.2 (M+H)+

Example 107

Preparation of 1-(4-(4-(8-oxa-3-azabicyclo[3.2.1]octan-3-yl)-6-(piperazin-1-yl)-1,3,5-triazin-2-yl)phenyl)-3-(pyridin-4-yl)urea Crude tert-butyl 4-(4-(8-oxa-3-azabicyclo[3.2.1]octan-3-yl)-6-(4-(3-pyridin-4-ylureido)phenyl)-1,3,5-triazin-2-yl)piperazine-1-carboxylate (approx 1.4 mmol) was taken up in dichloromethane (20 mL) and treated with trifluoroacetic acid (5 mL). The mixture was concentrated under reduced the pressure. To the residue was added diethyl ether to give the title compound as a solid di-TFA salt, which was collected by filtration and dried under house vacuum; MS (ES+) 488.1 (M+H)+

Example 108

Preparation of 1-{4-[4-(4-methylpiperazin-1-yl)-6-(8-oxa-3-azabicyclo[3.2.1]oct-3-yl)-1,3,5-triazin-2-yl]phenyl}-3-pyridin-4-ylurea 1-(4-(4-(8-oxa-3-azabicyclo[3.2.1]octan-3-yl)-6-(piperazin-1-yl)-1,3,5-triazin-2-yl)phenyl)-3-(pyridin-4-yl)urea-2TFA (115 mg) in 1:1 98% formic acid and 37% formalin (4 mL) was heated at 75° C. for 90 minutes, then concentrated to dryness and purified on HPLC to give the title compound as its di-TFA salt; MS (ES+) 502.3 (M+H)+

Example 109

Preparation of 1-{4-[4-(4-benzylpiperazin-1-yl)-6-(8-oxa-3-azabicyclo[3.2.1]oct-3-yl)-1,3,5-triazin-2-yl]phenyl}-3-pyridin-4-ylurea 1-(4-(4-(8-oxa-3-azabicyclo[3.2.1]octan-3-yl)-6-(piperazin-1-yl)-1,3,5-triazin-2-yl)phenyl)-3-(pyridin-4-yl)urea-2TFA (130 mg) in dichloromethane (4 mL) and triethylamine (0.10 mL) was treated with benzaldehyde (0.10 mL), followed by sodium triacetoxyborohydride (80 mg). The mixture was concentrated to dryness and purified on HPLC to give the title compound as its di-TFA salt; MS (ES+) 578.3 (M+H)+.

Example 110

Preparation of 1-(4-{4-(8-oxa-3-azabicyclo[3.2.1]oct-3-yl)-6-[4-(pyridin-3-ylmethyl)piperazin-1-yl]-1,3,5-triazin-2-yl}phenyl)-3-pyridin-4-ylurea 1-(4-(4-(8-oxa-3-azabicyclo[3.2.1]octan-3-yl)-6-(piperazin-1-yl)-1,3,5-triazin-2-yl)phenyl)-3-(pyridin-4-yl)urea-2TFA (150 mg) in dichloromethane (4 mL) and triethylamine (0.12 mL) was treated with 3-pyridinecarboxaldehyde (0.1 mL), followed by sodium triacetoxyborohydride (80 mg). The mixture was concentrated to dryness and purified on HPLC to give the title compound as its tri-TFA salt; MS (ES+) 579.3 (M+H)+

Example 111

Preparation of 1-{4-[4-(4-acetylpiperazin-1-yl)-6-(8-oxa-3-azabicyclo[3.2.1]oct-3-yl)-1,3,5-triazin-2-yl]phenyl}-3-pyridin-4-ylurea 1-(4-(4-(8-oxa-3-azabicyclo[3.2.1]octan-3-yl)-6-(piperazin-1-yl)-1,3,5-triazin-2-yl)phenyl)-3-(pyridin-4-yl)urea-2TFA (230 mg) in dichloromethane (4 mL) and triethylamine (1 mL) was treated with acetyl chloride. The mixture was concentrated to dryness and purified on HPLC to give the title compound as its TFA salt; MS (ES+) 530.3 (M+H)+.

Example 112

Preparation of 1-(4-{4-[4-(N,N-dimethylglycyl)piperazin-1-yl]-6-(8-oxa-3-azabicyclo[3.2.1]oct-3-yl)-1,3,5-triazin-2-yl}phenyl)-3-pyridin-4-ylurea 1-(4-(4-(8-oxa-3-azabicyclo[3.2.1]octan-3-yl)-6-(piperazin-1-yl)-1,3,5-triazin-2-yl)phenyl)-3-(pyridin-4-yl)urea-2TFA (64 mg) in dichloromethane (4 mL) and triethylamine (1 mL) was treated with dimethylaminoacetyl chloride hydrochloride (100 mg). The mixture was heated with a heat gun, then concentrated to dryness and purified on HPLC to give the title compound as its di-TFA salt; MS (ES+) 573.3 (M+H)+.

Example 113

Preparation of 1-{4-[4-(4-isonicotinoylpiperazin-1-yl)-6-(8-oxa-3-azabicyclo[3.2.1]oct-3-yl)-1,3,5-triazin-2-yl]phenyl}-3-pyridin-4-ylurea 1-(4-(4-(8-oxa-3-azabicyclo[3.2.1]octan-3-yl)-6-(piperazin-1-yl)-1,3,5-triazin-2-yl)phenyl)-3-(pyridin-4-yl)urea-2TFA (100 mg) in dichloromethane (4 mL) and triethylamine (1 mL) was treated with isonicotinoyl chloride (100 mg). The mixture was concentrated to dryness and purified on HPLC to give the title compound as its di-TFA salt; MS (ES+) 593.1 (M+H)+

Example 114

Preparation of Methyl 4-[4-(8-oxa-3-azabicyclo [3.2.1]oct-3-yl)-6-{4-[(pyridin-4-ylcarbamoyl) amino]phenyl}-1,3,5-triazin-2-yl]piperazine-1-carboxylate 1-(4-(4-(8-oxa-3-azabicyclo[3.2.1]octan-3-yl)-6-(piperazin-1-yl)-1,3,5-triazin-2-yl)phenyl)-3-(pyridin-4-yl)urea-2TFA (75 mg) in dichloromethane (2 mL), tetrahydrofuran (2 mL), and triethylamine (1 mL) was treated with methyl chloroformate (0.10 mL). The mixture was concentrated to dryness and purified on RP-HPLC to give the title compound as its TFA salt. MS (ES+) 546.3 (M+H)+

Example 115

Preparation of 1-(4-(4-(8-oxa-3-azabicyclo[3.2.1] octan-3-yl)-6-(4-oxopiperidin-1-yl)-1,3,5-triazin-2-yl)phenyl)-3-(pyridin-4-yl)urea Step 1: Preparation of 1-(4,6-dichloro-1,3,5-triazin-2-yl)piperidin-4-one To magnetically stirred ice-water (72 mL) was added a solution of cyanuric chloride (2.2 g, 12 mmol) in acetone (48 mL), followed by piperidone monohydrate hydrochloride (1.8 g, 12 mmol) as a suspension in acetone (20 mL) and water (10 mL). To the mixture was added a suspension of sodium hydrogen carbonate (2.2 g, 24 mmol) in water (25 mL). The mixture was stirred at 0° C. for two hours. The title compound was collected by filtration, washed with water, and dried under vacuum.
MS (ES+) 248.8 (M+H)+

Step 2: Preparation of 1-(4-(8-oxa-3-azabicyclo [3.2.1]octan-3-yl)-6-chloro-1,3,5-triazin-2-yl)piperidin-4-one To an aqueous solution of 8-oxa-3-azabicyclo[3.2.1]octane hydrochloride (66 mL) was added 1-(4,6-dichloro-1,3,5-triazin-2-yl)piperidin-4-one (2.7 g, 11 mmol) as a suspension in acetone (40 mL). To the mixture was added solid sodium carbonate (2.5 g, 24 mmol). The suspension was stirred at 80° C. for two hours and then allowed to cool to room temperature. The title compound was collected by filtration, washed with water, and dried under vacuum; MS (ES+) 324.4 (M+H)+

Step 3: Preparation of 1-(4-(4-aminophenyl)-6-(8-oxa-3-azabicyclo[3.2.1]octan-3-yl)-1,3,5-triazin-2-yl)piperidin-4-one A suspension of 1-(4-(8-oxa-3-azabicyclo[3.2.1]octan-3-yl)-6-chloro-1,3,5-triazin-2-yl)piperidin-4-one (1.0 g, 3.1 mmol), 4-aminophenylboronic acid, pinacol ester (1.0 g, 4.7 mmol), and tetrakis(triphenylphosphine)palladium (0.20 g, 0.17 mmol) in aqueous 2 M sodium carbonate solution (3 mL) and 1:1 ethanol/toluene (12 mL) was irradiated in the microwave at 120° C. for 1 hour. After cooling, the biphasic mixture was extracted thrice with ethyl acetate. The extracts were washed with saturated aqueous sodium chloride solution, dried over anhydrous magnesium sulfate, filtered, and concentrated to dryness under reduced pressure to give the title compound as a golden yellow foam.
MS (ES+)=381.6 (M+H)+

Step 4: Preparation of 1-(4-(4-(8-oxa-3-azabicyclo [3.2.1]octan-3-yl)-6-(4-oxopiperidin-1-yl)-1,3,5-triazin-2-yl)phenyl)-3-(pyridin-4-yl)urea A mixture of crude 1-(4-(4-aminophenyl)-6-(8-oxa-3-azabicyclo[3.2.1]octan-3-yl)-1,3,5-triazin-2-yl)piperidin-4-one (approx. 3.1 mmol) and triethylamine (4 mL) in dichloromethane (30 mL) was treated with triphosgene (0.71 g, 2.4 mmol). The mixture was then treated with a solution of 4-aminopyridine (1.8 g, 19 mmol) in tetrahydrofuran (20 mL). The mixture was concentrated to dryness under reduced pressure and the residue purified by HPLC to give the title compound as its TFA salt. MS (ES+) 501.2 (M+H)+

Example 116

Preparation of 1-{4-[4-(4-hydroxypiperidin-1-yl)-6-(8-oxa-3-azabicyclo[3.2.1]oct-3-yl)-1,3,5-triazin-2-yl]phenyl}-3-pyridin-4-ylurea 1-(4-(4-(8-oxa-3-azabicyclo[3.2.1]octan-3-yl)-6-(4-oxopiperidin-1-yl)-1,3,5-triazin-2-yl)phenyl)-3-(pyridin-4-yl)urea-TFA (56 mg) was taken up in methanol/tetrahydrofuran (1:1, 6 mL), and the mixture at 0° C. was treated with sodium borohydride (10 mg). After warming to room temperature, the mixture was concentrated to a residue which then was purified by HPLC to give the title compound as its TFA salt.; MS (ES+) 503.0 (M+H)+

Example 117

Preparation of 1-(4-{4-[4-(benzylamino)piperidin-1-yl]-6-(8-oxa-3-azabicyclo[3.2.1]oct-3-yl)-1,3,5-triazin-2-yl}phenyl)-3-pyridin-4-ylurea 1-(4-(4-(8-oxa-3-azabicyclo[3.2.1]octan-3-yl)-6-(4-oxopiperidin-1-yl)-1,3,5-triazin-2-yl)phenyl)-3-(pyridin-4-yl)urea-TFA (85 mg) in dichloromethane (3 mL) and tetrahydrofuran (3 mL) was treated with benzylamine (0.030 mL), followed by glacial acetic acid (0.016 mL) and sodium triacetoxyborohydride (89 mg). After completion of the reaction, methanol was added and mixture was concentrated to dryness. The residue was purified by HPLC to give the title compound as its di-TFA salt.
MS (ES+) 592.3 (M+H)+

Example 118

Preparation of 1-(4-{4-[4-(methylamino)piperidin-1-yl]-6-(8-oxa-3-azabicyclo[3.2.1]oct-3-yl)-1,3,5-triazin-2-yl}phenyl)-3-pyridin-4-ylurea 1-(4-(4-(8-oxa-3-azabicyclo[3.2.1]octan-3-yl)-6-(4-oxopiperidin-1-yl)-1,3,5-triazin-2-yl)phenyl)-3-(pyridin-4-yl)urea-TFA (50 mg) in tetrahydrofuran (5 mL) was treated with methylamine (2.0 M solution in tetrahydrofuran, 0.16 mL), followed by glacial acetic acid (0.009 mL) and sodium triacetoxyborohydride (51 mg). After completion of the reaction, methanol was added and mixture was concentrated to dryness. The residue was purified by HPLC to give the title compound as its di-TFA salt; MS (ES+) 516.3 (M+H)+

Example 119

Preparation of 1-(4-{4-[4-(ethylamino)piperidin-1-yl]-6-(8-oxa-3-azabicyclo[3.2.1]oct-3-yl)-1,3,5-triazin-2-yl}phenyl)-3-pyridin-4-ylurea 1-(4-(4-(8-oxa-3-azabicyclo[3.2.1]octan-3-yl)-6-(4-oxopiperidin-1-yl)-1,3,5-triazin-2-yl)phenyl)-3-(pyridin-4-yl)urea-TFA (50 mg) in tetrahydrofuran (5 mL) was treated with ethylamine (2.0 M solution in tetrahydrofuran, 0.16 mL), followed by glacial acetic acid (0.009 mL) and sodium triacetoxyborohydride (51 mg). After completion of the reaction, methanol was added and mixture was concentrated to dryness. The residue was purified by HPLC to give the title compound as its di-TFA salt; MS (ES+) 530.3 (M+H)+

Example 120

Preparation of 1-{4-[4-(4-{[2-(dimethylamino)ethyl]amino}piperidin-1-yl)-6-(8-oxa-3-azabicyclo[3.2.1]oct-3-yl)-1,3,5-triazin-2-yl]phenyl}-3-pyridin-4-ylurea The titled compound was prepared by the procedure as outlined in example 118, by reacting 1-(4-(4-(8-oxa-3-azabicyclo[3.2.1]octan-3-yl)-6-(4-oxopiperidin-1-yl)-1,3,5-triazin-2-yl)phenyl)-3-(pyridin-4-yl)urea-TFA (50 mg) with N,N-dimethylethylenediamine (0.026 mL) and purified by HPLC and isolated as its tri-TFA salt; MS (ES+) 573.7 (M+H)+.

Example 121

Preparation of 1-{4-[4-(4-morpholin-4-ylpiperidin-1-yl)-6-(8-oxa-3-azabicyclo[3.2.1]oct-3-yl)-1,3,5-triazin-2-yl]phenyl}-3-pyridin-4-ylurea By reacting 1-(4-(4-(8-oxa-3-azabicyclo[3.2.1]octan-3-yl)-6-(4-oxopiperidin-1-yl)-1,3,5-triazin-2-yl)phenyl)-3-(pyridin-4-yl)urea-TFA (50 mg) with 1-(2-aminoethyl)pyrrolidine (0.030 mL) and following the procedure as mentioned in Experimental 118, the title product was isolated as its tri-TFA salt; MS (ES+) 599.8 (M+H)+.

Example 122

Preparation of 1-(4-(4-(8-oxa-3-azabicyclo[3.2.1]octan-3-yl)-6-(4-(4-methylpiperazin-1-yl)piperidin-1-yl)-1,3,5-triazin-2-yl)phenyl)-3-(pyridin-4-yl)urea By reacting 1-(4-(4-(8-oxa-3-azabicyclo[3.2.1]octan-3-yl)-6-(4-oxopiperidin-1-yl)-1,3,5-triazin-2-yl)phenyl)-3-(pyridin-4-yl)urea-TFA (40 mg) and 1-methylpiperazine (0.050 mL) and following the procedure as outlined in example 118, the titled compound was isolated after HPLC purification as its tri-TFA salt; MS (ES+) 585.9 (M+H)+

Example 123

Preparation of 1-(4-(4-(8-oxa-3-azabicyclo[3.2.1]octan-3-yl)-6-(4-(2-hydroxyethylamino)piperidin-1-yl)-1,3,5-triazin-2-yl)phenyl)-3-(pyridin-4-yl)urea Starting from 1-(4-(4-(8-oxa-3-azabicyclo[3.2.1]octan-3-yl)-6-(4-oxopiperidin-1-yl)-1,3,5-triazin-2-yl)phenyl)-3-(pyridin-4-yl)urea-TFA (50 mg) and ethanolamine (0.020 mL) and following the procedure as outlined in example 118, the title compound was isolated as its di-TFA salt after HPLC purification. MS (ES+) 546.7 (M+H)+

Example 124

Preparation of 1-(4-(4-(8-oxa-3-azabicyclo[3.2.1]octan-3-yl)-6-(4-(2-morpholinoethylamino)piperidin-1-yl)-1,3,5-triazin-2-yl)phenyl)-3-(pyridin-4-yl)urea Starting from 1-(4-(4-(8-oxa-3-azabicyclo[3.2.1]octan-3-yl)-6-(4-oxopiperidin-1-yl)-1,3,5-triazin-2-yl)phenyl)-3-(pyridin-4-yl)urea-TFA (50 mg) and 1-(2-aminoethyl)morpholine (0.031 mL) and following the procedure as outlined in example 118, the titled compound was isolated as its tri-TFA salt after HPLC purification; MS (ES+) 615.9 (M+H)+

Example 125

Preparation of Methyl 2-(1-(4-(8-oxa-3-azabicyclo[3.2.1]octan-3-yl)-6-(4-(3-pyridin-4-ylureido)phenyl)-1,3,5-triazin-2-yl)piperidin-4-ylamino)acetate Starting from 1-(4-(4-(8-oxa-3-azabicyclo[3.2.1]octan-3-yl)-6-(4-oxopiperidin-1-yl)-1,3,5-triazin-2-yl)phenyl)-3-(pyridin-4-yl)urea-TFA (50 mg) and glycine methyl ester hydrochloride (20 mg) and triethylamine (10 drops) and following the procedure as outlined in example 118 the title compound was isolated as its di-TFA salt after HPLC purification; MS (ES+) 574.8 (M+H)+.

Example 126

Preparation of 2-(1-(4-(8-oxa-3-azabicyclo[3.2.1]octan-3-yl)-6-(4-(3-pyridin-4-ylureido)phenyl)-1,3,5-triazin-2-yl)piperidin-4-ylamino)acetamide Starting from 1-(4-(4-(8-oxa-3-azabicyclo[3.2.1]octan-3-yl)-6-(4-oxopiperidin-1-yl)-1,3,5-triazin-2-yl)phenyl)-3-(pyridin-4-yl)urea-TFA (50 mg) and glycinamide hydrochloride (18 mg) and triethylamine (10 drops) and following the procedure as outlined in example 118 the title compound was isolated as its di-TFA salt after HPLC purification; MS (ES+) 559.8 (M+H)+

Example 127

Preparation of Tert-butyl 2-(1-(4-(8-oxa-3-azabicyclo[3.2.1]octan-3-yl)-6-(4-(3-pyridin-4-ylureido)phenyl)-1,3,5-triazin-2-yl)piperidin-4-ylamino)acetate Starting from 1-(4-(4-(8-oxa-3-azabicyclo[3.2.1]octan-3-yl)-6-(4-oxopiperidin-1-yl)-1,3,5-triazin-2-yl)phenyl)-3-(pyridin-4-yl)urea-TFA (60 mg) and glycine tert-butyl ester hydrochloride (33 mg) and triethylamine (10 drops) and following the procedure as outlined in example 118, the title compound was isolated as its di-TFA salt after HPLC purification; MS (ES+) 616.9 (M+H)+.

Example 128

Preparation of 2-(1-(4-(8-oxa-3-azabicyclo[3.2.1]octan-3-yl)-6-(4-(3-pyridin-4-ylureido)phenyl)-1,3,5-triazin-2-yl)piperidin-4-ylamino)acetic acid Tert-butyl 2-(1-(4-(8-oxa-3-azabicyclo[3.2.1]octan-3-yl)-6-(4-(3-pyridin-4-ylureido)phenyl)-1,3,5-triazin-2-yl)piperidin-4-ylamino)acetate (28 mg) in dichloromethane (3 mL) was treated with trifluoroacetic acid (1 mL) and then concentrated to dryness to give the title compound as its TFA salt.
MS (ES+) 560.2 (M+H)+.

Example 129

Preparation of 4-[4-(1,4-dioxa-8-azaspiro[4.5]dec-8-yl)-6-morpholin-4-yl-1,3,5-triazin-2-yl]aniline

MS (ES+) 399.47 (M+H)+.

Example 130

Preparation of 1-{4-[4-(1,4-dioxa-8-azaspiro[4.5]dec-8-yl)-6-morpholin-4-yl-1,3,5-triazin-2-yl]phenyl}-3-pyridin-4-ylurea

MS (ES+) 519.58 (M+H)+.

Example 131

Preparation of 1-{4-[4-(1,4-dioxa-8-azaspiro[4.5]dec-8-yl)-6-morpholin-4-yl-1,3,5-triazin-2-yl]phenyl}-3-pyridin-3-ylurea

MS (ES+) 519.58 (M+H)+.

Example 132

Preparation of 1-{4-[4-(1,4-dioxa-8-azaspiro[4.5]dec-8-yl)-6-morpholin-4-yl-1,3,5-triazin-2-yl]phenyl}-3-phenylurea

MS (ES+) 518.59 (M+H)+.

Example 133

Preparation of 1-[4-(dimethylamino)phenyl]-3-{4-[4-(1,4-dioxa-8-azaspiro[4.5]dec-8-yl)-6-morpholin-4-yl-1,3,5-triazin-2-yl]phenyl}urea

MS (ES+) 561.66 (M+H)+.

Example 134

Preparation of 1-(4-cyanophenyl)-3-{4-[4-(1,4-dioxa-8-azaspiro[4.5]dec-8-yl)-6-morpholin-4-yl-1,3,5-triazin-2-yl]phenyl}urea

MS (ES+) 543.60 (M+H)+.

Example 135

Preparation of 1-{4-[4-(1,4-dioxa-8-azaspiro[4.5]dec-8-yl)-6-morpholin-4-yl-1,3,5-triazin-2-yl]phenyl}-3-(2-methylpyridin-4-yl)urea

MS (ES+) 533.61 (M+H)+

Example 136

Preparation of 1-[2-(dimethylamino)ethyl]-3-{4-[4-(1,4-dioxa-8-azaspiro[4.5]dec-8-yl)-6-morpholin-4-yl-1,3,5-triazin-2-yl]phenyl}urea

MS (ES+) 513.62 (M+H)+

Example 137

Preparation of 1-[4-(4-morpholin-4-yl-6-quinolin-3-yl-1,3,5-triazin-2-yl)phenyl]-3-pyridin-4-ylurea HRMS: calcd for C28H24N8O2+H+, 505.20950. found (ESI, [M+H]+ Obs'd), 505.2098.
HRMS: calcd for C28H24N8O2+H+, 505.20950. found (ESI, [M+H]+ Calc'd), 505.2095.

Example 138

Preparation of 2-(difluoromethyl)-1-(4,6-di-8-oxa-3-azabicyclo[3.2.1]oct-3-yl-1,3,5-triazin-2-yl)-1H-benzimidazole A solution of cyanuric chloride (922 mg, 5 mmol) in acetone (5 mL) was added to ice. A solution of 8-oxa-3-azabicyclo[3.2.1]octane hydrochloride (750 mg, 5 mmol) and triethylamine (2.1 mL, 15 mmol) in aqueous acetone was then added. After 20 min the precipitate was collected to give 1.0 g of a white powder which was a 7:3 mixture of 3-(4,6-dichloro-1,3,5-triazine-2,4-diyl)-8-oxa-3-azabicyclo[3.2.1]octane and 3,3'-(6-chloro-1,3,5-triazine-2,4-diyl)bis(8-oxa-3-azabicyclo[3.2.1]octane). Treatment of the mixture (400 mg) with 2-(difluoromethyl)-1H-benzo[d]imidazole (146 mg, 0.87 mmol) and K2CO3 (967 mg, 7 mmol) in DMF (2.5 mL) for 18 hours, followed by addition of 8-oxa-3-azabicyclo[3.2.1]octane hydrochloride (150 mg) gave, after 1 h, 3,3'-(6-(2-(difluoromethyl)-1H-benzo[d]imidazol-1-yl)-1,3,5-triazine-2,4-diyl)bis(8-oxa-3-azabicyclo[3.2.1]octane) after purification by HPLC. (M+H) 475.

Example 139

Preparation of 2-(difluoromethyl)-1-[4-morpholin-4-yl-6-(8-oxa-3-azabicyclo[3.2.1]oct-3-yl)-1,3,5-triazin-2-yl]-1H-benzimidazole To a stirred solution of 3-(4,6-dichloro-1,3,5-triazine-2,4-diyl)(8-oxa-3-azabicyclo[3.2.1]octane) (2.61 g, 10 mmol) in acetone/ice, morpholine (900 mg, 12 mmol) and triethylamine (5 ml) was added. The reaction mixture was stirred at room temperature for 3 hours. Separated white solid was filtered and washed with water. The crude product obtained was pure enough and taken to next step without purification. Treatment of the mixture (270 mg. 0.87 mmol) with 2-(difluoromethyl)-1H-benzo[d]imidazole (146 mg, 0.87 mmol) and K2CO3 (967 mg, 7 mmol) in DMF (2.5 mL) for 18 hours gave 2-(difluoromethyl)-1-[4-morpholin-4-yl-6-(8-oxa-3-azabicyclo[3.2.1]oct-3-yl)-1,3,5-triazin-2-yl]-1H-benzimidazole after purification by HPLC. (M+H) 445.

Example 140

Preparation of 1-[4-(4-azetidin-1-yl-6-morpholin-4-yl-1,3,5-triazin-2-yl)phenyl]-3-pyridin-4-ylurea mp 212° C.; MS (ESI) m/z 433.3.

Example 141

Preparation of methyl 4-({[4-(4-azetidin-1-yl-6-morpholin-4-yl-1,3,5-triazin-2-yl)phenyl]carbamoyl}amino)benzoate mp 212° C.; MS (ESI) m/z 490.2.

Example 142

Preparation of 1-[4-(4-isopropoxy-6-morpholin-4-yl-1,3,5-triazin-2-yl)phenyl]-3-{4-[(4-methylpiperazin-1-yl)carbonyl]phenyl}urea MS (ESI) m/z 561.6.

Example 143

Preparation of 4-({[4-(4-isopropoxy-6-morpholin-4-yl-1,3,5-triazin-2-yl)phenyl]carbamoyl}amino)-N-(1-methylpiperidin-4-yl)benzamide MS (ESI) m/z 575.6

Example 144

Preparation of 1-{4-[4-(8-oxa-3-azabicyclo[3.2.1]oct-3-yl)-6-(2-piperidin-1-ylethoxy)-1,3,5-triazin-2-yl]phenyl}-3-pyridin-4-ylurea MS (ESI) m/z 531.5

Example 145

Preparation of methyl(4-{4-[4-({[4-(4-methylpiperazin-1-yl)phenyl]carbamoyl}amino)phenyl]-6-(8-oxa-3-azabicyclo[3.2.1]oct-3-yl)-1,3,5-triazin-2-yl}phenyl)carbamate MS (ESI) m/z 650.7

Example 146

Preparation of 1-cyclopropyl-3-(4-{4-[4-({[4-(4-methylpiperazin-1-yl)phenyl]carbamoyl}amino)phenyl]-6-(8-oxa-3-azabicyclo[3.2.1]oct-3-yl)-1,3,5-triazin-2-yl}phenyl)urea MS (ESI) m/z 675.8

Example 147

Preparation of N',N'''-{[6-(8-oxa-3-azabicyclo[3.2.1]oct-3-yl)-1,3,5-triazine-2,4-diyl]di-4,1-phenylene}bis{1-[4-(4-methylpiperazin-1-yl)phenyl]urea}

MS (ESI) m/z 809.9

Example 148

Preparation of 1-[4-(4-methylpiperazin-1-yl)phenyl]-3-{4-[4-(8-oxa-3-azabicyclo[3.2.1]oct-3-yl)-6-{4-[(pyridin-4ylcarbamoyl)amino]phenyl}-1,3,5-triazin-2-yl]phenyl}urea MS (ESI) m/z 712.8

Example 149

Preparation of 1-(4-{4-[(2-aminoethyl)amino]-6-(8-oxa-3-azabicyclo[3.2.1]oct-3-yl)-1,3,5-triazin-2-yl}phenyl)-3-pyridin-3-ylurea HRMS: calcd for C23H27N9O2+H+, 462.23605. found (ESI, [M+H]+ Obs'd), 462.2358.

Example 150

Preparation of 1-{4-[4-anilino-6-(8-oxa-3-azabicyclo[3.2.1]oct-3-yl)-1,3,5-triazin-2-yl]phenyl}-3-pyridin-3-ylurea HRMS: calcd for C27H26N8O2+H+, 495.22515. found (ESI, [M+H]+ Obs'd), 495.2249.

Example 151

Preparation of 4-({[4-(4,6-dimorpholin-4-yl-1,3,5-triazin-2-yl)phenyl]carbamoyl}amino)-N-(2-piperidin-1-ylethyl)benzamide MS (ESI) m/2 308.6; HRMS: calcd for C32H41N9O4+H+, 616.33543. found (ESI, [M+H]+ Obs'd), 616.3347; HRMS: calcd for C32H41N9O4+H+, 616.33543. found (ESI, [M+H]+ Calc'd), 616.3354.

Example 152

Preparation of 1-[4-(4,6-dimorpholin-4-yl-1,3,5-triazin-2-yl)phenyl]-3-[4-(morpholin-4-ylcarbonyl)phenyl]urea MS (ESI) m/z 575.3; HRMS: calcd for C29H34N8O5+H+, 575.27249. found (ESI, [M+H]+ Obs'd), 575.2722; HRMS: calcd for C29H34N8O5+H+, 575.27249. found (ESI, [M+H]+ Calc'd), 575.2725.

Example 153

Preparation of 1-(4-{4-[(2-hydroxyethyl)amino]-6-(8-oxa-3-azabicyclo[3.2.1]oct-3-yl)-1,3,5-triazin-2-yl}phenyl)-3-pyridin-3-ylurea MS (ESI) m/z 463.5.

Example 154

Preparation of 1-{4-[4-(azetidin-3-ylamino)-6-(8-oxa-3-azabicyclo[3.2.1]oct-3-yl)-1,3,5-triazin-2-yl]phenyl}-3-pyridin-3-ylurea MS (ESI) m/z 474.5

Example 155

Preparation of 1-(4-{4-[(2-morpholin-4-ylethyl)amino]-6-(8-oxa-3-azabicyclo[3.2.1]oct-3-yl)-1,3,5-triazin-2-yl}phenyl)-3-pyridin-3-ylurea MS (ESI) m/z 532.6.

Example 156

Preparation of 1-(4-{4-[(3-aminopropyl)amino]-6-(8-oxa-3-azabicyclo[3.2.1]oct-3-yl)-1,3,5-triazin-2-yl}phenyl)-3-pyridin-3-ylurea MS (ESI) m/z 476.5.

Example 157

Preparation of 1-(4-{4-[(4-cyclopentylpiperazin-1-yl)amino]-6-(8-oxa-3-azabicyclo[3.2.1]oct-3-yl)-1,3,5-triazin-2-yl}phenyl)-3-pyridin-3-ylurea MS (ESI) m/z 571.7

Example 158

1-{4-[4-isopropoxy-6-(8-oxa-3-azabicyclo[3.2.1]oct-3-yl)-1,3,5-triazin-2-yl]phenyl}-3-pyridin-4-ylurea MS (ESI) m/z 462.53

Example 159

Preparation of 1-{4-[4-isopropoxy-6-(8-oxa-3-azabicyclo[3.2.1]oct-3-yl)-1,3,5-triazin-2-yl]phenyl}-3-[4-(4-methylpiperazin-1-yl)phenyl]urea

Example 160

Preparation of 1-{4-[4-chloro-6-(8-oxa-3-azabicyclo[3.2.1]oct-3-yl)-1,3,5-triazin-2-yl]phenyl}-3-pyridin-4-ylurea MS (ESI) m/z 438.8

Example 161

Preparation of 1-[4-(4-methyl-6-morpholin-4-yl-1,3,5-triazin-2-yl)phenyl]-3-pyridin-4-ylurea MS (ESI) m/z 391.5

Example 162

Preparation of methyl 4-({[4-(4-methyl-6-morpholin-4-yl-1,3,5-triazin-2-yl)phenyl]carbamoyl}amino)benzoate MS (ESI) m/z 449.2.

Example 163

Preparation of 1-{4-[4-(3,6-dihydro-2H-pyran-4-yl)-6-morpholin-4-yl-1,3,5-triazin-2-yl]phenyl}-3-{4-[(4-methylpiperazin-1-yl)carbonyl]phenyl}urea MS (ESI) m/z 584.7

Example 164

Preparation of 4-({[4-(4-methyl-6-morpholin-4-yl-1,3,5-triazin-2-yl)phenyl]carbamoyl}amino)-N-(1-methylpiperidin-4-yl)benzamide MS (ESI) m/z 530.63.

Example 165

Preparation of N-[2-(dimethylamino)ethyl]-N-methyl-4-({[4-(4-methyl-6-morpholin-4-yl-1,3,5-triazin-2-yl)phenyl]carbamoyl}amino)benzamide MS (ESI) m/z 518.6

Example 166

Preparation of 1-[4-(4-methyl-6-morpholin-4-yl-1,3,5-triazin-2-yl)phenyl]-3-{4-[(4-methylpiperazin-1-yl)carbonyl]phenyl}urea MS (ESI) m/z 516.6.

Example 167

Preparation of 1-(4-{[3-(dimethylamino)pyrrolidin-1-yl]carbonyl}phenyl)-3-[4-(4,6-dimorpholin-4-yl-1,3,5-triazin-2-yl)phenyl]urea HRMS: calcd for $C_{31}H_{39}N_9O_4+H+$, 602.31978. found (ESI, [M+H]+ Obs'd), 602.3192.

Example 168

Preparation of 1-[4-({4-[2-(dimethylamino)ethyl]piperazin-1-yl}carbonyl)phenyl]-3-[4-(4,6-dimorpholin-4-yl-1,3,5-triazin-2-yl)phenyl]urea HRMS: calcd for $C_{33}H_{44}N_{10}O_4+H+$, 645.36198. found (ESI, [M+H]+ Obs'd), 645.3615.

Example 169

Preparation of 1-(4-{4-(8-oxa-3-azabicyclo[3.2.1]oct-3-yl)-6-[(piperidin-4-ylmethyl)amino]-1,3,5-triazin-2-yl}phenyl)-3-pyridin-3-ylurea MS (ESI) m/z 515.6

Example 170

Preparation of 1-(4-{4-(8-oxa-3-azabicyclo[3.2.1]oct-3-yl)-6-[(2-piperidin-4-ylethyl)amino]-1,3,5-triazin-2-yl}phenyl)-3-pyridin-3-ylurea MS (ESI) m/z 529.65.

Example 171

Preparation of 1-{4-[4-(3-methylimidazolidin-1-yl)-6-(8-oxa-3-azabicyclo[3.2.1]oct-3-yl)-1,3,5-triazin-2-yl]phenyl}-3-pyridin-3-ylurea MS (ESI) m/z 487.5

Example 172

Preparation of 1-{4-[4-(3-methyltetrahydropyrimidin-1(2H)-yl)-6-(8-oxa-3-azabicyclo[3.2.1]oct-3-yl)-1,3,5-triazin-2-yl]phenyl}-3-pyridin-3-ylurea MS (ESI) m/z 501.6

Example 173

Preparation of 1-{4-[4-(8-oxa-3-azabicyclo[3.2.1]oct-3-yl)-6-(2-piperidin-1-ylethoxy)-1,3,5-triazin-2-yl]phenyl}-3-pyridin-3-ylurea MS (ESI) m/z 530.6

Example 174

Preparation of 1-(4-{4-[2-methoxy-1-(methoxymethyl)ethoxy]-6-(8-oxa-3-azabicyclo[3.2.1]oct-3-yl)-1,3,5-triazin-2-yl}phenyl)-3-pyridin-4-ylurea MS (ESI) m/z 521.58

Example 175

Preparation of 1-(4-{4-[2-methoxy-1-(methoxymethyl)ethoxy]-6-(8-oxa-3-azabicyclo[3.2.1]oct-3-yl)-1,3,5-triazin-2-yl}phenyl)-3-[4-(4-methylpiperazin-1-yl)phenyl]urea MS (ESI) m/z 618.7.

Example 176

Preparation of 2-hydroxyethyl(4-{4-[2-methoxy-1-(methoxymethyl)ethoxy]-6-(8-oxa-3-azabicyclo[3.2.1]oct-3-yl)-1,3,5-triazin-2-yl}phenyl)carbamate MS (ESI) m/z 489.53.

Example 177

Preparation of 1-(4-{4-[2-methoxy-1-(methoxymethyl)ethoxy]-6-(8-oxa-3-azabicyclo[3.2.1]oct-3-yl)-1,3,5-triazin-2-yl}phenyl)-3-methylurea MS (ESI) m/z 458.52.

Example 178

Preparation of 1-cyclopropyl-3-(4-{4-[2-methoxy-1-(methoxymethyl)ethoxy]-6-(8-oxa-3-azabicyclo[3.2.1]oct-3-yl)-1,3,5-triazin-2-yl}phenyl)urea MS (ESI) m/z 484.56.

Example 179

Preparation of 1-[4-(4,6-dimorpholin-4-yl-1,3,5-triazin-2-yl)phenyl]-3-{4-[(4-pyrrolidin-1-ylpiperidin-1-yl)carbonyl]phenyl}urea MS (ESI) m/z 642.4; HRMS: calcd for C34H43N9O4+H+, 642.35108. found (ESI-FTMS, [M+H]1+), 642.3491.

Example 180

Preparation of 1-{4-[4-(8-oxa-3-azabicyclo[3.2.1]oct-3-yl)-6-(piperidin-3-ylmethoxy)-1,3,5-triazin-2-yl]phenyl}-3-pyridin-3-ylurea MS (ESI) m/z 516.61

Example 181

Preparation of 1-{4-[4-(4-aminobutoxy)-6-(8-oxa-3-azabicyclo[3.2.1]oct-3-yl)-1,3,5-triazin-2-yl]phenyl}-3-pyridin-3-ylurea MS (ESI) m/z 490.57

Example 182

Preparation of 1-{4-[4-(8-oxa-3-azabicyclo[3.2.1]oct-3-yl)-6-(2-piperidin-4-ylethoxy)-1,3,5-triazin-2-yl]phenyl}-3-pyridin-3-ylurea MS (ESI) m/z 530.63

Example 183

Preparation of 1-{4-[4-(8-oxa-3-azabicyclo[3.2.1]oct-3-yl)-6-(piperidin-4-ylmethoxy)-1,3,5-triazin-2-yl]phenyl}-3-pyridin-3-ylurea MS (ESI) m/z 516.61

Example 184

Preparation 4-({[4-(4-butyl-6-morpholin-4-yl-1,3,5-triazin-2-yl)phenyl]carbamoyl}amino)benzoic acid MS (ESI) m/z 476.53

Example 185

Preparation of N-[2-(dimethylamino)ethyl]-4-({[4-(4-isopropoxy-6-morpholin-4-yl-1,3,5-triazin-2-yl)phenyl]carbamoyl}amino)-N-methylbenzamide MS (ESI) m/z 562.6

Example 186

Preparation of 1-[4-(4-butyl-6-morpholin-4-yl-1,3,5-triazin-2-yl)phenyl]-3-pyridin-4-ylurea MS (ESI) m/z 433.5

Example 187

Preparation of N-[2-(dimethylamino)ethyl]-4-({[4-(4-isopropoxy-6-morpholin-4-yl-1,3,5-triazin-2-yl)phenyl]carbamoyl}amino)benzamide MS (ESI) m/z 548.67

Example 188

Preparation of methyl 4-({[4-(4-butyl-6-morpholin-4-yl-1,3,5-triazin-2-yl)phenyl]carbamoyl}amino)benzoate MS (ESI) m/z 490.56.

Example 189

Preparation of 1-(4-{4-morpholin-4-yl-6-[(1S,4S)-2-oxa-5-azabicyclo[2.2.1]hept-5-yl]-1,3,5-triazin-2-yl}phenyl)-3-pyridin-4-ylurea HRMS: calcd for C24H26N8O3+H+, 475.22006. found (ESI, [M+H]+ Obs'd), 475.2201.

Example 190

Preparation of 1-{4-[4-(methylamino)-6-(8-oxa-3-azabicyclo[3.2.1]oct-3-yl)-1,3,5-triazin-2-yl]phenyl}-3-pyridin-3-ylurea MS (ESI) m/z 432.49.

Example 191

Preparation of 1-{4-[4-(ethylamino)-6-(8-oxa-3-azabicyclo[3.2.1]oct-3-yl)-1,3,5-triazin-2-yl]phenyl}-3-pyridin-3-ylurea MS (ESI) m/z 446.52

Example 192

Preparation of 1-{4-[4-(dimethylamino)-6-(8-oxa-3-azabicyclo[3.2.1]oct-3-yl)-1,3,5-triazin-2-yl]phenyl}-3-pyridin-3-ylurea MS (ESI) m/z 446.52.

Example 193

Preparation of 1-{4-[4-(isopropylamino)-6-(8-oxa-3-azabicyclo[3.2.1]oct-3-yl)-1,3,5-triazin-2-yl]phenyl}-3-pyridin-3-ylurea MS (ESI) m/z 460.54

Example 194

Preparation of 1-{4-[4-(diethylamino)-6-(8-oxa-3-azabicyclo[3.2.1]oct-3-yl)-1,3,5-triazin-2-yl]phenyl}-3-pyridin-3-ylurea MS (ESI) m/z 474.57.

Example 195

Preparation of 4-({[4-(4-azetidin-1-yl-6-morpholin-4-yl-1,3,5-triazin-2yl)phenyl]carbamoyl}amino)benzoic acid mp 204° C.; MS (ESI) m/z 476.2;

Example 196

Preparation of 1-[4-(4-azetidin-1-yl-6-morpholin-4-yl-1,3,5-triazin-2-yl)phenyl]-3-{4-[(4-methylpiperazin-1-yl)carbonyl]phenyl}urea mp 170° C.; MS (ESI) m/z 558.2.

Example 197

Preparation of 4-({[4-(4-azetidin-1-yl-6-morpholin-4-yl-1,3,5-triazin-2-yl)phenyl]carbamoyl}amino)-N-[2-(dimethylamino)ethyl]-N-methylbenzamide MS (ESI) m/z 280.7;

Example 198

Preparation of 4-({[4-(4-butyl-6-morpholin-4-yl-1,3,5-triazin-2-yl)phenyl]carbamoyl}amino)-N-[2-(dimethylamino)ethyl]-N-methylbenzamide

Example 199

Preparation of 1-{4-[4-(1-ethoxyvinyl)-6-morpholin-4-yl-1,3,5-triazin-2-yl]phenyl}-3-pyridin-4-ylurea MS (ESI) m/z 447.499.

Example 200

Preparation of 1-{4-[4-(2-methoxyethoxy)-6-morpholin-4-yl-1,3,5-triazin-2-yl]phenyl}-3-pyridin-4-ylurea HRMS: calcd for C22H25N7O4+H+, 452.20408. found (ESI, [M+H]+ Obs'd), 452.2047.

Example 201

Preparation of 1-(diethylcarbamoyl)-4-[({4-[4-morpholin-4-yl-6-(3-oxa-8-azabicyclo[3.2.1]oct-8-yl)-1,3,5-triazin-2-yl]phenyl}carbamoyl)amino]pyridinium HRMS: calcd for C30H38N9O4+H+, 589.31195. found (ESI, [M+H]+), 589.3035.

Example 202

Preparation of 1-(4-{4-[ethyl(methyl)amino]-6-(8-oxa-3-azabicyclo[3.2.1]oct-3-yl)-1,3,5-triazin-2-yl}phenyl)-3-pyridin-3-ylurea MS (ESI) m/z 460.54.

Example 203

Preparation of 1-{4-[4-(sec-butylamino)-6-(8-oxa-3-azabicyclo[3.2.1]oct-3-yl)-1,3,5-triazin-2-yl]phenyl}-3-pyridin-3-ylurea MS (ESI) m/z 474.57.

Example 204

Preparation of 1-{4-[4-{[2-hydroxy-1-(hydroxymethyl)ethyl]amino}-6-(8-oxa-3-azabicyclo[3.2.1]oct-3-yl)-1,3,5-triazin-2-yl]phenyl}-3-pyridin-3-ylurea MS (ESI) m/z 492.54.

Example 205

Preparation of 1-(4-{4-[bis(2-hydroxyethyl)amino]-6-(8-oxa-3-azabicyclo[3.2.1]oct-3-yl)-1,3,5-triazin-2-yl}phenyl)-3-pyridin-3-ylurea MS (ESI) m/z 506.57

Example 206

Preparation of 1-(4-{4-[(1S,4S)-2,5-diazabicyclo[2.2.1]hept-2-yl]-6-(8-oxa-3-azabicyclo[3.2.1]oct-3-yl)-1,3,5-triazin-2-yl}phenyl)-3-pyridin-3-ylurea MS (ESI) m/z 499.58.

Example 207

Preparation of 1-{4-[4-{[4-(4-methylpiperazin-1-yl)phenyl]amino}-6-(8-oxa-3-azabicyclo[3.2.1]oct-3-yl)-1,3,5-triazin-2-yl]phenyl}-3-pyridin-3-ylurea MS (ESI) m/z 592.71.

Example 208

Preparation of 1-(4-{4-(8-oxa-3-azabicyclo[3.2.1]oct-3-yl)-6-[(4-piperazin-1-ylphenyl)amino]-1,3,5-triazin-2-yl}phenyl)-3-pyridin-3-ylurea MS (ESI) m/z 578.68.

Example 209

Preparation of 1-[4-(4-acetyl-6-morpholin-4-yl-1,3,5-triazin-2-yl)phenyl]-3-pyridin-4-ylurea MS (ESI) m/z 419.406

Example 210

Preparation of 1-(4-{4-morpholin-4-yl-6-[(1S,4S)-2-oxa-5-azabicyclo[2.2.1]hept-5-yl]-1,3,5-triazin-2-yl}phenyl)-3-{4-[(4-pyrrolidin-1-ylpiperidin-1-yl)carbonyl]phenyl}urea MS (ESI) m/z 654.3; HRMS: calcd for C35H43N9O4+H+, 654.35108. found (ESI-FTMS, [M+H]1+), 654.35129.

Example 211

Preparation of methyl 4-[({4-[4-(2-methoxyethoxy)-6-morpholin-4-yl-1,3,5-triazin-2-yl]phenyl}carbamoyl)amino]benzoate HRMS: calcd for C25H28N6O6+H+, 509.21431. found (ESI, [M+H]+ Obs'd), 509.214.

Example 212

Preparation of 1-methyl-3-(4-{4-[(1-methylethyl)amino]-6-(8-oxa-3-azabicyclo[3.2.1]oct-3-yl)-1,3,5-triazin-2-yl}phenyl)urea MS (ESI) m/z 397.48.

Example 213

Preparation of 1-cyclopropyl-3-(4-{4-[(1-methylethyl)amino]-6-(8-oxa-3-azabicyclo[3.2.1]oct-3-yl)-1,3,5-triazin-2-yl}phenyl)urea MS (ESI) m/z 423.52.

Example 214

Preparation of 1-(2-hydroxyethyl)-3-(4-{4-[(1-methylethyl)amino]-6-(8-oxa-3-azabicyclo[3.2.1]oct-3-yl)-1,3,5-triazin-2-yl}phenyl)urea MS (ESI) m/z 427.51.

Example 215

Preparation of 1-(4-{4-[(1-methylethyl)amino]-6-(8-oxa-3-azabicyclo[3.2.1]oct-3-yl)-1,3,5-triazin-2-yl}phenyl)-3-pyridin-4-ylurea MS (ESI) m/z 460.54.

Example 216

Preparation of 1-(4-{4-[(1-methylethyl)amino]-6-(8-oxa-3-azabicyclo[3.2.1]oct-3-yl)-1,3,5-triazin-2-yl}phenyl)-3-[6-(4-methylpiperazin-1-yl)pyridin-3-yl]urea MS (ESI) m/z 460.54.

Example 217

Preparation of 1-(4-{4-[(1-methylethyl)amino]-6-(8-oxa-3-azabicyclo[3.2.1]oct-3-yl)-1,3,5-triazin-2-yl}phenyl)-3-[4-(4-methylpiperazin-1-yl)phenyl]urea MS (ESI) m/z 557.70.

Example 218

Preparation of 1-{4-[(2,2-dimethylhydrazino)carbonyl]phenyl}-3-(4-{4-[(1-methylethyl)amino]-6-(8-oxa-3-azabicyclo[3.2.1]oct-3-yl)-1,3,5-triazin-2-yl}phenyl)urea MS (ESI) m/z 545.65.

Example 219

Preparation of 4-{[(4-{4-[(1-methylethyl)amino]-6-(8-oxa-3-azabicyclo[3.2.1]oct-3-yl)-1,3,5-triazin-2-yl}phenyl)carbamoyl]amino}-N-pyrrolidin-1-ylbenzamide MS (ESI) m/z 571.69.

Example 220

Preparation of 1-{4-[2-(dimethylamino)ethoxy]phenyl}-3-(4-{4-[(1-methylethyl)amino]-6-(8-oxa-3-azabicyclo[3.2.1]oct-3-yl)-1,3,5-triazin-2-yl}phenyl)urea MS (ESI) m/z 546.68.

Example 221

Preparation of 1-[4-(hydroxymethyl)phenyl]-3-(4-{4-[(1-methylethyl)amino]-6-(8-oxa-3-azabicyclo[3.2.1]oct-3-yl)-1,3,5-triazin-2-yl}phenyl)urea MS (ESI) m/z 489.58

Example 222

Preparation of 1-[4-(2-hydroxyethyl)phenyl]-3-(4-{4-[(1-methylethyl)amino]-6-(8-oxa-3-azabicyclo[3.2.1]oct-3-yl)-1,3,5-triazin-2-yl}phenyl)urea MS (ESI) m/z 503.61.

Example 223

Preparation of 1-{4-[4-(1-hydroxyethyl)-6-morpholin-4-yl-1,3,5-triazin-2-yl]phenyl}-3-pyridin-4-ylurea MS (ESI) m/z 421.46.

Example 224

Preparation of 1-[4-(4,6-di-3-oxa-8-azabicyclo[3.2.1]oct-8-yl-1,3,5-triazin-2-yl)phenyl]-3-pyridin-4-ylurea MS (ESI) m/z 514.59.

Example 225

Preparation of methyl 4-({[4-(4-ethyl-6-morpholin-4-yl-1,3,5-triazin-2-yl)phenyl]carbamoyl}amino)benzoate MS (ESI) m/z 462.51

Example 226

Preparation of methyl 4-[({4-[4-(3,6-dihydro-2H-pyran-4-yl)-6-morpholin-4-yl-1,3,5-triazin-2-yl]phenyl}carbamoyl)amino]benzoate MS (ESI) m/z 516.55.

Example 227

Preparation of 4-[({4-[4-(3,6-dihydro-2H-pyran-4-yl)-6-morpholin-4-yl-1,3,5-triazin-2-yl]phenyl}carbamoyl)amino]benzoic acid MS (ESI) m/z 502.53

Example 228

Preparation of 1-(4-{4-morpholin-4-yl-6-[2-(pyridin-4-ylamino)ethyl]-1,3,5-triazin-2-yl}phenyl)-3-pyridin-4-ylurea HRMS: calcd for C26H27N9O2+H+, 498.23605. found (ESI, [M+H]+ Obs'd), 498.2383.

Example 229

Preparation of 1-[4-(4-methylpiperazin-1-yl)phenyl]-3-{4-[4-morpholin-4-yl-6-(3-oxa-8-azabicyclo[3.2.1]oct-8-yl)-1,3,5-triazin-2-yl]phenyl}urea HRMS: calcd for C31H39N9O3+H+, 586.32486. found (ESI, [M+H]+ Obs'd), 586.3245.

Example 230

Preparation of 1-(4-acetylphenyl)-3-{4-[4-morpholin-4-yl-6-(3-oxa-8-azabicyclo[3.2.1]oct-8-yl)-1,3,5-triazin-2-yl]phenyl}urea HRMS: calcd for C28H31N7O4+H+, 530.25103. found (ESI, [M+H]+ Obs'd), 530.2508.

Example 231

Preparation of 4-({[4-(4-butyl-6-morpholin-4-yl-1,3,5-triazin-2-yl)phenyl]carbamoyl}amino)-N-[2-(dimethylamino)ethyl]benzamide MS (ESI) m/z 546.676.

Example 232

Preparation of 1-[4-(4-butyl-6-morpholin-4-yl-1,3,5-triazin-2-yl)phenyl]-3-{4-[(4-methylpiperazin-1-yl)carbonyl]phenyl}urea MS (ESI) m/z 559.4.

Example 233

Preparation of 4-({[4-(4-ethyl-6-morpholin-4-yl-1,3,5-triazin-2-yl)phenyl]carbamoyl}amino)benzoic acid MS (ESI) m/z 448.483

Example 234

Preparation of 1-methyl-3-{4-[4-(8-oxa-3-azabicyclo[3.2.1]oct-3-yl)-6-(9-oxa-3,7-diazabicyclo[3.3.1]non-3-yl)-1,3,5-triazin-2-yl]phenyl}urea HRMS: calcd for C23H30N8O3+H+, 467.25136. found (ESI, [M+H]+ Obs'd), 467.2525.

Example 235

Preparation of 1-{4-[4-(8-oxa-3-azabicyclo[3.2.1]oct-3-yl)-6-(9-oxa-3,7-diazabicyclo[3.3.1]non-3-yl)-1,3,5-triazin-2-yl]phenyl}-3-pyridin-3-ylurea HRMS: calcd for C27H31N9O3+H+, 530.26226. found (ESI, [M+H]+ Obs'd), 530.2638.

Example 236

Preparation of 1-[4-(4-ethyl-6-morpholin-4-yl-1,3,5-triazin-2-yl)phenyl]-3-{4-[(4-methylpiperazin-1-yl)carbonyl]phenyl}urea MS (ESI) m/z 531.1.

Example 237

Preparation of N-[2-(dimethylamino)ethyl]-4-({[4-(4-ethyl-6-morpholin-4-yl-1,3,5-triazin-2-yl)phenyl]carbamoyl}amino)benzamide

Example 238

Preparation of 1-(4-{[4-(dimethylamino)piperidin-1-yl]carbonyl}phenyl)-3-[4-(4-ethyl-6-morpholin-4-yl-1,3,5-triazin-2-yl)phenyl]urea MS (ESI) m/z 558.711

Example 239

Preparation of 1-[4-(4-butyl-6-morpholin-4-yl-1,3,5-triazin-2-yl)phenyl]-3-[4-(hydroxymethyl)phenyl]urea MS (ESI) m/z 462.554.

Example 240

Preparation of 4-[({4-[4-(3,6-dihydro-2H-pyran-4-yl)-6-morpholin-4-yl-1,3,5-triazin-2-yl]phenyl}carbamoyl)amino]-N-[2-(dimethylamino)ethyl]-N-methylbenzamide MS (ESI) m/z 586.721.

Example 241

Preparation of 1-[4-(4-butyl-6-morpholin-4-yl-1,3,5-triazin-2-yl)phenyl]-3-(4-{[4-(dimethylamino)piperidin-1-yl]carbonyl}phenyl)urea MS (ESI) m/z 586.741.

Example 242

Preparation of N-[2-(dimethylamino)ethyl]-4-({[4-(4-ethyl-6-morpholin-4-yl-1,3,5-triazin-2-yl)phenyl]carbamoyl}amino)-N-methylbenzamide MS (ESI) m/z 532.649.

Example 243

Preparation of N-[2-(dimethylamino)ethyl]-4-({[4-(4-methoxy-6-morpholin-4-yl-1,3,5-triazin-2-yl)phenyl]carbamoyl}amino)-N-methylbenzamide MS (ESI) m/z 534.62.

Example 244

Preparation of N-[2-(dimethylamino)ethyl]-4-({[4-(4-methoxy-6-morpholin-4-yl-1,3,5-triazin-2-yl)phenyl]carbamoyl}amino)benzamide MS (ESI) m/z 520.60.

Example 245

Preparation of 4-({[4-(4-methoxy-6-morpholin-4-yl-1,3,5-triazin-2-yl)phenyl]carbamoyl}amino)-N-methyl-N-[2-(methylamino)ethyl]benzamide MS (ESI) m/z 520.60.

Example 246

Preparation of 1-[4-(4-methoxy-6-morpholin-4-yl-1,3,5-triazin-2-yl)phenyl]-3-{4-[(4-methylpiperazin-1-yl)carbonyl]phenyl}urea MS (ESI) m/z 532.61.

Example 247

Preparation of 1-{4-[(3,3-dimethylpiperazin-1-yl)carbonyl]phenyl}-3-[4-(4-methoxy-6-morpholin-4-yl-1,3,5-triazin-2-yl)phenyl]urea MS (ESI) m/z 546.63.

Example 248

Preparation of 4-({[4-(4-methoxy-6-morpholin-4-yl-1,3,5-triazin-2-yl)phenyl]carbamoyl}amino)-N-(2-piperidin-1-ylethyl)benzamide MS (ESI) m/z 560.66.

Example 249

Preparation of 1-(4-ethenylphenyl)-3-{4-[4-morpholin-4-yl-6-(3-oxa-8-azabicyclo[3.2.1]oct-8-yl)-1,3,5-triazin-2-yl]phenyl}urea MS (ESI) m/z 514.3;
HRMS: calcd for C28H31N7O3+H+, 514.25611. found (ESI, [M+H]+ Obs'd), 514.2561.

Example 250

Preparation of 1-{4-[(4-methylpiperazin-1-yl)methyl]phenyl}-3-{4-[4-morpholin-4-yl-6-(3-oxa-8-azabicyclo[3.2.1]oct-8-yl)-1,3,5-triazin-2-yl]phenyl}urea HRMS: calcd for C32H41N9O3+H+, 600.34051. found (ESI, [M+H]+ Obs'd), 600.3405.

Example 251

Preparation of 4-({[4-(4-ethyl-6-morpholin-4-yl-1,3,5-triazin-2-yl)phenyl]carbamoyl}amino)-N-[4-(4-methylpiperazin-1-yl)phenyl]benzamide MS (ESI) m/z 621.77.

Example 252

Preparation of 1-[4-(4-butyl-6-morpholin-4-yl-1,3,5-triazin-2-yl)phenyl]-3-[4-({[2-(dimethylamino)ethyl]amino}methyl)phenyl]urea MS (ESI) m/z 532.71.

Example 253

Preparation of 4-({[4-(4-butyl-6-morpholin-4-yl-1,3,5-triazin-2-yl)phenyl]carbamoyl}amino)-N-[4-(4-methylpiperazin-1-yl)phenyl]benzamide MS (ESI) m/z 649.82.

Example 254

Preparation of 1-[4-(4-butyl-6-morpholin-4-yl-1,3,5-triazin-2-yl)phenyl]-3-{4-[(4-methylpiperazin-1-yl)methyl]phenyl}urea MS (ESI) m/z 544.728.

Example 255

Preparation of 1-[4-(4-butyl-6-morpholin-4-yl-1,3,5-triazin-2-yl)phenyl]-3-(4-formylphenyl)urea MS (ESI) m/z 461.2.

Example 256

Preparation of tert-butyl(1R,4R)-5-(4-morpholin-4-yl-6-{4-[(pyridin-4-ylcarbamoyl)amino]phenyl}-1,3,5-triazin-2-yl)-2,5-diazabicyclo[2.2.1]heptane-2-carboxylate mp 192° C.; MS (ESI) m/z 574.3.

Example 257

Preparation of tert-butyl(1R,4R)-5-[4-(4-{[(4-acetylphenyl)carbamoyl]amino}phenyl)-6-morpholin-4-yl-1,3,5-triazin-2-yl]-2,5-diazabicyclo[2.2.1]heptane-2-carboxylate mp 202° C.; MS (ESI) m/z 615.3;

Example 258

Preparation of 1-(4-{4-[(2-methoxyethyl)amino]-6-(8-oxa-3-azabicyclo[3.2.1]oct-3-yl)-1,3,5-triazin-2-yl}phenyl)-3-pyridin-3-ylurea MS (ESI) m/z 476.54

Example 259

Preparation of 1-{4-[4-{[(1S)-2-hydroxy-1-methylethyl]amino}-6-(8-oxa-3-azabicyclo[3.2.1]oct-3-yl)-1,3,5-triazin-2-yl]phenyl}-3-pyridin-3-ylurea MS (ESI) m/z 476.54.

Example 260

Preparation of 1-{4-[4-{[(1R)-2-hydroxy-1-methylethyl]amino}-6-(8-oxa-3-azabicyclo[3.2.1]oct-3-yl)-1,3,5-triazin-2-yl]phenyl}-3-pyridin-3-ylurea MS (ESI) m/z 476.54.

Example 261

Preparation of 1-(4-{4-[(2-hydroxy-1,1-dimethylethyl)amino]-6-(8-oxa-3-azabicyclo[3.2.1]oct-3-yl)-1,3,5-triazin-2-yl}phenyl)-3-pyridin-3-ylurea MS (ESI) m/z 490.57.

Example 262

Preparation of 1-{4-[4-(tert-butylamino)-6-(8-oxa-3-azabicyclo[3.2.1]oct-3-yl)-1,3,5-triazin-2-yl]phenyl}-3-pyridin-3-ylurea MS (ESI) m/z 474.57.

Example 263

Preparation of 4-({[4-(4,6-dimorpholin-4-yl-1,3,5-triazin-2-yl)phenyl]carbamoyl}amino)-N-(pyridin-2-ylmethyl)benzamide mp 296-298° C.; MS (ESI) m/z 298.6;
HRMS: calcd for C31H33N9O4+H+, 596.27283. found (ESI, [M+H]+ Obs'd), 596.2724.
HRMS: calcd for C31H33N9O4+H+, 596.27283. found (ESI, [M+H]+ Calc'd), 596.2728.

Example 264

Preparation of 1-[4-(4,6-di-3-oxa-8-azabicyclo[3.2.1]oct-8-yl-1,3,5-triazin-2-yl)phenyl]-3-(4-piperazin-1-ylphenyl)urea HRMS: calcd for C32H39N9O3+H+, 598.32486. found (ESI, [M+H]+ Obs'd), 598.3247.
HRMS: calcd for C32H39N9O3+H+, 598.32486. found (ESI, [M+H]+ Calc'd), 598.3249.

Example 265

Preparation of 1-[4-(4,6-di-3-oxa-8-azabicyclo[3.2.1]oct-8-yl-1,3,5-triazin-2-yl)phenyl]-3-[4-(4-methylpiperazin-1-yl)phenyl]urea HRMS: calcd for C33H41N9O3+H+, 612.34051. found (ESI, [M+H]+ Obs'd), 612.3402.

Example 266

Preparation of 1-{4-[2-(dimethylamino)ethoxy]phenyl}-3-{4-[4-morpholin-4-yl-6-(3-oxa-8-azabicyclo[3.2.1]oct-8-yl)-1,3,5-triazin-2-yl]phenyl}urea HRMS: calcd for C30H38N8O4+H+, 575.30888. found (ESI, [M+H]+ Obs'd), 575.3088.
HRMS: calcd for C30H38N8O4+H+, 575.30888. found (ESI, [M+H]+ Calc'd), 575.3089.

Example 267

Preparation of 1-(4-{4-[2-(1,3-dioxan-2-yl)ethyl]-6-morpholin-4-yl-1,3,5-triazin-2-yl}phenyl)-3-pyridin-4-ylurea HRMS: calcd for C25H29N7O4+H+, 492.23538. found (ESI, [M+H]+ Obs'd), 492.2364.

Example 268

Preparation of 1-(4-{4-[2,5-bis(hydroxymethyl)pyrrolidin-1-yl]-6-morpholin-4-yl-1,3,5-triazin-2-yl}phenyl)-3-pyridin-4-ylurea HRMS: calcd for C25H30N8O4+H+, 507.24628. found (ESI, [M+H]+ Obs'd), 507.2471.

Example 269

Preparation of 4-({[4-(4-butyl-6-morpholin-4-yl-1,3,5-triazin-2-yl)phenyl]carbamoyl}amino)-N-{4-[2-(dimethylamino)ethoxy]phenyl}benzamide MS (ESI) m/z 638.773.

Example 270

Preparation of 1-{4-[(4-benzylpiperidin-1-yl)carbonyl]phenyl}-3-[4-(4-butyl-6-morpholin-4-yl-1,3,5-triazin-2-yl)phenyl]urea MS (ESI) m/z 633.821.

Example 271

Preparation of 4-({[4-(4-ethyl-6-morpholin-4-yl-1,3,5-triazin-2-yl)phenyl]carbamoyl}amino)-N-(1-methylpiperidin-4-yl)benzamide MS (ESI) m/z 545.3.

Example 272

Preparation of 4-({[4-(4-butyl-6-morpholin-4-yl-1,3,5-triazin-2-yl)phenyl]carbamoyl}amino)-N-(1-methylpiperidin-4-yl)benzamide MS (ESI) m/z 573.4.

Example 273

Preparation of 1-{4-[4-(6-hydroxy-3-oxa-8-azabicyclo[3.2.1]oct-8-yl)-6-morpholin-4-yl-1,3,5-triazin-2-yl]phenyl}-3-pyridin-4-ylurea MS (ESI) m/z 504.551.

Example 274

Preparation of 1-(4-{4-[3-(dimethylamino)propyl]-6-morpholin-4-yl-1,3,5-triazin-2-yl}phenyl)-3-pyridin-4-ylurea MS (ESI) m/z 462.56.

Example 275

Preparation of 1-[4-(4-{3-[(1-methylethyl)amino]propyl}-6-morpholin-4-yl-1,3,5-triazin-2-yl)phenyl]-3-pyridin-4-ylurea MS (ESI) m/z 476.59.

Example 276

Preparation of 1-{4-[4-morpholin-4-yl-6-(3-pyrrolidin-1-ylpropyl)-1,3,5-triazin-2-yl]phenyl}-3-pyridin-4-ylurea MS (ESI) m/z 488.60.

Example 277

Preparation of 1-(4-{4-[3-(4-methylpiperazin-1-yl)propyl]-6-morpholin-4-yl-1,3,5-triazin-2-yl}phenyl)-3-pyridin-4-ylurea MS (ESI) m/z 517.64.

Example 278

Preparation of 1-{4-[4-(3-{[2-(dimethylamino)ethyl]amino}propyl)-6-morpholin-4-yl-1,3,5-triazin-2-yl]phenyl}-3-pyridin-4-ylurea MS (ESI) m/z 505.63.

Example 279

Preparation of 1-{4-[4-(3-hydroxypropyl)-6-morpholin-4-yl-1,3,5-triazin-2-yl]phenyl}-3-pyridin-4-ylurea MS (ESI) m/z 435.49.

Example 280

Preparation of 1-{4-[4-morpholin-4-yl-6-(3-oxopropyl)-1,3,5-triazin-2-yl]phenyl}-3-pyridin-4-ylurea MS (ESI) m/z 433.47.

Example 281

Preparation of tert-butyl-7-(4-morpholin-4-yl-6-{4-[(pyridin-4-ylcarbamoyl)amino]phenyl}-1,3,5-triazin-2-yl)-9-oxa-3,7-diazabicyclo[3.3.1]nonane-3-carboxylate HRMS: calcd for C30H37N9O5+H+, 604.29904. found (ESI, [M+H]+ Obs'd), 604.2993.

Example 282

Preparation of 1-{4-[4-(6,8-dioxa-3-azabicyclo[3.2.1]oct-3-yl)-6-morpholin-4-yl-1,3,5-triazin-2-yl]phenyl}-3-pyridin-4-ylurea HRMS: calcd for C24H26N8O4+H+, 491.21498. found (ESI, [M+H]+ Obs'd), 491.2155.

Example 283

Preparation of 1-{4-[4-(3,6-dihydro-2H-pyran-4-yl)-6-morpholin-4-yl-1,3,5-triazin-2-yl]phenyl}-3-(4-{[4-(dimethylamino)piperidin-1-yl]carbonyl}phenyl)urea MS (ESI) m/z 612.759.

Example 284

Preparation of 4-[({4-[4-(3,6-dihydro-2H-pyran-4-yl)-6-morpholin-4-yl-1,3,5-triazin-2-yl]phenyl}carbamoyl)amino]-N-[2-(dimethylamino)ethyl]benzamide MS (ESI) m/z 572.694.

Example 285

Preparation of 1-[4-(4,6-di-3-oxa-8-azabicyclo[3.2.1]oct-8-yl-1,3,5-triazin-2-yl)phenyl]-3-{4-[(4-methylpiperazin-1-yl)methyl]phenyl}urea MS (ESI) m/z 625.78

Example 286

Preparation of N-[4-(4,6-di-3-oxa-8-azabicyclo[3.2.1]oct-8-yl-1,3,5-triazin-2-yl)phenyl]piperazine-1-carboxamide MS (ESI) m/z 506.61

Example 287

Preparation of 1-[4-(4,6-di-3-oxa-8-azabicyclo[3.2.1]oct-8-yl-1,3,5-triazin-2-yl)phenyl]-3-[4-(hydroxymethyl)phenyl]urea MS (ESI) m/z 543.63.

Example 288

Preparation of 1-[4-(4,6-di-3-oxa-8-azabicyclo[3.2.1]oct-8-yl-1,3,5-triazin-2-yl)phenyl]-3-{4-[(methylamino)methyl]phenyl}urea MS (ESI) m/z 556.67.

Example 289

Preparation of 1-{4-[2-(dimethylamino)ethoxy]phenyl}-3-[4-(4,6-di-3-oxa-8-azabicyclo[3.2.1]oct-8-yl-1,3,5-triazin-2-yl)phenyl]urea MS (ESI) m/z 600.73.

Example 290

Preparation of 1-{4-[4-morpholin-4-yl-6-(9-oxa-3,7-diazabicyclo[3.3.1]non-3-yl)-1,3,5-triazin-2-yl]phenyl}-3-pyridin-4-ylurea MS (ESI) m/z 503.57.

Example 291

Preparation of 1-{4-[4-(7-methyl-9-oxa-3,7-diazabicyclo[3.3.1]non-3-yl)-6-morpholin-4-yl-1,3,5-triazin-2-yl]phenyl}-3-pyridin-4-ylurea MS (ESI) m/z 517.60.

Example 292

Preparation of 1-{4-[4-(7-acetyl-9-oxa-3,7-diazabicyclo[3.3.1]non-3-yl)-6-morpholin-4-yl-1,3,5-triazin-2-yl]phenyl}-3-pyridin-4-ylurea MS (ESI) m/z 545.61.

Example 293

Preparation of 1-(4-{4-[7-(methylsulfonyl)-9-oxa-3,7-diazabicyclo[3.3.1]non-3-yl]-6-morpholin-4-yl-1,3,5-triazin-2-yl}phenyl)-3-pyridin-4-ylurea MS (ESI) m/z 581.66.

Example 294

Preparation of 1-[4-(4-methylpiperazin-1-yl)phenyl]-3-[4-(4-morpholin-4-yl-6-propyl-1,3,5-triazin-2-yl)phenyl]urea MS (ESI) m/z 517.4.

Example 295

Preparation of 1-{4-[2-(dimethylamino)ethoxy]phenyl}-3-[4-(4-ethyl-6-morpholin-4-yl-1,3,5-triazin-2-yl)phenyl]urea MS (ESI) m/z 492.2.

Example 296

Preparation of 1-[4-(4-ethyl-6-morpholin-4-yl-1,3,5-triazin-2-yl)phenyl]-3-[4-(4-methylpiperazin-1-yl)phenyl]urea MS (ESI) m/z 503.

Example 297

Preparation of 1-[4-(4-methylpiperazin-1-yl)phenyl]-3-{4-[4-(2-methylpropyl)-6-morpholin-4-yl-1,3,5-triazin-2-yl]phenyl}urea MS (ESI) m/z 530.701.

Example 298

Preparation of 1-{4-[(3,3-dimethylpiperazin-1-yl)carbonyl]phenyl}-3-[4-(4-ethyl-6-morpholin-4-yl-1,3,5-triazin-2-yl)phenyl]urea MS (ESI) m/z 544.684.

Example 299

Preparation of 4-({[4-(4-ethyl-6-morpholin-4-yl-1,3,5-triazin-2-yl)phenyl]carbamoyl}amino)-N-(1-methylazetidin-3-yl)benzamide MS (ESI) m/z 517.3;
MS (ESI) m/z 259.2;

Example 300

Preparation of methyl 4-[({4-[4-(1-methylethyl)-6-morpholin-4-yl-1,3,5-triazin-2-yl]phenyl}carbamoyl)amino]benzoate mp 218° C.;
MS (ESI) m/z 477.3.

Example 301

Preparation of 4-[({4-[4-(1-methylethyl)-6-morpholin-4-yl-1,3,5-triazin-2-yl]phenyl}carbamoyl)amino]benzoic acid MS (ESI) m/z 463.3.

Example 302

Preparation of tert-butyl-(1R,4R)-5-{4-[4-({[4-(1-hydroxyethyl)phenyl]carbamoyl}amino)phenyl]-6-morpholin-4-yl-1,3,5-triazin-2-yl}-2,5-diazabicyclo[2.2.1]heptane-2-carboxylate MS (ESI) m/z 617.4.

Example 303

Preparation of 1-[4-(4-methylpiperazin-1-yl)phenyl]-3-{4-[4-(3-oxa-8-azabicyclo[3.2.1]oct-8-yl)-6-(8-oxa-3-azabicyclo[3.2.1]oct-3-yl)-1,3,5-triazin-2-yl]phenyl}urea HRMS: calcd for C33H41N9O3+H+, 612.34051. found (ESI, [M+H]+ Obs'd), 612.3402.
HRMS: calcd for C33H41N9O3+H+, 612.34051. found (ESI, [M+H]+ Calc'd), 612.3405.

Example 304

Preparation of 1-{4-[4-(1-methylethyl)-6-morpholin-4-yl-1,3,5-triazin-2-yl]phenyl}-3-{4-[(4-methylpiperazin-1-yl)carbonyl]phenyl}urea MS (ESI) m/z 544.66.

Example 305

Preparation of N-[2-(dimethylamino)ethyl]-4-[({4-[4-(1-methylethyl)-6-morpholin-4-yl-1,3,5-triazin-2-yl]phenyl}carbamoyl)amino]benzamide MS (ESI) m/z 532.65.

Example 306

Preparation of N-[2-(dimethylamino)ethyl]-N-methyl-4-[({4-[4-(1-methylethyl)-6-morpholin-4-yl-1,3,5-triazin-2-yl]phenyl}carbamoyl)amino]benzamide MS (ESI) m/z 546.68.

Example 307

Preparation of N-(1-methylazetidin-3-yl)-4-[({4-[4-(1-methylethyl)-6-morpholin-4-yl-1,3,5-triazin-2-yl]phenyl}carbamoyl)amino]benzamide MS (ESI) m/z 530.63.

Example 308

Preparation of 1-(4-{[4-(dimethylamino)piperidin-1-yl]carbonyl}phenyl)-3-{4-[4-(1-methylethyl)-6-morpholin-4-yl-1,3,5-triazin-2-yl]phenyl}urea MS (ESI) m/z 572.72.

Example 309

Preparation of 4-[({4-[4-(1-methylethyl)-6-morpholin-4-yl-1,3,5-triazin-2-yl]phenyl}carbamoyl)amino]-N-pyridin-4-ylbenzamide MS (ESI) m/z 538.61.

Example 310

Preparation of 4-[({4-[4-(1-methylethyl)-6-morpholin-4-yl-1,3,5-triazin-2-yl]phenyl}carbamoyl)amino]-N-pyridin-3-ylbenzamide MS (ESI) m/z 538.61.

Example 311

Preparation of N-cyclobutyl-4-[({4-[4-(1-methylethyl)-6-morpholin-4-yl-1,3,5-triazin-2-yl]phenyl}carbamoyl)amino]benzamide MS (ESI) m/z 515.62.

Example 312

Preparation of 1-{4-[4,6-di-(1S,4S)-2-oxa-5-azabicyclo[2.2.1]hept-5-yl-1,3,5-triazin-2-yl]phenyl}-3-[4-(4-methylpiperazin-1-yl)phenyl]urea MS (ESI) m/z 583.70.

Example 313

Preparation of 1-{4-[4,6-di-(1S,4S)-2-oxa-5-azabicyclo[2.2.1]hept-5-yl-1,3,5-triazin-2-yl]phenyl}-3-(4-piperazin-1-ylphenyl)urea MS (ESI) m/z 569.67.

Example 314

Preparation of 1-{4-[4,6-di-(1R,4R)-2-oxa-5-azabicyclo[2.2.1]hept-5-yl-1,3,5-triazin-2-yl]phenyl}-3-[4-(4-methylpiperazin-1-yl)phenyl]urea MS (ESI) m/z 583.70.

Example 315

Preparation of 1-(2-fluoroethyl)-3-{4-[4-{[4-(4-methylpiperazin-1-yl)phenyl]amino}-6-(8-oxa-3-azabicyclo[3.2.1]oct-3-yl)-1,3,5-triazin-2-yl]phenyl}urea MS (ESI) m/z 561.6.

Example 316

Preparation of 1-cyclopropyl-3-{4-[4-{[4-(4-methylpiperazin-1-yl)phenyl]amino}-6-(8-oxa-3-azabicyclo[3.2.1]oct-3-yl)-1,3,5-triazin-2-yl]phenyl}urea MS (ESI) m/z 555.71.

Example 317

Preparation of 1-methyl-3-{4-[4-{[4-(4-methylpiperazin-1-yl)phenyl]amino}-6-(8-oxa-3-azabicyclo[3.2.1]oct-3-yl)-1,3,5-triazin-2-yl]phenyl}urea MS (ESI) m/z 529.67.

Example 318

Preparation of 4-[({4-[4-{[4-(4-methylpiperazin-1-yl)phenyl]amino}-6-(8-oxa-3-azabicyclo[3.2.1]oct-3-yl)-1,3,5-triazin-2-yl]phenyl}carbamoyl)amino]benzamide MS (ESI) m/z 634.745.

Example 319

1-{4-[4-{[4-(4-methylpiperazin-1-yl)phenyl]amino}-6-(8-oxa-3-azabicyclo[3.2.1]oct-3-yl)-1,3,5-triazin-2-yl]phenyl}-3-phenylurea MS (ESI) m/z 591.72.

Example 320

Preparation of 1-[4-(4-ethyl-6-morpholin-4-yl-1,3,5-triazin-2-yl)phenyl]-3-{4-[(4-phenylpiperidin-1-yl)carbonyl]phenyl}urea MS m/z 08-301429LMS.

Example 321

Preparation of 4-({[4-(4-ethyl-6-morpholin-4-yl-1,3,5-triazin-2-yl)phenyl]carbamoyl}amino)-N-(pyridin-4-ylmethyl)benzamide MS (ESI) m/z 539.4;
MS (ESI) m/z 270.2.

Example 322

Preparation of 1-{4-[(4-methylpiperazin-1-yl)carbonyl]phenyl}-3-{4-[4-(2-methylpropyl)-6-morpholin-4-yl-1,3,5-triazin-2-yl]phenyl}urea MS (ESI) m/z 558.711.

Example 323

Preparation of 1-(4-{[4-(dimethylamino)piperidin-1-yl]carbonyl}phenyl)-3-{4-[4-(2-methylpropyl)-6-morpholin-4-yl-1,3,5-triazin-2-yl]phenyl}urea MS (ESI) m/z 586.765.

Example 324

Preparation of N-[2-(dimethylamino)ethyl]-N-methyl-4-[({4-[4-(2-methylpropyl)-6-morpholin-4-yl-1,3,5-triazin-2-yl]phenyl}carbamoyl)amino]benzamide MS (ESI) m/z 560.727.

Example 325

Preparation of 1-methyl-3-(4-{4-(8-oxa-3-azabicyclo[3.2.1]oct-3-yl)-6-[(4-piperazin-1-ylphenyl)amino]-1,3,5-triazin-2-yl}phenyl)urea MS (ESI) m/z 515.62.

Example 326

Preparation of 1-cyclopropyl-3-(4-{4-(8-oxa-3-azabicyclo[3.2.1]oct-3-yl)-6-[(4-piperazin-1-ylphenyl)amino]-1,3,5-triazin-2-yl}phenyl)urea MS (ESI) m/z 541.66.

Example 327

Preparation of 1-(2-fluoroethyl)-3-(4-{4-(8-oxa-3-azabicyclo[3.2.1]oct-3-yl)-6-[(4-piperazin-1-ylphenyl)amino]-1,3,5-triazin-2-yl}phenyl)urea MS (ESI) m/z 547.64.

Example 328

Preparation of 1-(2-hydroxyethyl)-3-(4-{4-(8-oxa-3-azabicyclo[3.2.1]oct-3-yl)-6-[(4-piperazin-1-ylphenyl)amino]-1,3,5-triazin-2-yl}phenyl)urea MS (ESI) m/z 545.65.

Example 329

Preparation of 4-{[(4-{4-(8-oxa-3-azabicyclo[3.2.1]oct-3-yl)-6-[(4-piperazin-1-ylphenyl)amino]-1,3,5-triazin-2-yl}phenyl)carbamoyl]amino}benzamide MS (ESI) m/z 620.72.

Example 330

Preparation of 1-(4-{4-(8-oxa-3-azabicyclo[3.2.1]oct-3-yl)-6-[(4-piperazin-1-ylphenyl)amino]-1,3,5-triazin-2-yl}phenyl)-3-phenylurea MS (ESI) m/z 577.69.

Example 331

Preparation of 1-methyl-3-{4-[4-{[4-(4-methylpiperazin-1-yl)phenyl]amino}-6-(8-oxa-3-azabicyclo[3.2.1]oct-3-yl)-1,3,5-triazin-2-yl]phenyl}urea MS (ESI) m/z 529.67.

Example 332

Preparation of 1-cyclopropyl-3-{4-[4-{[4-(4-methylpiperazin-1-yl)phenyl]amino}-6-(8-oxa-3-azabicyclo[3.2.1]oct-3-yl)-1,3,5-triazin-2-yl]phenyl}urea MS (ESI) m/z 555.71.

Example 333

Preparation of 1-(2-fluoroethyl)-3-{4-[4-{[4-(4-methylpiperazin-1-yl)phenyl]amino}-6-(8-oxa-3-azabicyclo[3.2.1]oct-3-yl)-1,3,5-triazin-2-yl]phenyl}urea MS (ESI) m/z 561.69.

Example 334

Preparation of 4-[({4-[4-{[4-(4-methylpiperazin-1-yl)phenyl]amino}-6-(8-oxa-3-azabicyclo[3.2.1]oct-3-yl)-1,3,5-triazin-yl]phenyl}carbamoyl)amino]benzamide MS (ESI) m/z 634.745.

Example 335

Preparation of 1-{4-[4-{[4-(4-methylpiperazin-1-yl)phenyl]amino}-6-(8-oxa-3-azabicyclo[3.2.1]oct-3-yl)-1,3,5-triazin-2-yl]phenyl}-3-phenylurea MS (ESI) m/z 591.72;

Example 336

Preparation of 1-(2,3'-bipyridin-4-yl)-3-{4-[4-morpholin-4-yl-6-(3-oxa-8-azabicyclo[3.2.1]oct-8-yl)-1,3,5-triazin-2-yl]phenyl}urea MS (ESI) m/z 566.4; HRMS: calcd for C30H31N9O3+H+, 566.26226. found (ESI, [M+H]+ Calc'd), 566.2623.

Example 337

Preparation of 1-{4-[4-(4-methylphenyl)-6-morpholin-4-yl-1,3,5-triazin-2-yl]phenyl}-3-{4-[(4-methylpiperazin-1-yl)carbonyl]phenyl}urea MS (ESI) m/z 593.5.

Example 338

Preparation of N-[2-(dimethylamino)ethyl]-N-methyl-4-[({4-[4-(4-methylphenyl)-6-morpholin-4-yl-1,3,5-triazin-2-yl]phenyl}carbamoyl)amino]benzamide MS (ESI) m/z 595.5.

Example 339

Preparation of 1-{4-[4-(dimethylamino)piperidin-1-yl]phenyl}-3-{4-[4-(4-methylphenyl)-6-morpholin-4-yl-1,3,5-triazin-2-yl]phenyl}urea MS (ESI) m/z 593.4.

Example 340

Preparation of 1-{4-[4-(4-methylphenyl)-6-morpholin-4-yl-1,3,5-triazin-2-yl]phenyl}-3-pyridin-4-ylurea MS (ESI) m/z 468.3.

Example 341

Preparation of 1-{4-[4-(dimethylamino)piperidin-1-yl]phenyl}-3-[4-(4-ethyl-6-morpholin-4-yl-1,3,5-triazin-2-yl)phenyl]urea MS (ESI) m/z 531.4.

Example 342

Preparation of 4-[({4-[4-(4-methylphenyl)-6-morpholin-4-yl-1,3,5-triazin-2-yl]phenyl}carbamoyl)amino]benzoic acid MS (ESI) m/z 511.4.

Example 343

Preparation of 1-{4-[4-(4-methylphenyl)-6-morpholin-4-yl-1,3,5-triazin-2-yl]phenyl}-3-[4-(4-methylpiperazin-1-yl)phenyl]urea MS (ESI) m/z 565.4.

Example 344

Preparation of methyl 4-[({4-[4-(4-methylphenyl)-6-morpholin-4-yl-1,3,5-triazin-2-yl]phenyl}carbamoyl)amino]benzoate MS (ESI) m/z 525.4.

Example 345

Preparation of 1-{4-[4-(dimethylamino)piperidin-1-yl]phenyl}-3-[4-(4-morpholin-4-yl-6-phenyl-1,3,5-triazin-2-yl)phenyl]urea MS (ESI) m/z 578.745

Example 346

Preparation of 1-[4-(4-morpholin-4-yl-6-phenyl-1,3,5-triazin-2-yl)phenyl]-3-pyridin-4-ylurea MS (ESI) m/z 454.1.

Preparation of (2S,5R)-pyrrolidine-2,5-diyldimethanol hydrochloride ((2S,5R)-1-benzylpyrrolidine-2,5-diyl)dimethanol (2.2 g, 10 mmol) was dissolved in ethanol/tetrahydrofuran (200 mL, 1:1), and the mixture was treated with 10% palladium on carbon (250 mg). The suspension was shaken under 50 psi of hydrogen until the consumption of hydrogen had ceased. The mixture was filtered through a pad of Celite™ diatomaceous earth, eluting with ethanol. The filtrate was concentrated to dryness to provide the title compound as a golden oil that solidified upon prolonged storage. MS (ES$^+$)=132.2 (M+H)$^+$ Preparation of ((2S,5R)-1-(4-chloro-6-(4-nitrophenyl)-1,3,5-triazin-2-yl)pyrrolidine-2,5-diyl)dimethanol A suspension of 2,4-dichloro-6-(4-nitrophenyl)-1,3,5-triazine (2.2 g, 8.0 mmol) in acetone (40 mL) was added to magnetically stirred ice water (60 mL). The mixture was treated with a solution of (2S,5R)-pyrrolidine-2,5-diyldimethanol hydrochloride (1.0 g, 6.0 mmol) in acetone/water (20 mL, 3:1), followed by a suspension of sodium hydrogen carbonate (1.0 g, 12 mmol) in water (12 mL). After 30 minutes of stirring at 0° C., the mixture was treated with an additional quantity of (2S,5R)-pyrrolidine-2,5-diyldimethanol hydrochloride (0.26 g, 1.6 mmol) in water (3 mL), followed by sodium hydrogen carbonate (0.35 g) in water (5 mL). The suspension was allowed to stir overnight while regaining room temperature. The title compound was isolated by Buchner filtration, washed with water, and dried under house vacuum. Compound identification by mass spectrometry was achieved via the analysis of the product reaction product of ((2S,5R)-1-(4-chloro-6-(4-nitrophenyl)-1,3,5-triazin-2-yl)pyrrolidine-2,5-diyl)dimethanol with excess morpholine in ethanol. MS (ES$^+$)=417.2 (M+morpholine–Cl)$^+$ Preparation of ((2S,5R)-1-(4-(3-oxa-8-azabicyclo[3.2.1]octan-8-yl)-6-(4-nitrophenyl)-1,3,5-triazin-2-yl)pyrrolidine-2,5-diyl)dimethanol A suspension of ((2S,5R)-1-(4-chloro-6-(4-nitrophenyl)-1,3,5-triazin-2-yl)pyrrolidine-2,5-diyl)dimethanol (0.91 g, 2.5 mmol), 3-oxa-8-azabicyclo[3.2.1]octane hydrochloride (0.37 g, 2.5 mmol) in ethanol (13 mL) was treated with triethylamine (1 mL) and heated in a microwave reactor for 20 minutes at 130° C. The reaction mixture was purified by automated flash chromatography (methanol/chloroform) to provide the title compound as a hard peach colored foam. MS (ES$^+$)=443.2 (M+H)$^+$ Preparation of 8-(4-((2S,5R)-2,5-bis((tert-butyldimethylsilyloxy)methyl)pyrrolidin-1-yl)-6-(4-nitrophenyl)-1,3,5-triazin-2-yl)-3-oxa-8-azabicyclo[3.2.1]octane A solution of ((2S,5R)-1-(4-(3-oxa-8-azabicyclo[3.2.1]octan-8-yl)-6-(4-nitrophenyl)-1,3,5-triazin-2-yl)pyrrolidine-2,5-diyl)dimethanol (approximately 2.7 mmol) in dichloromethane (15 mL) was treated successively with tert-butyl dimethyl chlorosilane (1.0 g, 6.8 mmol) and imidazole (0.55 g, 8.1 mmol). The resulting suspension was stirred overnight at room temperature and then quenched with water. The aqueous phase was extracted three times with dichloromethane. The combined extracts were dried over anhydrous magnesium sulfate, filtered, and concentrated to dryness under reduced pressure. The crude residue was purified by automated flash chromatography (hexanes/ethyl acetate) to provide the title material. MS (ES$^+$)=671.4 (M+H)$^+$ Preparation of 4-(4-(3-oxa-8-azabicyclo[3.2.1]octan-8-yl)-6-((2S,5R)-2,5-bis((tert-butyldimethylsilyloxy)methyl)pyrrolidin-1-yl)-1,3,5-triazin-2-yl)aniline A suspension of palladium on charcoal (10%, 50 mg) and 8-(4-((2S,5R)-2,5-bis((tert-butyldimethylsilyloxy)methyl)pyrrolidin-1-yl)-6-(4-nitrophenyl)-1,3,5-triazin-2-yl)-3-oxa-8-azabicyclo[3.2.1]octane (0.55 g, 1.2 mmol) in tetrahydrofuran (20 mL) was stirred under a balloon of hydrogen overnight. The mixture was filtered through a pad of Celite™ diatomaceous earth and concentrated under reduced pressure to provide the title compound as a tan foam (0.42 g, 80%). MS (ES$^+$)=642.4 (M+H)$^+$ Example 347

Preparation of 1-(4-{4-[(2R,5S)-2,5-bis(hydroxymethyl)pyrrolidin-1-yl]-6-(3-oxa-8-azabicyclo[3.2.1]oct-8-yl)-1,3,5-triazin-2-yl}phenyl)-3-pyridin-4-ylurea A solution of 4-(4-(3-oxa-8-azabicyclo[3.2.1]octan-8-yl)-6-((2S,5R)-2,5-bis((tert-butyldimethylsilyloxy)methyl)pyrrolidin-1-yl)-1,3,5-triazin-2-yl)aniline (0.16 mmol) in dichloromethane (4 mL) was treated successively with triethylamine (1.6 mmol, 210 µL) and a triphosgene (24 mg, 0.08 mmol) solution in dichloromethane (500 µL). After 5 minutes, the mixture was treated with a solution of 4-aminopyridine (45 mg, 0.48 mmol) in warm tetrahydrofuran. After 1 hour, the reaction mixture was quenched with methanol and concentrated to dryness. The crude residue was treated with a saturated solution of hydrogen chloride in methanol. Upon complete desilylation, the mixture was concentrated to dryness and the residue purified by reverse-phase high performance liquid chromatography using a Phenomenex Prodigy column running a gradient elution of 5% acetonitrile/95% of 0.1% aqueous trifluoroacetic acid to 50% acetonitrile over 25 minutes. After concentration, the title compound was obtained as it trifluoroacetic acid salt (132 mg). MS (ES$^+$)=533.3 (M+H)$^+$ Example 348

Preparation of 1-(4-{4-[(2R,5S)-2,5-bis(hydroxymethyl)pyrrolidin-1-yl]-6-(3-oxa-8-azabicyclo[3.2.1]oct-8-yl)-1,3,5-triazin-2-yl}phenyl)-3-[4-(4-methylpiperazin-1-yl)phenyl]urea A solution of 4-(4-(3-oxa-8-azabicyclo[3.2.1]octan-8-yl)-6-((2S,5R)-2,5-bis((tert-butyldimethylsilyloxy)methyl)pyrrolidin-1-yl)-1,3,5-triazin-2-yl)aniline (0.16 mmol) in dichloromethane (4 mL) was treated successively with triethylamine (1.6 mmol, 210 µL) and a triphosgene (24 mg, 0.08 mmol) solution in dichloromethane (500 µL). After 5 minutes, the mixture was treated with 4-(4-methylpiperazin-1-yl)aniline (61 mg, 0.32 mmol). After 1 hour, the reaction mixture was quenched with methanol and concentrated to dryness. The crude residue was treated with a saturated solution of hydrogen chloride in methanol. Upon complete desilylation, the mixture was concentrated to dryness and the residue purified by reverse-phase high performance liquid chromatography using a Phenomenex Prodigy column running a gradient elution of 5% acetonitrile/95% of 0.1% aqueous trifluoroacetic acid to 50% acetonitrile over 25 minutes.

After concentration, the title compound was obtained as it trifluoroacetic acid salt (100 mg). MS (ES$^+$)=630.4 (M+H)$^+$

Example 349

Preparation of 1-(6-chloropyridin-3-yl)-3-{4-[4-morpholin-4-yl-6-(3-oxa-8-azabicyclo[3.2.1]oct-8-yl)-1,3,5-triazin-2-yl]phenyl}urea HRMS: calcd for C25H27ClN8O3+H+. 523.19674. found (ESI, [M+H]+ Obs'd), 523.1975.

Example 350

Preparation of 1-(4-{[4-(dimethylamino)piperidin-1-yl]carbonyl}phenyl)-3-{4-[4-morpholin-4-yl-6-(tetrahydro-2H-pyran-4-yl)-1,3,5-triazin-2-yl]phenyl}urea MS (ESI) m/z 614.8

Example 351

Preparation of 1-(4-aminophenyl)-3-[4-(4,6-dimorpholin-4-yl-1,3,5-triazin-2-yl)phenyl]urea MS (ESI) m/z 477.1.

Example 352

Preparation of N-[4-({[4-(4,6-di-8-oxa-3-azabicyclo[3.2.1]oct-3-yl-1,3,5-triazin-2-yl)phenyl]carbamoyl}amino)phenyl]-N2,N2-dimethylglycinamide The 4-(4,6-di-8-oxa-3-azabicyclo[3.2.1]oct-3-yl-1,3,5-triazin-2-yl)aniline (50 mg, 0.127 mmol) was dissolved in dichloromethane (1.5 mL) and triethylamine (0.120 mL) and added to a solution of triphosgene (17 mg) in dichloromethane (0.5 mL). Stir for 5 minutes then added N-(4-aminophenyl)-N2,N2-dimethylglycinamide (27 mg, 0.14 mmol). Purified by Gilson HPLC to provide the title compound as the TFA salt: 31.8 mg (35%) (M+H) m/z 614.3.

Example 353

Preparation of N-[4-({[4-(4,6-di-8-oxa-3-azabicyclo[3.2.1]oct-3-yl-1,3,5-triazin-2-yl)phenyl]carbamoyl}amino)phenyl]-2-pyrrolidin-1-ylacetamide The 4-(4,6-di-8-oxa-3-azabicyclo[3.2.1]oct-3-yl-1,3,5-triazin-2-yl)aniline (50 mg, 0.127 mmol) was dissolved in dichloromethane (1.5 mL) and triethylamine (0.120 mL) and added to a solution of triphosgene (17 mg) in dichloromethane (0.5 mL). Stir for 5 minutes then added N-(4-aminophenyl)-2-pyrrolidin-1-ylacetamide (30 mg, 0.14 mmol) Purified by Gilson HPLC to provide the title compound as the TFA salt: 63.1 mg (66%) (M+H) m/z 640.3.

Example 354

Preparation of 1-(4-(4-(8-oxa-3-azabicyclo[3.2.1]octan-3-yl)-6-(4-(piperazin-1-yl)phenylamino)-1,3,5-triazin-2-yl)phenyl)-3-methylurea Prepared as shown in Scheme 1, using commercially available tert-butyl 4-(4-aminophenyl)piperazine-1-carboxylate in the second nucleophilic aromatic substitution step. Following urea formation using methylamine, the Boc-piperazine intermediate was treated with TFA to provide the title compound. (M+H) 516.3.

Example 355

Preparation of 1-(4-(4-(8-oxa-3-azabicyclo[3.2.1]octan-3-yl)-6-(4-(piperazin-1-yl)phenylamino)-1,3,5-triazin-2-yl)phenyl)-3-cyclopropylurea Prepared as shown in Scheme 1, using commercially available tert-butyl 4-(4-aminophenyl)piperazine-1-carboxylate in the second nucleophilic aromatic substitution step. Following urea formation using cyclopropylamine, the Boc-piperazine intermediate was treated with TFA to provide the title compound. (M+H) 542.3.

Example 356

Preparation of 1-(4-(4-(8-oxa-3-azabicyclo[3.2.1]octan-3-yl)-6-(4-(piperazin-1-yl)phenylamino)-1,3,5-triazin-2-yl)phenyl)-3-(2-fluoroethyl)urea Prepared as shown in Scheme 1, using commercially available tert-butyl 4-(4-aminophenyl)piperazine-1-carboxylate in the second nucleophilic aromatic substitution step. Following urea formation using 2-fluoroethylamine, the Boc-piperazine intermediate was treated with TFA to provide the title compound. (M+H) 548.3.

Example 357

Preparation of 1-(4-(4-(8-oxa-3-azabicyclo[3.2.1]octan-3-yl)-6-(4-(piperazin-1-yl)phenylamino)-1,3,5-triazin-2-yl)phenyl)-3-(2-hydroxyethyl)urea Prepared as shown in Scheme 1, using commercially available tert-butyl 4-(4-aminophenyl)piperazine-1-carboxylate in the second nucleophilic aromatic substitution step. Following urea formation using 2-aminoethanol, the Boc-piperazine intermediate was treated with TFA to provide the title compound. (M+H) 546.3.

Example 358

Preparation of 4-(3-(4-(4-(8-oxa-3-azabicyclo[3.2.1]octan-3-yl)-6-(4-(piperazin-1-yl)phenylamino)-1,3,5-triazin-2-yl)phenyl)ureido)benzamide Prepared as shown in Scheme 1, using commercially available tert-butyl 4-(4-aminophenyl)piperazine-1-carboxylate in the second nucleophilic aromatic substitution step. Following urea formation using 4-aminobenzamide, the Boc-piperazine intermediate was treated with TFA to provide the title compound. (M+H) 621.3.

Example 359

Preparation of 1-(4-(4-(8-oxa-3-azabicyclo[3.2.1]octan-3-yl)-6-(4-(piperazin-1-yl)phenylamino)-1,3,5-triazin-2-yl)phenyl)-3-phenylurea Prepared as shown in Scheme 1, using commercially available tert-butyl 4-(4-aminophenyl)piperazine-1-carboxylate in the second nucleophilic aromatic substitution step. Following urea formation using aniline, the Boc-piperazine intermediate was treated with TFA to provide the title compound. (M+H) 578.3.

Example 360

Preparation of 1-(4-(4-(3-oxa-8-azabicyclo[3.2.1]octan-8-yl)-6-(piperidin-4-ylamino)-1,3,5-triazin-2-yl)phenyl)-3-ethylurea Prepared as shown in Scheme 1, using commercially available tert-butyl 4-aminopiperidine-1-carboxylate in the second nucleophilic aromatic substitution step. Following urea formation using ethylamine, the Boc-piperidine intermediate was treated with TFA to provide the title compound. (M+H) 453.6.

Example 361

Preparation of 1-(4-(4-(3-oxa-8-azabicyclo[3.2.1]octan-8-yl)-6-(piperidin-4-ylamino)-1,3,5-triazin-2-yl)phenyl)-3-ethylurea Prepared as shown in Scheme 1, using N1-(2-(dimethylamino)ethyl)-N1-methylbenzene-1,4-diamine in the urea formation step. (M+H) 614.3.

The required benzene-1,4-diamine intermediates for the following compounds were prepared as outlined in Scheme 4.

Example 362

Preparation of 1-(4-(4-(3-oxa-8-azabicyclo[3.2.1]octan-8-yl)-6-(piperidin-4-ylamino)-1,3,5-triazin-2-yl)phenyl)-3-ethylurea Prepared as shown in Scheme 1, using 1-(4-aminophenyl)-N,N-dimethylpiperidin-4-amine in the urea formation step. (M+H) 640.4.

Preparation of 1-(4-aminophenyl)-N,N-dimethylpiperidin-4-amine

Prepared from 4-fluoronitrobenzene and the appropriate amine as shown in Scheme 4.

Example 363

Preparation of 1-(4-(4-(3-oxa-8-azabicyclo[3.2.1]octan-8-yl)-6-(piperidin-4-ylamino)-1,3,5-triazin-2-yl)phenyl)-3-ethylurea Prepared as shown in Scheme 1, using N1-(2-methoxyethyl)benzene-1,4-diamine in the urea formation step. (M+H) 587.3.

Preparation of N1-(2-methoxyethyl)benzene-1,4-diamine

Prepared from 4-fluoronitrobenzene and the appropriate amine as shown in Scheme 4.

Example 364

Preparation of 1-(4-(4-(3-oxa-8-azabicyclo[3.2.1]octan-8-yl)-6-(piperidin-4-ylamino)-1,3,5-triazin-2-yl)phenyl)-3-ethylurea Prepared as shown in Scheme 1, using 2-(4-aminophenylamino)ethanol in the urea formation step. (M+H) 573.3.

Preparation of 2-(4-aminophenylamino)ethanol

Prepared from 4-fluoronitrobenzene and the appropriate amine as shown in Scheme 4.

Example 365

Preparation of 1-(4-(4-(3-oxa-8-azabicyclo[3.2.1]octan-8-yl)-6-(piperidin-4-ylamino)-1,3,5-triazin-2-yl)phenyl)-3-ethylurea Prepared as shown in Scheme 1, using N1-(1-methylpiperidin-4-yl)benzene-1,4-diamine in the urea formation step. (M+H) 626.3.

Preparation of N1-(1-methylpiperidin-4-yl)benzene-1,4-diamine

Prepared from 4-fluoronitrobenzene and the appropriate amine as shown in Scheme 4.

Example 366

Preparation of 1-(4-(4,6-di(3-oxa-8-azabicyclo[3.2.1]octan-8-yl)-1,3,5-triazin-2-yl)phenyl)-3-(4-(piperazin-1-ylmethyl)phenyl)urea Prepared as shown in Scheme 1, using commercially available tert-butyl 4-(4-aminobenzyl)piperazine-1-carboxylate in the urea formation step. Following urea formation, the Boc-piperidine intermediate was treated with TFA to provide the title compound. (M+H) 612.3.

Example 367

Preparation of 1-(4-(4,6-di(3-oxa-8-azabicyclo[3.2.1]octan-8-yl)-1,3,5-triazin-2-yl)phenyl)-3-(4-((dimethylamino)methyl)phenyl)urea Prepared as shown in Scheme 1, using commercially available 4-((dimethylamino)methyl)aniline in the urea formation step. (M+H) 571.3.

Example 368

Preparation of 1-(4-(aminomethyl)phenyl)-3-(4-(4,6-di(3-oxa-8-azabicyclo[3.2.1]octan-8-yl)-1,3,5-triazin-2-yl)phenyl)urea Prepared as shown in Scheme 1, using commercially available tert-butyl 4-aminobenzylcarbamate in the urea formation step. Following urea formation, the Boc-amine intermediate was treated with TFA to provide the title compound. (M+H) 543.3.

Example 369

Preparation of 1-(4-(4,6-di(3-oxa-8-azabicyclo[3.2.1]octan-8-yl)-1,3,5-triazin-2-yl)phenyl)-3-(4-(pyrrolidin-1-ylmethyl)phenyl)urea Prepared as shown in Scheme 1, using commercially available 4-(pyrrolidin-1-ylmethyl)aniline in the urea formation step. (M+H) 597.3.

Example 370

Preparation of 1-(4-(4,6-di(3-oxa-8-azabicyclo[3.2.1]octan-8-yl)-1,3,5-triazin-2-yl)phenyl)-3-(4-(2-(4-methylpiperazin-1-yl)ethoxy)phenyl)urea Prepared as shown in Scheme 1, using 4-(2-(4-methylpiperazin-1-yl)ethoxy)aniline in the urea formation step. (M+H) 656.4.

The required 4-(alkoxy)aniline intermediates for the following compounds were prepared as outlined in Scheme 5.

Example 371

Preparation of 1-(4-(4,6-di(3-oxa-8-azabicyclo[3.2.1]octan-8-yl)-1,3,5-triazin-2-yl)phenyl)-3-(4-(2-(pyrrolidin-1-yl)ethoxy)phenyl)urea Prepared as shown in Scheme 1, using 4-(2-(pyrrolidin-1-yl)ethoxy)aniline in the urea formation step. (M+H) 627.3.

Preparation of 4-(2-(pyrrolidin-1-yl)ethoxy)aniline

Prepared from 4-fluoronitrobenzene and the appropriate alcohol as shown in Scheme 5.

Example 372

Preparation of 1-(4-(4,6-di(3-oxa-8-azabicyclo[3.2.1]octan-8-yl)-1,3,5-triazin-2-yl)phenyl)-3-(4-(2-hydroxyethoxy)phenyl)urea Prepared as shown in Scheme 1, using 2-(4-aminophenoxy)ethanol in the urea formation step. (M+H) 574.3.

Preparation of 2-(4-aminophenoxy)ethanol

Prepared from 4-fluoronitrobenzene and the appropriate alcohol as shown in Scheme 5.

Example 373

Preparation of N-(4-(3-(4-(4,6-di(3-oxa-8-azabicyclo[3.2.1]octan-8-yl)-1,3,5-triazin-2-yl)phenyl)ureido)phenyl)-2-(dimethylamino)acetamide Prepared as shown in Scheme 1, using commercially available N-(4-aminophenyl)-2-(dimethylamino)acetamide in the urea formation step. (M+H) 614.3.

Example 374

Preparation of N-(4-(3-(4-(4,6-di(3-oxa-8-azabicyclo[3.2.1]octan-8-yl)-1,3,5-triazin-2-yl)phenyl)ureido)phenyl)-2-(4-methylpiperazin-1-yl)acetamide Prepared as shown in Scheme 1, using commercially available N-(4-aminophenyl)-2-(4-methylpiperazin-1-yl)acetamide in the urea formation step. (M+H) 669.4.

Example 375

Preparation of N-(4-(3-(4-(4,6-di(3-oxa-8-azabicyclo[3.2.1]octan-8-yl)-1,3,5-triazin-2-yl)phenyl)ureido)phenyl)-2-(pyrrolidin-1-yl)acetamide Prepared as shown in Scheme 1, using commercially available N-(4-aminophenyl)-2-(pyrrolidin-1-yl)acetamide in the urea formation step. (M+H) 640.3.

Example 376

Preparation of 1-(4-(4-(3-oxa-8-azabicyclo[3.2.1]octan-8-yl)-6-(isopropylamino)-1,3,5-triazin-2-yl)phenyl)-3-(pyridin-3-yl)urea Prepared as shown in Scheme 1, using commercially available pyridin-3-amine in the urea formation step. (M+H) 461.2.

Example 377

Preparation of 1-(4-(4-(3-oxa-8-azabicyclo[3.2.1]octan-8-yl)-6-(isopropylamino)-1,3,5-triazin-2-yl)phenyl)-3-(pyridin-4-yl)urea Prepared as shown in Scheme 1, using commercially available pyridin-4-amine in the urea formation step. (M+H) 461.2.

Example 378

Preparation of 1-(4-(4-(3-oxa-8-azabicyclo[3.2.1]octan-8-yl)-6-(isopropylamino)-1,3,5-triazin-2-yl)phenyl)-3-(4-(4-methylpiperazin-1-yl)phenyl)urea Prepared as shown in Scheme 1, using commercially available 4-(4-methylpiperazin-1-yl)aniline in the urea formation step. (M+H) 558.3.

Example 379

Preparation of 1-(4-(4-(3-oxa-8-azabicyclo[3.2.1]octan-8-yl)-6-(isopropylamino)-1,3,5-triazin-2-yl)phenyl)-3-(4-((4-methylpiperazin-1-yl)methyl)phenyl)urea Prepared as shown in Scheme 1, using commercially available 4-((4-methylpiperazin-1-yl)methyl)aniline in the urea formation step. (M+H) 572.3.

Example 380

Preparation of 1-(4-(4-(3-oxa-8-azabicyclo[3.2.1]octan-8-yl)-6-(isopropylamino)-1,3,5-triazin-2-yl)phenyl)-3-(4-(piperazin-1-ylmethyl)phenyl)urea Prepared as shown in Scheme 1, using commercially available tert-butyl 4-(4-aminobenzyl)piperazine-1-carboxylate in the urea formation step. Following urea formation, the Boc-piperazine intermediate was treated with TFA to provide the title compound. (M+H) 558.3.

Example 381

Preparation of 1-(4-(4-(3-oxa-8-azabicyclo[3.2.1]
octan-8-yl)-6-(isopropylamino)-1,3,5-triazin-2-yl)
phenyl)-3-(4-((dimethylamino)methyl)phenyl)urea Prepared as shown in Scheme 1, using commercially available 4-((dimethylamino)methyl)aniline in the urea formation step. (M+H) 517.3.

Example 382

Preparation of 1-(4-(4-(3-oxa-8-azabicyclo[3.2.1]
octan-8-yl)-6-(isopropylamino)-1,3,5-triazin-2-yl)
phenyl)-3-(4-(aminomethyl)phenyl)urea Prepared as shown in Scheme 1, using commercially available tert-butyl 4-aminobenzylcarbamate in the urea formation step. Following urea formation, the Boc-amine intermediate was treated with TFA to provide the title compound. (M+H) 489.3.

Example 383

Preparation of 1-(4-(4-(3-oxa-8-azabicyclo[3.2.1]
octan-8-yl)-6-(isopropylamino)-1,3,5-triazin-2-yl)
phenyl)-3-(4-(pyrrolidin-1-ylmethyl)phenyl)urea Prepared as shown in Scheme 1, using commercially available 4-(pyrrolidin-1-ylmethyl)aniline in the urea formation step. (M+H) 543.3.

Example 384

Preparation of 1-(4-(4-(3-oxa-8-azabicyclo[3.2.1]
octan-8-yl)-6-(isopropylamino)-1,3,5-triazin-2-yl)
phenyl)-3-(4-(2-(pyrrolidin-1-yl)ethoxy)phenyl)urea Prepared as shown in Scheme 1, using 4-(2-(pyrrolidin-1-yl)ethoxy)aniline in the urea formation step. (M+H) 573.3.

Example 385

Preparation of 1-(4-(4-(3-oxa-8-azabicyclo[3.2.1]
octan-8-yl)-6-(isopropylamino)-1,3,5-triazin-2-yl)
phenyl)-3-(4-(2-(dimethylamino)ethoxy)phenyl)urea Prepared as shown in Scheme 1, using 4-(2-(dimethylamino)ethoxy)aniline in the urea formation step. (M+H) 547.3.

Preparation of 4-(2-(dimethylamino)ethoxy)aniline

Prepared from 4-fluoronitrobenzene and the appropriate alcohol as shown in Scheme 5.

Example 386

Preparation of 1-(4-(4-(3-oxa-8-azabicyclo[3.2.1]
octan-8-yl)-6-(isopropylamino)-1,3,5-triazin-2-yl)
phenyl)-3-(6-(4-methylpiperazin-1-yl)pyridin-3-yl)
urea Prepared as shown in Scheme 1, using commercially available 5-(4-methylpiperazin-1-yl)pyridin-2-amine in the urea formation step. (M+H) 559.3.

Example 387

Preparation of 1-(4-(4-(3-oxa-8-azabicyclo[3.2.1]
octan-8-yl)-6-(isopropylamino)-1,3,5-triazin-2-yl)
phenyl)-3-(4-(piperazin-1-yl)phenyl)urea Prepared as shown in Scheme 1, using commercially available tert-butyl 4-(4-aminophenyl)piperazine-1-carboxylate in the urea formation step. Following urea formation, the Boc-amine intermediate was treated with TFA to provide the title compound. (M+H) 544.3.

Example 388

Preparation of 1-(4-(4-(3-oxa-8-azabicyclo[3.2.1]
octan-8-yl)-6-(isopropylamino)-1,3,5-triazin-2-yl)
phenyl)-3-(4-(4-(dimethylamino)piperidin-1-yl)phenyl)urea Prepared as shown in Scheme 1, using 1-(4-aminophenyl)-N,N-dimethylpiperidin-4-amine in the urea formation step. (M+H) 586.4.

Example 389

Preparation of 1-(4-(4-(3-oxa-8-azabicyclo[3.2.1]
octan-8-yl)-6-(isopropyl(methyl)amino)-1,3,5-triazin-2-yl)phenyl)-3-(4-(4-methylpiperazin-1-yl)phenyl)urea Prepared as shown in Scheme 1, using commercially available 4-(4-methylpiperazin-1-yl)aniline in the urea formation step. (M+H) 572.3.

Example 390

Preparation of 1-(4-(4-(3-oxa-8-azabicyclo[3.2.1]
octan-8-yl)-6-(isopropyl(methyl)amino)-1,3,5-triazin-2-yl)phenyl)-3-(4-((dimethylamino)methyl)
phenyl)urea Prepared as shown in Scheme 1, using commercially available 4-((dimethylamino)methyl)aniline in the urea formation step. (M+H) 531.3.

Example 391

Preparation of 1-(4-(4-(3-oxa-8-azabicyclo[3.2.1]
octan-8-yl)-6-(isopropyl(methyl)amino)-1,3,5-triazin-2-yl)phenyl)-3-(4-(2-(dimethylamino)ethoxy)
phenyl)urea Prepared as shown in Scheme 1, using 4-(2-(dimethylamino)ethoxy)aniline in the urea formation step. (M+H) 561.3.

Example 392

Preparation of 1-(4-(4-(3-oxa-8-azabicyclo[3.2.1]
octan-8-yl)-6-thiomorpholino-1,3,5-triazin-2-yl)phenyl)-3-(pyridin-3-yl)urea (Scheme 6)

Step 1: Preparation of 8-(4-chloro-6-(4-nitrophenyl)-1,3,5-triazin-2-yl)-3-oxa-8-azabicyclo[3.2.1]octane A solution of 2,4-dichloro-6-(4-nitrophenyl)-1,3,5-triazine (1.25 g, 4.61 mmol) in acetone (20 mL) and ice water (20 mL) was prepared. To this was added dropwise over 10 minutes a suspension of 3-oxa-8-azabicyclo[3.2.1]octane-hydrochloride (0.655 g, 4.38 mmol) and sodium bicarbonate (0.775 g, 9.22 mmol) in acetone (15 mL) and water (15 mL). The resulting tan solution was allowed to stir at 0° C. for 2 hours, then gradually allowed to warm to room temperature over 18 hours. The light brown suspension was filtered and washed with water. The crude product was purified by silica gel column chromatography, eluting with 0-1.5% methanol in methylene chloride to provide 8-(4-chloro-6-(4-nitrophenyl)-1,3,5-triazin-2-yl)-3-oxa-8-azabicyclo[3.2.1]octane (0.89 g, 56%) as an off-white solid. (M+H) 348.1.

Step 2: Preparation of 8-(4-(4-nitrophenyl)-6-thiomorpholino-1,3,5-triazin-2-yl)-3-oxa-8-azabicyclo[3.2.1]octane A solution of 8-(4-chloro-6-(4-nitrophenyl)-1,3,5-triazin-2-yl)-3-oxa-8-azabicyclo[3.2.1]octane (0.450 g, 1.29 mmol) in acetone (5 mL) and water (10 mL) was prepared. To this was added sodium carbonate (0.274 g, 2.59 mmoles), followed by thiomorpholine (0.134 ml, 1.42 mmol).

The resulting light tan suspension was allowed to stir at 60° C. for 2.5 hours. The suspension was filtered and the solid was washed with water and dried in vacuo to provide 8-(4-(4-nitrophenyl)-6-thiomorpholino-1,3,5-triazin-2-yl)-3-oxa-8-azabicyclo[3.2.1]octane (0.455 g, 85%) as a white solid. HRMS 415.1546 (M+H, calc.), 415.1526 (M+H, obs.).

Step 3: Preparation of 4-(4-(3-oxa-8-azabicyclo[3.2.1]octan-8-yl)-6-thiomorpholino-1,3,5-triazin-2-yl)aniline A suspension of 8-(4-(4-nitrophenyl)-6-thiomorpholino-1,3,5-triazin-2-yl)-3-oxa-8-azabicyclo[3.2.1]octane (0.418 g, 1.01 mmol) in pyridine (3 ml) and DMF (6 ml) was prepared. Tin(II) chloride dihydrate (0.569 g, 2.52 mmol) was then added and the off-white suspension was allowed to stir at room temperature for 16 hours, at which time the suspension was light yellow. The suspension was filtered, washing with methanol, and concentrated. LCMS indicated reaction had not gone to completion. The crude product was dissolved in DMF (6 ml) and pyridine (3 ml) and additional tin(II) chloride dihydrate (0.569 g, 2.52 mmol) was added. The solution was allowed to stir at room temperature for 18 hours, then filtered. The precipitate was washed with methanol and the filtrate was concentrated to provide 4-(4-(3-oxa-8-azabicyclo[3.2.1]octan-8-yl)-6-thiomorpholino-1,3,5-triazin-2-yl)aniline (0.195 g, 50%) as a yellow solid. (M+H) 385.1.

Step 4: Preparation of 1-(4-(4-(3-oxa-8-azabicyclo[3.2.1]octan-8-yl)-6-thiomorpholino-1,3,5-triazin-2-yl)phenyl)-3-(pyridin-3-yl)urea The method of urea formation using triphosgene and triethylamine in methylene chloride, described in Scheme 1, was utilized using commercially available pyridin-3-amine as the amine component. Purification by HPLC (5-95% acetonitrile in water over 20 minutes, 0.05% TFA buffer, Waters Atlantis column) provided 1-(4-(4-(3-oxa-8-azabicyclo[3.2.1]octan-8-yl)-6-thiomorpholino-1,3,5-triazin-2-yl)phenyl)-3-(pyridin-3-yl)urea (0.032 g, 63%) as an off-white solid. (M+H) 505.2.

Example 393

Preparation of 1-(4-(4-(3-oxa-8-azabicyclo[3.2.1]octan-8-yl)-6-thiomorpholino-1,3,5-triazin-2-yl)phenyl)-3-(pyridin-4-yl)urea Prepared as shown in Scheme 6, using commercially available pyridin-4-amine in the urea formation step. Yield; 28 mg (54%); (M+H) 505.2.

Example 394

Preparation of 1-(4-(4-(3-oxa-8-azabicyclo[3.2.1]octan-8-yl)-6-thiomorpholino-1,3,5-triazin-2-yl)phenyl)-3-(4-(4-methylpiperazin-1-yl)phenyl)urea Prepared as shown in Scheme 6, using commercially available 4-(4-methylpiperazin-1-yl)aniline in the urea formation step. Yield; 44 mg (73%); (M+H) 602.3.

Example 395

Preparation of 1-(4-(4-(3-oxa-8-azabicyclo[3.2.1]octan-8-yl)-6-thiomorpholino-1,3,5-triazin-2-yl)phenyl)-3-(4-((dimethylamino)methyl)phenyl)urea Prepared as shown in Scheme 6, using commercially available 4-((dimethylamino)methyl)aniline in the urea formation step. Yield; 19 mg (34%); (M+H) 561.3.

Example 365

Preparation of 1-(4-(4-(3-oxa-8-azabicyclo[3.2.1]octan-8-yl)-6-thiomorpholino-1,3,5-triazin-2-yl)phenyl)-3-(4-(2-(dimethylamino)ethoxy)phenyl)urea Prepared as shown in Scheme 6, using 4-(2-(dimethylamino)ethoxy)aniline in the urea formation step. Yield; 35 mg (59%); (M+H) 591.3.

Example 397

Preparation of 1-(4-(4,6-bis((R)-3-methylmorpholino)-1,3,5-triazin-2-yl)phenyl)-3-(pyridin-4-yl)urea Prepared as shown in Scheme 1, using commercially available pyridin-4-amine in the urea formation step. Yield; 44 mg (75%); (M+H) 491.2.

Example 398

Preparation of 1-(4-(4,6-bis((R)-3-methylmorpholino)-1,3,5-triazin-2-yl)phenyl)-3-(pyridin-3-yl)urea Prepared as shown in Scheme 1, using commercially available pyridin-3-amine in the urea formation step. Yield; 46 mg (79%); (M+H) 491.2.

Example 399

Preparation of 1-(4-(4,6-bis((R)-3-methylmorpholino)-1,3,5-triazin-2-yl)phenyl)-3-(4-(4-methylpiperazin-1-yl)phenyl)urea Prepared as shown in Scheme 1, using commercially available 4-((dimethylamino)methyl)aniline in the urea formation step. Yield; 57 mg (81%); (M+H) 588.3.

Example 400

Preparation of 1-(4-(4,6-bis((R)-3-methylmorpholino)-1,3,5-triazin-2-yl)phenyl)-3-(6-(4-methylpiperazin-1-yl)pyridin-3-yl)urea Prepared as shown in Scheme 1, using commercially available 5-(4-methylpiperazin-1-yl)pyridin-2-amine in the urea formation step. Yield; 56 mg (79%); (M+H) 589.3.

Example 401

Preparation of 1-(4-(4,6-bis((R)-3-methylmorpholino)-1,3,5-triazin-2-yl)phenyl)-3-(4-((dimethylamino)methyl)phenyl)urea Prepared as shown in Scheme 1, using commercially available 4-((dimethylamino)methyl)aniline in the urea formation step. Yield; 28 mg (43%); (M+H) 547.3.

Example 402

Preparation of 1-(4-(4,6-bis((R)-3-methylmorpholino)-1,3,5-triazin-2-yl)phenyl)-3-(4-(2-(dimethylamino)ethoxy)phenyl)urea Prepared as shown in Scheme 1, using 4-(2-(dimethylamino)ethoxy)aniline in the urea formation step. Yield; 50 mg (72%); (M+H) 577.3.

Example 403

Preparation of 1-(4-(4,6-bis((R)-3-methylmorpholino)-1,3,5-triazin-2-yl)phenyl)-3-(4-(2-(pyrrolidin-1-yl)ethoxy)phenyl)urea Prepared as shown in Scheme 1, using 4-(2-(pyrrolidin-1-yl)ethoxy)aniline in the urea formation step. Yield; 41 mg (57%); (M+H) 603.3.

Example 404

Preparation of 1-(4-(4-(3-oxa-8-azabicyclo[3.2.1]octan-8-yl)-6-(3,6-dihydro-2H-pyran-4-yl)-1,3,5-triazin-2-yl)phenyl)-3-(pyridin-4-yl)urea (Scheme 7)

Step 1: Preparation of 8-(4-chloro-6-(4-nitrophenyl)-1,3,5-triazin-2-yl)-3-oxa-8-azabicyclo[3.2.1]octane Prepared as shown in Scheme 6, described in Example 392, Step 1.

Step 2: Preparation of 8-(4-(3,6-dihydro-2H-pyran-4-yl)-6-(4-nitrophenyl)-1,3,5-triazin-2-yl)-3-oxa-8-azabicyclo[3.2.1]octane A microwave vial was charged with 8-(4-chloro-6-(4-nitrophenyl)-1,3,5-triazin-2-yl)-3-oxa-8-azabicyclo[3.2.1]octane (0.440 g, 1.27 mmoles). Toluene (6 mL) was then added and the solution was sparged with nitrogen for 10 minutes. Tetrakis(triphenylphosphine)palladium(0) (0.088 g, 0.076 mmol) and tributyl(3,6-dihydro-2H-pyran-4-yl)stannane (0.567 g, 1.52 mmol) were added. The vial was sealed and heated to 100° C. for 40 minutes via microwave. Additional tributyl(3,6-dihydro-2H-pyran-4-yl)stannane (0.283 g, 0.76 mmoles) and tetrakis(triphenylphosphine)palladium(0) (0.022 g, 0.019 mmol) were added and the suspension was heated to 110° C. by microwave for additional 90 minutes. The suspension was then cooled to room temperature and filtered through Celite™. The filter cake was washed with ethyl acetate and the filtrate was concentrated under reduced pressure. The crude product was purified by silica gel chromatography, eluting with 0-2% methanol in methylene chloride, to provide 8-(4-(3,6-dihydro-2H-pyran-4-yl)-6-(4-nitrophenyl)-1,3,5-triazin-2-yl)-3-oxa-8-azabicyclo[3.2.1]octane (0.430 g, 86%) as a light yellow solid. HRMS 396.1666 (M+H, calc.), 396.1668 (M+H, obs.).

Step 3: Preparation of 4-(4-(3-oxa-8-azabicyclo[3.2.1]octan-8-yl)-6-(3,6-dihydro-2H-pyran-4-yl)-1,3,5-triazin-2-yl)aniline A mixture of iron powder (0.071 g, 1.27 mmoles) in acetic acid (2 ml) was heated to 55° C. for 15 minutes. Water (2 ml) was then added and oil bath was turned off. A solution of 8-(4-(3,6-dihydro-2H-pyran-4-yl)-6-(4-nitrophenyl)-1,3,5-triazin-2-yl)-3-oxa-8-azabicyclo[3.2.1]octane (0.100 g, 0.253 mmol) in ethyl acetate (2 ml) was then added to this warm solution over 5 minutes. The mixture was cooled to RT and allowed to stir for 16 hours. The mixture was extracted with ethyl acetate by decantation (4×) into a sep. funnel containing saturated aqueous sodium carbonate. The combined organic extracts were washed with water, brine, dried, and concentrated to provide 4-(4-(3-oxa-8-azabicyclo[3.2.1]octan-8-yl)-6-(3,6-dihydro-2H-pyran-4-yl)-1,3,5-triazin-2-yl)aniline (0.068 g, 74%), which was used in the next step without purification. (M+H) 366.4.

Step 4: Preparation of 1-(4-(4-(3-oxa-8-azabicyclo[3.2.1]octan-8-yl)-6-(3,6-dihydro-2H-pyran-4-yl)-1,3,5-triazin-2-yl)phenyl)-3-(pyridin-4-yl)urea The method of urea formation using triphosgene and triethylamine in methylene chloride, described in Scheme 1, was utilized using commercially available pyridin-4-amine as the amine component. Purification by HPLC (5-95% acetonitrile in water over 20 minutes, 0.05% TFA buffer, Waters Atlantis column) provided 1-(4-(4-(3-oxa-8-azabicyclo[3.2.1]octan-8-yl)-6-(3,6-dihydro-2H-pyran-4-yl)-1,3,5-triazin-2-yl)phenyl)-3-(pyridin-4-yl)urea (0.034 g, 75%) as a light yellow solid. (M+H) 486.2.

Example 405

Preparation of 1-(4-(4-(3-oxa-8-azabicyclo[3.2.1]octan-8-yl)-6-(3,6-dihydro-2H-pyran-4-yl)-1,3,5-triazin-2-yl)phenyl)-3-(4-(4-methylpiperazin-1-yl)phenyl)urea Prepared as shown in Scheme 7, using commercially available 4-(4-methylpiperazin-1-yl)aniline in the urea formation step. Yield; 44 mg (82%); (M+H) 583.3.

Example 406

Preparation of 1-(4-(4-(3-oxa-8-azabicyclo[3.2.1]octan-8-yl)-6-(tetrahydro-2H-pyran-4-yl)-1,3,5-triazin-2-yl)phenyl)-3-(pyridin-4-yl)urea Prepared as shown in Scheme 7; representative synthesis described below.

Preparation of 4-(4-(3-oxa-8-azabicyclo[3.2.1]octan-8-yl)-6-(tetrahydro-2H-pyran-4-yl)-1,3,5-triazin-2-yl)aniline A solution of 8-(4-(3,6-dihydro-2H-pyran-4-yl)-6-(4-nitrophenyl)-1,3,5-triazin-2-yl)-3-oxa-8-azabicyclo[3.2.1]octane (prepared as described in Example DJR-51, Step 2) (0.260 g, 0.658 mmol) in ethyl acetate (5 ml), methanol (5 ml), and methylene chloride (2 ml—added due to poor solubility of SM in EA/methanol) was prepared and 10% palladium on carbon (0.078 g, 30% by weight) was added. The flask was purged with hydrogen gas (balloon) and allowed to stir under positive pressure of hydrogen for 16 hours. Additional palladium on carbon (0.039 g) was added and the suspension was purged with hydrogen gas (balloon) and stirred for an additional 3 hours. The flask was purged with hydrogen gas and stirred for an additional 1 hour. The suspension was filtered through Celite™, the filter cake was washed with ethyl acetate, and the filtrate was concentrated to provide 4-(4-(3-oxa-8-azabicyclo[3.2.1]octan-8-yl)-6-(tetrahydro-2H-pyran-4-yl)-1,3,5-triazin-2-yl)aniline (0.220 g, 91%) as an off-white solid. HRMS 368.2080 (M+H, calc.), 368.2085 (M+H, obs.).

Preparation of 1-(4-(4-(3-oxa-8-azabicyclo[3.2.1]octan-8-yl)-6-(tetrahydro-2H-pyran-4-yl)-1,3,5-triazin-2-yl)phenyl)-3-(pyridin-4-yl)urea The method of urea formation using triphosgene and triethylamine in methylene chloride, described in Scheme 1, was utilized using commercially available pyridin-4-amine as the amine component. Purification by HPLC (5-95% acetonitrile in water over 20 minutes, 0.05% TFA buffer, Waters Atlantis column) provided 1-(4-(4-(3-oxa-8-azabicyclo[3.2.1]octan-8-yl)-6-(tetrahydro-2H-pyran-4-yl)-1,3,5-triazin-2-yl)phenyl)-3-(pyridin-4-yl)urea (0.0461 g, 82%) as an off-white solid. (M+H) 488.2.

Example 407

Preparation of 1-(4-(4-(3-oxa-8-azabicyclo[3.2.1]octan-8-yl)-6-(tetrahydro-2H-pyran-4-yl)-1,3,5-triazin-2-yl)phenyl)-3-(4-(4-methylpiperazin-1-yl)phenyl)urea Prepared as shown in Scheme 7, using commercially available 4-(4-methylpiperazin-1-yl)aniline in the urea formation step. Yield; 54 mg (79%); (M+H) 585.3.

Example 408

Preparation of 1-(4-(4-(3-oxa-8-azabicyclo[3.2.1]octan-8-yl)-6-(tetrahydro-2H-pyran-4-yl)-1,3,5-triazin-2-yl)phenyl)-3-(4-(2-(dimethylamino)ethoxy)phenyl)urea Prepared as shown in Scheme 7, using 4-(2-(dimethylamino)ethoxy)aniline in the urea formation step. Yield; 49 mg (73%); (M+H) 572.3.

Example 409

Preparation of 1-(4-(4-(3-oxa-8-azabicyclo[3.2.1]octan-8-yl)-6-(tetrahydro-2H-pyran-4-yl)-1,3,5-triazin-2-yl)phenyl)-3-(4-((dimethylamino)methyl)phenyl)urea Prepared as shown in Scheme 7, using commercially available 4-((dimethylamino)methyl)aniline in the urea formation step. Yield; 21 mg (33%); (M+H) 544.3.

Example 410

Preparation of 1-(4-(4-((1S,4S)-2-oxa-5-azabicyclo[2.2.1]heptan-5-yl)-6-((R)-3-methylmorpholino)-1,3,5-triazin-2-yl)phenyl)-3-(pyridin-4-yl)urea Prepared as shown in Scheme 1, using commercially available pyridin-4-amine in the urea formation step. Yield; 45 mg (70%); (M+H) 489.2.

Example 411

Preparation of 1-(4-(4-((1S,4S)-2-oxa-5-azabicyclo[2.2.1]heptan-5-yl)-6-((R)-3-methylmorpholino)-1,3,5-triazin-2-yl)phenyl)-3-(pyridin-3-yl)urea Prepared as shown in Scheme 1, using commercially available pyridin-3-amine in the urea formation step. Yield; 60 mg (95%); (M+H) 489.2.

Example 412

Preparation of 1-(4-(4-((1S,4S)-2-oxa-5-azabicyclo[2.2.1]heptan-5-yl)-6-((R)-3-methylmorpholino)-1,3,5-triazin-2-yl)phenyl)-3-(4-(4-methylpiperazin-1-yl)phenyl)urea Prepared as shown in Scheme 1, using commercially available 4-(4-methylpiperazin-1-yl)aniline in the urea formation step. Yield; 69 mg (90%); (M+H) 586.3.

Example 413

Preparation of 1-(4-(4-((1S,4S)-2-oxa-5-azabicyclo[2.2.1]heptan-5-yl)-6-((R)-3-methylmorpholino)-1,3,5-triazin-2-yl)phenyl)-3-(4-((4-methylpiperazin-1-yl)methyl)phenyl)urea Prepared as shown in Scheme 1, using commercially available 4-((4-methylpiperazin-1-yl)methyl)aniline in the urea formation step. Yield; 73 mg (94%); (M+H) 600.3.

Example 414

Preparation of 1-(4-(4-((1S,4S)-2-oxa-5-azabicyclo[2.2.1]heptan-5-yl)-6-((R)-3-methylmorpholino)-1,3,5-triazin-2-yl)phenyl)-3-(4-(pyrrolidin-1-ylmethyl)phenyl)urea Prepared as shown in Scheme 1, using commercially available 4-(pyrrolidin-1-ylmethyl)aniline in the urea formation step. Yield; 56 mg (75%); (M+H) 571.3.

Example 415

Preparation of 1-(4-(4-(3-oxa-8-azabicyclo[3.2.1] octan-8-yl)-6-((R)-3-methylmorpholino)-1,3,5-triazin-2-yl)phenyl)-3-(pyridin-3-yl)urea Prepared as shown in Scheme 1, using commercially available pyridin-3-amine in the urea formation step. Yield; 44 mg (66%); (M+H) 503.2.

Example 416

Preparation of 1-(4-(4-(3-oxa-8-azabicyclo[3.2.1] octan-8-yl)-6-((R)-3-methylmorpholino)-1,3,5-triazin-2-yl)phenyl)-3-(pyridin-4-yl)urea Prepared as shown in Scheme 1, using commercially available pyridin-4-amine in the urea formation step. Yield; 35 mg (53%); (M+H) 503.2.

Example 417

Preparation of 1-(4-(4-(3-oxa-8-azabicyclo[3.2.1] octan-8-yl)-6-((R)-3-methylmorpholino)-1,3,5-triazin-2-yl)phenyl)-3-(4-(4-methylpiperazin-1-yl)phenyl)urea Prepared as shown in Scheme 1, using commercially available 4-(4-methylpiperazin-1-yl)aniline in the urea formation step. Yield; 58 mg (62%); (M+H) 600.3.

Example 418

Preparation of 1-(4-(4-(3-oxa-8-azabicyclo[3.2.1] octan-8-yl)-6-((R)-3-methylmorpholino)-1,3,5-triazin-2-yl)phenyl)-3-(4-(pyrrolidin-1-ylmethyl)phenyl)urea Prepared as shown in Scheme 1, using commercially available 4-(pyrrolidin-1-ylmethyl)aniline in the urea formation step. Yield; 41 mg (45%); (M+H) 585.5.

Example 419

Preparation of 1-(4-(4-(3-oxa-8-azabicyclo[3.2.1] octan-8-yl)-6-((R)-3-methylmorpholino)-1,3,5-triazin-2-yl)phenyl)-3-(4-(2-(dimethylamino)ethoxy) phenyl)urea Prepared as shown in Scheme 1, using 4-(2-(dimethylamino)ethoxy)aniline in the urea formation step. Yield; 43 mg (47%); (M+H) 589.3.

Example 420

Preparation of (R)-1-(4-(4-(3-methylmorpholino)-6-(tetrahydro-2H-pyran-4-yl)-1,3,5-triazin-2-yl)phenyl)-3-(pyridin-3-yl)urea Prepared as shown in Scheme 7, using commercially available pyridin-3-amine in the urea formation step. Yield; 45 mg (77%); (M+H) 476.2.

Example 421

Preparation of (R)-1-(4-(4-(3-methylmorpholino)-6-(tetrahydro-2H-pyran-4-yl)-1,3,5-triazin-2-yl)phenyl)-3-(4-(4-methylpiperazin-1-yl)phenyl)urea Prepared as shown in Scheme 7, using commercially available 4-(4-methylpiperazin-1-yl)aniline in the urea formation step. Yield; 53 mg (75%); (M+H) 573.3.

Example 422

Preparation of (R)-1-(4-(4-(3-methylmorpholino)-6-(tetrahydro-2H-pyran-4-yl)-1,3,5-triazin-2-yl)phenyl)-3-(4-(piperazin-1-yl)phenyl)urea Prepared as shown in Scheme 7, using commercially available tert-butyl 4-(4-aminophenyl)piperazine-1-carboxylate in the urea formation step. Following urea formation, the Boc-piperazine intermediate was treated with TFA to provide the title compound. Yield; 63 mg (90%); (M+H) 559.3.

Example 423

Preparation of 1-(4-(4-((R)-3-methylmorpholino)-6-(tetrahydro-2H-pyran-4-yl)-1,3,5-triazin-2-yl)phenyl)-3-(4-((S)-3-methylpiperazin-1-yl)phenyl)urea Prepared as shown in Scheme 7, using (S)-tert-butyl 4-(4-aminophenyl)-3-methylpiperazine-1-carboxylate in the urea formation step. Following urea formation, the Boc-piperazine intermediate was treated with TFA to provide the title compound. Yield; 60 mg (71%); (M+H) 573.3.

Preparation of (S)-tert-butyl 4-(4-aminophenyl)-3-methylpiperazine-1-carboxylate Prepared from 4-fluoronitrobenzene and the appropriate amine as shown in Scheme 4.

Example 424

Preparation of 1-(4-(4-((R)-3-methylmorpholino)-6-(tetrahydro-2H-pyran-4-yl)-1,3,5-triazin-2-yl)phenyl)-3-(4-((R)-3-methylpiperazin-1-yl)phenyl)urea Prepared as shown in Scheme 7, using (R)-tert-butyl 4-(4-aminophenyl)-3-methylpiperazine-1-carboxylate in the urea formation step. Following urea formation, the Boc-piperazine intermediate was treated with TFA to provide the title compound. Yield; 68 mg (90%); (M+H) 573.3.

Preparation of (R)-tert-butyl 4-(4-aminophenyl)-3-methylpiperazine-1-carboxylate Prepared from 4-fluoronitrobenzene and the appropriate amine as shown in Scheme 4.

Example 425

Preparation of 1-(4-((3R,5S)-3,5-dimethylpiperazin-1-yl)phenyl)-3-(4-(4-((R)-3-methylmorpholino)-6-(tetrahydro-2H-pyran-4-yl)-1,3,5-triazin-2-yl)phenyl)urea Prepared as shown in Scheme 7, using (3,5-cis)-tert-butyl 4-(4-aminophenyl)-3,5-dimethylpiperazine-1-carboxylate in the urea formation step. Following urea formation, the Boc-piperazine intermediate was treated with TFA to provide the title compound. Yield; 67 mg (77%); (M+H) 587.3.

Preparation of (3,5-cis)-tert-butyl 4-(4-aminophenyl)-3,5-dimethylpiperazine-1-carboxylate Prepared from 4-fluoronitrobenzene and the appropriate amine as shown in Scheme 4.

Example 426

Preparation of 1-(4-(4-(3-oxa-8-azabicyclo[3.2.1]octan-8-yl)-6-sulfoxymorpholino-1,3,5-triazin-2-yl)phenyl)-3-(4-(4-methylpiperazin-1-yl)phenyl)urea Prepared as shown in Scheme 6. A solution of 1-(4-(4-(3-oxa-8-azabicyclo[3.2.1]octan-8-yl)-6-thiomorpholino-1,3,5-triazin-2-yl)phenyl)-3-(4-(4-methylpiperazin-1-yl)phenyl)urea (0.020 g, 0.033 mmol) in acetonitrile (1.5 ml) and water (0.5 ml) was prepared and oxone (0.020 g, 0.033 mmol) was added. The solution was stirred at room temperature for 16 hours. The suspension was diluted with ethyl acetate and washed with saturated sodium bicarbonate. The organic phase was washed with brine, dried, and concentrated, then purified by HPLC (5-95% acetonitrile in water over 20 minutes, 0.05% TFA buffer, Waters Atlantis column) to provide the TFA salt of the sulfoxide of 1-(4-(4-(3-oxa-8-azabicyclo[3.2.1]octan-8-yl)-6-sulfoxymorpholino-1,3,5-triazin-2-yl)phenyl)-3-(4-(4-methylpiperazin-1-yl)phenyl)urea (0.0029 g, 14%) as a white solid. (M+H) 618.4.

Example 427

Preparation of (R)-1-(4-(2-(dimethylamino)ethoxy)phenyl)-3-(4-(4-(3-methylmorpholino)-6-(tetrahydro-2H-pyran-4-yl)-1,3,5-triazin-2-yl)phenyl)urea Prepared as shown in Scheme 7, using 4-(2-(dimethylamino)ethoxy)aniline in the urea formation step. Yield; 34 mg (51%); (M+H) 562.3.

Example 428

Preparation of (R)-1-(4-(4-ethylpiperazin-1-yl)phenyl)-3-(4-(4-(3-methylmorpholino)-6-(tetrahydro-2H-pyran-4-yl)-1,3,5-triazin-2-yl)phenyl)urea Prepared as shown in Scheme 7, using commercially available 4-(4-ethylpiperazin-1-yl)aniline in the urea formation step. Yield; 66 mg (93%); (M+H) 587.3.

Example 429

Preparation of (R)-1-(4-(4-isopropylpiperazin-1-yl)phenyl)-3-(4-(4-(3-methylmorpholino)-6-(tetrahydro-2H-pyran-4-yl)-1,3,5-triazin-2-yl)phenyl)urea Prepared as shown in Scheme 7, using 4-(4-isopropylpiperazin-1-yl)aniline in the urea formation step. Yield; 66 mg (91%); (M+H) 601.4.

Preparation of 4-(4-isopropylpiperazin-1-yl)aniline

Prepared from 4-fluoronitrobenzene and the appropriate amine as shown in Scheme 4.

Example 430

Preparation of (R)-1-(4-(4-(dimethylamino)piperidin-1-yl)phenyl)-3-(4-(4-(3-methylmorpholino)-6-(tetrahydro-2H-pyran-4-yl)-1,3,5-triazin-2-yl)phenyl)urea Prepared as shown in Scheme 7, using 1-(4-aminophenyl)-N,N-dimethylpiperidin-4-amine in the urea formation step. Yield; 69 mg (95%); (M+H) 601.4.

Example 431

Preparation of (R)-1-(4-(4-(3-methylmorpholino)-6-(tetrahydro-2H-pyran-4-yl)-1,3,5-triazin-2-yl)phenyl)-3-(4-(4-methylpiperazine-1-carbonyl)phenyl)urea Prepared as shown in Scheme 7, using (4-aminophenyl)(4-methylpiperazin-1-yl)methanone in the urea formation step. Yield; 38 mg (52%); (M+H) 601.3.

The (4-aminophenyl)(piperazin-1-yl)methanone intermediates prepared as shown in Scheme 8 were used to make the following compounds.

Example 432

Preparation of (R)-1-(4-(4-isopropylpiperazine-1-carbonyl)phenyl)-3-(4-(4-(3-methylmorpholino)-6-(tetrahydro-2H-pyran-4-yl)-1,3,5-triazin-2-yl)phenyl)urea Prepared as shown in Scheme 7, using (4-aminophenyl)(4-isopropylpiperazin-1-yl)methanone in the urea formation step. Yield; 68 mg (89%); (M+H) 629.3.

Preparation of (4-aminophenyl)(4-isopropylpiperazin-1-yl)methanone

Prepared from 4-nitrobenzoyl chloride and the appropriate amine as shown in Scheme 8.

Example 433

Preparation of (R)-1-(4-(4-(3-methylmorpholino)-6-(tetrahydro-2H-pyran-4-yl)-1,3,5-triazin-2-yl)phenyl)-3-(6-(4-methylpiperazin-1-yl)pyridin-3-yl)urea Prepared as shown in Scheme 7, using commercially available 6-(4-methylpiperazin-1-yl)pyridin-3-amine in the urea formation step. Yield; 69 mg (99%); (M+H) 574.3.

Example 434

Preparation of 1-(4-(4-(3-oxa-8-azabicyclo[3.2.1]octan-8-yl)-6-(tetrahydro-2H-pyran-4-yl)-1,3,5-triazin-2-yl)phenyl)-3-(4-(4-ethylpiperazin-1-yl)phenyl)urea Prepared as shown in Scheme 7, using commercially available 4-(4-ethylpiperazin-1-yl)aniline in the urea formation step. Yield; 32 mg (43%); (M+H) 599.3.

Example 435

Preparation of 1-(4-(4-(3-oxa-8-azabicyclo[3.2.1] octan-8-yl)-6-(tetrahydro-2H-pyran-4-yl)-1,3,5-triazin-2-yl)phenyl)-3-(4-(4-isopropylpiperazin-1-yl) phenyl)urea Prepared as shown in Scheme 7, using 4-(4-isopropylpiperazin-1-yl)aniline in the urea formation step. Yield; 51 mg (66%); (M+H) 613.4.

Example 436

Preparation of 1-(4-(4-(3-oxa-8-azabicyclo[3.2.1] octan-8-yl)-6-(tetrahydro-2H-pyran-4-yl)-1,3,5-triazin-2-yl)phenyl)-3-(4-(4-cyclopropylpiperazin-1-yl) phenyl)urea Prepared as shown in Scheme 7, using 4-(4-cyclopropylpiperazin-1-yl)aniline in the urea formation step. Yield; 11 mg (14%); (M+H) 611.3.

Preparation of 4-(4-cyclopropylpiperazin-1-yl)aniline

Prepared from 4-fluoronitrobenzene and the appropriate amine as shown in Scheme 4.

Example 437

Preparation of 1-(4-(4-(3-oxa-8-azabicyclo[3.2.1] octan-8-yl)-6-(tetrahydro-2H-pyran-4-yl)-1,3,5-triazin-2-yl)phenyl)-3-(4-(4-(dimethylamino)piperidin-1-yl)phenyl)urea Prepared as shown in Scheme 7, using 1-(4-aminophenyl)-N,N-dimethylpiperidin-4-amine in the urea formation step. Yield; 28 mg (36%); (M+H) 613.4.

Example 438

Preparation of 1-(4-(4-(3-oxa-8-azabicyclo[3.2.1] octan-8-yl)-6-(tetrahydro-2H-pyran-4-yl)-1,3,5-triazin-2-yl)phenyl)-3-(4-(4-methylpiperazine-1-carbonyl)phenyl)urea Prepared as shown in Scheme 7, using (4-aminophenyl)(4-methylpiperazin-1-yl)methanone in the urea formation step. Yield; 36 mg (46%); (M+H) 613.3.

Example 439

Preparation of 1-(4-(4-(3-oxa-8-azabicyclo[3.2.1] octan-8-yl)-6-(tetrahydro-2H-pyran-4-yl)-1,3,5-triazin-2-yl)phenyl)-3-(4-(4-isopropylpiperazine-1-carbonyl)phenyl)urea Prepared as shown in Scheme 7, using (4-aminophenyl)(4-isopropylpiperazin-1-yl)methanone in the urea formation step. Yield; 41 mg (50%); (M+H) 641.3.

The following 1-(4-(4-(3-oxa-8-azabicyclo[3.2.1]octan-8-yl)-6-((R)-3-methylmorpholino)-1,3,5-triazin-2-yl)phenyl)-3-urea compounds were prepared as shown in Scheme 9.

Example 440

Preparation of 1-(4-(4-(3-oxa-8-azabicyclo[3.2.1] octan-8-yl)-6-((R)-3-methylmorpholino)-1,3,5-triazin-2-yl)phenyl)-3-(4-(4-ethylpiperazin-1-yl)phenyl)urea Step 1: Preparation of (R)-4-(4-chloro-6-(4-nitrophenyl)-1,3,5-triazin-2-yl)-3-methylmorpholine A solution of 2,4-dichloro-6-(4-nitrophenyl)-1,3,5-triazine (1.25 g, 4.61 mmol) and sodium bicarbonate (0.775 g, 9.22 mmol) in acetone (20 mL) and ice water (20 mL) was prepared. To this was added dropwise over 5 minutes (R)-3-methylmorpholine (0.466 g, 4.61 mmol). The resulting tan solution was allowed to stir at 0° C. for 2 hours, then gradually allowed to warm to room temperature over 18 hours. The light brown suspension was filtered and washed with water to provide (R)-4-(4-chloro-6-(4-nitrophenyl)-1,3,5-triazin-2-yl)-3-methylmorpholine (1.40 g, 90%) as a light brown solid. HRMS 336.0857 (M+H, calc.), 336.0845 (M+H, obs.).

Step 2: Preparation of 8-(4-((R)-3-methylmorpholino)-6-(4-nitrophenyl)-1,3,5-triazin-2-yl)-3-oxa-8-azabicyclo[3.2.1]octane A solution of (R)-4-(4-chloro-6-(4-nitrophenyl)-1,3,5-triazin-2-yl)-3-methylmorpholine (0.94 g, 2.80 mmol) in acetone (10 mL) and ice water (10 mL) was prepared. To this was added dropwise over 10 minutes a suspension of 3-oxa-8-azabicyclo[3.2.1]octane-hydrochloride (0.419 g, 2.80 mmol) and sodium bicarbonate (0.470 g, 5.60 mmol) in acetone (10 mL) and water (10 mL). The resulting tan solution was allowed to stir at 0° C. for 2 hours, then gradually allowed to warm to room temperature over 3 hours. The light brown suspension was filtered and washed with water to provide 8-(4-chloro-6-(4-nitrophenyl)-1,3,5-triazin-2-yl)-3-oxa-8-azabicyclo[3.2.1]octane (0.964 g, 83%) as a brown solid. HRMS 413.1931 (M+H, calc.), 413.1936 (M+H, obs.).

Step 3: Preparation of 4-(4-(3-oxa-8-azabicyclo [3.2.1]octan-8-yl)-6-((R)-3-methylmorpholino)-1,3, 5-triazin-2-yl)aniline A solution of 8-(4-((R)-3-methylmorpholino)-6-(4-nitrophenyl)-1,3,5-triazin-2-yl)-3-oxa-8-azabicyclo[3.2.1]octane (0.915 g, 2.22 mmol) in ethyl acetate (10 ml), methanol (10 ml), and methylene chloride (5 ml—added due to poor solubility of SM in EA/methanol) was prepared and 10% palladium on carbon (0.270 g, 30% by weight) was added. The flask was purged with hydrogen gas (balloon) and allowed to stir under positive pressure of hydrogen for 16 hours. The suspension was filtered through Celite™, the filter cake was washed with ethyl acetate, and the filtrate was concentrated to provide 4-(4-(3-oxa-8-azabicyclo[3.2.1]octan-8-yl)-6-((R)-3-methylmorpholino)-1,3,5-triazin-2-yl)aniline (0.587 g, 69%) as an off-white solid. (M+H) 383.3.

Step 4: Preparation of 1-(4-(4-(3-oxa-8-azabicyclo [3.2.1]octan-8-yl)-6-((R)-3-methylmorpholino)-1,3, 5-triazin-2-yl)phenyl)-3-(4-(4-ethylpiperazin-1-yl) phenyl)urea The method of urea formation using triphosgene and triethylamine in methylene chloride, described in Scheme 1, was utilized using commercially available 4-(4-ethylpiperazin-1-yl)aniline as the amine component. Purification by HPLC (5-95% acetonitrile in water over 20 minutes, 0.05% TFA buffer, Waters Atlantis column) provided 1-(4-(4-(3-oxa-8-azabicyclo[3.2.1]octan-8-yl)-6-((R)-3-methylmorpholino)-1,3,5-triazin-2-yl)phenyl)-3-(4-(4-ethylpiperazin-1-yl)phenyl)urea (0.0761 g, 95%) as a light yellow solid. (M+H) 614.3.

Example 441

Preparation of 1-(4-(4-(3-oxa-8-azabicyclo[3.2.1]octan-8-yl)-6-((R)-3-methylmorpholino)-1,3,5-triazin-2-yl)phenyl)-3-(4-(4-isopropylpiperazin-1-yl)phenyl)urea Prepared as shown in Scheme 9, using 4-(4-isopropylpiperazin-1-yl)aniline in the urea formation step. Yield; 82 mg (100%); (M+H) 628.4.

Example 442

Preparation of 1-(4-(4-(3-oxa-8-azabicyclo[3.2.1]octan-8-yl)-6-((R)-3-methylmorpholino)-1,3,5-triazin-2-yl)phenyl)-3-(4-(4-cyclopropylpiperazin-1-yl)phenyl)urea Prepared as shown in Scheme 9, using 4-(4-cyclopropylpiperazin-1-yl)aniline in the urea formation step. Yield; 32 mg (39%); (M+H) 626.3.

Example 443

Preparation of 1-(4-(4-(3-oxa-8-azabicyclo[3.2.1]octan-8-yl)-6-((R)-3-methylmorpholino)-1,3,5-triazin-2-yl)phenyl)-3-(4-(4-(dimethylamino)piperidin-1-yl)phenyl)urea Prepared as shown in Scheme 9, using 1-(4-aminophenyl)-N,N-dimethylpiperidin-4-amine in the urea formation step. Yield; 77 mg (93%); (M+H) 628.4.

Example 444

Preparation of 1-(4-(4-(3-oxa-8-azabicyclo[3.2.1]octan-8-yl)-6-((R)-3-methylmorpholino)-1,3,5-triazin-2-yl)phenyl)-3-(4-(4-methylpiperazine-1-carbonyl)phenyl)urea Prepared as shown in Scheme 9, using (4-aminophenyl)(4-methylpiperazin-1-yl)methanone in the urea formation step. Yield; 43 mg (52%); (M+H) 628.3.

Example 445

Preparation of 1-(4-(4-(3-oxa-8-azabicyclo[3.2.1]octan-8-yl)-6-((R)-3-methylmorpholino)-1,3,5-triazin-2-yl)phenyl)-3-(4-(4-isopropylpiperazine-1-carbonyl)phenyl)urea Prepared as shown in Scheme 9, using (4-aminophenyl)(4-isopropylpiperazin-1-yl)methanone in the urea formation step. Yield; 72 mg (84%); (M+H) 656.4.

Example 446

Preparation of 1-(4-(4-(3-oxa-8-azabicyclo[3.2.1]octan-8-yl)-6-((R)-3-methylmorpholino)-1,3,5-triazin-2-yl)phenyl)-3-(6-(4-methylpiperazin-1-yl)pyridin-3-yl)urea Prepared as shown in Scheme 9, using commercially available 6-(4-methylpiperazin-1-yl)pyridin-3-amine in the urea formation step. Yield; 74 mg (94%); (M+H) 601.3.

Example 447

Preparation of 1-(4-(4,6-bis((R)-3-methylmorpholino)-1,3,5-triazin-2-yl)phenyl)-3-(4-(4-ethylpiperazin-1-yl)phenyl)urea Prepared as shown in Scheme 1, using commercially available 4-(4-ethylpiperazin-1-yl)aniline in the urea formation step. Yield; 80 mg (99%); (M+H) 602.3.

Example 448

Preparation of 1-(4-(4,6-bis((R)-3-methylmorpholino)-1,3,5-triazin-2-yl)phenyl)-3-(4-(4-isopropylpiperazin-1-yl)phenyl)urea Prepared as shown in Scheme 1, using 4-(4-isopropylpiperazin-1-yl)aniline in the urea formation step. Yield; 74 mg (88%); (M+H) 616.4.

Example 449

Preparation of 1-(4-(4,6-bis((R)-3-methylmorpholino)-1,3,5-triazin-2-yl)phenyl)-3-(4-(4-(dimethylamino)piperidin-1-yl)phenyl)urea Prepared as shown in Scheme 1, using 1-(4-aminophenyl)-N,N-dimethylpiperidin-4-amine in the urea formation step. Yield; 80 mg (96%); (M+H) 616.4.

Example 450

Preparation of 1-(4-(4,6-bis((R)-3-methylmorpholino)-1,3,5-triazin-2-yl)phenyl)-3-(4-(4-methylpiperazine-1-carbonyl)phenyl)urea Prepared as shown in Scheme 1, using (4-aminophenyl)(4-methylpiperazin-1-yl)methanone in the urea formation step. Yield; 79 mg (95%); (M+H) 616.3.

Example 451

Preparation of 1-(4-(4,6-bis((R)-3-methylmorpholino)-1,3,5-triazin-2-yl)phenyl)-3-(4-(4-isopropylpiperazine-1-carbonyl)phenyl)urea Prepared as shown in Scheme 1, using (4-aminophenyl)(4-isopropylpiperazin-1-yl)methanone in the urea formation step. Yield; 18 mg (20%); (M+H) 644.4.

Example 452

Preparation of 4-(3-(4-(4,6-bis((R)-3-methylmorpholino)-1,3,5-triazin-2-yl)phenyl)ureido)-N,N-dimethylbenzamide Prepared as shown in Scheme 1, using commercially available 4-amino-N,N-dimethylbenzamide in the urea formation step. Yield; 43 mg (57%); (M+H) 561.3.

Example 453

Preparation of 1-(4-(4,6-bis((R)-3-methylmorpholino)-1,3,5-triazin-2-yl)phenyl)-3-(4-(pyrrolidin-1-ylmethyl)phenyl)urea Prepared as shown in Scheme 1, using commercially available 4-(pyrrolidin-1-ylmethyl)aniline in the urea formation step. Yield; 61 mg (79%); (M+H) 573.3.

Example 454

Preparation of 4-(3-(4-(4-(3-oxa-8-azabicyclo[3.2.1]octan-8-yl)-6-(tetrahydro-2H-pyran-4-yl)-1,3,5-triazin-2-yl)phenyl)ureido)benzamide Prepared as shown in Scheme 7, using commercially available 4-aminobenzamide in the urea formation step. Yield; 22 mg (21%); (M+H) 530.2.

Example 455

Preparation of 4-(3-(4-(4-(3-oxa-8-azabicyclo[3.2.1]octan-8-yl)-6-(tetrahydro-2H-pyran-4-yl)-1,3,5-triazin-2-yl)phenyl)ureido)-N,N-dimethylbenzamide Prepared as shown in Scheme 7, using commercially available 4-amino-N,N-dimethylbenzamide in the urea formation step. Yield; 22 mg (21%); (M+H) 558.3.

Example 456

Preparation of 1-(4-(4-(3-oxa-8-azabicyclo[3.2.1]octan-8-yl)-6-(tetrahydro-2H-pyran-4-yl)-1,3,5-triazin-2-yl)phenyl)-3-(4-(pyrrolidine-1-carbonyl)phenyl)urea Prepared as shown in Scheme 7, using (4-aminophenyl)(pyrrolidin-1-yl)methanone in the urea formation step. Yield; 41 mg (36%); (M+H) 584.3.

Preparation of (4-aminophenyl)(pyrrolidin-1-yl)methanone

Prepared from 4-nitrobenzoyl chloride and the appropriate amine as shown in Scheme 8.

Example 457

Preparation of 4-(3-(4-(4-(3-oxa-8-azabicyclo[3.2.1]octan-8-yl)-6-(tetrahydro-2H-pyran-4-yl)-1,3,5-triazin-2-yl)phenyl)ureido)-N-(2-(dimethylamino)ethyl)benzamide Prepared as shown in Scheme 7, using 4-amino-N-(2-(dimethylamino)ethyl)benzamide in the urea formation step. Yield; 36 mg (32%); (M+H) 601.3.

Preparation of 4-amino-N-(2-(dimethylamino)ethyl)benzamide

Prepared from 4-nitrobenzoyl chloride and the appropriate amine as shown in Scheme 8.

Example 458

Preparation of 4-(3-(4-(4-(3-oxa-8-azabicyclo[3.2.1]octan-8-yl)-6-(tetrahydro-2H-pyran-4-yl)-1,3,5-triazin-2-yl)phenyl)ureido)-N-(2-(methylamino)ethyl)benzamide Prepared as shown in Scheme 7, using tert-butyl 2-(4-aminobenzamido)ethyl(methyl)carbamate in the urea formation step. Following urea formation, the Boc-amine intermediate was treated with TFA to provide the title compound. Yield; 25 mg (22%); (M+H) 587.3.

Preparation of tert-butyl 2-(4-aminobenzamido)ethyl(methyl)carbamate

Prepared from 4-nitrobenzoyl chloride and the appropriate amine as shown in Scheme 8.

Example 459

Preparation of 4-(3-(4-(4-(3-oxa-8-azabicyclo[3.2.1]octan-8-yl)-6-(tetrahydro-2H-pyran-4-yl)-1,3,5-triazin-2-yl)phenyl)ureido)-N-(2-(dimethylamino)ethyl)-N-methylbenzamide Prepared as shown in Scheme 7, using 4-amino-N-(2-(dimethylamino)ethyl)-N-methylbenzamide in the urea formation step. Yield; 10 mg (9%); (M+H) 615.3.

Preparation of 4-amino-N-(2-(dimethylamino)ethyl)-N-methylbenzamide

Prepared from 4-nitrobenzoyl chloride and the appropriate amine as shown in Scheme 8.

Example 460

Preparation of 1-(4-(4-(3-oxa-8-azabicyclo[3.2.1]octan-8-yl)-6-(tetrahydro-2H-pyran-4-yl)-1,3,5-triazin-2-yl)phenyl)-3-(4-(morpholine-4-carbonyl)phenyl)urea Prepared as shown in Scheme 7, using (4-aminophenyl)(morpholino)methanone in the urea formation step. Yield; 25 mg (21%); (M+H) 600.3.

Preparation of (4-aminophenyl)(morpholino)methanone

Prepared from 4-nitrobenzoyl chloride and the appropriate amine as shown in Scheme 8.

Example 461

Preparation of 1-(4-(2-aminoethylamino)phenyl)-3-(4-(4,6-di(3-oxa-8-azabicyclo[3.2.1]octan-8-yl)-1,3,5-triazin-2-yl)phenyl)urea Prepared as shown in Scheme 1, using di-Boc protected N1-(2-aminoethyl)benzene-1,4-diamine in the urea formation step. Following urea formation, the di-Boc-amine intermediate was treated with TFA to provide the title compound. Yield; x mg (x %); HRMS 572.3092 (M+H, calc.), 572.3098 (M+H, obs.).

Preparation of di-Boc protected N1-(2-aminoethyl)benzene-1,4-diamine

Prepared from 4-fluoronitrobenzene and the appropriate amine as shown in Scheme 4.

Example 462

Preparation of 4-({[4-(4-{4-[(methylcarbamoyl) amino]phenyl}-6-morpholin-4-yl-1,3,5-triazin-2-yl) phenyl]carbamoyl}amino)benzamide Step 1: Preparation of phenyl 4-(4,4,5,5-tetramethyl-1,3,2-dioxaborolan-2-yl)phenylcarbamate To a solution of 4-(4,4,5,5-tetramethyl-1,3,2-dioxaborolan-2-yl)aniline (25.0 g, 114 mmol) and pyridine (4 mL, 57 mmol) in dry dichloromethane (250 mL)phenyl chloroformate (12 mL, 114 mmol) was added drop wise at –10° C. The reaction mixture was stirred at –10° C. for 30 min and then at room temperature for 30 minutes. The reaction mixture was diluted with dichloromethane (100 mL) and washed with water (2×70 mL). The organic layer was dried over anhydrous $Na_2SO_4$ and concentrated to get the crude product. Then the crude product was dissolved in diethyl ether (15 mL) and sonicated for 10 min and then pentane (30 mL) was added. the resulting solid was filtered and washed with pentane to give phenyl 4-(4,4,5,5-tetramethyl-1,3,2-dioxaborolan-2-yl)phenylcarbamate (26 g, 88% yield).
$^1$HNMR (300 MHz, $CDC_3$): δ 7.8 (d, 2H) 7.5 (d, 2H), 7.4 (m, 2H), 7.2 (m, 3H), 7.0 (s, 1H), 1.3 (s, 12H).

Step 2: Preparation of 1-methyl-3-(4-(4,4,5,5-tetramethyl-1,3,2-dioxaborolan-2-yl)phenyl) urea A mixture of phenyl 4-(4,4,5,5-tetramethyl-1,3,2-dioxaborolan-2-yl)phenylcarbamate (26 g, 76.6 mmol)), 2.0M Methylamine/THF (265 mL, 530 mmol) in 150 mL of THF was stirred at room temperature for 6 hours, then excess solvent was distilled off from the reaction mixture; residue was dissolved into water, extracted with ethyl acetate. The organic layer was dried over anhydrous $Na_2SO_4$, concentrated under reduced pressure. The crude product was purified by silica gel column chromatography by using 5-60% ethyl acetate in pet-ether as an eluent. to give 1-methyl-3-[4-(4,4,5,5-tetramethyl-[1,3,2]dioxaborolan-2-yl)-phenyl]-urea. (20 g, 88% yield) as white solid.
$^1$HNMR (300 MHz, $CDC_3$): δ 7.7 (d, 2H), 7.2 (d, 2H), 6.7 (s, 1H), 5.0 (s, 1H), 2.8 (s, 3H), 1.2 (s, 12H).

Step 3: Preparation of 4-(4,6-dichloro-1,3,5-triazin-2-yl) morpholine

Morpholine (9.5 mL, 108 mmol)) was added to a solution of cyanuric chloride (20 g, 108 mmol) in chloroform (10 mL) and stirred at –5° C. for 1 hour. Reaction mixture was diluted with water, extracted with dichloromethane. The organic layer was dried over anhydrous $Na_2SO_4$, filtered and concentrated under reduced pressure. Crude product was purified by silica gel (100-200 mesh) column chromatography using 5% ethyl acetate in pet-ether as an eluent to give 4-(4,6-dichloro-1,3,5-triazin-2-yl)morpholine (10 g, 39% yield).

Step 4: Preparation of 1-(4-(4-chloro-6-morpholino-1,3,5-triazin-2-yl)phenyl)-3-methylurea A mixture of compound 4-(4,6-dichloro-1,3,5-triazin-2-yl)morpholine (10 g, 42.7 mmol), $Pd(PPh_3)_4$ (2.46 g, 2.1 mmol), 1-methyl-3-[4-(4,4,5,5-tetramethyl-[1,3,2]dioxaborolan-2-yl)-phenyl]-urea. (11.7 g, 42.4 mmol) and 1N $Na_2CO_3$ (168 mL, 168 mmol) in degassed 1,2-dimethoxyethane (400 mL) was heated to 65° C. for 8 hours under $N_2$ atmosphere. The reaction mixture filtered, diluted with water, extracted with ethyl acetate and washed with water, brine, dried over anhydrous $Na_2SO_4$, filtered and concentrated under reduced pressure. Crude product was purified by silica gel (100-200 mesh) column chromatography using 20-60% ethyl acetate in pet-ether as an eluent. To give 1-(4-(4-chloro-6-morpholino-1,3,5-triazin-2-yl)phenyl)-3-methylurea (5.0 g, 34% yield).
$^1$HNMR (300 MHz, DMSO-d6): δ 9.4 (br, 1H), 8.2 (d, 2H), 7.6 (d, 2H), 6.6 (br, 1H), 4.0 (m, 2H), 3.8 (m, 6H), 2.8 (s, 3H).

Step 5: Preparation of 1-(4-(4-(4-aminophenyl)-6-morpholino-1,3,5-triazin-2-yl)phenyl)-3-methylurea The title compound was prepared by following the procedure of Example 462 step 4 using 1-(4-(4-chloro-6-morpholino-1,3,5-triazin-2-yl)phenyl)-3-methylurea and 4-(4,4,5,5-tetramethyl-1,3,2-dioxaborolan-2-yl)aniline. Yield 2 g, 45% yield.

Step 6: Preparation of phenyl 4-carbamoylphenylcarbamate

To a solution of 4-aminobenzamide (5.0 g, 36.7 mmol) and pyridine (2.9 g, 36.7 mmol)) in dry $CH_2Cl_2$ (100 mL) at –10° C., phenyl chloroformate (6.9 g, 44.1 mmol) was added dropwise, stirred at –10° C. for 30 min and then at room temperature for 30 minutes The reaction mixture was diluted with $CH_2Cl_2$ (100 mL) and washed with water (2×70 mL). The organic layer was dried over anhydrous $Na_2SO_4$ and concentrated to get the crude product. The crude product was dissolved in diethyl ether (15 mL) and sonicated for 10 minutes and then pentane (30 mL) was added, the resulting solid was filtered and washed with pentane to give phenyl 4-carbamoylphenylcarbamate (7.2 g, 77% yield).

Step 7: Preparation of 4-({[4-(4-{4-[(methylcarbamoyl)amino]phenyl}-6-morpholin-4-yl-1,3,5-triazin-2-yl)phenyl]carbamoyl}amino)benzamide To a solution of 1-(4-(4-(4-aminophenyl)-6-morpholino-1,3,5-triazin-2-yl)phenyl)-3-methylurea (0.6 g, 1.5 mmol) and triethylamine (4-5 mL) in dry DMF (10 mL), phenyl 4-carbamoylphenylcarbamate (1.15 g, 4.5 mmol).) was added at room temperature and mixture was heated to 90° C. for 10 hours under nitrogen atmosphere. After cooling to room temperature reaction mixture was quenched with ice water and resulting solid was filtered to get crude product. Crude product was purified by Preparative HPLC to give 4-({[4-(4-{4-[(methylcarbamoyl)amino]phenyl}-6-morpholin-4-yl-1,3,5-triazin-2-yl)phenyl]carbamoyl}amino)benzamide (45 mg, 5.3% yield).

159

Example 463

Preparation of 1-{4-[4-(3,5-dimethylmorpholin-4-yl)-6-{4-[(methylcarbamoyl)amino]phenyl}-1,3,5-triazin-2-yl]phenyl}-3-pyridin-3-ylurea Step 1: Preparation of 4-(4,6-dichloro-1,3,5-triazin-2-yl)-3,5-dimethylmorpholine The title compound was prepared by following the procedure of Example 462 step 3 using cyanuric chloride and 3,5-dimethylmorpholine. Yield 5 g, 35% yield.
$^1$HNMR (300 MHz, CDC$_3$): δ 4.6 (m, 2H), 3.6 (m, 2H), 2.8 (m, 2H), 1.2 (d, 6H).

Step 2: Preparation of 1-(4-(4-chloro-6-(3,5-dimethylmorpholino)-1,3,5-triazin-2-yl)phenyl)-3-methylurea The title compound was prepared by following the procedure of example 462 step 4 using 4-(4,6-dichloro-1,3,5-triazin-2-yl)-3,5-dimethylmorpholine and 1-methyl-3-[4-(4,4,5,5-tetramethyl-[1,3,2]dioxaborolan-2-yl)-phenyl]-urea. Yield 1.15 g, 16% yield.

Step 3: Preparation of 1-(4-(4-(4-aminophenyl)-6-(3,5-dimethylmorpholino)-1,3,5-triazin-2-yl)phenyl)-3-methylurea The title compound was prepared by following the procedure of example 462 step 4 using 1-(4-(4-chloro-6-(3,5-dimethylmorpholino)-1,3,5-triazin-2-yl)phenyl)-3-methylurea and 4-(4,4,5,5-tetramethyl-1,3,2-dioxaborolan-2-yl)aniline. Yield 2 g, 86% yield.

Step 4: Preparation of phenyl pyridin-3-ylcarbamate

The title compound was prepared by following the procedure of example 462 step 6 using 3-aminopyridine and phenyl chloroformate. Yield 7 g, 62% yield.

Step 5: Preparation of 1-{4-[4-(3,5-dimethylmorpholin-4-yl)-6-{4-[(methylcarbamoyl)amino]phenyl}-1,3,5-triazin-2-yl]phenyl}-3-pyridin-3-ylurea The title compound was prepared by following the procedure of example 462 step 7 using 1-(4-(4-(4-aminophenyl)-6-(3,5-dimethylmorpholino)-1,3,5-triazin-2-yl)phenyl)-3-methylurea and phenyl pyridin-3-ylcarbamate. Yield 77 mg, 6% yield.

Example 464

Preparation of 4-[({4-[4-{4-[(methylcarbamoyl)amino]phenyl}-6-(8-oxa-3-azabicyclo[3.2.1]oct-3-yl)-1,3,5-triazin-2-yl]phenyl}carbamoyl)amino]benzamide Step 1: Preparation of 3-(4,6-dichloro-1,3,5-triazin-2-yl)-8-oxa-3-azabicyclo[3.2.1]octane The title compound was prepared by following the procedure of example 462 step 3 using cyanuric chloride and 8-oxa-3-azabicyclo[3.2.1]octane. Yield 10 g, 47% yield.

160

Step 2: Preparation of 1-(4-(4-(8-oxa-3-azabicyclo[3.2.1]octan-3-yl)-6-chloro-1,3,5-triazin-2-yl)phenyl)-3-methylurea The title compound was prepared by following the procedure of example 462 step 4 using 3-(4,6-dichloro-1,3,5-triazin-2-yl)-8-oxa-3-azabicyclo[3.2.1]octane and 1-methyl-3-[4-(4,4,5,5-tetramethyl-[1,3,2]dioxaborolan-2-yl)-phenyl]-urea. Yield 5 g, 29% yield.

Step 3: Preparation of 1-(4-(4-(4-aminophenyl)-6-(8-oxa-3-azabicyclo[3.2.1]octan-3-yl)-1,3,5-triazin-2-yl)phenyl)-3-methylurea The title compound was prepared by following the procedure of example 462 step 4 using 1-(4-(4-(8-oxa-3-azabicyclo[3.2.1]octan-3-yl)-6-chloro-1,3,5-triazin-2-yl)phenyl)-3-methylurea and 4-(4,4,5,5-tetramethyl-1,3,2-dioxaborolan-2-yl)aniline. Yield 2.8 g, 49% yield.

Step 4: Preparation of 4-[({4-[4-{4-[(methylcarbamoyl)amino]phenyl}-6-(8-oxa-3-azabicyclo[3.2.1]oct-3-yl)-1,3,5-triazin-2-yl]phenyl}carbamoyl)amino]benzamide The title compound was prepared by following the procedure of example 462 step 7 using 1-(4-(4-(4-aminophenyl)-6-(8-oxa-3-azabicyclo[3.2.1]octan-3-yl)-1,3,5-triazin-2-yl)phenyl)-3-methylurea and phenyl 4-carbamoylphenylcarbamate. Yield 90 mg, 13% yield.

Example 465

Preparation of 3-[({4-[4-{4-[(methylcarbamoyl)amino]phenyl}-6-(8-oxa-3-azabicyclo[3.2.1]oct-3-yl)-1,3,5-triazin-2-yl]phenyl}carbamoyl)amino]benzamide Step 1: Preparation of phenyl 3-carbacarbamoylphenylcarbamate The title compound was prepared by following the procedure of example 462 step 6 using 3-aminobenzamide and phenyl chloroformate. Yield 7 g, 74% yield.

Step 2: Preparation of 3-[({4-[4-{4-[(methylcarbamoyl)amino]phenyl}-6-(8-oxa-3-azabicyclo[3.2.1]oct-3-yl)-1,3,5-triazin-2-yl]phenyl}carbamoyl)amino]benzamide The title compound was prepared by following the procedure of example 462 step 7 using 1-(4-(4-(4-aminophenyl)-6-(8-oxa-3-azabicyclo[3.2.1]octan-3-yl)-1,3,5-triazin-2-yl)phenyl)-3-methylurea and phenyl 3-carbamoylphenylcarbamate. Yield 90 mg, 13% yield.

Example 466

Preparation of 3-({[4-(4-{4-[(methylcarbamoyl)amino]phenyl}-6-morpholin-4-yl-1,3,5-triazin-2-yl)phenyl]carbamoyl}amino)benzamide The title compound was prepared by following the procedure of example 462 step 7 using 1-(4-(4-(4-aminophenyl)-6-morpholino-1,3,5-triazin-2-yl)phenyl)-3-methylurea and phenyl 3-carbamoylphenylcarbamate. Yield 51 mg, 4% yield.

Example 467

Preparation of 1-methyl-3-[4-(4-morpholin-4-yl-6-{4-[(pyridin-3-ylcarbamoyl)amino]phenyl}-1,3,5-triazin-2-yl)phenyl]urea The title compound was prepared by following the procedure of example 462 step 7 using 1-(4-(4-(4-aminophenyl)-6-morpholino-1,3,5-triazin-2-yl)phenyl)-3-methylurea and phenyl pyridin-3-ylcarbamate. Yield 77 mg, 6% yield.

Example 468

Preparation of 1-methyl-3-[4-(4-morpholin-4-yl-6-{4-[(pyridin-4-ylcarbamoyl)amino]phenyl}-1,3,5-triazin-2-yl)phenyl]urea

Step 1: Preparation of phenyl pyridin-4-ylcarbamate

The title compound was prepared by following the procedure of example 462 step 6 using 4-aminopyridine and phenyl chloroformate. Yield 6 g, 534% yield.

Step 2: Preparation of 1-methyl-3-[4-(4-morpholin-4-yl-6-{4-[(pyridin-4-ylcarbamoyl)amino]phenyl}-1,3,5-triazin-2-yl)phenyl]urea The title compound was prepared by following the procedure of example 462 step 7 using 1-(4-(4-(4-aminophenyl)-6-morpholino-1,3,5-triazin-2-yl)phenyl)-3-methylurea and phenyl pyridin-4-ylcarbamate. Yield 75 mg, 3.9% yield.

Example 469

Preparation of 3-[({4-[4-(3,5-dimethylmorpholin-4-yl)-6-{4-[(methylcarbamoyl)amino]phenyl}-1,3,5-triazin-2-yl]phenyl}carbamoyl)amino]benzamide The title compound was prepared by following the procedure of example 462 step 7 using 1-(4-(4-(4-aminophenyl)-6-(3,5-dimethylmorpholino)-1,3,5-triazin-2-yl)phenyl)-3-methylurea and phenyl 3-carbamoylphenylcarbamate. Yield 56 mg, 4.1% yield.

Example 470

Preparation of 4-[({4-[4-(3,5-dimethylmorpholin-4-yl)-6-{4-[(methylcarbamoyl)amino]phenyl}-1,3,5-triazin-2-yl]phenyl}carbamoyl)amino]benzamide The title compound was prepared by following the procedure of example 462 step 7 using 1-(4-(4-(4-aminophenyl)-6-(3,5-dimethylmorpholino)-1,3,5-triazin-2-yl)phenyl)-3-methylurea and phenyl 4-carbamoylphenylcarbamate. Yield 70 mg, 12.8% yield.

Example 471

Preparation of 1-methyl-3-{4-[4-(8-oxa-3-azabicyclo[3.2.1]oct-3-yl)-6-{4-[(pyridin-4-ylcarbamoyl)amino]phenyl}-1,3,5-triazin-2-yl]phenyl}urea The title compound was prepared by following the procedure of example 462 step 7 using 1-(4-(4-(4-aminophenyl)-6-(8-oxa-3-azabicyclo[3.2.1]octan-3-yl)-1,3,5-triazin-2-yl)phenyl)-3-methylurea and phenyl pyridin-4-ylcarbamate. Yield 51 mg, 4% yield.

Example 472

Preparation of 1-{4-[4-(3,5-dimethylmorpholin-4-yl)-6-{4-[(methylcarbamoyl)amino]phenyl}-1,3,5-triazin-2-yl]phenyl}-3-pyridin-4-ylurea The title compound was prepared by following the procedure of example 462 step 7 using 1-(4-(4-(4-aminophenyl)-6-(3,5-dimethylmorpholino)-1,3,5-triazin-2-yl)phenyl)-3-methylurea and phenyl pyridin-4-ylcarbamate. Yield 15 mg, 0.8% yield.

Example 473

Preparation of N-[4-(4,6-dimorpholin-4-yl-1,3,5-triazin-2-yl)phenyl]-2,2-difluoroacetamide

Step 1: Preparation of 4,4'-(6-chloro-1,3,5-triazine-2,4-diyl)dimorpholine

A solution of morpholine (8.71 g, 100 mmol) in 100 mL of methylene was added dropwise to a mixture of cyanuric chloride (9.22 g, 50.0 mmol) and triethylamine (10.1 g, 100 mmol) in 200 mL of methylene chloride at 0° C. Then the reaction mixture was stirred at 0° C. for 1 hr and slowly warmed up to room temperature. After stirring at room temperature for 1 hr, the reaction mixture was filtered to remove the triethylamine hydrochloride salt. The filtrate was concentrated to give 4,4'-(6-chloro-1,3,5-triazine-2,4-diyl)dimorpholine (14.2 g, 100 yield) as a white solid. HPLC: Rt=2.43 min; MS 286, 288 [M+H].

Step 2: Preparation of 4-(4,6-dimorpholino-1,3,5-triazin-2-yl)aniline

A mixture of 4,4'-(6-chloro-1,3,5-triazine-2,4-diyl)dimorpholine (1.40 g, 4.90 mmol), 4-(4,4,5,5-tetramethyl-1,3,2-dioxaborolan-2-yl)aniline (2.62 g, 11.9 mmol) and tetrakis(triphenylphosphine) palladium (0) (282 mg, 0.240 mmol) in 2M sodium carbonate aqueous solution (10 mL, 20 mmol) and 40 mL of DME was stirred at 80° C. for 2 hr. The reaction mixture was diluted with 300 mL of ethyl acetate and washed with water. The organic layer was concentrated and purified by flash chromatography (ISCO, 120 g silica gel column, eluting with 0-100% EtOAc/Hexane) to give 4-(4,6-dimorpholino-1,3,5-triazin-2-yl)aniline (0.68 g, 40% yield). HPLC: Rt=2.09 min; MS 343 [M+H].

Step 3: Preparation of N-[4-(4,6-dimorpholin-4-yl-1,3,5-triazin-2-yl)phenyl]-2,2-difluoroacetamide To a mixture of 2,2-difluoroacetic acid (20 mg, 0.21 mmol), HBTU (76 mg, 0.2 mmol), and DIEA (52 mg, 0.40 mmol) in 2 mL of DMF was added 4-(4,6-dimorpholino-1,3,5-triazin-2-yl) aniline (40 mg, 0.12 mmol). The reaction was stirred at 60° C. 16 hr. Then the reaction mixture was cooled to room temperature and purified by reverse phase chromatography to give N-[4-(4,6-dimorpholin-4-yl-1,3,5-triazin-2-yl)phenyl]-2,2-difluoroacetamide (23 mg, 46% yield). HPLC: Rt=2.19 min; MS 421 [M+H].

Example 474

Preparation of N-[4-(4,6-dimorpholin-4-yl-1,3,5-triazin-2-yl)phenyl]-4,5-dihydro-1H-imidazol-2-amine A mixture of 4-(4,6-dimorpholino-1,3,5-triazin-2-yl) aniline (40 mg, 0.12 mmol), imidazolidine-2-thione (15 mg, 0.15 mmol0 and mercury(II) chloride (40 mg, 0.15 mmol) in 2 mL of DMF was stirred at 140° C. 16 hr. Then the reaction mixture was cooled to room temperature and filtered through Celite™. The filtration was concentrated and purified by reverse phase chromatography to give N-[4-(4,6-dimorpholin-4-yl-1,3,5-triazin-2-yl)phenyl]-4,5-dihydro-1H-imidazol-2-amine (9.0 mg, 22% yield). HPLC: Rt=1.74 min; MS 411 [M+H].

Example 475

Preparation of 2,4-dimorpholin-4-yl-6-[4-(2H-tetrazol-5-yl)phenyl]-1,3,5-triazine Step 1: Preparation of 4-(4,6-dimorpholino-1,3,5-triazin-2-yl)benzonitrile The title compound was prepared by following the procedure of example 473 step 2 using 4,4'-(6-chloro-1,3,5-triazine-2,4-diyl)dimorpholine and 4-cyanophenyl-boronic acid. Yield 86 mg, 50% yield; HPLC: Rt=2.60 min; MS 353 [M+H].

Step 2: Preparation of 2,4-dimorpholin-4-yl-6-[4-(2H-tetrazol-5-yl)phenyl]-1,3,5-triazine A mixture of 4-(4,6-dimorpholino-1,3,5-triazin-2-yl)benzonitrile (11 mg, 0.031 mmol), sodium azide (5.5 mg, 0.085 mmol) and triethylamine hydrochloride (6.0 mg, 0.043 mmol) in 2 mL of DMF was stirred at 120° C. for 6 hr. Then the reaction mixture was cooled to room temperature and purified by reverse phase chromatography to give 2,4-dimorpholin-4-yl-6-[4-(2H-tetrazol-5-yl)phenyl]-1,3,5-triazine. Yield 12 mg, 97% yield; HPLC: Rt=2.09 min; MS 394 [M–H].

Example 476

Preparation of 1-[4-(4,6-dimorpholin-4-yl-1,3,5-triazin-2-yl)phenyl]-3-methylurea Step 1: Preparation of 1-Methyl-3-[4-(4,4,5,5-tetramethyl-[1,3,2]dioxaborolan-2-yl)-phenyl]-urea A mixture of 2-(4-isocyanatophenyl)-4,4,5,5-tetramethyl-1,3,2-dioxaborolane (750 mg, 3.06 mmol), 2.0M Methylamine/THF (2.3 mL, 4.60 mmol) in 50 mL of THF was stirred at room temperature for 6 hr. Then the traction mixture was concentrated to give 1-methyl-3-[4-(4,4,5,5-tetramethyl-[1,3,2]dioxaborolan-2-yl)-phenyl]-urea. (760 mg, 90% yield). Rt=2.21 min; 277 [M+H].

Step 2: Preparation of 1-[4-(4,6-dimorpholin-4-yl-1,3,5-triazin-2-yl)phenyl]-3-methylurea The title compound was prepared by following the procedure of example 473 step 2 using 4,4'-(6-chloro-1,3,5-triazine-2,4-diyl)dimorpholine and 1-Methyl-3-[4-(4,4,5,5-tetramethyl-[1,3,2]dioxaborolan-2-yl)-phenyl]-urea. Yield 13 mg, 11% yield; HPLC: Rt=1.98 min; MS 400 [M+H].

Example 477

Preparation of 2-[4-(4,6-dimorpholin-4-yl-1,3,5-triazin-2-yl)phenyl]-N-pyridin-3-ylacetamide Step 1: Preparation of 2-(4-(4,6-dimorpholino-1,3,5-triazin-2-yl)phenyl)acetic acid A mixture of 4,4'-(6-chloro-1,3,5-triazine-2,4-diyl)dimorpholine (285 mg, 1.0 mmol), 2-(4-(4,4,5,5-tetramethyl-1,3,2-dioxaborolan-2-yl)phenyl)acetic acid. (315 mg, 1.2 mmol) and tetrakis(triphenylphosphine)palladium (0) (58 mg, 0.05 mmol) in 2M sodium carbonate aqueous solution (3 mL, 8 mmol) and 20 mL of DME was stirred at 80° C. for 2 hr. Then the reaction mixture was diluted with 50 mL of ethyl acetate and extracted with 1N NaOH (50 mL, three times)). The combined aqueous layers were neutralized to pH=6. Then the aqueous solution was extracted with ethyl acetate (50 mL, three times). The combined organic layers were washed with saturated sodium carbonate and brine. Then the organic layer was dried over anhydrous sodium sulfate and concentrated to give 2-(4-(4,6-dimorpholino-1,3,5-triazin-2-yl)phenyl) acetic acid (68 mg, 18% yield). HPLC: Rt=2.04 min; MS 386 [M+H].

Step 2: Preparation of 2-[4-(4,6-dimorpholin-4-yl-1,3,5-triazin-2-yl)phenyl]-N-pyridin-3-ylacetamide The title compound was prepared by following the procedure of example 473 step 3 using 2-(4-(4,6-dimorpholino-1,3,5-triazin-2-yl)phenyl) acetic acid and 3-aminopyridine. Yield 21 mg, 44% yield; HPLC: Rt=1.91 min; MS 462 [M+H].

Preparation of ((2S,5R)-1-(4-(8-oxa-3-azabicyclo[3.2.1]octan-3-yl)-6-(4-nitrophenyl)-1,3,5-triazin-2-yl)pyrrolidine-2,5-diyl)dimethanol A suspension of ((2S,5R)-1-(4-chloro-6-(4-nitrophenyl)-1,3,5-triazin-2-yl)pyrrolidine-2,5-diyl)dimethanol (1.3 g, 2.7 mmol), 8-oxa-3-azabicyclo[3.2.1]octane hydrochloride (0.51 g, 3.4 mmol) in ethanol (15 mL) was treated with triethylamine (1.35 mL, 10 mmol) and heated with a heat gun briefly to reflux. The reaction mixture was purified by automated flash chromatography (methanol/chloroform) to provide the title compound as a hard peach colored foam. MS (ES$^+$)=443.2 (M+H)$^+$ Preparation of 3-(4-((2S,5R)-2,5-bis((tert-butyldimethylsilyloxy)methyl)pyrrolidin-1-yl)-6-(4-nitrophenyl)-1,3,5-triazin-2-yl)-8-oxa-3-azabicyclo[3.2.1]octane A solution of ((2S,5R)-1-(4-(8-oxa-3-azabicyclo[3.2.1]octan-3-yl)-6-(4-nitrophenyl)-1,3,5-triazin-2-yl)pyrrolidine-2,5-diyl)dimethanol (1.5 g, 3.4 mmol) in dichloromethane (15 mL) was treated successively with tert-butyl dimethyl chlorosilane (1.3 g, 8.5 mmol) and imidazole (0.69 g, 10 mmol). The resulting suspension was stirred overnight at room temperature and then quenched with water. The aqueous phase was extracted three times with dichloromethane. The combined extracts were dried over anhydrous magnesium sulfate, filtered, and concentrated to dryness under reduced pressure. The crude residue (a peach-colored solid) was carried on to the following step without further purification. MS (ES$^+$)=671.4 (M+H)$^+$ Preparation of 4-(4-(8-oxa-3-azabicyclo[3.2.1]octan-3-yl)-6-((2S,5R)-2,5-bis((tert-butyldimethylsilyloxy)methyl)pyrrolidin-1-yl)-1,3,5-triazin-2-yl)aniline A suspension of palladium on charcoal (10%, 100 mg) and crude 3-(4-((2S,5R)-2,5-bis((tert-butyldimethylsilyloxy)methyl)pyrrolidin-1-yl)-6-(4-nitrophenyl)-1,3,5-triazin-2-yl)-8-oxa-3-azabicyclo[3.2.1]octane (3.4 mmol maximum) in tetrahydrofuran (30 mL) was shaken for 8 hours under 50 psi of hydrogen. The mixture was filtered through a pad of Celite™ diatomaceous earth and concentrated under reduced pressure to provide the title compound as an orange foam. MS (ES$^+$)=642.4 (M+H)$^+$ Example 667

Preparation of 1-(4-{4-[(2R,5S)-2,5-bis(hydroxymethyl)pyrrolidin-1-yl]-6-(8-oxa-3-azabicyclo[3.2.1]oct-3-yl)-1,3,5-triazin-2-yl}phenyl)-3-pyridin-4-ylurea A solution of 4-(4-(8-oxa-3-azabicyclo[3.2.1]octan-3-yl)-6-((2S,5R)-2,5-bis((tert-butyldimethylsilyloxy)methyl)pyrrolidin-1-yl)-1,3,5-triazin-2-yl)aniline (0.24 g, 0.37 mmol) in dichloromethane (5 mL) was treated successively with triethylamine (500 µL) and a triphosgene (56 mg) solution in dichloromethane (1 mL). After 5 minutes, the mixture was treated with a solution of 4-aminopyridine (70 mg) in warm tetrahydrofuran. After 1 hour, the reaction mixture was quenched with methanol and concentrated to dryness. Half of the crude residue was treated with a saturated solution of hydrogen chloride in methanol. Upon complete desilylation, the mixture was concentrated to dryness and the residue purified by reverse-phase high performance liquid chromatography using a Phenomenex Prodigy column running a gradient elution of 5% acetonitrile/95% of 0.1% aqueous trifluoroacetic acid to 50% acetonitrile over 25 minutes. After concentration, the title compound was obtained as it trifluoroacetic acid salt (75 mg). MS (ES$^+$)=533.3 (M+H)$^+$ Example 668

Preparation of 1-(4-{4-[(2R,5S)-2,5-bis(hydroxymethyl)pyrrolidin-1-yl]-6-(8-oxa-3-azabicyclo[3.2.1]oct-3-yl)-1,3,5-triazin-2-yl}phenyl)-3-[4-(4-methylpiperazin-1-yl)phenyl]urea A solution of 4-(4-(8-oxa-3-azabicyclo[3.2.1]octan-3-yl)-6-((2S,5R)-2,5-bis((tert-butyldimethylsilyloxy)methyl)pyrrolidin-1-yl)-1,3,5-triazin-2-yl)aniline (0.25 g, 0.39 mmol) in dichloromethane (5 mL) was treated successively with triethylamine (500 µL) and a triphosgene (59 mg, 0.08 mmol) solution in dichloromethane (1 mL). After 5 minutes, the mixture was treated with 4-(4-methylpiperazin-1-yl)aniline (150 mg). After 1 hour, the reaction mixture was quenched with methanol and concentrated to dryness. The crude residue was treated with a saturated solution of hydrogen chloride in methanol. Upon complete desilylation, the mixture was concentrated to dryness and the residue purified by reverse-phase high performance liquid chromatography using a Phenomenex Gemini column running a gradient elution of 5% acetonitrile/55% of 0.1% aqueous trifluoroacetic acid to 50% acetonitrile over 15 minutes. After concentration, the title compound was obtained as it trifluoroacetic acid salt (130 mg). MS (ES$^+$)=630.4 (M+H)$^+$ Example 823

Preparation of 1-[4-(4,6-di-3,7-dioxa-9-azabicyclo[3.3.1]non-9-yl-1,3,5-triazin-2-yl)phenyl]-3-[4-(4-methylpiperazin-1-yl)phenyl]urea To a solution of cyanuric chloride (0.368 g, 2 mmol) in CH$_2$Cl$_2$ (20 mL) was added 3,7-dioxa-9-azabicyclo[3.3.1]nonane. HCO$_2$H (0.718 g, 4.1 mmol), followed by addition of Et$_3$N (0.98 mL, 7 mmol). The resulting reaction mixture was stirred for 24 h, and then diluted with CH$_2$Cl$_2$. The organic phase was washed with aqueous 1N HCl (3×) and dried over MgSO$_4$. The solvent was removed in vacuum to give 9,9'-(6-chloro-1,3,5-triazine-2,4-diyl)bis(3,7-dioxa-9-azabicyclo[3.3.1]nonane) as white solid (0.15 g, 95% yield).

To a 10 mL vial were added 9,9'-(6-chloro-1,3,5-triazine-2,4-diyl)bis(3,7-dioxa-9-azabicyclo[3.3.1]nonane) (150 mg, 0.406 mmol), 4-aminophenylboronic acid pinacol ester (133 mg, 0.61 mmol), Pd(PPh$_3$)$_4$ (10 mg), toluene (1 mL), EtOH (1 mL) and 2M Na$_2$CO$_3$ aqueous solution (0.305 mL). The resulting mixture was heated at 120° C. for 20 minutes in microwave oven. The reaction mixture was cooled to room temperature. The aqueous phase was extracted with EtOAc, and the combined organic phases were dried over (MgSO$_4$). The solvent was removed under reduced pressure and the residue was subjected to HPLC separation to give 4-(4,6-di(3,7-dioxa-9-azabicyclo[3.3.1]nonan-9-yl)-1,3,5-triazin-2-yl)aniline as a white solid (120 mg).

To a solution of 4-(4,6-di(3,7-dioxa-9-azabicyclo[3.3.1]nonan-9-yl)-1,3,5-triazin-2-yl)aniline (120 mg, 0.281 mmol) in CH$_2$Cl$_2$ was added Et$_3$N (0.237 mL, 1.69 mmol) and triphosgene (42 mg, 0.14 mmol). The mixture was stirred at room temperature for 15 minutes and 4-(4-methylpiperazin-1-yl)aniline (107 mg, 0.56 mmol) was added. The mixture was stirred at room temperature overnight. The solvent was removed, and the residue was subjected to HPLC separation to give the title compound (1TFA salt) MS (ESI) m/z 644.3306.

Preparation of (6S)-tert-butyl 6-hydroxy-3-oxa-8-azabicyclo[3.2.1]octane-8-carboxylate (Scheme 10)

Step 1

(2R',5S')-1-tert-butyl 2,5-dimethyl 1H-pyrrole-1,2,5(2H,5H)-tricarboxylate (cis-diester) was synthesized by following the procedure described in literature: *Organic Letters* 2004, 6(18), 3055-8.

Step 2: Reduction of cis-diester to (2R',5S')-tert-butyl 2,5-bis(hydroxymethyl)-2,5-dihydro-1H-pyrrole-1-carboxylate (cis-diol)

To a solution of (2R',5S')-1-tert-butyl 2,5-dimethyl 1H-pyrrole-1,2,5(2H,5H)-tricarboxylate (6.6 g, 23.1 mmol) in THF (100 mL) was added slowly of LiBH$_4$ solution (2M in THF, 34.7 mL, 69.4 mmol) at 0° C. The resulting mixture was stirred at room temperature for 3 hours, then cooled to 0° C. again. HCl solution (1M, 30 mL) was added to the reaction mixture, and stirred for 10 minutes before diluted with EtOAc. The organic layer was separated, and the aqueous phase was extracted with EtOAc. The combined organic phases were washed with water and brine, and dried (MgSO$_4$). The organic solvent was removed in vacuo to give the crude product, which was purified by flash chromatography in silica gel with EtOAc:Hex:MeOH (50:50:10) to give the cis-diol (3.8 g, 72%).

Step 3: Preparation of (2R',5S')-tert-butyl 2,5-bis((tert-butyldimethylsilyloxy)methyl)-2,5-dihydro-1H-pyrrole-1-carboxylate To a solution of the cis-diol (3.57 g, 15.6 mmol) in DMF (15 mL) were added TBSCl (5.16 g, 34.3 mmol) and imidazole (3.18 g, 46.7 mmol). The mixture was heated at 80° C. for 30 minutes in microwave oven (150 watt). Cooled to room temperature, the mixture was taken up in water (50 mL) and EtOAc (50 mL). The organic layer was separated, and the aqueous phase was extracted with EtOAc. Combined organic phases were washed with water and brine, and dried (MgSO$_4$). The organic solvent was removed in vacuo to give the crude product, which was purified by flash chromatography in silica gel with EtOAc:Hex (10:90) to give the title compound (7.12 g, 98%).

Step 4: Synthesis of (2R',3S',5R')-tert-butyl 2,5-bis ((tert-butyldimethylsilyloxy)methyl)-3-hydroxypyrrolidine-1-carboxylate (trans-alcohol)

To a solution of (2R',5S')-tert-butyl 2,5-bis((tert-butyldimethylsilyloxy)methyl)-2,5-dihydro-1H-pyrrole-1-carboxylate (4.8 g, 10.5 mmol) in THF (50 mL) was added slowly of BH$_3$ DMS solution (2M in THF, 6.97 mL, 13.9 mmol) at 0° C. The resulting mixture was stirred at room temperature for 3 hours, then cooled to 0° C. again. NaOH solution (5M, 12.6 mL, 63.2 mmol) was added to the reaction mixture, followed by addition of H$_2$O$_2$ (30%, 6.33 mL, 62.0 mmol). The resulting mixture was stirred for 5 hours before diluted with EtOAc. The organic layer was separated, and the aqueous phase was extracted with EtOAc. Combined organic phases were washed with water and brine, and dried (MgSO$_4$). The organic solvent was removed in vacuo to give the crude product, which was purified by flash chromatography in silica gel with EtOAc:Hex (30:70) to give the title compound (3.8 g, 77%).

Step 5: Benzyl protection of the trans alcohol

To a solution of (2R',3S',5R')-tert-butyl 2,5-bis((tert-butyldimethylsilyloxy)methyl)-3-hydroxypyrrolidine-1-carboxylate (2.515 g, 5.3 mmol) in THF (50 mL) were added NaH (60%, 0.423 g, 10.6 mmol). The mixture was stirred at room temperature for 30 minutes, and benzyl bromide (1.085 g, 6.3 mmol) and TBAI (0.195 g, 0.5 mmol) were added. The mixture was stirred at room temperature for 12 hours, and quenched by addition of sat. NH$_4$Cl solution (20 mL). Concentrated in vacuo, and the residue was taken up in water and EtOAc. The organic layer was separated, and the aqueous phase was extracted with EtOAc. Combined organic phases were washed with water and brine, and dried (MgSO$_4$). The organic solvent was removed in vacuo to give the crude product, which was purified by flash chromatography in silica gel with EtOAc:Hex (10:90) to give (2R',3S',5R')-tert-butyl 3-(benzyloxy)-2,5-bis((tert-butyldimethylsilyloxy)methyl) pyrrolidine-1-carboxylate (3.0 g, 100%) as colorless oil.

Step 6: Synthesis of (2R',3S',5R')-tert-butyl 3-(benzyloxy)-2,5-bis(hydroxymethyl)pyrrolidine-1-carboxylate (benzyloxy diol)

To a solution of (2R',3S',5R')-tert-butyl 3-(benzyloxy)-2,5-bis((tert-butyldimethylsilyloxy)methyl)pyrrolidine-1-carboxylate (3.0 g, 5.3 mmol) in THF (50 mL) was added slowly of TBAF solution (1M in THF, 21.8 mL, 21.8 mmol) at 0° C. The resulting mixture was stirred at room temperature for 6, and quenched by addition of sat. NH$_4$Cl solution (10 mL). Concentrated in vacuo, and the residue was treated with water and EtOAc. The organic layer was separated, and the aqueous phase was extracted with EtOAc. Combined organic phases were washed with water and brine, and dried (MgSO$_4$). The organic solvent was removed in vacuo to give the crude product, which was purified by flash chromatography in silica gel with EtOAc:Hex:MeOH (50:50:5) to give the title compound (1.15 g, 62.5%).

Step 7: Synthesis of (6S')-tert-butyl 6-(benzyloxy)-3-oxa-8-azabicyclo[3.2.1]octane-8-carboxylate by cyclization To a solution of (2R',3S',5R')-tert-butyl 3-(benzyloxy)-2,5-bis(hydroxymethyl)pyrrolidine-1-carboxylate (1.15 g, 3.4 mmol) in THF (50 mL) was added NaH (60%, 0.409 g, 10.2 mmol). The mixture was stirred at room temperature for 30 minutes, and cooled down to 0° C. A solution of p-TsCl (0.65 g, 3.4 mmol) in THF (5 mL) was slowly added to the mixture. The reaction mixture was then stirred at room temperature for 12 hours, and quenched by addition of sat. NH$_4$Cl solution (20 mL). Concentrated in vacuo, and the residue was taken up in water and EtOAc. The organic layer was separated, and the aqueous phase was extracted with EtOAc. Combined organic phases were washed with water and brine, and dried (MgSO$_4$). The organic solvent was removed in vacuo to give the crude product, which was purified by flash chromatography in silica gel with EtOAc:Hex (20:80) to give the title compound (716 mg, 66%) as off-white solid.

The compounds in Table I were made by the proceeding methods.

TABLE I

| Example | Name | MS (ESI) m/z |
|---|---|---|
| 478 | 1-(4-{[4-(dimethylamino)piperidin-1-yl]carbonyl}phenyl)-3-{4-[4-morpholin-4-yl-6-(tetrahydro-2H-pyran-4-yl)-1,3,5-triazin-2-yl]phenyl}urea | 615.5 |
| 479 | 1-{4-[(4-methylpiperazin-1-yl)carbonyl]phenyl}-3-(4-{4-morpholin-4-yl-6-[(3S)-tetrahydrofuran-3-yloxy]-1,3,5-triazin-2-yl}phenyl)urea | 589.6 |
| 480 | 1-{4-[4-(5-hydroxy-3-oxa-7-azabicyclo[4.1.1]oct-7-yl)-6-morpholin-4-yl-1,3,5-triazin-2-yl]phenyl}-3-pyridin-4-ylurea | 505.3 253.2 273.8 |
| 481 | 1-[4-(4,6-dimorpholin-4-yl-1,3,5-triazin-2-yl)phenyl]-3-pyridazin-4-ylurea | 464.2 253.1 |
| 482 | 1-{4-[(4-methylpiperazin-1-yl)carbonyl]phenyl}-3-{4-[4-morpholin-4-yl-6-(oxetan-3-yloxy)-1,3,5-triazin-2-yl]phenyl}urea | 575.5 |
| 483 | 1-{4-[4-morpholin-4-yl-6-(3-oxa-8-azabicyclo[3.2.1]oct-8-yl)-1,3,5-triazin-2-yl]phenyl}-3-pyridazin-4-ylurea | 490.6 |
| 484 | 1-(4-{[(3R)-3-(dimethylamino)pyrrolidin-1-yl]carbonyl}phenyl)-3-[4-(4,6-dimorpholin-4-yl-1,3,5-triazin-2-yl)phenyl]urea | 602.5 |

TABLE I-continued

| Example | Name | MS (ESI) m/z |
|---|---|---|
| 485 | 1-(4-{[(3S)-3-(dimethylamino)pyrrolidin-1-yl]carbonyl}phenyl)-3-[4-(4,6-dimorpholin-4-yl-1,3,5-triazin-2-yl)phenyl]urea | 602.6 |
| 486 | 1-[4-(4-isopropyl-6-morpholin-4-yl-1,3,5-triazin-2-yl)phenyl]-3-{4-[(4-methylpiperazin-1-yl)carbonyl]phenyl}urea | 545.1 293.5 273 |
| 487 | 1-{4-[4-(1-methylethyl)-6-morpholin-4-yl-1,3,5-triazin-2-yl]phenyl}-3-(4-pyrimidin-5-ylphenyl)urea | 497.3 |
| 488 | 1-(4-{4-[(2,2-dimethoxyethyl)amino]-6-morpholin-4-yl-1,3,5-triazin-2-yl}phenyl)-3-pyridin-3-ylurea | 481.2 241.1 261.6 |
| 489 | 1-{4-[4-(1-methylethyl)-6-morpholin-4-yl-1,3,5-triazin-2-yl]phenyl}-3-(4-pyridin-4-ylphenyl)urea | 496.3 248.6 269.1 |
| 490 | 1-(4-iodophenyl)-3-{4-[4-(1-methylethyl)-6-morpholin-4-yl-1,3,5-triazin-2-yl]phenyl}urea | 545.1 |
| 491 | 1-{4-[4-(1-methylethyl)-6-morpholin-4-yl-1,3,5-triazin-2-yl]phenyl}-3-(4-{[4-(1-methylethyl)piperazin-1-yl]carbonyl}phenyl)urea | 573.4 287.2 |
| 492 | 1-[4-(4-azetidin-1-yl-6-morpholin-4-yl-1,3,5-triazin-2-yl)phenyl]-3-(4-{[4-(1-methylethyl)piperazin-1-yl]carbonyl}phenyl)urea | 586.6 |
| 493 | 1-{4-[2-(dimethylamino)pyrimidin-5-yl]phenyl}-3-{4-[4-(1-methylethyl)-6-morpholin-4-yl-1,3,5-triazin-2-yl]phenyl}urea | 540.5 |
| 494 | tert-butyl 3-[(4-morpholin-4-yl-6-{4-[(pyridin-4-ylcarbamoyl)amino]phenyl}-1,3,5-triazin-2-yl)oxy]azetidine-1-carboxylate | 549.6 |
| 495 | 1-(4-{[4-(dimethylamino)piperidin-1-yl]carbonyl}phenyl)-3-[4-(4,6-dimorpholin-4-yl-1,3,5-triazin-2-yl)phenyl]urea | 616.4 308.7 |
| 496 | 1-[4-(4,6-dimorpholin-4-yl-1,3,5-triazin-2-yl)phenyl]-3-(4-nitrophenyl)urea | 507.1 |
| 497 | 1-(4-aminophenyl)-3-[4-(4,6-dimorpholin-4-yl-1,3,5-triazin-2-yl)phenyl]urea | 477.1 259.6 |
| 498 | N-[4-({[4-(4,6-dimorpholin-4-yl-1,3,5-triazin-2-yl)phenyl]carbamoyl}amino)phenyl]-4-methylpiperazine-1-carboxamide | 603.2 302.1 322.6 |
| 499 | 4-(dimethylamino)-N-[4-({[4-(4,6-dimorpholin-4-yl-1,3,5-triazin-2-yl)phenyl]carbamoyl}amino)phenyl]piperidine-1-carboxamide | 631.3 |
| 500 | 1-[2-(dimethylamino)ethyl]-3-[4-({[4-(4,6-dimorpholin-4-yl-1,3,5-triazin-2-yl)phenyl]carbamoyl}amino)phenyl]-1-methylurea | 605.3 |
| 501 | 1-[4-(4,6-dimorpholin-4-yl-1,3,5-triazin-2-yl)phenyl]-3-(4-{[(2-piperidin-1-ylethyl)carbamoyl]amino}phenyl)urea | 631.3 |
| 502 | N-[4-({[4-(4,6-dimorpholin-4-yl-1,3,5-triazin-2-yl)phenyl]carbamoyl}amino)phenyl]-4-methyl-1,4-diazepane-1-carboxamide | 617.3 |
| 503 | N-[4-({[4-(4,6-dimorpholin-4-yl-1,3,5-triazin-2-yl)phenyl]carbamoyl}amino)phenyl]-4-ethylpiperazine-1-carboxamide | 617.3 |
| 504 | 1-{4-[(dimethylcarbamoyl)amino]phenyl}-3-[4-(4,6-dimorpholin-4-yl-1,3,5-triazin-2-yl)phenyl]urea | 548.3 |
| 505 | 1-{4-[4-(3,6-dihydro-2H-pyran-4-yl)-6-morpholin-4-yl-1,3,5-triazin-2-yl]phenyl}-3-(4-{[4-(dimethylamino)piperidin-1-yl]carbonyl}phenyl)urea | 613.4 |
| 506 | 4-[({4-[4-(3,6-dihydro-2H-pyran-4-yl)-6-morpholin-4-yl-1,3,5-triazin-2-yl]phenyl}carbamoyl)amino]-N-[2-(dimethylamino)ethyl]-N-methylbenzamide | 587.4 |
| 507 | 1-{4-[4-(3,6-dihydro-2H-pyran-4-yl)-6-morpholin-4-yl-1,3,5-triazin-2-yl]phenyl}-3-{4-[(4-methylpiperazin-1-yl)carbonyl]phenyl}urea | 585.3 |
| 508 | 4-[({4-[4-(3,6-dihydro-2H-pyran-4-yl)-6-morpholin-4-yl-1,3,5-triazin-2-yl]phenyl}carbamoyl)amino]-N-[2-(dimethylamino)ethyl]benzamide | 573.3 |
| 509 | N-[4-({[4-(4,6-di-8-oxa-3-azabicyclo[3.2.1]oct-3-yl-1,3,5-triazin-2-yl)phenyl]carbamoyl}amino)phenyl]-2-(4-methylpiperazin-1-yl)acetamide | 668.4 |
| 510 | 1-(4-{[4-(dimethylamino)piperidin-1-yl]carbonyl}phenyl)-3-{4-[4-morpholin-4-yl-6-(tetrahydro-2H-pyran-4-yl)-1,3,5-triazin-2-yl]phenyl}urea | 615.5 |
| 511 | 1-{4-[(4-methylpiperazin-1-yl)carbonyl]phenyl}-3-{4-[4-morpholin-4-yl-6-(tetrahydro-2H-pyran-4-yl)-1,3,5-triazin-2-yl]phenyl}urea | 587.3 |

TABLE I-continued

| Example | Name | MS (ESI) m/z |
|---|---|---|
| 512 | N-[2-(dimethylamino)ethyl-4-[({4-[4-morpholin-4-yl-6-(tetrahydro-2H-pyran-4-yl)-1,3,5-triazin-2-yl]phenyl}carbamoyl)amino]benzamide | 575.3 |
| 513 | 4-[({4-[4-morpholin-4-yl-6-(tetrahydro-2H-pyran-4-yl)-1,3,5-triazin-2-yl]phenyl}carbamoyl)amino]-N-(2-pyrrolidin-1-ylethyl)benzamide | 601.3 |
| 514 | 4-[({4-[4-morpholin-4-yl-6-(tetrahydro-2H-pyran-4-yl)-1,3,5-triazin-2-yl]phenyl}carbamoyl)amino]-N-(2-piperidin-1-ylethyl)benzamide | 615.3 |
| 515 | 1-[4-(4,6-dimorpholin-4-yl-1,3,5-triazin-2-yl)phenyl]-3-(4-{[4-(1-methylethyl)piperazin-1-yl]carbonyl}phenyl)urea | 616.3 308.6 329.2 |
| 516 | 1-(4-{[(3S)-3-(dimethylamino)pyrrolidin-1-yl]carbonyl}phenyl)-3-{4-[4-morpholin-4-yl-6-(3-oxa-8-azabicyclo[3.2.1]oct-8-yl)-1,3,5-triazin-2-yl]phenyl}urea | 627.7 |
| 517 | 1-(4-{[(3S)-3-(dimethylamino)pyrrolidin-1-yl]carbonyl}phenyl)-3-{4-[4-morpholin- | 449.4 |
| 518 | 4-yl-6-(3-oxa-8-azabicyclo[3.2.1]oct-8-yl)-1,3,5-triazin-2-yl]phenyl}urea | 616.4 |
| 519 | N-[2-(dimethylamino)ethyl]-N-methyl-4-[[(4-{4-morpholin-4-yl-6-[(3S)-tetrahydrofuran-3-yloxy]-1,3,5-triazin-2-yl}phenyl)carbamoyl]amino}benzamide | 616.4 |
| 520 | 4-{[(4-{4-morpholin-4-yl-6-[(3S)-tetrahydrofuran-3-yloxy]-1,3,5-triazin-2-yl}phenyl)carbamoyl]amino}-N-(2-piperidin-1-ylethyl)benzamide | 616.4 |
| 521 | 4-{[(4-{4-morpholin-4-yl-6-[(3S)-tetrahydrofuran-3-yloxy]-1,3,5-triazin-2-yl}phenyl)carbamoyl]amino}-N-(2-pyrrolidin-1-ylethyl)benzamide | 616.4 |
| 522 | 1-(4-{[4-(1-methylethyl)piperazin-1-yl]carbonyl}phenyl)-3-(4-{4-morpholin-4-yl-6-[(3S)-tetrahydrofuran-3-yloxy]-1,3,5-triazin-2-yl}phenyl)urea | 616.4 |
| 523 | 1-(4-{[4-(1-methylethyl)piperazin-1-yl]carbonyl}phenyl)-3-{4-[4-morpholin-4-yl-6-(tetrahydro-2H-pyran-4-yl)-1,3,5-triazin-2-yl]phenyl}urea | 616.4 |
| 524 | N-[2-(dimethylamino)ethyl]-N-methyl-4-[({4-[4-morpholin-4-yl-6-(tetrahydro-2H-pyran-4-yl)-1,3,5-triazin-2-yl]phenyl}carbamoyl)amino]benzamide | 616.4 |
| 525 | 4-[({4-[4-(2-methylpropyl)-6-morpholin-4-yl-1,3,5-triazin-2-yl]phenyl}carbamoyl)amino]benzoic acid | 477.3 |
| 526 | 1-{4-[4-(4-methylphenyl)-6-morpholin-4-yl-1,3,5-triazin-2-yl]phenyl}-3-[4-(4-methylpiperazin-1-yl)phenyl]urea | 565.4 |
| 527 | 4-[({4-[4-(4-methylphenyl)-6-morpholin-4-yl-1,3,5-triazin-2-yl]phenyl}carbamoyl)amino]benzoic acid | 511.4 |
| 528 | methyl 4-[({4-[4-(4-methylphenyl)-6-morpholin-4-yl-1,3,5-triazin-2-yl]phenyl}carbamoyl)amino]benzoate | 525.4 |
| 529 | 1-{4-[4-(dimethylamino)piperidin-1-yl]phenyl}-3-[4-(4-ethyl-6-morpholin-4-yl-1,3,5-triazin-2-yl)phenyl]urea | 531.4 |
| 530 | 1-{4-[4-(4-methylphenyl)-6-morpholin-4-yl-1,3,5-triazin-2-yl]phenyl}-3-pyridin-4-ylurea | 468.3 |
| 531 | 1-{4-[4-(dimethylamino)piperidin-1-yl]phenyl}-3-{4-[4-(4-methylphenyl)-6-morpholin-4-yl-1,3,5-triazin-2-yl]phenyl}urea | 593.4 |
| 532 | N-[2-(dimethylamino)ethyl]-N-methyl-4-[({4-[4-(4-methylphenyl)-6-morpholin-4-yl-1,3,5-triazin-2-yl]phenyl}carbamoyl)amino]benzamide | 595.5 |
| 533 | 1-{4-[4-(4-methylphenyl)-6-morpholin-4-yl-1,3,5-triazin-2-yl]phenyl}-3-{4-[(4-methylpiperazin-1-yl)carbonyl]phenyl}urea | 593.5 |
| 534 | 1-[4-(4-ethyl-6-morpholin-4-yl-1,3,5-triazin-2-yl)phenyl]-3-{4-[(4-pyridin-2-ylpiperazin-1-yl)carbonyl]phenyl}urea | 594.5 |
| 535 | 1-{4-[4-(dimethylamino)piperidin-1-yl]phenyl}-3-[4-(4-morpholin-4-yl-6-phenyl-1,3,5-triazin-2-yl)phenyl]urea | 579.5 |
| 536 | 1-[4-(4-ethyl-6-morpholin-4-yl-1,3,5-triazin-2-yl)phenyl]-3-{4-[(4-methylpiperazin-1-yl)carbonyl]phenyl}urea | 531.1 |
| 537 | 1-[4-(4-morpholin-4-yl-6-phenyl-1,3,5-triazin-2-yl)phenyl]-3-pyridin-4-ylurea | 454.1 |
| 538 | methyl 4-({[4-(4-morpholin-4-yl-6-phenyl-1,3,5-triazin-2-yl)phenyl]carbamoyl}amino)benzoate | 511 |

TABLE I-continued

| Example | Name | MS (ESI) m/z |
|---|---|---|
| 539 | N-[2-(dimethylamino)ethyl-N-methyl-4-({[4-(4-morpholin-4-yl-6-phenyl-1,3,5-triazin-2-yl]phenyl]carbamoyl}amino)benzamide | 581.2 |
| 540 | methyl 4-{[(4-{4,6-bis[(3S)-3-methylmorpholin-4-yl]-1,3,5-triazin-2-yl}phenyl)carbamoyl]amino}benzoate | 548 |
| 541 | 4-({[4-(4-morpholin-4-yl-6-phenyl-1,3,5-triazin-2-yl)phenyl]carbamoyl}amino)benzoic acid | 497 |
| 542 | N-[2-(dimethylamino)ethyl]-4-[({4-[4-(4-methylphenyl)-6-morpholin-4-yl-1,3,5-triazin-2-yl]phenyl}carbamoyl)amino]benzamide | 581.3 |
| 543 | 1-{4-[(4-methylpiperazin-1-yl)carbonyl]phenyl}-3-[4-(4-morpholin-4-yl-6-phenyl-1,3,5-triazin-2-yl)phenyl]urea | 579.2 |
| 544 | 1-(4-{[4-(dimethylamino)piperidin-1-yl]carbonyl}phenyl)-3-[4-(4-morpholin-4-yl-6-phenyl-1,3,5-triazin-2-yl)phenyl]urea | 661.5 |
| 545 | N-[2-(dimethylamino)ethyl]-4-({[4-(4-morpholin-4-yl-6-phenyl-1,3,5-triazin-2-yl)phenyl]carbamoyl}amino)benzamide | 567.2 |
| 546 | 4-{[(4-{4,6-bis[(3S)-3-methylmorpholin-4-yl]-1,3,5-triazin-2-yl}phenyl)carbamoyl]amino}-N-[2-(dimethylamino)ethyl]benzamide | 604.4 |
| 547 | 1-{4-[(4-isopropylpiperazin-1-yl)carbonyl]phenyl}-3-{4-[4-(4-methylphenyl)-6-morpholin-4-yl-1,3,5-triazin-2-yl]phenyl}urea | 621.5 |
| 548 | 4-[({4-[4-(4-methylphenyl)-6-morpholin-4-yl-1,3,5-triazin-2-yl]phenyl}carbamoyl)amino]-N-(2-pyrrolidin-1-ylethyl)benzamide | 607.5 |
| 549 | 4-{[(4-{4,6-bis[(3S)-3-methylmorpholin-4-yl]-1,3,5-triazin-2-yl}phenyl)carbamoyl]amino}benzoic acid | 534.5 |
| 550 | N-(2-methoxyethyl)-4-[({4-[4-(4-methylphenyl)-6-morpholin-4-yl-1,3,5-triazin-2-yl]phenyl}carbamoyl)amino]benzamide | 568.2 |
| 551 | N-(2-methoxyethyl)-4-({[4-(4-morpholin-4-yl-6-phenyl-1,3,5-triazin-2-yl)phenyl]carbamoyl}amino)benzamide | 554.2 |
| 552 | 4-({[4-(4-morpholin-4-yl-6-phenyl-1,3,5-triazin-2-yl)phenyl]carbamoyl}amino)-N-(2-pyrrolidin-1-ylethyl)benzamide | 593.5 |
| 553 | 1-{4-[4-(4-methylphenyl)-6-morpholin-4-yl-1,3,5-triazin-2-yl]phenyl}-3-[4-(pyrrolidin-1-ylcarbonyl)phenyl]urea | 567.6 |
| 554 | N-[3-(dimethylamino)propyl]-4-[({4-[4-(4-methylphenyl)-6-morpholin-4-yl-1,3,5-triazin-2-yl]phenyl}carbamoyl)amino]benzamide | 595.4 |
| 555 | 1-{4-[4-(4-methylphenyl)-6-morpholin-4-yl-1,3,5-triazin-2-yl]phenyl}-3-[4-(piperidin-1-ylcarbonyl)phenyl]urea | 578.1 |
| 556 | N-[3-(dimethylamino)propyl]-4-({[4-(4-morpholin-4-yl-6-phenyl-1,3,5-triazin-2-yl)phenyl]carbamoyl}amino)benzamide | 581.4 291.2 |
| 557 | 1-{4-[4-morpholin-4-yl-6-(2-thienyl)-1,3,5-triazin-2-yl]phenyl}-3-pyridin-4-ylurea | 460.2 230.6 |
| 558 | 4-[({4-[4-morpholin-4-yl-6-(2-thienyl)-1,3,5-triazin-2-yl]phenyl}carbamoyl)amino]benzoic acid | 503.4 |
| 559 | 1-{4-[(4-methylpiperazin-1-yl)carbonyl]phenyl}-3-{4-[4-morpholin-4-yl-6-(2-thienyl)-1,3,5-triazin-2-yl]phenyl}urea | 585.5 |
| 560 | methyl 4-[({4-[4-morpholin-4-yl-6-(2-thienyl)-1,3,5-triazin-2-yl]phenyl}carbamoyl)amino]benzoate | 517.2 |
| 561 | N-(2-methoxyethyl)-4-[({4-[4-morpholin-4-yl-6-(2-thienyl)-1,3,5-triazin-2-yl]phenyl}carbamoyl)amino]benzamide | 560.3 |
| 562 | N-[2-(dimethylamino)ethyl]-N-methyl-4-[({4-[4-morpholin-4-yl-6-(2-thienyl)-1,3,5-triazin-2-yl]phenyl}carbamoyl)amino]benzamide | 587.3 294.1 |
| 563 | N-[2-(dimethylamino)ethyl]-4-[({4-[4-morpholin-4-yl-6-(2-thienyl)-1,3,5-triazin-2-yl]phenyl}carbamoyl)amino]benzamide | 573.1 |
| 564 | 4-{[(4-{4,6-bis[(3S)-3-methylmorpholin-4-yl]-1,3,5-triazin-2-yl}phenyl)carbamoyl]amino}-N-[2-(dimethylamino)ethyl]-N-methylbenzamide | 618.4 309.7 |
| 565 | 1-(4-{4,6-bis[(3S)-3-methylmorpholin-4-yl]-1,3,5-triazin-2-yl}phenyl)-3-{4-[(4-methylpiperazin-1-yl)carbonyl]phenyl}urea | 616.4 329.2 308.7 |
| 566 | 1-{4-[4-morpholin-4-yl-6-(1,4-oxazepan-4-yl)-1,3,5-triazin-2-yl]phenyl}-3-pyridin-4-ylurea | 477.2 |

TABLE I-continued

| Example | Name | MS (ESI) m/z |
|---|---|---|
| 567 | methyl 4-[({4-[4-morpholin-4-yl-6-(1,4-oxazepan-4-yl)-1,3,5-triazin-2-yl]phenyl}carbamoyl)amino]benzoate | 534.4 |
| 568 | 1-(4-{[4-(dimethylamino)piperidin-1-yl]carbonyl}phenyl)-3-{4-[4-morpholin-4-yl-6-(2-thienyl)-1,3,5-triazin-2-yl]phenyl}urea | 613.4 307.2 |
| 569 | 4-[({4-[4-morpholin-4-yl-6-(1,4-oxazepan-4-yl)-1,3,5-triazin-2-yl]phenyl}carbamoyl)amino]benzoic acid | 520.3 |
| 570 | N-[3-(dimethylamino)propyl]-4-[({4-[4-morpholin-4-yl-6-(2-thienyl)-1,3,5-triazin-2-yl]phenyl}carbamoyl)amino]benzamide | 587.3 294.2 |
| 571 | 1-(4-{4,6-bis[(3S)-3-methylmorpholin-4-yl]-1,3,5-triazin-2-yl}phenyl)-3-[4-(pyrrolidin-1-ylcarbonyl)phenyl]urea | 587.5 |
| 572 | N-[2-(dimethylamino)ethyl]-4-[({4-[4-morpholin-4-yl-6-(1,4-oxazepan-4-yl)-1,3,5-triazin-2-yl]phenyl}carbamoyl)amino]benzamide | 590.3 295.6 |
| 573 | 1-{4-[(4-methylpiperazin-1-yl)carbonyl]phenyl}-3-{4-[4-morpholin-4-yl-6-(1,4-oxazepan-4-yl)-1,3,5-triazin-2-yl]phenyl}urea | 602.3 322.2 301.7 |
| 574 | N-(2-methoxyethyl)-4-[({4-[4-morpholin-4-yl-6-(1,4-oxazepan-4-yl)-1,3,5-triazin-2-yl]phenyl}carbamoyl)amino]benzamide | 577.2 |
| 575 | 1-{4-[(4-ethylpiperazin-1-yl)carbonyl]phenyl}-3-{4-[4-morpholin-4-yl-6-(2-thienyl)-1,3,5-triazin-2-yl]phenyl}urea | 599.3 300.2 320.7 |
| 576 | 1-{4-[4-(4-methylphenyl)-6-morpholin-4-yl-1,3,5-triazin-2-yl]phenyl}-3-{3-[(4-methylpiperazin-1-yl)carbonyl]phenyl}urea | 593.3 317.7 521.3 |
| 577 | 3-[({4-[4-(4-methylphenyl)-6-morpholin-4-yl-1,3,5-triazin-2-yl]phenyl}carbamoyl)amino]benzoic acid | 511.2 |
| 578 | methyl 3-[({4-[4-(4-methylphenyl)-6-morpholin-4-yl-1,3,5-triazin-2-yl]phenyl}carbamoyl)amino]benzoate | 525.2 |
| 579 | 1-(3-{[4-(dimethylamino)piperidin-1-yl]carbonyl}phenyl)-3-{4-[4-(4-methylphenyl)-6-morpholin-4-yl-1,3,5-triazin-2-yl]phenyl}urea | 521.3 |
| 580 | N-[2-(dimethylamino)ethyl]-N-methyl-3-[({4-[4-(4-methylphenyl)-6-morpholin-4-yl-1,3,5-triazin-2-yl]phenyl}carbamoyl)amino]benzamide | 595.3 298.2 |
| 581 | methyl 3-({[4-(4-ethyl-6-morpholin-4-yl-1,3,5-triazin-2-yl)phenyl]carbamoyl}amino)benzoate | 463.5 |
| 582 | methyl 3-({[4-(4-morpholin-4-yl-6-thiophen-2-yl-1,3,5-triazin-2-yl)phenyl]carbamoyl}amino)benzoate | 517.2 |
| 583 | N-[2-(dimethylamino)ethyl]-3-[({4-[4-(4-methylphenyl)-6-morpholin-4-yl-1,3,5-triazin-2-yl]phenyl}carbamoyl)amino]benzamide | 581.3 291.1 |
| 584 | N-[2-(dimethylamino)ethyl]-N-methyl-4-[({4-[4-morpholin-4-yl-6-(1,4-oxazepan-4-yl)-1,3,5-triazin-2-yl]phenyl}carbamoyl)amino]benzamide | 604.4 302.7 |
| 585 | 3-({[4-(4-ethyl-6-morpholin-4-yl-1,3,5-triazin-2-yl)phenyl]carbamoyl}amino)benzoic acid | 449.4 |
| 586 | methyl 3-({[4-(4-morpholin-4-yl-6-phenyl-1,3,5-triazin-2-yl)phenyl]carbamoyl}amino)benzoate | 511.4 |
| 587 | 1-[4-(4-ethyl-6-morpholin-4-yl-1,3,5-triazin-2-yl)phenyl]-3-{3-[(4-pyridin-2-ylpiperazin-1-yl)carbonyl]phenyl}urea | 594.6 |
| 588 | N-[2-(dimethylamino)ethyl]-3-({[4-(4-ethyl-6-morpholin-4-yl-1,3,5-triazin-2-yl)phenyl]carbamoyl}amino)-N-methylbenzamide | 533.3 267.1 |
| 589 | 1-[4-(4-ethyl-6-morpholin-4-yl-1,3,5-triazin-2-yl)phenyl]-3-{3-[(4-methylpiperazin-1-yl)carbonyl]phenyl}urea | 531.3 266.1 286.7 |
| 590 | 3-({[4-(4-morpholin-4-yl-6-phenyl-1,3,5-triazin-2-yl)phenyl]carbamoyl}amino)benzoic acid | 497.3 |
| 591 | methyl 4-({[4-(4-morpholin-4-yl-6-piperidin-1-yl-1,3,5-triazin-2-yl)phenyl]carbamoyl}amino)benzoate | 518.3 |
| 592 | 1-[4-(4-morpholin-4-yl-6-piperidin-1-yl-1,3,5-triazin-2-yl)phenyl]-3-pyridin-4-ylurea | 461.3 |
| 593 | 4-({[4-(4-morpholin-4-yl-6-piperidin-1-yl-1,3,5-triazin-2-yl)phenyl]carbamoyl}amino)benzoic acid | 504..3 |
| 594 | methyl 4-({[4-(4-morpholin-4-yl-6-pyrrolidin-1-yl-1,3,5-triazin-2-yl)phenyl]carbamoyl}amino)benzoate | 504.5 |
| 595 | 1-(4-{[4-(1-methylethyl)piperazin-1-yl]carbonyl}phenyl)-3-[4-(4-morpholin-4-yl-6-piperidin-1-yl-1,3,5-triazin-2-yl)phenyl]urea | 604.5 |

TABLE I-continued

| Example | Name | MS (ESI) m/z |
|---|---|---|
| 596 | 1-{4-[(4-ethylpiperazin-1-yl)carbonyl]phenyl}-3-[4-(4-morpholin-4-yl-6-piperidin-1-yl-1,3,5-triazin-2-yl)phenyl]urea | 600.5 |
| 597 | 1-{4-[(4-methylpiperazin-1-yl)carbonyl]phenyl}-3-[4-(4-morpholin-4-yl-6-piperidin-1-yl-1,3,5-triazin-2-yl)phenyl]urea | 586.5 |
| 598 | 1-(4-{[4-(dimethylamino)piperidin-1-yl]carbonyl}phenyl)-3-[4-(4-morpholin-4-yl-6-piperidin-1-yl-1,3,5-triazin-2-yl)phenyl]urea | 614.5 |
| 599 | 4-({[4-(4-morpholin-4-yl-6-pyrrolidin-1-yl-1,3,5-triazin-2-yl)phenyl]carbamoyl}amino)benzoic acid | 490.5 |
| 600 | 1-[4-(4-morpholin-4-yl-6-pyrrolidin-1-yl-1,3,5-triazin-2-yl)phenyl]-3-pyridin-4-ylurea | 447.5 |
| 601 | N-[2-(dimethylamino)ethyl]-4-({[4-(4-morpholin-4-yl-6-piperidin-1-yl-1,3,5-triazin-2-yl)phenyl]carbamoyl}amino)benzamide | 474.6 |
| 602 | 1-(4-{[4-(dimethylamino)piperidin-1-yl]carbonyl}phenyl)-3-[4-(4-morpholin-4-yl-6-pyrrolidin-1-yl-1,3,5-triazin-2-yl)phenyl]urea | 600.4 300.7 |
| 603 | 1-(4-{[4-(1-methylethyl)piperazin-1-yl]carbonyl}phenyl)-3-[4-(4-morpholin-4-yl-6-pyrrolidin-1-yl-1,3,5-triazin-2-yl)phenyl]urea | 600.4 300.7 |
| 604 | N-[2-(dimethylamino)ethyl]-N-methyl-4-({[4-(4-morpholin-4-yl-6-pyrrolidin-1-yl-1,3,5-triazin-2-yl)phenyl]carbamoyl}amino)benzamide | 574.6 |
| 605 | N-[2-(dimethylamino)ethyl]-N-methyl-4-({[4-(4-morpholin-4-yl-6-piperidin-1-yl-1,3,5-triazin-2-yl)phenyl]carbamoyl}amino)benzamide | 588.3 294.6 |
| 606 | 1-{4-[(4-ethylpiperazin-1-yl)carbonyl]phenyl}-3-[4-(4-morpholin-4-yl-6-pyrrolidin-1-yl-1,3,5-triazin-2-yl)phenyl]urea | 586.3 293.7 286.7 |
| 607 | 1-{4-[(4-methylpiperazin-1-yl)carbonyl]phenyl}-3-[4-(4-morpholin-4-yl-6-pyrrolidin-1-yl-1,3,5-triazin-2-yl)phenyl]urea | 572.3 |
| 608 | N-[2-(dimethylamino)ethyl]-4-({[4-(4-morpholin-4-yl-6-pyrrolidin-1-yl-1,3,5-triazin-2-yl)phenyl]carbamoyl}amino)benzamide | 560.1 280.6 |
| 609 | 1-(4-{4,6-bis[(3S)-3-methylmorpholin-4-yl]-1,3,5-triazin-2-yl}phenyl)-3-pyridin-4-ylurea | 491.2 266.6 246.1 |
| 610 | N-[3-(dimethylamino)propyl]-4-({[4-(4-morpholin-4-yl-6-piperidin-1-yl-1,3,5-triazin-2-yl)phenyl]carbamoyl}amino)benzamide | 588.3 294.6 |
| 611 | N-(2-methoxyethyl)-4-({[4-(4-morpholin-4-yl-6-piperidin-1-yl-1,3,5-triazin-2-yl)phenyl]carbamoyl}amino)benzamide | 561.4 281.2 |
| 612 | 1-[4-(4-morpholin-4-yl-6-pyrrolidin-1-yl-1,3,5-triazin-2-yl)phenyl]-3-[4-(pyrrolidin-1-ylcarbonyl)phenyl]urea | 543.3 |
| 613 | 1-(4-{4,6-bis[(3S)-3-methylmorpholin-4-yl]-1,3,5-triazin-2-yl}phenyl)-3-{4-[(4-ethylpiperazin-1-yl)carbonyl]phenyl}urea | 630.6 |
| 614 | 1-(4-{4,6-bis[(3S)-3-methylmorpholin-4-yl]-1,3,5-triazin-2-yl}phenyl)-3-(4-{[4-(1-methylethyl)piperazin-1-yl]carbonyl}phenyl)urea | 644.7 |
| 615 | methyl 4-{[(4-{4-[(3S)-3-methylmorpholin-4-yl]-6-morpholin-4-yl-1,3,5-triazin-2-yl}phenyl)carbamoyl]amino}benzoate | 534.3 |
| 616 | 1-(4-{4,6-bis[(3S)-3-methylmorpholin-4-yl]-1,3,5-triazin-2-yl}phenyl)-3-(4-{[4-(dimethylamino)piperidin-1-yl]carbonyl}phenyl)urea | 644.6 |
| 617 | 1-(4-{4-[(3S)-3-methylmorpholin-4-yl]-6-morpholin-4-yl-1,3,5-triazin-2-yl}phenyl)-3-{4-[(4-methylpiperazin-1-yl)carbonyl]phenyl}urea | 602.3 322.2 301.7 |
| 618 | 1-(4-{[4-(1-methylethyl)piperazin-1-yl]carbonyl}phenyl)-3-(4-{4-[(3S)-3-methylmorpholin-4-yl]-6-morpholin-4-yl-1,3,5-triazin-2-yl}phenyl)urea | 630.4 315.7 |
| 619 | 4-{[(4-{4-[(3S)-3-methylmorpholin-4-yl]-6-morpholin-4-yl-1,3,5-triazin-2-yl}phenyl)carbamoyl]amino}benzoic acid | 520.2 |
| 620 | 1-{4-[(4-ethylpiperazin-1-yl)carbonyl]phenyl}-3-(4-{[(3S)-3-methylmorpholin-4-yl]-6-morpholin-4-yl-1,3,5-triazin-2-yl}phenyl)urea | 616.4 308.7 329.2 |
| 621 | N-[3-(dimethylamino)propyl]-4-{[(4-{4-[(3S)-3-methylmorpholin-4-yl]-6-morpholin-4-yl-1,3,5-triazin-2-yl}phenyl)carbamoyl]amino}benzamide | 604.6 |
| 622 | 4-{[(4-{4-[(3S)-3-methylmorpholin-4-yl]-6-morpholin-4-yl-1,3,5-triazin-2-yl}phenyl)carbamoyl]amino}-N-(2-pyrrolidin-1-ylethyl)benzamide | 616.5 |

TABLE I-continued

| Example | Name | MS (ESI) m/z |
|---|---|---|
| 623 | 1-(4-{4-[(3R)-3-methylmorpholin-4-yl]-6-[(3S)-3-methylmorpholin-4-yl]-1,3,5-triazin-2-yl}phenyl)-3-{4-[(4-methylpiperazin-1-yl)carbonyl]phenyl}urea | 616.4 308.7 329.2 |
| 624 | 1-(4-{4,6-bis[(3S)-3-methylmorpholin-4-yl]-1,3,5-triazin-2-yl}phenyl)-3-(4-{[4-(dipropylamino)piperidin-1-yl]carbonyl}phenyl)urea | 700.6 350.8 |
| 625 | 1-{4-[(4-ethylpiperazin-1-yl)carbonyl]phenyl}-3-(4-{4-[(3R)-3-methylmorpholin-4-yl]-6-[(3S)-3-methylmorpholin-4-yl]-1,3,5-triazin-2-yl}phenyl)urea | 630.5 315.7 |
| 626 | 4-{[(4-{4-[(3R)-3-methylmorpholin-4-yl]-6-[(3S)-3-methylmorpholin-4-yl]-1,3,5-triazin-2-yl}phenyl)carbamoyl]amino}benzoic acid | 534.3 |
| 627 | 1-{4-[(4-butylpiperazin-1-yl)carbonyl]phenyl}-3-(4-{4-[(3R)-3-methylmorpholin-4-yl]-6-[(3S)-3-methylmorpholin-4-yl]-1,3,5-triazin-2-yl}phenyl)urea | 658.6 |
| 628 | methyl 4-{[(4-{4-[(3R)-3-methylmorpholin-4-yl]-6-[(3S)-3-methylmorpholin-4-yl]-1,3,5-triazin-2-yl}phenyl)carbamoyl]amino}benzoate | 548.2 |
| 629 | 1-(4-{4,6-bis[(3S)-3-methylmorpholin-4-yl]-1,3,5-triazin-2-yl}phenyl)-3-{4-[(4-butylpiperazin-1-yl)carbonyl]phenyl}urea | 658.5 329.7 |
| 630 | 1-(4-{[4-(1-methylethyl)piperazin-1-yl]carbonyl}phenyl)-3-(4-{4-[(3R)-3-methylmorpholin-4-yl]-6-[(3S)-3-methylmorpholin-4-yl]-1,3,5-triazin-2-yl}phenyl)urea | 644.5 |
| 631 | 1-(4-{4,6-bis[(3S)-3-methylmorpholin-4-yl]-1,3,5-triazin-2-yl}phenyl)-3-(4-{[4-(2-methylpropyl)piperazin-1-yl]carbonyl}phenyl)urea | 658.5 |
| 632 | 1-(4-{4,6-bis[(3S)-3-methylmorpholin-4-yl]-1,3,5-triazin-2-yl}phenyl)-3-(4-{[4-(1-methylpropyl)piperazin-1-yl]carbonyl}phenyl)urea | 658.6 |
| 633 | 4-{[(4-{4,6-bis[(3S)-3-methylmorpholin-4-yl]-1,3,5-triazin-2-yl}phenyl)carbamoyl]amino}-N-[2-(4-methylpiperazin-1-yl)ethyl]benzamide | 659.6 |
| 634 | N-[2-(dimethylamino)ethyl]-4-{[(4-{4-[(3R)-3-methylmorpholin-4-yl]-6-[(3S)-3-methylmorpholin-4-yl]-1,3,5-triazin-2-yl}phenyl)carbamoyl]amino}benzamide | 604.5 |
| 635 | 4-{[(4-{4,6-bis[(3S)-3-methylmorpholin-4-yl]-1,3,5-triazin-2-yl}phenyl)carbamoyl]amino}-N-(2-pyrrolidin-1-ylethyl)benzamide | 626.5 |
| 636 | 1-(4-{4,6-bis[(3S)-3-methylmorpholin-4-yl]-1,3,5-triazin-2-yl}phenyl)-3-{4-[(4-propylpiperidin-1-yl)carbonyl]phenyl}urea | 643.4 322.2 |
| 637 | 1-(4-{4,6-bis[(3S)-3-methylmorpholin-4-yl]-1,3,5-triazin-2-yl}phenyl)-3-[4-(piperidin-1-ylcarbonyl)phenyl]urea | 601.5 |
| 638 | 1-(4-{4,6-bis[(3S)-3-methylmorpholin-4-yl]-1,3,5-triazin-2-yl}phenyl)-3-{4-[(4-propylpiperazin-1-yl)carbonyl]phenyl}urea | 643.5 |
| 639 | 4-{[(4-{4,6-bis[(3S)-3-methylmorpholin-4-yl]-1,3,5-triazin-2-yl}phenyl)carbamoyl]amino}-N-(2-methoxyethyl)benzamide | 591.6 |
| 640 | 1-{4-[4-morpholin-4-yl-6-(4-tricyclo[3.3.1.1³,⁷]dec-1-ylpiperazin-1-yl)-1,3,5-triazin-2-yl]phenyl}-3-pyridin-4-ylurea | 596.7 |
| 641 | methyl 4-{[(4-{4-[4-(dimethylcarbamoyl)piperazin-1-yl]-6-morpholin-4-yl-1,3,5-triazin-2-yl}phenyl)carbamoyl]amino}benzoate | 590.5 |
| 642 | N,N-dimethyl-4-(4-morpholin-4-yl-6-{4-[(pyridin-4-ylcarbamoyl)amino]phenyl}-1,3,5-triazin-2-yl)piperazine-1-carboxamide | 533.6 |
| 643 | N,N-dimethyl-4-(4-{4-[({4-[(4-methylpiperazin-1-yl)carbonyl]phenyl}carbamoyl)amino]phenyl}-6-morpholin-4-yl-1,3,5-triazin-2-yl)piperazine-1-carboxamide | 658.3 329.7 |
| 644 | N,N-dimethyl-4-{4-morpholin-4-yl-6-[4-({[4-(pyridazin-4-ylcarbamoyl)phenyl]carbamoyl}amino)phenyl]-1,3,5-triazin-2-yl}piperazine-1-carboxamide | 653.3 |
| 645 | N,N-dimethyl-4-(4-morpholin-4-yl-6-{4-[({4-[(4-propylpiperidin-1-yl)carbonyl]phenyl}carbamoyl)amino]phenyl}-1,3,5-triazin-2-yl)piperazine-1-carboxamide | 685.6 |
| 646 | 4-{[(4-{4-[4-(dimethylcarbamoyl)piperazin-1-yl]-6-morpholin-4-yl-1,3,5-triazin-2-yl}phenyl)carbamoyl]amino}benzoic acid | 576.2 |

TABLE I-continued

| Example | Name | MS (ESI) m/z |
|---|---|---|
| 647 | 4-(4-{4-[({4-[(2-methoxyethyl)carbamoyl]phenyl}carbamoyl)amino]phenyl}-6-morpholin-4-yl-1,3,5-triazin-2-yl)-N,N-dimethylpiperazine-1-carboxamide | 633.3 317.1 |
| 648 | 4-[4-(4-{[(4-{[2-(dimethylamino)ethyl](methyl)carbamoyl}phenyl)carbamoyl]amino}phenyl)-6-morpholin-4-yl-1,3,5-triazin-2-yl]-N,N-dimethylpiperazine-1-carboxamide | 660.3 330.7 |
| 649 | 4-(4-{4-[({4-[(4-ethylpiperazin-1-yl)carbonyl]phenyl}carbamoyl)amino]phenyl}-6-morpholin-4-yl-1,3,5-triazin-2-yl)-N,N-dimethylpiperazine-1-carboxamide | 672.6 |
| 650 | 1-(4-{4-[4-(ethylsulfonyl)piperazin-1-yl]-6-morpholin-4-yl-1,3,5-triazin-2-yl}phenyl)-3-pyridin-4-ylurea | 554.2 |
| 651 | methyl 4-{[(4-{4-[4-(ethylsulfonyl)piperazin-1-yl]-6-morpholin-4-yl-1,3,5-triazin-2-yl}phenyl)carbamoyl]amino}benzoate | 611.2 |
| 652 | 4-{[(4-{4-[4-(ethylsulfonyl)piperazin-1-yl]-6-morpholin-4-yl-1,3,5-triazin-2-yl}phenyl)carbamoyl]amino}benzoic acid | 597.7 |
| 653 | N-[3-(dimethylamino)propyl]-4-{[(4-{4-[4-(ethylsulfonyl)piperazin-1-yl]-6-morpholin-4-yl-1,3,5-triazin-2-yl}phenyl)carbamoyl]amino}benzamide | 681.2 341.1 |
| 654 | N-[2-(dimethylamino)ethyl]-4-{[(4-{4-[4-(ethylsulfonyl)piperazin-1-yl]-6-morpholin-4-yl-1,3,5-triazin-2-yl}phenyl)carbamoyl]amino}benzamide | 667.3 334.2 |
| 655 | 4-{[(4-{4-[4-(1-methylethyl)-1,4-diazepan-1-yl]-6-morpholin-4-yl-1,3,5-triazin-2-yl}phenyl)carbamoyl]amino}benzoic acid | 561.5 |
| 656 | methyl 4-{[(4-{4-[4-(acetylamino)piperidin-1-yl]-6-morpholin-4-yl-1,3,5-triazin-2-yl}phenyl)carbamoyl]amino}benzoate | 575.4 |
| 657 | 1-(4-{4-[4-(1-methylethyl)-1,4-diazepan-1-yl]-6-morpholin-4-yl-1,3,5-triazin-2-yl}phenyl)-3-{4-[(4-methylpiperazin-1-yl)carbonyl]phenyl}urea | 643.6 |
| 658 | N-[1-(4-morpholin-4-yl-6-{4-[(pyridin-4-ylcarbamoyl)amino]phenyl}-1,3,5-triazin-2-yl)piperidin-4-yl]acetamide | 518.5 |
| 659 | 4-{[(4-{4-[4-(acetylamino)piperidin-1-yl]-6-morpholin-4-yl-1,3,5-triazin-2-yl}phenyl)carbamoyl]amino}benzoic acid | 561.5 |
| 660 | N-[2-(dimethylamino)ethyl]-4-{[(4-{4-[4-(1-methylethyl)-1,4-diazepan-1-yl]-6-morpholin-4-yl-1,3,5-triazin-2-yl}phenyl)carbamoyl]amino}benzamide | 631.5 |
| 661 | N-{1-[(4-{[(4-{4-[4-(1-methylethyl)-1,4-diazepan-1-yl]-6-morpholin-4-yl-1,3,5-triazin-2-yl}phenyl)carbamoyl]amino}phenyl)carbonyl]piperidin-4-yl}acetamide | 685.6 |
| 662 | 1-{4-[(4-ethylpiperazin-1-yl)carbonyl]phenyl}-3-(4-{4-[4-(1-methylethyl)-1,4-diazepan-1-yl]-6-morpholin-4-yl-1,3,5-triazin-2-yl}phenyl)urea | 657.4 329.2 219.8 |
| 663 | 1-(4-{4-[4-(1-methylethyl)-1,4-diazepan-1-yl]-6-morpholin-4-yl-1,3,5-triazin-2-yl}phenyl)-3-(4-{[4-(1-methylethyl)piperazin-1-yl]carbonyl}phenyl)urea | 671.4 336.2 224.5 |
| 664 | 1-(4-{4,6-bis[(3S)-3-methylmorpholin-4-yl]-1,3,5-triazin-2-yl}phenyl)-3-(4-{[(3S)-3-methylmorpholin-4-yl]carbonyl}phenyl)urea | 617.5 |
| 665 | 1-{4-[(4-butylpiperazin-1-yl)carbonyl]phenyl}-3-(4-{4-[4-(1-methylethyl)-1,4-diazepan-1-yl]-6-morpholin-4-yl-1,3,5-triazin-2-yl}phenyl)urea | 685.6 |
| 666 | N-[4-({[4-(4,6-di-8-oxa-3-azabicyclo[3.2.1]oct-3-yl-1,3,5-triazin-2-yl)phenyl]carbamoyl}amino)phenyl]-2-(4-methylpiperazin-1-yl)acetamide | |
| 667 | 1-(4-{4-[(2R,5S)-2,5-bis(hydroxymethyl)pyrrolidin-1-yl]-6-(8-oxa-3-azabicyclo[3.2.1]oct-3-yl)-1,3,5-triazin-2-yl}phenyl)-3-pyridin-4-ylurea | 533.3 |
| 668 | 1-(4-{4-[(2R,5S)-2,5-bis(hydroxymethyl)pyrrolidin-1-yl]-6-(8-oxa-3-azabicyclo[3.2.1]oct-3-yl)-1,3,5-triazin-2-yl}phenyl)-3-[4-(4-methylpiperazin-1-yl)phenyl]urea | 630.4 |
| 669 | 1-{4-[4-morpholin-4-yl-6-(3-oxa-8-azabicyclo[3.2.1]oct-8-yl)-1,3,5-triazin-2-yl]phenyl}-3-pyridin-4-ylurea | 489.3 |
| 670 | 4-[({4-[4-morpholin-4-yl-6-(3-oxa-8-azabicyclo[3.2.1]oct-8-yl)-1,3,5-triazin-2-yl]phenyl}carbamoyl)amino]benzamide | 531.2 |

TABLE I-continued

| Example | Name | MS (ESI) m/z |
|---|---|---|
| 671 | 1-{4-[4-morpholin-4-yl-6-(3-oxa-8-azabicyclo[3.2.1]oct-8-yl)-1,3,5-triazin-2-yl]phenyl}-3-pyridin-3-ylurea | 489.5 |
| 672 | 1-(4-fluorophenyl)-3-{4-[4-morpholin-4-yl-6-(3-oxa-8-azabicyclo[3.2.1]oct-8-yl)-1,3,5-triazin-2-yl]phenyl}urea | 506.5 |
| 673 | 1-[4-(hydroxymethyl)phenyl]-3-{4-[4-morpholin-4-yl-6-(3-oxa-8-azabicyclo[3.2.1]oct-8-yl)-1,3,5-triazin-2-yl]phenyl}urea | 518.5 |
| 674 | 1-[4-(2-hydroxyethyl)phenyl]-3-{4-[4-morpholin-4-yl-6-(3-oxa-8-azabicyclo[3.2.1]oct-8-yl)-1,3,5-triazin-2-yl]phenyl}urea | 532.5 |
| 675 | 2-(diethylamino)ethyl 4-[({4-[4-morpholin-4-yl-6-(3-oxa-8-azabicyclo[3.2.1]oct-8-yl)-1,3,5-triazin-2-yl]phenyl}carbamoyl)amino]benzoate | 631.6 |
| 676 | 1-(4-methylphenyl)-3-{4-[4-morpholin-4-yl-6-(3-oxa-8-azabicyclo[3.2.1]oct-8-yl)-1,3,5-triazin-2-yl]phenyl}urea | 502.5 |
| 677 | 1-(4-cyanophenyl)-3-{4-[4-morpholin-4-yl-6-(3-oxa-8-azabicyclo[3.2.1]oct-8-yl)-1,3,5-triazin-2-yl]phenyl}urea | 513.5 |
| 678 | 1-[4-(4-methylpiperazin-1-yl)phenyl]-3-{4-[4-morpholin-4-yl-6-(3-oxa-8-azabicyclo[3.2.1]oct-8-yl)-1,3,5-triazin-2-yl]phenyl}urea | 586.6 |
| 679 | 1-isopropyl-3-{4-[4-morpholin-4-yl-6-(3-oxa-8-azabicyclo[3.2.1]oct-8-yl)-1,3,5-triazin-2-yl]phenyl}urea | 454.5 |
| 680 | 1-(2-hydroxyethyl)-3-{4-[4-morpholin-4-yl-6-(3-oxa-8-azabicyclo[3.2.1]oct-8-yl)-1,3,5-triazin-2-yl]phenyl}urea | 456.5 |
| 681 | 4-[4-morpholin-4-yl-6-(3-oxa-8-azabicyclo[3.2.1]oct-8-yl)-1,3,5-triazin-2-yl]aniline | 369.2 |
| 682 | {3-[4-morpholin-4-yl-6-(3-oxa-8-azabicyclo[3.2.1]oct-8-yl)-1,3,5-triazin-2-yl]phenyl}methanol | 384.4 |
| 683 | 3-[4-morpholin-4-yl-6-(3-oxa-8-azabicyclo[3.2.1]oct-8-yl)-1,3,5-triazin-2-yl]phenol | 370.4 |
| 684 | 5-[4-morpholin-4-yl-6-(3-oxa-8-azabicyclo[3.2.1]oct-8-yl)-1,3,5-triazin-2-yl]-1H-benzimidazol-2-amine | 409.4 |
| 685 | 1-{4-[4-(3-hydroxy-8-azabicyclo[3.2.1]oct-8-yl)-6-morpholin-4-yl-1,3,5-triazin-2-yl]phenyl}-3-phenylurea | 502.5 |
| 686 | 1-(4-{4-[(4-methylpiperazin-1-yl)amino]-6-morpholin-4-yl-1,3,5-triazin-2-yl}phenyl)-3-phenylurea | 490.5 |
| 687 | 1-(4-{4-[(1-methylpiperidin-4-yl)oxy]-6-morpholin-4-yl-1,3,5-triazin-2-yl}phenyl)-3-pyridin-4-ylurea | 491.5 |
| 688 | 1-{4-[4-morpholin-4-yl-6-(piperidin-4-yloxy)-1,3,5-triazin-2-yl]phenyl}-3-pyridin-4-ylurea | 477.5 |
| 689 | ethyl 4-[(4-morpholin-4-yl-6-{4-[(pyridin-4-ylcarbamoyl)amino]phenyl}-1,3,5-triazin-2-yl)oxy]piperidine-1-carboxylate | 549.5 |
| 690 | N-ethyl-4-[(4-morpholin-4-yl-6-{4-[(pyridin-4-ylcarbamoyl)amino]phenyl}-1,3,5-triazin-2-yl)oxy]piperidine-1-carboxamide | 548.5 |
| 691 | tert-butyl 4-[(4-morpholin-4-yl-6-{4-[(pyridin-4-ylcarbamoyl)amino]phenyl}-1,3,5-triazin-2-yl)oxy]piperidine-1-carboxylate | 577.3 |
| 692 | 4-[(4-morpholin-4-yl-6-{4-[(pyridin-4-ylcarbamoyl)amino]phenyl}-1,3,5-triazin-2-yl)oxy]piperidine-1-sulfonamide | 556.5 |
| 693 | methyl 4-[({4-[4-morpholin-4-yl-6-(3-oxa-8-azabicyclo[3.2.1]oct-8-yl)-1,3,5-triazin-2-yl]phenyl}carbamoyl)amino]benzoate | 546.3 |
| 694 | N-[2-(dimethylamino)ethyl]-4-[({4-[4-morpholin-4-yl-6-(3-oxa-8-azabicyclo[3.2.1]oct-8-yl)-1,3,5-triazin-2-yl]phenyl}carbamoyl)amino]benzamide | 602.4 |
| 695 | N,N-dimethyl-4-[({4-[4-morpholin-4-yl-6-(3-oxa-8-azabicyclo[3.2.1]oct-8-yl)-1,3,5-triazin-2-yl]phenyl}carbamoyl)amino]benzamide | 559.2 |
| 696 | N-methyl-4-[({4-[4-morpholin-4-yl-6-(3-oxa-8-azabicyclo[3.2.1]oct-8-yl)-1,3,5-triazin-2-yl]phenyl}carbamoyl)amino]benzamide | 545.2 |
| 697 | 1-{4-[(4-methylpiperazin-1-yl)carbonyl]phenyl}-3-{4-[4-morpholin-4-yl-6-(3-oxa-8-azabicyclo[3.2.1]oct-8-yl)-1,3,5-triazin-2-yl]phenyl}urea | 614.3 |

TABLE I-continued

| Example | Name | MS (ESI) m/z |
|---|---|---|
| 698 | N-[2-(dimethylamino)ethyl]-N-methyl-4-[({4-[4-morpholin-4-yl-6-(3-oxa-8-azabicyclo[3.2.1]oct-8-yl)-1,3,5-triazin-2-yl]phenyl}carbamoyl)amino]benzamide | 616.4 |
| 699 | N-(2-hydroxyethyl)-4-[({4-[4-morpholin-4-yl-6-(3-oxa-8-azabicyclo[3.2.1]oct-8-yl)-1,3,5-triazin-2-yl]phenyl}carbamoyl)amino]benzamide | 575.4 |
| 700 | N-[3-(dimethylamino)propyl]-4-[({4-[4-morpholin-4-yl-6-(3-oxa-8-azabicyclo[3.2.1]oct-8-yl)-1,3,5-triazin-2-yl]phenyl}carbamoyl)amino]benzamide | 616.4 |
| 701 | N-methyl-N-[2-(methylamino)ethyl]-4-[({4-[4-morpholin-4-yl-6-(3-oxa-8-azabicyclo[3.2.1]oct-8-yl)-1,3,5-triazin-2-yl]phenyl}carbamoyl)amino]benzamide | 602.4 |
| 702 | N-(2-morpholin-4-ylethyl)-4-[({4-[4-morpholin-4-yl-6-(3-oxa-8-azabicyclo[3.2.1]oct-8-yl)-1,3,5-triazin-2-yl]phenyl}carbamoyl)amino]benzamide | 644.4 |
| 703 | 1-{4-[(3,5-dimethylpiperazin-1-yl)carbonyl]phenyl}-3-{4-[4-morpholin-4-yl-6-(3-oxa-8-azabicyclo[3.2.1]oct-8-yl)-1,3,5-triazin-2-yl]phenyl}urea | 628.4 |
| 704 | 4-[4-(1,4-dioxa-8-azaspiro[4.5]dec-8-yl)-6-morpholin-4-yl-1,3,5-triazin-2-yl]aniline | 399.3 |
| 705 | 1-{4-[4-(1,4-dioxa-8-azaspiro[4.5]dec-8-yl)-6-morpholin-4-yl-1,3,5-triazin-2-yl]phenyl}-3-pyridin-4-ylurea | 519.7 |
| 706 | 1-{4-[4-(1,4-dioxa-8-azaspiro[4.5]dec-8-yl)-6-morpholin-4-yl-1,3,5-triazin-2-yl]phenyl}-3-pyridin-3-ylurea | 519.2 |
| 707 | 1-{4-[4-(1,4-dioxa-8-azaspiro[4.5]dec-8-yl)-6-morpholin-4-yl-1,3,5-triazin-2-yl]phenyl}-3-phenylurea | 518.2 |
| 708 | 1-[4-(dimethylamino)phenyl]-3-{4-[4-(1,4-dioxa-8-azaspiro[4.5]dec-8-yl)-6-morpholin-4-yl-1,3,5-triazin-2-yl]phenyl}urea | 561.3 |
| 709 | 1-(4-cyanophenyl)-3-{4-[4-(1,4-dioxa-8-azaspiro[4.5]dec-8-yl)-6-morpholin-4-yl-1,3,5-triazin-2-yl]phenyl}urea | 543.2 |
| 710 | 1-{4-[4-(1,4-dioxa-8-azaspiro[4.5]dec-8-yl)-6-morpholin-4-yl-1,3,5-triazin-2-yl]phenyl}-3-(2-methylpyridin-4-yl)urea | 533.7 |
| 711 | 1-[2-(dimethylamino)ethyl]-3-{4-[4-(1,4-dioxa-8-azaspiro[4.5]dec-8-yl)-6-morpholin-4-yl-1,3,5-triazin-2-yl]phenyl}urea | 513.7 |
| 712 | 1-[4-(4-morpholin-4-yl-6-quinolin-3-yl-1,3,5-triazin-2-yl)phenyl]-3-pyridin-4-ylurea | 505.7 |
| 713 | 1-(diethylcarbamoyl)-4-[({4-[4-morpholin-4-yl-6-(3-oxa-8-azabicyclo[3.2.1]oct-8-yl)-1,3,5-triazin-2-yl]phenyl}carbamoyl)amino]pyridinium | 588.3 |
| 714 | 1-{4-[4-(2-methoxyethoxy)-6-morpholin-4-yl-1,3,5-triazin-2-yl]phenyl}-3-pyridin-4-ylurea | 452.6 |
| 715 | methyl 4-[({4-[4-(2-methoxyethoxy)-6-morpholin-4-yl-1,3,5-triazin-2-yl]phenyl}carbamoyl)amino]benzoate | 509.4 |
| 716 | 4-(4,6-di-3-oxa-8-azabicyclo[3.2.1]oct-8-yl-1,3,5-triazin-2-yl)aniline | 395.3 |
| 717 | 1-[4-(4,6-di-3-oxa-8-azabicyclo[3.2.1]oct-8-yl-1,3,5-triazin-2-yl)phenyl]-3-pyridin-4-ylurea | 515.8 |
| 718 | 1-(4-{morpholin-4-yl-6-[2-(pyridin-4-ylamino)ethyl]-1,3,5-triazin-2-yl}phenyl)-3-pyridin-4-ylurea | 498.6 |
| 719 | 1-(4-acetylphenyl)-3-{4-[4-morpholin-4-yl-6-(3-oxa-8-azabicyclo[3.2.1]oct-8-yl)-1,3,5-triazin-2-yl]phenyl}urea | 530.4 |
| 720 | N-[2-(dimethylamino)ethyl]-4-({[4-(4-methoxy-6-morpholin-4-yl-1,3,5-triazin-2-yl)phenyl]carbamoyl}amino)-N-methylbenzamide | 535.5 |
| 721 | N-[2-(dimethylamino)ethyl]-4-({[4-(4-methoxy-6-morpholin-4-yl-1,3,5-triazin-2-yl)phenyl]carbamoyl}amino)benzamide | 521.5 |
| 722 | 4-({[4-(4-methoxy-6-morpholin-4-yl-1,3,5-triazin-2-yl)phenyl]carbamoyl}amino)-N-methyl-N-[2-(methylamino)ethyl]benzamide | 521.5 |
| 723 | 1-[4-(4-methoxy-6-morpholin-4-yl-1,3,5-triazin-2-yl)phenyl]-3-{4-[(4-methylpiperazin-1-yl)carbonyl]phenyl}urea | 533.5 |
| 724 | 1-{4-[(3,3-dimethylpiperazin-1-yl)carbonyl]phenyl}-3-[4-(4-methoxy-6-morpholin-4-yl-1,3,5-triazin-2-yl)phenyl]urea | 547.5 |

TABLE I-continued

| Example | Name | MS (ESI) m/z |
|---|---|---|
| 725 | 4-({[4-(4-methoxy-6-morpholin-4-yl-1,3,5-triazin-2-yl)phenyl]carbamoyl}amino)-N-(2-piperidin-1-ylethyl)benzamide | 561.5 |
| 726 | 1-(4-ethenylphenyl)-3-{4-[4-morpholin-4-yl-6-(3-oxa-8-azabicyclo[3.2.1]oct-8-yl)-1,3,5-triazin-2-yl]phenyl}urea | 514.3 |
| 727 | 1-{4-[(4-methylpiperazin-1-yl)methyl]phenyl}-3-{4-[4-morpholin-4-yl-6-(3-oxa-8-azabicyclo[3.2.1]oct-8-yl)-1,3,5-triazin-2-yl]phenyl}urea | 601.1 |
| 728 | 1-(4-{4-[2,5-bis(hydroxymethyl)pyrrolidin-1-yl]-6-morpholin-4-yl-1,3,5-triazin-2-yl}phenyl)-3-pyridin-4-ylurea | 508 |
| 729 | 1-{4-[2-(dimethylamino)ethoxy]phenyl}-3-{4-[4-morpholin-4-yl-6-(3-oxa-8-azabicyclo[3.2.1]oct-8-yl)-1,3,5-triazin-2-yl]phenyl}urea | 575.5 |
| 730 | 1-(4-{4-[2-(1,3-dioxan-2-yl)ethyl]-6-morpholin-4-yl-1,3,5-triazin-2-yl}phenyl)-3-pyridin-4-ylurea | 492.9 |
| 731 | 1-(4-{4-[3-(dimethylamino)propyl]-6-morpholin-4-yl-1,3,5-triazin-2-yl}phenyl)-3-pyridin-4-ylurea | 463.4 |
| 732 | 1-[4-(4-{3-[(1-methylethyl)amino]propyl}-6-morpholin-4-yl-1,3,5-triazin-2-yl)phenyl]-3-pyridin-4-ylurea | 477.4 |
| 733 | 1-{4-[4-morpholin-4-yl-6-(3-pyrrolidin-1-ylpropyl)-1,3,5-triazin-2-yl]phenyl}-3-pyridin-4-ylurea | 489.4 |
| 734 | 1-(4-{4-[3-(4-methylpiperazin-1-yl)propyl]-6-morpholin-4-yl-1,3,5-triazin-2-yl}phenyl)-3-pyridin-4-ylurea | 518.4 |
| 735 | 1-{4-[4-(3-{[2-(dimethylamino)ethyl]amino}propyl)-6-morpholin-4-yl-1,3,5-triazin-2-yl]phenyl}-3-pyridin-4-ylurea | 506.5 |
| 736 | 1-{4-[4-(3-hydroxypropyl)-6-morpholin-4-yl-1,3,5-triazin-2-yl]phenyl}-3-pyridin-4-ylurea | 436.3 |
| 737 | 1-{4-[4-morpholin-4-yl-6-(3-oxopropyl)-1,3,5-triazin-2-yl]phenyl}-3-pyridin-4-ylurea | 434.3 |
| 738 | 4-[4-(6,8-dioxa-3-azabicyclo[3.2.1]oct-3-yl)-6-morpholin-4-yl-1,3,5-triazin-2-yl]aniline | 371.3 |
| 739 | tert-butyl 7-[4-(4-aminophenyl)-6-morpholin-4-yl-1,3,5-triazin-2-yl]-9-oxa-3,7-diazabicyclo[3.3.1]nonane-3-carboxylate | 484.4 |
| 740 | 1-{4-[4-(6,8-dioxa-3-azabicyclo[3.2.1]oct-3-yl)-6-morpholin-4-yl-1,3,5-triazin-2-yl]phenyl}-3-pyridin-4-ylurea | 491.3 |
| 741 | tert-butyl 7-(4-morpholin-4-yl-6-{4-[(pyridin-4-ylcarbamoyl)amino]phenyl}-1,3,5-triazin-2-yl)-9-oxa-3,7-diazabicyclo[3.3.1]nonane-3-carboxylate | 604.4 |
| 742 | 1-{4-[4-morpholin-4-yl-6-(9-oxa-3,7-diazabicyclo[3.3.1]non-3-yl)-1,3,5-triazin-2-yl]phenyl}-3-pyridin-4-ylurea | 504.4 |
| 743 | 1-{4-[4-(7-methyl-9-oxa-3,7-diazabicyclo[3.3.1]non-3-yl)-6-morpholin-4-yl-1,3,5-triazin-2-yl]phenyl}-3-pyridin-4-ylurea | 518.4 |
| 744 | 1-{4-[4-(7-acetyl-9-oxa-3,7-diazabicyclo[3.3.1]non-3-yl)-6-morpholin-4-yl-1,3,5-triazin-2-yl]phenyl}-3-pyridin-4-ylurea | 546.4 |
| 745 | 1-(4-{4-[7-(methylsulfonyl)-9-oxa-3,7-diazabicyclo[3.3.1]non-3-yl]-6-morpholin-4-yl-1,3,5-triazin-2-yl}phenyl)-3-pyridin-4-ylurea | 582.5 |
| 746 | 1-(2-chloropyridin-4-yl)-3-{4-[4-morpholin-4-yl-6-(3-oxa-8-azabicyclo[3.2.1]oct-8-yl)-1,3,5-triazin-2-yl]phenyl}urea | 523.3 |
| 747 | 1-(2,3'-bipyridin-4-yl)-3-{4-[4-morpholin-4-yl-6-(3-oxa-8-azabicyclo[3.2.1]oct-8-yl)-1,3,5-triazin-2-yl]phenyl}urea | 566.4 |
| 748 | tert-butyl N-[4-morpholin-4-yl-6-(4-nitrophenyl)-1,3,5-triazin-2-yl]glycinate | 417.2 |
| 749 | 1-(6-chloropyridin-3-yl)-3-{4-[4-morpholin-4-yl-6-(3-oxa-8-azabicyclo[3.2.1]oct-8-yl)-1,3,5-triazin-2-yl]phenyl}urea | 523.3 |
| 750 | N-[4-morpholin-4-yl-6-(4-nitrophenyl)-1,3,5-triazin-2-yl]glycine | 361.3 |
| 751 | 1,3-bis{4-[4-morpholin-4-yl-6-(3-oxa-8-azabicyclo[3.2.1]oct-8-yl)-1,3,5-triazin-2-yl]phenyl}urea | 763.5 |
| 752 | 1-(4-{[4-(dimethylamino)piperidin-1-yl]carbonyl}phenyl)-3-{4-[4-morpholin-4-yl-6-(3-oxa-8-azabicyclo[3.2.1]oct-8-yl)-1,3,5-triazin-2-yl]phenyl}urea | 642.4 |

TABLE I-continued

| Example | Name | MS (ESI) m/z |
|---|---|---|
| 753 | N-[2-(4-methylpiperazin-1-yl)ethyl]-4-[({4-[4-morpholin-4-yl-6-(3-oxa-8-azabicyclo[3.2.1]oct-8-yl)-1,3,5-triazin-2-yl]phenyl}carbamoyl)amino]benzamide | 657.4 |
| 754 | 1-{4-[(4-isopropylpiperazin-1-yl)carbonyl]phenyl}-3-{4-[4-morpholin-4-yl-6-(3-oxa-8-azabicyclo[3.2.1]oct-8-yl)-1,3,5-triazin-2-yl]phenyl}urea | 642.4 |
| 755 | 1-{4-[(4-cyclopentylpiperazin-1-yl)carbonyl]phenyl}-3-{4-[4-morpholin-4-yl-6-(3-oxa-8-azabicyclo[3.2.1]oct-8-yl)-1,3,5-triazin-2-yl]phenyl}urea | 668.4 |
| 756 | 1-{4-[4-morpholin-4-yl-6-(3-oxa-8-azabicyclo[3.2.1]oct-8-yl)-1,3,5-triazin-2-yl]phenyl}-3-[4-(piperazin-1-ylcarbonyl)phenyl]urea | 600.4 |
| 757 | 1-{4-[4-morpholin-4-yl-6-(3-oxa-8-azabicyclo[3.2.1]oct-8-yl)-1,3,5-triazin-2-yl]phenyl}-3-{4-[(4-morpholin-4-ylpiperidin-1-yl)carbonyl]phenyl}urea | 684.4 |
| 758 | 4-[({4-[4-morpholin-4-yl-6-(3-oxa-8-azabicyclo[3.2.1]oct-8-yl)-1,3,5-triazin-2-yl]phenyl}carbamoyl)amino]-N-(2-pyrrolidin-1-ylethyl)benzamide | 628.4 |
| 759 | 4-[({4-[4-morpholin-4-yl-6-(3-oxa-8-azabicyclo[3.2.1]oct-8-yl)-1,3,5-triazin-2-yl]phenyl}carbamoyl)amino]-N-(2-piperidin-1-ylethyl)benzamide | 642.4 |
| 760 | 1-[4-(1,4'-bipiperidin-1'-ylcarbonyl)phenyl]-3-{4-[4-morpholin-4-yl-6-(3-oxa-8-azabicyclo[3.2.1]oct-8-yl)-1,3,5-triazin-2-yl]phenyl}urea | 682.5 |
| 761 | 1-{4-[4-morpholin-4-yl-6-(3-oxa-8-azabicyclo[3.2.1]oct-8-yl)-1,3,5-triazin-2-yl]phenyl}-3-{4-[(4-pyrrolidin-1-ylpiperidin-1-yl)carbonyl]phenyl}urea | 668.5 |
| 762 | 1-{4-[4-morpholin-4-yl-6-(3-oxa-8-azabicyclo[3.2.1]oct-8-yl)-1,3,5-triazin-2-yl]phenyl}-3-[4-(thiomorpholin-4-ylcarbonyl)phenyl]urea | 617.3 |
| 763 | 1-[4-(morpholin-4-ylcarbonyl)phenyl]-3-{4-[4-morpholin-4-yl-6-(3-oxa-8-azabicyclo[3.2.1]oct-8-yl)-1,3,5-triazin-2-yl]phenyl}urea | 601.4 |
| 764 | 4-[({4-[4-morpholin-4-yl-6-(3-oxa-8-azabicyclo[3.2.1]oct-8-yl)-1,3,5-triazin-2-yl]phenyl}carbamoyl)amino]benzoic acid | 532.3 |
| 765 | 1-{4-[4-(3,7-dioxa-9-azabicyclo[3.3.1]non-9-yl)-6-morpholin-4-yl-1,3,5-triazin-2-yl]phenyl}-3-pyridin-4-ylurea | 505.3 |
| 766 | 1-[6-(4-methylpiperazin-1-yl)pyridin-3-yl]-3-{4-[4-morpholin-4-yl-6-(3-oxa-8-azabicyclo[3.2.1]oct-8-yl)-1,3,5-triazin-2-yl]phenyl}urea | 587.4 |
| 767 | 1-(4-{[4-(dimethylamino)piperidin-1-yl]carbonyl}phenyl)-3-{4-[4-(3,7-dioxa-9-azabicyclo[3.3.1]non-9-yl)-6-morpholin-4-yl-1,3,5-triazin-2-yl]phenyl}urea | 658.4 |
| 768 | N-[2-(dimethylamino)ethyl]-4-[({4-[4-(3,7-dioxa-9-azabicyclo[3.3.1]non-9-yl)-6-morpholin-4-yl-1,3,5-triazin-2-yl]phenyl}carbamoyl)amino]-N-methylbenzamide | 632.4 |
| 769 | 1-{4-[4-(3,7-dioxa-9-azabicyclo[3.3.1]non-9-yl)-6-morpholin-4-yl-1,3,5-triazin-2-yl]phenyl}-3-{4-[(4-methylpiperazin-1-yl)carbonyl]phenyl}urea | 630.4 |
| 770 | methyl 4-[({4-[4-(3,7-dioxa-9-azabicyclo[3.3.1]non-9-yl)-6-morpholin-4-yl-1,3,5-triazin-2-yl]phenyl}carbamoyl)amino]benzoate | 562.3 |
| 771 | 4-[({4-[4-(3,7-dioxa-9-azabicyclo[3.3.1]non-9-yl)-6-morpholin-4-yl-1,3,5-triazin-2-yl]phenyl}carbamoyl)amino]benzoic acid | 548.3 |
| 772 | 1-{4-[4-(3,7-dioxa-9-azabicyclo[3.3.1]non-9-yl)-6-morpholin-4-yl-1,3,5-triazin-2-yl]phenyl}-3-[4-(piperazin-1-ylcarbonyl)phenyl]urea | 616.3 |
| 773 | 1-{4-[4-(3,7-dioxa-9-azabicyclo[3.3.1]non-9-yl)-6-morpholin-4-yl-1,3,5-triazin-2-yl]phenyl}-3-{4-[(4-isopropylpiperazin-1-yl)carbonyl]phenyl}urea | 658.3 |
| 774 | 4-[({4-[4-(3,7-dioxa-9-azabicyclo[3.3.1]non-9-yl)-6-morpholin-4-yl-1,3,5-triazin-2-yl]phenyl}carbamoyl)amino]-N-(2-pyrrolidin-1-ylethyl)benzamide | 644.3 |

TABLE I-continued

| Example | Name | MS (ESI) m/z |
|---|---|---|
| 775 | 4-[({4-[4-(3,7-dioxa-9-azabicyclo[3.3.1]non-9-yl)-6-morpholin-4-yl-1,3,5-triazin-2-yl]phenyl}carbamoyl)amino]-N-(2-piperidin-1-ylethyl)benzamide | 658.4 |
| 776 | 1-{4-[4-(3,7-dioxa-9-azabicyclo[3.3.1]non-9-yl)-6-morpholin-4-yl-1,3,5-triazin-2-yl]phenyl}-3-{4-[(4-pyrrolidin-1-ylpiperidin-1-yl)carbonyl]phenyl}urea | 684.4 |
| 777 | 1-[4-(1,4'-bipiperidin-1'-ylcarbonyl)phenyl]-3-{4-[4-(3,7-dioxa-9-azabicyclo[3.3.1]non-9-yl)-6-morpholin-4-yl-1,3,5-triazin-2-yl]phenyl}urea | 698.4 |
| 778 | 4-[({4-[4-(3,7-dioxa-9-azabicyclo[3.3.1]non-9-yl)-6-morpholin-4-yl-1,3,5-triazin-2-yl]phenyl}carbamoyl)amino]-N-(2-pyridin-2-ylethyl)benzamide | 652.4 |
| 779 | 4-[({4-[4-(3,7-dioxa-9-azabicyclo[3.3.1]non-9-yl)-6-morpholin-4-yl-1,3,5-triazin-2-yl]phenyl}carbamoyl)amino]-N-(2-pyridin-4-ylethyl)benzamide | 652.4 |
| 780 | N-[4-(4-aminophenyl)-6-morpholin-4-yl-1,3,5-triazin-2-yl]benzenesulfonamide | 413.2 |
| 781 | N-(4-morpholin-4-yl-6-{4-[(pyridin-4-ylcarbamoyl)amino]phenyl}-1,3,5-triazin-2-yl)benzenesulfonamide | 533.4 |
| 782 | N-{4-[4-({[4-(4-methylpiperazin-1-yl)phenyl]carbamoyl}amino)phenyl]-6-morpholin-4-yl-1,3,5-triazin-2-yl}benzenesulfonamide | 630.3 |
| 783 | N-(4-{4-[({4-[2-(dimethylamino)ethoxy]phenyl}carbamoyl)amino]phenyl}-6-morpholin-4-yl-1,3,5-triazin-2-yl)benzenesulfonamide | 619.3 |
| 784 | N-(4-{4-[({4-[(4-methylpiperazin-1-yl)carbonyl]phenyl}carbamoyl)amino]phenyl}-6-morpholin-4-yl-1,3,5-triazin-2-yl)benzenesulfonamide | 658.3 |
| 785 | N-{4-morpholin-4-yl-6-[4-({[4-(piperazin-1-ylcarbonyl)phenyl]carbamoyl}amino)phenyl]-1,3,5-triazin-2-yl}benzenesulfonamide | 644.4 |
| 786 | N-[4-(4-{[(4-{[4-(dimethylamino)piperidin-1-yl]carbonyl}phenyl)carbamoyl]amino}phenyl)-6-morpholin-4-yl-1,3,5-triazin-2-yl]benzenesulfonamide | 686.4 |
| 787 | N-[2-(dimethylamino)ethyl]-N-methyl-4-{[(4-{4-morpholin-4-yl-6-[(phenylsulfonyl)amino]-1,3,5-triazin-2-yl}phenyl)carbamoyl]amino}benzamide | 660.4 |
| 788 | N-[2-(dimethylamino)ethyl]-4-{[(4-{4-morpholin-4-yl-6-[(phenylsulfonyl)amino]-1,3,5-triazin-2-yl}phenyl)carbamoyl]amino}benzamide | 646.4 |
| 789 | methyl 4-{[(4-{4-morpholin-4-yl-6-[(phenylsulfonyl)amino]-1,3,5-triazin-2-yl}phenyl)carbamoyl]amino}benzoate | 590.3 |
| 790 | 4-{[(4-{4-morpholin-4-yl-6-[(phenylsulfonyl)amino]-1,3,5-triazin-2-yl}phenyl)carbamoyl]amino}benzoic acid | 576.2 |
| 791 | 1-{4-[4-morpholin-4-yl-6-(3-oxa-9-azabicyclo[3.3.1]non-9-yl)-1,3,5-triazin-2-yl]phenyl}-3-pyridin-4-ylurea | 503.2 |
| 792 | 1-{4-[(4-methylpiperazin-1-yl)carbonyl]phenyl}-3-{4-[4-morpholin-4-yl-6-(3-oxa-9-azabicyclo[3.3.1]non-9-yl)-1,3,5-triazin-2-yl]phenyl}urea | 628.5 |
| 793 | 1-{4-[4-morpholin-4-yl-6-(3-oxa-9-azabicyclo[3.3.1]non-9-yl)-1,3,5-triazin-2-yl]phenyl}-3-[4-(piperazin-1-ylcarbonyl)phenyl]urea | 614.5 |
| 794 | 1-(4-{[4-(dimethylamino)piperidin-1-yl]carbonyl}phenyl)-3-{4-[4-morpholin-4-yl-6-(3-oxa-9-azabicyclo[3.3.1]non-9-yl)-1,3,5-triazin-2-yl]phenyl}urea | 656.5 |
| 795 | N-[2-(dimethylamino)ethyl]-N-methyl-4-[({4-[4-morpholin-4-yl-6-(3-oxa-9-azabicyclo[3.3.1]non-9-yl)-1,3,5-triazin-2-yl]phenyl}carbamoyl)amino]benzamide | 630.4 |
| 796 | N-[2-(dimethylamino)ethyl]-4-[({4-[4-morpholin-4-yl-6-(3-oxa-9-azabicyclo[3.3.1]non-9-yl)-1,3,5-triazin-2-yl]phenyl}carbamoyl)amino]benzamide | 616.4 |
| 797 | N-(2-methoxyethyl)-4-[({4-[4-morpholin-4-yl-6-(3-oxa-9-azabicyclo[3.3.1]non-9-yl)-1,3,5-triazin-2-yl]phenyl}carbamoyl)amino]benzamide | 603.4 |

TABLE I-continued

| Example | Name | MS (ESI) m/z |
|---|---|---|
| 798 | 4-[({4-[4-morpholin-4-yl-6-(3-oxa-9-azabicyclo[3.3.1]non-9-yl)-1,3,5-triazin-2-yl]phenyl}carbamoyl)amino]-N-(2-pyrrolidin-1-ylethyl)benzamide | 642.4 |
| 799 | 4-[({4-[4-morpholin-4-yl-6-(3-oxa-9-azabicyclo[3.3.1]non-9-yl)-1,3,5-triazin-2-yl]phenyl}carbamoyl)amino]-N-(2-piperidin-1-ylethyl)benzamide | 656.4 |
| 800 | 1-{4-[4-morpholin-4-yl-6-(3-oxa-9-azabicyclo[3.3.1]non-9-yl)-1,3,5-triazin-2-yl]phenyl}-3-{4-[(4-pyrrolidin-1-ylpiperidin-1-yl)carbonyl]phenyl}urea | 682.5 |
| 801 | N-[2-(1-methylpyrrolidin-2-yl)ethyl]-4-[({4-[4-morpholin-4-yl-6-(3-oxa-9-azabicyclo[3.3.1]non-9-yl)-1,3,5-triazin-2-yl]phenyl}carbamoyl)amino]benzamide | 656.6 |
| 802 | N-methyl-N-[2-(methylamino)ethyl]-4-[({4-[4-morpholin-4-yl-6-(3-oxa-9-azabicyclo[3.3.1]non-9-yl)-1,3,5-triazin-2-yl]phenyl}carbamoyl)amino]benzamide | 616.5 |
| 803 | 1-{4-[(4-ethylpiperazin-1-yl)carbonyl]phenyl}-3-{4-[4-morpholin-4-yl-6-(3-oxa-8-azabicyclo[3.2.1]oct-8-yl)-1,3,5-triazin-2-yl]phenyl}urea | 628.3 |
| 804 | 1-{4-[(4-ethylpiperazin-1-yl)carbonyl]phenyl}-3-{4-[4-morpholin-4-yl-6-(3-oxa-9-azabicyclo[3.3.1]non-9-yl)-1,3,5-triazin-2-yl]phenyl}urea | 642.5 |
| 805 | 1-(4-{[4-(1-methylethyl)piperazin-1-yl]carbonyl}phenyl)-3-{4-[4-morpholin-4-yl-6-(3-oxa-9-azabicyclo[3.3.1]non-9-yl)-1,3,5-triazin-2-yl]phenyl}urea | 656.3 |
| 806 | 1-{4-[4-(3,7-dioxa-9-azabicyclo[3.3.1]non-9-yl)-6-morpholin-4-yl-1,3,5-triazin-2-yl]phenyl}-3-{4-[(4-ethylpiperazin-1-yl)carbonyl]phenyl}urea | 644.5 |
| 807 | 1-{4-[4-morpholin-4-yl-6-(2-oxa-5-azabicyclo[2.2.2]oct-5-yl)-1,3,5-triazin-2-yl]phenyl}-3-pyridin-4-ylurea | 489.2 |
| 808 | 1-(1,3-dimethyl-1H-pyrazol-5-yl)-3-{4-[4-morpholin-4-yl-6-(2-oxa-5-azabicyclo[2.2.2]oct-5-yl)-1,3,5-triazin-2-yl]phenyl}urea | 506.2 |
| 809 | 1-{4-[4-morpholin-4-yl-6-(2-oxa-5-azabicyclo[2.2.2]oct-5-yl)-1,3,5-triazin-2-yl]phenyl}-3-(1H-pyrazol-3-yl)urea | 478.2 |
| 810 | 1-(4-{[4-(dimethylamino)piperidin-1-yl]carbonyl}phenyl)-3-{4-[4-morpholin-4-yl-6-(2-oxa-5-azabicyclo[2.2.2]oct-5-yl)-1,3,5-triazin-2-yl]phenyl}urea | 642.2 |
| 811 | 1-(4-{[4-(1-methylethyl)piperazin-1-yl]carbonyl}phenyl)-3-{4-[4-morpholin-4-yl-6-(2-oxa-5-azabicyclo[2.2.2]oct-5-yl)-1,3,5-triazin-2-yl]phenyl}urea | 642.5 |
| 812 | 1-{4-[(4-ethylpiperazin-1-yl)carbonyl]phenyl}-3-{4-[4-morpholin-4-yl-6-(2-oxa-5-azabicyclo[2.2.2]oct-5-yl)-1,3,5-triazin-2-yl]phenyl}urea | 628.2 |
| 813 | 1-{4-[(4-methylpiperazin-1-yl)carbonyl]phenyl}-3-{4-[4-morpholin-4-yl-6-(2-oxa-5-azabicyclo[2.2.2]oct-5-yl)-1,3,5-triazin-2-yl]phenyl}urea | 614.2 |
| 814 | 1-{4-[4-morpholin-4-yl-6-(2-oxa-5-azabicyclo[2.2.2]oct-5-yl)-1,3,5-triazin-2-yl]phenyl}-3-[4-(piperazin-1-ylcarbonyl)phenyl]urea | 600.3 |
| 815 | N-[2-(dimethylamino)ethyl]-4-[({4-[4-morpholin-4-yl-6-(2-oxa-5-azabicyclo[2.2.2]oct-5-yl)-1,3,5-triazin-2-yl]phenyl}carbamoyl)amino]benzamide | 602.5 |
| 816 | N-[2-(dimethylamino)ethyl]-N-methyl-4-[({4-[4-morpholin-4-yl-6-(2-oxa-5-azabicyclo[2.2.2]oct-5-yl)-1,3,5-triazin-2-yl]phenyl}carbamoyl)amino]benzamide | 616.3 |
| 817 | 2-tert-butoxy-4-morpholin-4-yl-6-(4-nitrophenyl)-1,3,5-triazine | 360.1 |
| 818 | 1-(4-{4-[(6S)-6-hydroxy-3-oxa-8-azabicyclo[3.2.1]oct-8-yl]-6-morpholin-4-yl-1,3,5-triazin-2-yl}phenyl)-3-pyridin-4-ylurea | 505.2 |
| 819 | 1-(4-{4-[6-(benzyloxy)-3-oxa-8-azabicyclo[3.2.1]oct-8-yl]-6-morpholin-4-yl-1,3,5-triazin-2-yl}phenyl)-3-pyridin-4-ylurea | 595.2 |
| 820 | 1-(4-{4-[(6R)-6-hydroxy-3-oxa-8-azabicyclo[3.2.1]oct-8-yl]-6-morpholin-4-yl-1,3,5-triazin-2-yl}phenyl)-3-pyridin-4-ylurea | 505.2 |

TABLE I-continued

| Example | Name | MS (ESI) m/z |
|---|---|---|
| 821 | 1-(4-{4-[(6R)-6-(benzyloxy)-3-oxa-8-azabicyclo[3.2.1]oct-8-yl]-6-morpholin-4-yl-1,3,5-triazin-2-yl}phenyl)-3-pyridin-4-ylurea | 595.2 |
| 822 | 1-{4-[(1,1-dioxidothiomorpholin-4-yl)carbonyl]phenyl}-3-{4-[4-morpholin-4-yl-6-(3-oxa-8-azabicyclo[3.2.1]oct-8-yl)-1,3,5-triazin-2-yl]phenyl}urea | 649.1 |
| 823 | 1-[4-(4,6-di-3,7-dioxa-9-azabicyclo[3.3.1]non-9-yl-1,3,5-triazin-2-yl)phenyl]-3-[4-(4-methylpiperazin-1-yl)phenyl]urea | 644.3306 |
| 824 | 1-(4-{[(3S)-3-(dimethylamino)pyrrolidin-1-yl]carbonyl}phenyl)-3-{4-[4-morpholin-4-yl-6-(3-oxa-8-azabicyclo[3.2.1]oct-8-yl)-1,3,5-triazin-2-yl]phenyl}urea | 628.5, 314.8, 356.8 |
| 825 | 1-(4-{[(3R)-3-(dimethylamino)pyrrolidin-1-yl]carbonyl}phenyl)-3-{4-[4-morpholin-4-yl-6-(3-oxa-8-azabicyclo[3.2.1]oct-8-yl)-1,3,5-triazin-2-yl]phenyl}urea | 628.5, 314.8, 356.8 |
| 826 | 1-{4-[(4-methylpiperazin-1-yl)carbonyl]phenyl}-3-[4-(6-morpholin-4-yl-4-oxo-4,5-dihydro-1,3,5-triazin-2-yl)phenyl]urea | 519.1, 280.5, 260 |
| 827 | 1-{4-[(4-butylpiperazin-1-yl)carbonyl]phenyl}-3-(4-{4-[4-(1-methylethyl)-1,4-diazepan-1-yl]-6-morpholin-4-yl-1,3,5-triazin-2-yl}phenyl)urea | |
| 828 | 1-(4-{4-[4-(1-methylethyl)-1,4-diazepan-1-yl]-6-morpholin-4-yl-1,3,5-triazin-2-yl}phenyl)-3-(4-{[4-(1-methylethyl)piperazin-1-yl]carbonyl}phenyl)urea | 671.4; 336.2; 224.5; |
| 829 | 1-{4-[(4-ethylpiperazin-1-yl)carbonyl]phenyl}-3-(4-{4-[4-(1-methylethyl)-1,4-diazepan-1-yl]-6-morpholin-4-yl-1,3,5-triazin-2-yl}phenyl)urea | 657.4; 329.2; 219.8; |
| 830 | 1-{4-[(4-methylpiperazin-1-yl)carbonyl]phenyl}-3-{4-[4-morpholin-4-yl-6-(tetrahydro-2H-pyran-4-yl)-1,3,5-triazin-2-yl]phenyl}urea | 587.6; 314.8; 294.3; |
| 831 | 1-(4-{[(3R)-3-(dimethylamino)pyrrolidin-1-yl]carbonyl}phenyl)-3-[4-(4,6-dimorpholin-4-yl-1,3,5-triazin-2-yl)phenyl]urea | |
| 832 | 1-(4-{[(3S)-3-(dimethylamino)pyrrolidin-1-yl]carbonyl}phenyl)-3-[4-(4,6-dimorpholin-4-yl-1,3,5-triazin-2-yl)phenyl]urea | |
| 833 | 1-(4-{[4-(1-methylethyl)piperazin-1-yl]carbonyl}phenyl)-3-{4-[4-morpholin-4-yl-6-(tetrahydro-2H-pyran-4-yl)-1,3,5-triazin-2-yl]phenyl}urea | 615.5; 308.3; 328.8; |
| 834 | N-[2-(dimethylamino)ethyl]-N-methyl-4-[({4-[4-morpholin-4-yl-6-(tetrahydro-2H-pyran-4-yl)-1,3,5-triazin-2-yl]phenyl}carbamoyl)amino]benzamide | 589.5; 295.3; |
| 835 | 1-{4-[4-(azetidin-3-yloxy)-6-morpholin-4-yl-1,3,5-triazin-2-yl]phenyl}-3-pyridin-4-ylurea | 449.1; 225.1; |
| 836 | N-(1-methylethyl)-3-[(4-morpholin-4-yl-6-{4-[(pyridin-4-ylcarbamoyl)amino]phenyl}-1,3,5-triazin-2-yl)oxy]azetidine-1-carboxamide | 534.4; 267.7; |
| 837 | N-{1-[(4-{[(4-{4,6-bis[(3S)-3-methylmorpholin-4-yl]-1,3,5-triazin-2-yl}phenyl)carbamoyl]amino}phenyl)carbonyl]piperidin-4-yl}acetamide | 658.5; 329.8; |
| 838 | 1-(4-{4,6-bis[(3S)-3-methylmorpholin-4-yl]-1,3,5-triazin-2-yl}phenyl)-3-(4-{[4-(1-methylethyl)-1,4-diazepan-1-yl]carbonyl}phenyl)urea | 658.8; 329.8; |
| 839 | 1-(4-{4,6-bis[(3S)-3-methylmorpholin-4-yl]-1,3,5-triazin-2-yl}phenyl)-3-[4-(3-oxa-8-azabicyclo[3.2.1]oct-8-ylcarbonyl)phenyl]urea | 629.7; 315.3; |
| 840 | 1-(4-{4,6-bis[(3S)-3-methylmorpholin-4-yl]-1,3,5-triazin-2-yl}phenyl)-3-{4-[(4-cyanopiperidin-1-yl)carbonyl]phenyl}urea | |
| 841 | 1-(4-{4,6-bis[(3S)-3-methylmorpholin-4-yl]-1,3,5-triazin-2-yl}phenyl)-3-(4-{[(3S)-3-(dimethylamino)pyrrolidin-1-yl]carbonyl}phenyl)urea | |
| 842 | 1-(4-{4,6-bis[(3S)-3-methylmorpholin-4-yl]-1,3,5-triazin-2-yl}phenyl)-3-(4-{[(3R)-3-(dimethylamino)pyrrolidin-1-yl]carbonyl}phenyl)urea | |
| 843 | 1-(4-{[(3S)-3-(dimethylamino)pyrrolidin-1-yl]carbonyl}phenyl)-3-(4-{4-(morpholin-4-yl)-6-[4-(propan-2-yl)-1,4-diazepan-1-yl]-1,3,5-triazin-2-yl}phenyl)urea | 657.6; 329.3; 233.6; |

TABLE I-continued

| Example | Name | MS (ESI) m/z |
|---|---|---|
| 844 | 1-(4-{[(3R)-3-(dimethylamino)pyrrolidin-1-yl]carbonyl}phenyl)-3-(4-{4-(morpholin-4-yl)-6-[4-(propan-2-yl)-1,4-diazepan-1-yl]-1,3,5-triazin-2-yl}phenyl)urea | 657.5; 329.3; |
| 845 | 1-{4-[4,6-di(morpholin-4-yl)-1,3,5-triazin-2-yl]phenyl}-3-{4-[(2-methylpiperazin-1-yl)carbonyl]phenyl}urea | |
| 846 | 1-(4-{4-(morpholin-4-yl)-6-[4-(propan-2-yl)-1,4-diazepan-1-yl]-1,3,5-triazin-2-yl}phenyl)-3-[4-(piperazin-1-ylcarbonyl)phenyl]urea | |
| 847 | 1-(4-{[(3R)-3-(dimethylamino)pyrrolidin-1-yl]carbonyl}phenyl)-3-(4-{4-(morpholin-4-yl)-6-[4-(propan-2-yl)-1,4-diazepan-1-yl]-1,3,5-triazin-2-yl}phenyl)urea | |
| 848 | 1-{4-[4,6-di(morpholin-4-yl)-1,3,5-triazin-2-yl]phenyl}-3-{4-[(3,3,4-trimethylpiperazin-1-yl)carbonyl]phenyl}urea | 616.3; 638.3; 654.3; |
| 849 | 1-{4-[4,6-di(morpholin-4-yl)-1,3,5-triazin-2-yl]phenyl}-3-(4-{[(3R)-3-methylpiperazin-1-yl]carbonyl}phenyl)urea | |
| 850 | 1-(4-{[(3R)-3,4-dimethylpiperazin-1-yl]carbonyl}phenyl)-3-{4-[4,6-di(morpholin-4-yl)-1,3,5-triazin-2-yl]phenyl}urea | |
| 851 | 1-(4-{[(3R)-4-cyclobutyl-3-methylpiperazin-1-yl]carbonyl}phenyl)-3-{4-[4,6-di(morpholin-4-yl)-1,3,5-triazin-2-yl]phenyl}urea | |
| 852 | 1-{4-[4,6-di(morpholin-4-yl)-1,3,5-triazin-2-yl]phenyl}-3-(4-{[(3R)-3-methyl-4-(propan-2-yl)piperazin-1-yl]carbonyl}phenyl)urea | |
| 853 | 1-{4-[4,6-di(morpholin-4-yl)-1,3,5-triazin-2-yl]phenyl}-3-(4-{[(3S)-3-methylpiperazin-1-yl]carbonyl}phenyl)urea | |
| 854 | N-[2-(dimethylamino)ethyl]-N-methyl-4-{[(4-{4-[(3S)-3-methylmorpholin-4-yl]-6-[4-(propan-2-yl)-1,4-diazepan-1-yl]-1,3,5-triazin-2-yl}phenyl)carbamoyl]amino}benzamide | |
| 855 | 1-(4-{4-[(3S)-3-methylmorpholin-4-yl]-6-[4-(propan-2-yl)-1,4-diazepan-1-yl]-1,3,5-triazin-2-yl}phenyl)-3-{4-[(4-methylpiperazin-1-yl)carbonyl]phenyl}urea | |
| 856 | 1-(4-{[(3S)-3-(dimethylamino)pyrrolidin-1-yl]carbonyl}phenyl)-3-(4-{4-[(3S)-3-methylmorpholin-4-yl]-6-[4-(propan-2-yl)-1,4-diazepan-1-yl]-1,3,5-triazin-2-yl}phenyl)urea | |
| 857 | N-[3-(dimethylamino)propyl]-4-{[(4-{4-(morpholin-4-yl)-6-[4-(propan-2-yl)-1,4-diazepan-1-yl]-1,3,5-triazin-2-yl}phenyl)carbamoyl]amino}benzamide | |
| 858 | N-[2-(dimethylamino)ethyl]-N-methyl-4-{[(4-{4-(morpholin-4-yl)-6-[4-(propan-2-yl)-1,4-diazepan-1-yl]-1,3,5-triazin-2-yl}phenyl)carbamoyl]amino}benzamide | |
| 859 | 1-[4-(morpholin-4-ylcarbonyl)phenyl]-3-(4-{4-(morpholin-4-yl)-6-[4-(propan-2-yl)-1,4-diazepan-1-yl]-1,3,5-triazin-2-yl}phenyl)urea | |
| 860 | N-(2-methoxyethyl)-4-{[(4-{4-(morpholin-4-yl)-6-[4-(propan-2-yl)-1,4-diazepan-1-yl]-1,3,5-triazin-2-yl}phenyl)carbamoyl]amino}benzamide | |
| 861 | 1-[4-(1,4-diazepan-1-ylcarbonyl)phenyl]-3-(4-{4-(morpholin-4-yl)-6-[4-(propan-2-yl)-1,4-diazepan-1-yl]-1,3,5-triazin-2-yl}phenyl)urea | 643.4; |
| 862 | 1-(4-{4-(morpholin-4-yl)-6-[4-(propan-2-yl)-1,4-diazepan-1-yl]-1,3,5-triazin-2-yl}phenyl)-3-(4-{[4-(propan-2-yl)-1,4-diazepan-1-yl]carbonyl}phenyl)urea | |
| 863 | 1-(4-{[(3S)-4-cyclobutyl-3-methylpiperazin-1-yl]carbonyl}phenyl)-3-{4-[4,6-di(morpholin-4-yl)-1,3,5-triazin-2-yl]phenyl}urea | |
| 864 | 1-(4-{[(3S)-3,4-dimethylpiperazin-1-yl]carbonyl}phenyl)-3-{4-[4,6-di(morpholin-4-yl)-1,3,5-triazin-2-yl]phenyl}urea | |
| 865 | 1-{4-[4-(morpholin-4-yl)-6-(tetrahydro-2H-pyran-4-yl)-1,3,5-triazin-2-yl]phenyl}-3-{4-[(3,3,4-trimethylpiperazin-1-yl)carbonyl]phenyl}urea | |
| 866 | 1-(4-{[(3S)-3,4-dimethylpiperazin-1-yl]carbonyl}phenyl)-3-{4-[4-(morpholin-4-yl)-6-(tetrahydro-2H-pyran-4-yl)-1,3,5-triazin-2-yl]phenyl}urea | |
| 867 | 1-(4-{[(3S)-3-methylpiperazin-1-yl]carbonyl}phenyl)-3-{4-[4-(morpholin-4-yl)-6-(tetrahydro-2H-pyran-4-yl)-1,3,5-triazin-2-yl]phenyl}urea | |

TABLE I-continued

| Example | Name | MS (ESI) m/z |
|---|---|---|
| 868 | 1-(4-{[(3R)-3-(dimethylamino)pyrrolidin-1-yl]carbonyl}phenyl)-3-{4-[4-morpholin-4-yl-6-(tetrahydro-2H-pyran-4-yl)-1,3,5-triazin-2-yl]phenyl}urea | |
| 869 | 1-(4-{[(3S)-3-(dimethylamino)pyrrolidin-1-yl]carbonyl}phenyl)-3-{4-[4-morpholin-4-yl-6-(tetrahydro-2H-pyran-4-yl)-1,3,5-triazin-2-yl]phenyl}urea | |

Biological Evaluation mTOR Kinase Assay Methods

Human mTOR assays (See Toral-Barza, et al. *Biochem Biophys. Res. Commun.* 2005 Jun. 24; 332(1):304-10) with purified enzyme are performed in 96-well plates by DELFIA format as follows. Enzymes are first diluted in kinase assay buffer (10 mM HEPES (pH 7.4), 50 mM NaCl, 50 mM β-glycerophosphate, 10 mM $MnCl_2$, 0.5 mM DTT, 0.25 mM microcystin LR, and 100 mg/mL BSA). To each well, 12 µL of the diluted enzyme is mixed briefly with 0.5 µL test inhibitor or control vehicle dimethylsulfoxide (DMSO). The kinase reaction is initiated by adding 12.5 µL kinase assay buffer containing ATP and His6-S6K to give a final reaction volume of 25 µL containing 800 ng/mL FLAG-TOR, 100 mM ATP and 1.25 mM His6-S6K. The reaction plate is incubated for 2 hours (linear at 1-6 hours) at room temperature with gentle shaking and then terminated by adding 25 µL Stop buffer (20 mM HEPES (pH 7.4), 20 mM EDTA, 20 mM EGTA). The DELFIA detection of the phosphorylated (Thr-389) His6-S6K is performed at room temperature using a monoclonal anti-P(T389)-p70S6K antibody (1A5, Cell Signaling) labeled with Europium-N1-ITC (Eu) (10.4 Eu per antibody, PerkinElmer). The DELFIA Assay buffer and Enhancement solution can be purchased from PerkinElmer. 45 µL of the terminated kinase reaction mixture is transferred to a Max-iSorp plate (Nunc) containing 55 µL PBS. The His6-S6K is allowed to attach for 2 hours after which the wells are aspirated and washed once with PBS. 100 µL of DELFIA Assay buffer with 40 ng/mL Eu-P(T389)-S6K antibody is added. The antibody binding is continued for 1 hour with gentle agitation. The wells are then aspirated and washed 4 times with PBS containing 0.05% Tween-20 (PBST). 100 µL of DELFIA Enhancement solution is added to each well and the plates are read in a PerkinElmer Victor model plate reader. Data obtained is used to calculate enzymatic activity and enzyme inhibition by potential inhibitors.

PI3K-Alpha and PI3K-Gamma Fluorescence Polarization Assay Protocols

The reaction buffer was 20 mM HEPES, pH 7.5, 2 mM $MgCl_2$, 0.05% CHAPS; and 0.01% βME (added fresh). The Stop/Detection Buffer was 100 mM HEPES, pH 7.5, 4 mM EDTA, 0.05% CHAPS; ATP 20 mM in water; PIP2 (diC8, Echelon, Salt Lake City Utah cat #P-4508) 1 mM in water (MW=856.5). The GST-GRP was 1.75 mg/mL or 1.4 mg/mL in 10% glycerol. The Red detector (TAMRA) was 2.5 µM. Nunc 384-well black polypropylene fluorescent plates were used for PI3K assays.

The assay is run by placing 5 µL of diluted enzyme per well, then 5 µL of diluted compound (or 9.5 µL enzyme then 0.5 µL compound in DMSO) is added and mixed. Then, 10 µL substrate is added to start the reaction. The samples are incubated 30-60 minutes, then the reaction is stopped by adding 20 µL stop/detector mix. PI3K is diluted with reaction buffer (e.g., 5 µL or 7.5 µL PI3K into 620 µL reaction buffer), and 5 µL of diluted enzyme is used per well. A 5 µL portion of reaction buffer or of drug diluted in buffer (e.g., 4 µL/100 so final DMSO is 1% in reaction) is added to each. Pipetting up and down mixes the samples. Alternatively, the enzyme can be diluted to 1215 µL. In this case 9.8 µL is added per well and 0.2 µL compound is added in DMSO.

To prepare 1 mL of substrate solution, 955 µL reaction buffer, 40 µL PIP2, and 2.5 µL ATP are mixed. 10 µL of substrate is added to each well to start the reaction. This results in 20 µM PIP2, and 25 µM ATP per reaction. The stop/detector mix is prepared by mixing 4 µL Red detector and 1.6 µL or 2.0 µL GST-GRP with 1 mL stop buffer, which results in 10 nM probe and 70 nM GST-GRP. 20 µL of the stop/detector mix is added to each well to stop the reaction. The plates are read after 30-90 minutes keeping the red probe solutions dark. For the zero time point, stop/detector mix is added to the enzyme just before adding substrate. For an extra control, stop/detector mix is added to buffer (no enzyme) and substrate or to just buffer (no substrate). Pooled PI3K preparations had a protein concentration of 0.25 mg/mL. The recommended reaction has 0.06 µL per 20 µL (0.015 µg/20 µL) or 0.01125 µg/15 µL or 0.75 µg/mL.

Plates are read on machines with filters for TAMRA. The units are mP with no enzyme controls reading app 190-220 mP units. Fully active enzyme reduces fluorescence polarization down to 70-100 mP after 30 minutes. An active compound raises the mP values halfway to control or to 120-150 mP units.

In Vitro Cell Culture Growth Assay Methods

Cell Lines used are human breast MDA-MB-361, human prostate PC3-mm2, and human prostate LNCap tumor cell lines. Cells are plated in 96-well culture plates at approximately 3000 cells per well. One day following plating, various concentrations of PI3K inhibitors in DMSO are added to cells (final DMSO concentration in cell assays is 0.25%). Three days after drug treatment, viable cell densities are determined by cell mediated metabolic conversion of the dye MTS, a well-established indicator of cell proliferation in vitro. Cell growth assays are performed using kits purchased from Promega Corporation (Madison, Wis.), following the protocol provided by the vendor. Measuring absorbance at 490 nm generates MTS assay results. Compound effect on cell proliferation is assessed relative to untreated control cell growth. The drug concentration that conferred 50% inhibition of growth is determined as $IC_{50}$ (µM).

hSMG-1 Kinase Assay

The human SMG-1 (hSMG-1) kinase assay employs the recombinant hSMG-1 protein prepared from transiently transfected HEK293 cells and a GST-p53 (aa 1-70) fusion substrate protein derived from cellular tumor suppressor gene p53. The routine assay is performed in a 96-well plate format as follows. Enzymes were first diluted in kinase assay buffer (10 mM HEPES, pH 7.4, 50 mM NaCl, 0.2 mM DTT, 50 mM β-glycerophosphate, 0.5 μM microcystin LR, 10 mM $MnCl_2$). To each well, 12 μL of the diluted enzyme were mixed briefly with 0.5 μL test inhibitor or control vehicle dimethylsulfoxide (DMSO). The kinase reaction was initiated by adding 12.5 μL kinase assay buffer containing ATP and GST-p53 to give a final reaction volume of 25 μL containing 400-800 ng/mL FLAG-hSMG-1, 0.5 μg GST-p53, 10 μM ATP. The reaction was carried out at room temperature for 1.0 hour before terminated by addition of 25 μl stop solution. The assay mixture was then transferred to FluoroNunc Plates with MaxiSorp Surface (Nunc #439454). The plates were incubated at room temperature for 2 hr (4° C. for overnight) to achieve efficient binding of substrate protein to the plate. The plates were aspirated, washed with PBS. Phospho-substrate proteins were detected by incubating for 1 hour with 125 ng of europium-labeled anti-mouse secondary antibody (PerkinElmer AD2027) and the primary phospho(S15)-p53 monoclonal antibody (Cell Signal #9286) in 100 μL DELFIA assay buffer (PerkinElmer #1244-111). Plates were then washed and incubated for 0.5 hour with 100 μl of DELFIA enhancement solution (PerkinElmer #1244-105). DELFIA assay results are recorded in a Victor Plate Reader (PerkinElmer). Data obtained were used to calculate enzymatic activity and enzyme inhibition by potential inhibitors.

Table 2 shows the results of the described PI3K-α, PI3K-γl-, and mTOR kinase assays.

TABLE 2

| Example | $IC_{50}$ PI3Kα nM | $IC_{50}$ PI3Kγ nM | $IC_{50}$ mTOR M |
|---|---|---|---|
| 1 | 3 | 29 | 0.0013 |
| 2 | 2 | 35 | 0.001 |
| 3 | 3 | 27 | 0.00385 |
| 4 | 2 | 23 | 0.0017 |
| 5 | 17 | 438 | 0.0063 |
| 6 | 6 | 53 | 0.006 |
| 7 | >10000 | >100000 | >4,0000 |
| 8 | 20 | 220 | 0.008 |
| 9 | 10 | 65 | 0.004 |
| 10 | 75 | 289 | 0.068 |
| 11 | 61 | 528 | 0.00925 |
| 12 | 248 | 815 | 0.011 |
| 13 | 51 | 879 | 0.0115 |
| 14 | 25 | 154 | 0.00845 |
| 15 | 23 | 177 | 0.0025 |
| 16 | >10,000 | >100000 | 0.01205 |
| 17 | 8 | 90 | 0.01395 |
| 18 | 9 | 71 | 0.036 |
| 19 | 23 | 206 | 0.039 |
| 20 | 41 | 258 | 0.0305 |
| 21 | 22 | 92 | 0.00175 |
| 22 | 12 | 142 | 0.00475 |
| 23 | 18 | 51 | 0.00205 |
| 24 | 22 | 99 | 0.0027 |
| 25 | 58 | 105 | 0.00405 |
| 26 | 680 | 10,000 | 0.0025 |
| 27 | 1230 | >10,000 | 0.00415 |
| 28 | 54 | 5550 | 0.00095 |
| 29 | 2690 | >10,000 | 0.0028 |
| 30 | 2120 | >10,000 | 0.00265 |
| 31 | 142 | 3520 | 0.00049 |
| 32 | 45 | 2540 | 0.00029 |
| 33 | NA | NA | 0.091 |
| 34 | 9 | 95 | 0.00049 |
| 35 | 6 | 54 | 0.00021 |
| 36 | 17 | 150 | 0.00051 |
| 37 | 39 | 155 | 0.00195 |
| 38 | 7 | 91 | 0.00028 |

TABLE 2-continued

| Example | $IC_{50}$ PI3Kα nM | $IC_{50}$ PI3Kγ nM | $IC_{50}$ mTOR M |
|---|---|---|---|
| 39 | 14 | 75 | 0.00032 |
| 40 | 21 | 136 | 0.00066 |
| 41 | 69 | 122 | 0.0013 |
| 42 | 86 | 290 | 0.00335 |
| 43 | 28 | 35 | 0.00165 |
| 44 | NA | NA | 0.0135 |
| 45 | NA | NA | 0.0036 |
| 46 | 208 | 4920 | 0.024 |
| 47 | 13 | 52 | 0.0016 |
| 48 | 6 | 40 | 0.0018 |
| 49 | 3 | 21 | 0.01 |
| 50 | 1 | 21 | 0.002 |
| 51 | 1 | 15 | 0.0019 |
| 52 | 2 | 38 | 0.001 |
| 53 | 45 | 403 | 0.024 |
| 54 | 10 | 88 | 0.00475 |
| 55 | 205 | 1580 | 0.05 |
| 56 | 122 | 444 | 0.015 |
| 57 | 8 | 74 | 0.0165 |
| 58 | 13 | 85 | 0.0025 |
| 59 | 3 | 30 | 0.00105 |
| 60 | 5 | 36 | 0.0018 |
| 61 | 9 | 32 | 0.00076 |
| 62 | 2 | 24 | 0.00068 |
| 63 | 5 | 36 | 0.00195 |
| 64 | 1457 | 1190 | 1.5 |
| 65 | 15 | 83 | 0.00505 |
| 66 | 7 | 30 | 0.00165 |
| 67 | 6 | 48 | 0.00145 |
| 68 | 0.3 | 7 | 0.00057 |
| 69 | 0.4 | 8 | 0.00085 |
| 70 | 2 | 20 | 0.0007 |
| 71 | 0.4 | 8 | 0.00067 |
| 72 | 2 | 19 | 0.00085 |
| 73 | 0.3 | 7 | 0.00077 |
| 74 | 0.4 | 8 | 0.00063 |
| 75 | 0.6 | 10 | 0.00075 |
| 76 | 0.4 | 8 | 0.00067 |
| 77 | 0.3 | 4 | 0.00068 |
| 78 | 3 | 23 | 0.00085 |
| 79 | 773 | 193 | 0.0051 |
| 80 | 851 | 2120 | 0.00715 |
| 81 | 2 | 38 | 0.001 |
| 82 | 3 | 21 | 0.0089 |
| 83 | 1 | 15 | 0.0019 |
| 84 | 10 | 88 | 0.00475 |
| 85 | 45 | 403 | 0.018 |
| 86 | 122 | 444 | 0.01 |
| 87 | 205 | 1580 | 0.05 |
| 88 | 8 | 74 | 0.0165 |
| 89 | 10 | 31 | 0.0016 |
| 90 | 8 | 42 | 0.00083 |
| 91 | 6 | 73 | 0.00071 |
| 92 | 11 | 92 | 0.00235 |
| 93 | 12 | 133 | 0.00855 |
| 94 | 5 | 56 | 0.001 |
| 95 | 48 | 101 | 0.00275 |
| 96 | NA | NA | 0.0012 |
| 97 | NA | NA | 0.0011 |
| 98 | 1350 | 9000 | 2.1 |
| 99 | 1520 | 7500 | 0.46 |
| 100 | 5 | 38 | 0.0035 |
| 101 | 6 | 33 | 0.00044 |
| 102 | 6 | 84 | 0.0061 |
| 103 | 3 | 73 | 0.0053 |
| 104 | 19 | 234 | 0.015 |
| 105 | 14 | 112 | 0.0305 |
| 106 | 393 | 1840 | 0.00755 |
| 107 | 115 | 1490 | 0.019 |
| 108 | 586 | 4150 | 0.019 |
| 109 | 1460 | 2960 | 0.0735 |
| 110 | 884 | 3510 | 0.029 |
| 111 | 116 | 1830 | 0.0023 |
| 112 | 488 | 777 | 0.012 |
| 113 | NA | NA | 0.0037 |
| 114 | 106 | 1180 | 0.00315 |
| 115 | 109 | 2000 | 0.0032 |
| 116 | 1740 | 2310 | 0.0027 |

TABLE 2-continued

| Example | IC$_{50}$ PI3Kα nM | IC$_{50}$ PI3Kγ nM | IC$_{50}$ mTOR M |
|---|---|---|---|
| 117 | 177 | 3000 | 0.083 |
| 118 | 379 | 297 | 0.195 |
| 119 | 1240 | 7530 | 0.14 |
| 120 | 262 | 1550 | 0.079 |
| 121 | 1850 | 4000 | 0.0435 |
| 122 | 1160 | 9500 | 0.0745 |
| 123 | 760 | 6350 | 0.115 |
| 124 | 1650 | 9650 | 0.155 |
| 125 | 840 | 8750 | 0.016 |
| 126 | 510 | 5510 | 0.0195 |
| 127 | 1390 | 4730 | 0.0515 |
| 128 | 1330 | 10,000 | 0.031 |
| 129 | 7217 | 10,000 | 2.35 |
| 130 | 14 | 132 | 0.008 |
| 131 | 25 | 336 | 0.0145 |
| 132 | 14 | 234 | 0.026 |
| 133 | 39 | 8890 | 0.043 |
| 134 | 20 | 183 | 0.0245 |
| 135 | 15 | 143 | 0.034 |
| 136 | 208 | 4920 | 0.024 |
| 137 | 9 | 117 | 0.00855 |
| 138 | 123.5 | 459 | 0.0435 |
| 139 | 24 | 43 | 0.074 |
| 140 | 27 | 100 | 0.027 |
| 141 | 241 | 3380 | 0.026 |
| 142 | 3 | 50 | 0.0011 |
| 143 | 2 | 22 | 0.0012 |
| 144 | NA | NA | NA |
| 145 | 574 | 1000 | 0.009 |
| 146 | >10000 | >100000 | 0.003 |
| 147 | 1930 | 6830 | 0.006 |
| 148 | 300 | 620 | 0.008 |
| 149 | 889 | 1400 | 0.08 |
| 150 | 832 | >10,000 | 0.005 |
| 151 | 0.6 | 8117 | 0.007 |
| 152 | 2 | 5 | 0.002 |
| 153 | 868 | 10,000 | 0.015 |
| 154 | 275 | 3820 | 0.064 |
| 155 | 2300 | 4940 | 0.016 |
| 156 | 746 | 10,000 | 0.053 |
| 157 | 1451 | 7090 | 0.17 |
| 158 | 300 | 1290 | 0.007 |
| 159 | 133 | 3920 | 0.002 |
| 160 | 358 | 9070 | 0.007 |
| 161 | 39 | 155 | 0.03 |
| 162 | 10 | 495 | 0.023 |
| 163 | 2 | 9 | 0.0039 |
| 164 | 378 | 1380 | 4 |
| 165 | 9 | 101 | 0.028 |
| 166 | 4 | 33 | 0.06 |
| 167 | 0.8 | 7 | 0.00068 |
| 168 | 1 | 3 | 0.0036 |
| 169 | 408 | 7960 | 0.0083 |
| 170 | 384 | 9500 | 0.004 |
| 171 | 300 | 9500 | 0.0012 |
| 172 | 435 | 10,000 | 0.008 |
| 173 | 1210 | 10,000 | 0.084 |
| 174 | 861 | 727 | 0.0021 |
| 175 | 549 | 453 | 0.0048 |
| 176 | 1120 | 3730 | 0.022 |
| 177 | 5840 | 4120 | 0.0016 |
| 178 | >10,000 | >10,000 | 0.014 |
| 179 | 1 | 13 | 0.001 |
| 180 | 531 | 8000 | 0.0016 |
| 181 | 426 | 6730 | 0.011 |
| 182 | 308 | 5000 | 0.003 |
| 183 | 526 | 11000 | 0.014 |
| 184 | 30 | 143 | 0.004 |
| 185 | 1 | 18 | 0.0029 |
| 186 | 28 | 221 | 0.006 |
| 187 | 3 | 24 | 0.0035 |
| 188 | 7540 | 2380 | 0.011 |
| 189 | 19 | 203 | 0.028 |
| 190 | 780 | 1320 | 0.0063 |
| 191 | 435 | 4630 | 0.016 |
| 192 | 1120 | 453 | 0.043 |
| 193 | 401 | 3133 | 0.0008 |
| 194 | NA | NA | 0.027 |
| 195 | 115 | 498 | 0.021 |
| 196 | 6 | 55 | 0.013 |
| 197 | 2 | 36 | 0.024 |
| 198 | 2 | 33 | 0.002 |
| 199 | 44 | 144 | 0.001 |
| 200 | 14 | 128 | 0.0065 |
| 201 | 28 | 606 | 0.0009 |
| 202 | NA | NA | 0.0055 |
| 203 | NA | NA | 0.001 |
| 204 | NA | NA | 0.0035 |
| 205 | NA | NA | 0.002 |
| 206 | NA | NA | 0.056 |
| 207 | NA | NA | 0.00084 |
| 208 | Na | NA | 0.0005 |
| 209 | 24 | 99 | 0.009 |
| 210 | 6 | 31 | NA |
| 211 | 80 | 108 | 0.006 |
| 212 | 902 | 8770 | 0.0064 |
| 213 | 5280 | 10,000 | 0.0095 |
| 214 | 2670 | 10,000 | 0.0029 |
| 215 | 187 | 3160 | 0.0012 |
| 216 | 521 | 7030 | 0.003 |
| 217 | 253 | 3230 | 0.0032 |
| 218 | 279 | 2780 | 0.0026 |
| 219 | 561 | 8280 | 0.0059 |
| 220 | 275 | 2830 | 0.0035 |
| 221 | 214 | 4280 | 0.0027 |
| 222 | 152 | 572 | 0.0005 |
| 223 | 2 | 200 | NA |
| 224 | 444 | 5870 | 0.0004 |
| 225 | 109 | 388 | 0.047 |
| 226 | 75 | 294 | 0.062 |
| 227 | 23 | 81 | 0.0073 |
| 228 | 46 | 280 | 0.051 |
| 229 | 19 | 70 | 0.00077 |
| 230 | 22 | 119 | 0.0012 |
| 231 | 4 | 63 | 0.0025 |
| 232 | 6 | 37 | 0.083 |
| 233 | 55 | 121 | 0.0079 |
| 234 | 4534 | 9534 | NA |
| 235 | 3206 | 4110 | NA |
| 236 | 3 | 15 | 0.011 |
| 237 | 2 | 23 | 0.003 |
| 238 | 1 | 10 | 0.0036 |
| 239 | 11 | 38 | 0.0032 |
| 240 | 1 | 6 | 0.0016 |
| 241 | 6 | 23 | 0.009 |
| 242 | 2 | 24 | 0.007 |
| 243 | 1 | 9 | 0.0077 |
| 244 | 1 | 9 | 0.0051 |
| 245 | 1 | 13 | 0.01 |
| 246 | 1 | 12 | 0.015 |
| 247 | 2 | 5 | 0.019 |
| 248 | 2 | 18 | 0.0064 |
| 249 | 25 | 216 | 0.002 |
| 250 | 21 | 190 | 0.0009 |
| 251 | 2 | 21 | 0.006 |
| 252 | 22 | 184 | 0.018 |
| 253 | 8 | 267 | 0.009 |
| 254 | 63 | 253 | 0.017 |
| 255 | 48 | 85 | 0.016 |
| 256 | 68 | 182 | 0.032 |
| 257 | 90 | 323 | 0.085 |
| 258 | 403 | 6170 | 0.0023 |
| 259 | 408 | 5410 | 0.0024 |
| 260 | 417 | 4730 | 0.0009 |
| 261 | 158 | 2530 | 0.00031 |
| 262 | 105 | 954 | 0.00029 |
| 263 | 3 | 20 | 0.001 |
| 264 | 947 | 5440 | NA |
| 265 | 1079 | 10,000 | 0.0015 |
| 266 | 16 | 93 | 0.0017 |
| 267 | 17 | 58 | 0.0035 |
| 268 | 12 | 41 | 0.00039 |
| 269 | 6 | 140 | 0.08 |
| 270 | 68 | 318 | 0.16 |
| 271 | 2 | 23 | 0.013 |
| 272 | 5 | 54 | 0.03 |

TABLE 2-continued

| Example | IC$_{50}$ PI3Kα nM | IC$_{50}$ PI3Kγ nM | IC$_{50}$ mTOR M |
|---|---|---|---|
| 273 | 4 | 33 | 0.0008 |
| 274 | 34 | 616 | 0.059 |
| 275 | 46 | 711 | 0.07 |
| 276 | 34 | 597 | 0.06 |
| 277 | 30 | 276 | 0.06 |
| 278 | 26 | 344 | 0.25 |
| 279 | 10 | 70 | 0.035 |
| 280 | 5 | 29 | 0.004 |
| 281 | 2188 | 4981 | 2.8 |
| 282 | 10 | 32 | 0.0047 |
| 283 | 1 | 11 | 0.0031 |
| 284 | 0.7 | 12 | 0.0009 |
| 285 | 1127 | 3433 | 0.001 |
| 286 | 4195 | 10,000 | 120 |
| 287 | 253 | 3304 | 0.00016 |
| 288 | 226 | 2784 | 0.00097 |
| 289 | 955 | 3880 | 0.0015 |
| 290 | 97 | 166 | 0.15 |
| 291 | 368 | 711 | 0.19 |
| 292 | 1501 | 3693 | 0.07 |
| 293 | 764 | 533 | 0.5 |
| 294 | 9 | 26 | 0.018 |
| 295 | 19 | 81 | 0.029 |
| 296 | 13 | 35 | 0.021 |
| 297 | 38 | 70 | 0.01 |
| 298 | 2 | 24 | 0.021 |
| 299 | 3 | 34 | 0.08 |
| 300 | 39 | 106 | 0.0053 |
| 301 | 21 | 58 | 0.0008 |
| 302 | 35 | 263 | 0.036 |
| 303 | NA | NA | 0.017 |
| 304 | 2 | 18 | 0.0025 |
| 305 | 1 | 18 | 0.0006 |
| 306 | 1 | 19 | 0.0021 |
| 307 | 3 | 30 | 0.0028 |
| 308 | 3 | 14 | 0.0029 |
| 309 | 12 | 95 | 0.0035 |
| 310 | 14 | 82 | 0.0059 |
| 311 | 40 | 125 | 0.012 |
| 312 | 3440 | 10,000 | 0.037 |
| 313 | 1730 | 7490 | 0.037 |
| 314 | 1820 | 10,000 | 0.08 |
| 315 | 1100 | 7900 | 0.005 |
| 316 | 1410 | 2690 | 0.071 |
| 317 | 216 | 6830 | 0.084 |
| 318 | 15.5 | 679 | 0.855 |
| 319 | 80 | 1446 | 0.0044 |
| 320 | 3.3 | 25 | 0.0129 |
| 321 | 25 | 116 | 0.0165 |
| 322 | 2.4 | 30 | 0.006 |
| 323 | 2.9 | 32 | 0.007 |
| 324 | 1 | 22 | 0.0052 |
| 325 | 74 | 6244 | 0.0046 |
| 326 | 830 | 6189 | 0.0122 |
| 327 | 394 | 5899 | 0.0063 |
| 328 | 261 | 14,000 | 0.0046 |
| 329 | 9.5 | 385 | 0.00068 |
| 330 | 42 | 827 | 0.0033 |
| 331 | NA | NA | 0.0035 |
| 332 | NA | NA | 0.011 |
| 333 | NA | NA | 0.0058 |
| 334 | 16 | 680 | 0.0009 |
| 335 | 81 | 144 | 0.004 |
| 336 | 40 | 44 | 0.0036 |
| 337 | 7 | 98 | 0.07 |
| 338 | 3 | 77 | 0.022 |
| 339 | 71 | 485 | 0.09 |
| 340 | 92 | 706 | 0.046 |
| 341 | 10 | 48 | 0.012 |
| 342 | 20 | 127 | 0.0066 |
| 343 | 97 | 6700 | 0.04 |
| 344 | 1610 | 4140 | 1.5 |
| 345 | 43 | 112 | 0.08 |
| 346 | 43 | 89 | 0.023 |
| 347 | 796 | 8440 | NA |
| 348 | 1030 | 10,000 | NA |
| 349 | 59 | 163 | NA |
| 350 | 1 | 7 | NA |
| 351 | 3 | 16 | 0.0042 |
| 352 | 13.5 | 732 | 0.00024 |
| 353 | 8.5 | 501 | 0.00022 |
| 354 | 69 | 6224 | 0.0046 |
| 355 | 830 | 6189 | 0.012 |
| 356 | 394 | 5899 | 0.0063 |
| 357 | 261 | 14000 | 0.0046 |
| 358 | 9 | 363 | 0.00068 |
| 359 | 42 | 827 | 0.0034 |
| 360 | 6672 | >10000 | 0.082 |
| 361 | 6028 | >10000 | 0.0013 |
| 362 | 3090 | >10000 | 0.00074 |
| 363 | 1097 | 7142 | 0.00077 |
| 364 | 1465 | 8038 | 0.0035 |
| 365 | 6340 | >10000 | 0.0012 |
| 366 | 585 | 2996 | 0.0011 |
| 367 | 499 | 4076 | 0.001 |
| 368 | 109 | 1936 | 0.00068 |
| 369 | 362 | 2560 | 0.0013 |
| 370 | 483 | 3502 | 0.00085 |
| 371 | 389 | 2256 | 0.00084 |
| 372 | 961 | 7245 | 0.00025 |
| 373 | 70 | 2962 | 0.00016 |
| 374 | 64 | 3915 | 0.00014 |
| 375 | 44 | 2589 | 0.00015 |
| 376 | 2602 | >10000 | 0.0023 |
| 377 | 2614 | 4718 | 0.0039 |
| 378 | 2506 | 5375 | 0.0054 |
| 379 | 4749 | 5255 | 0.0073 |
| 380 | 3344 | 3559 | 0.0051 |
| 381 | 2955 | 5395 | 0.0059 |
| 382 | 522 | 4306 | 0.0045 |
| 383 | 2978 | 3609 | 0.0061 |
| 384 | 4220 | 5381 | 0.0064 |
| 385 | 3397 | 4692 | 0.0057 |
| 386 | 5122 | 4476 | 0.0042 |
| 387 | 3416 | 2858 | 0.0032 |
| 388 | 3450 | 4285 | 0.0048 |
| 389 | 4766 | 5663 | 0.0065 |
| 390 | 2467 | 2354 | 0.012 |
| 391 | 2398 | 4000 | 0.0096 |
| 392 | 1178 | 2781 | 0.0055 |
| 393 | 444 | 1539 | 0.0036 |
| 394 | 592 | 3226 | 0.0088 |
| 395 | 584 | 2221 | 0.014 |
| 396 | 586 | 2432 | 0.01 |
| 397 | 173 | 2073 | 0.00016 |
| 398 | 644 | 3909 | 0.00021 |
| 399 | 330 | 1691 | 0.0011 |
| 400 | 846 | 4099 | 0.0017 |
| 401 | 413 | 3247 | 0.002 |
| 402 | 543 | 3643 | 0.0018 |
| 403 | 314 | 2383 | 0.00075 |
| 404 | 63 | 433 | 0.00069 |
| 405 | 50 | 193 | 0.00064 |
| 406 | 478 | 1881 | 0.00038 |
| 407 | 766 | 2255 | 0.00052 |
| 408 | 876 | 3342 | 0.00072 |
| 409 | 856 | 4487 | 0.0015 |
| 410 | 826 | 5684 | 0.0023 |
| 411 | 1896 | >10000 | 0.0036 |
| 412 | 1230 | 7483 | 0.0073 |
| 413 | 1518 | >10000 | 0.0092 |
| 414 | 969 | 5453 | 0.0069 |
| 415 | 787 | 3263 | 0.00038 |
| 416 | 446 | 2505 | 0.00055 |
| 417 | 656 | 4299 | 0.0011 |
| 418 | 520 | 3476 | 0.0015 |
| 419 | 610 | 4272 | 0.0017 |
| 420 | 593 | 4363 | 0.00063 |
| 421 | 414 | 1571 | 0.00072 |
| 422 | 269 | 1221 | 0.00079 |
| 423 | 610 | 1854 | 0.0011 |
| 424 | 576 | 1871 | 0.0014 |
| 425 | 309 | 2383 | 0.0012 |
| 426 | 1224 | 8477 | 0.053 |
| 427 | 580 | 1419 | 0.0013 |
| 428 | 450 | 840 | 0.0014 |

TABLE 2-continued

| Example | IC$_{50}$ PI3Kα nM | IC$_{50}$ PI3Kγ nM | IC$_{50}$ mTOR M |
|---|---|---|---|
| 429 | 483 | 1005 | 0.0019 |
| 430 | 402 | 484 | 0.0017 |
| 431 | 43 | 340 | 0.001 |
| 432 | 90 | 480 | 0.00069 |
| 433 | 220 | 1510 | 0.0023 |
| 434 | 571 | 4740 | 0.00056 |
| 435 | 643 | 4603 | 0.00075 |
| 436 | 749 | 3119 | 0.00062 |
| 437 | 381 | 1612 | 0.00056 |
| 438 | 77 | 663 | 0.00081 |
| 439 | 182 | 1283 | 0.00042 |
| 440 | 1006 | >10000 | 0.0012 |
| 441 | 970 | >10000 | 0.0012 |
| 442 | 1756 | >10000 | 0.0015 |
| 443 | 427 | 1883 | 0.00089 |
| 444 | 60 | 1099 | 0.00057 |
| 445 | 100 | 1002 | 0.00041 |
| 446 | 835 | 4013 | 0.00082 |
| 447 | 390 | 2802 | 0.0019 |
| 448 | 519 | >10000 | 0.0023 |
| 449 | 287 | 1640 | 0.0019 |
| 450 | 76 | 888 | 0.0017 |
| 451 | 85 | 702 | 0.0014 |
| 452 | 41 | 502 | 0.00055 |
| 453 | 659 | 4273 | 0.0033 |
| 454 | 278 | 1490 | 0.0002 |
| 455 | 113 | 1390 | 0.0003 |
| 456 | 150 | 1547 | 0.0007 |
| 457 | 63 | 839 | 0.0002 |
| 458 | 33 | 512 | 0.0002 |
| 459 | 26 | 483 | 0.0003 |
| 460 | 143 | 1083 | 0.0004 |
| 461 | 482 | 4415 | 0.0011 |
| 462 | | | <0.001 |
| 463 | | | 0.017 |
| 464 | | | 0.001 |
| 465 | | | 0.001 |
| 466 | | | 0.001 |
| 467 | | | <0.001 |
| 468 | | | <0.001 |
| 469 | | | 0.023 |
| 470 | | | 0.007 |
| 471 | | | 0.000 |
| 472 | | | 0.035 |
| 473 | | | 0.035 |
| 474 | | | 0.048 |
| 475 | | | 18.500 |
| 476 | | | 0.005 |
| 477 | | | 14.000 |
| 478 | 1.1 | 6.0 | 0.00089 |
| 479 | <2.1 | 14.0 | 0.0017 |
| 480 | 13.0 | 53.0 | 0.0029 |
| 481 | 11.0 | 65.0 | 0.0023 |
| 482 | 0.6 | 10.0 | 0.00305 |
| 483 | 28.5 | 150.0 | 0.00155 |
| 484 | 1.0 | 8.0 | 0.00063 |
| 485 | 1.4 | 10.0 | 0.00125 |
| 486 | 1.1 | 7.0 | 0.0045 |
| 487 | 32.3 | 27.0 | 0.0018 |
| 488 | 42.0 | 180.0 | 0.0034 |
| 489 | 3671.7 | 9045.0 | 0.0022 |
| 490 | 586.0 | 1077.0 | 0.0116 |
| 491 | 3.5 | 17.0 | 0.0011 |
| 492 | 6.5 | 35.0 | 0.018 |
| 493 | 2924.0 | 1078.0 | 0.0325 |
| 494 | 16.5 | 104.0 | 0.0042 |
| 495 | <1.00 | 6.0 | 0.00195 |
| 496 | NA | NA | NA |
| 497 | 3.0 | 19.0 | 0.0046 |
| 498 | <1.70 | 2.5 | 0.00235 |
| 499 | <1.90 | 4.5 | 0.0022 |
| 500 | 0.4 | 10.0 | 0.00109 |
| 501 | <1.75 | 6.5 | 0.00069 |
| 502 | 0.5 | 6.0 | 0.001 |
| 503 | 0.5 | 1.8 | |
| 504 | 1.8 | 10.0 | 0.00135 |
| 505 | 0.6 | 5.0 | NA |
| 506 | 0.3 | 7.0 | NA |
| 507 | 1.6 | 8.7 | 0.0032 |
| 508 | <1.9 | 12.5 | 0.00097 |
| 509 | 11.5 | 662.5 | 0.00045 |
| 510 | 1.1 | 6.3 | 0.00089 |
| 511 | 2.3 | 10.3 | 0.00052 |
| 512 | <1.9 | 10.0 | 0.00012 |
| 513 | <2.4 | 12.0 | 0.00012 |
| 514 | 1.6 | 15.0 | 0.00017 |
| 515 | 0.4 | 7.6 | 0.00155 |
| 516 | 2.1 | 17.0 | NA |
| 517 | 3.4 | 18.5 | 0.00106 |
| 518 | 0.9 | 6.5 | 0.0011 |
| 519 | <1.1 | 4.8 | 0.00071 |
| 520 | 1.4 | 8.0 | 0.00038 |
| 521 | 1.4 | 6.0 | 0.0003 |
| 522 | 1.4 | 7.5 | 0.00106 |
| 523 | 3.2 | 9.5 | 0.00043 |
| 524 | 0.8 | 10.0 | 0.00026 |
| 525 | NA | NA | NA |
| 526 | 96.5 | 6701.5 | 0.0475 |
| 527 | 20.5 | 127.0 | 0.0093 |
| 528 | 1612.0 | 4140.0 | 1.6 |
| 529 | 10.5 | 48.5 | 0.0155 |
| 530 | 92.0 | 705.5 | 0.0495 |
| 531 | 71.5 | 484.5 | 0.08 |
| 532 | 3.0 | 76.5 | 0.019 |
| 533 | 7.0 | 98.5 | 0.0705 |
| 534 | 2.1 | 11.1 | 0.0534 |
| 535 | 43.5 | 112.0 | 0.0815 |
| 536 | 1.5 | 13.0 | 0.0094 |
| 537 | 43.5 | 89.0 | 0.000022 |
| 538 | 333.0 | 197.0 | 0.000125 |
| 539 | 1.1 | 16.0 | 0.0000085 |
| 540 | 54.0 | 121.0 | 0.0000034 |
| 541 | 28.000 | 57.000 | 0.017 |
| 542 | 8.000 | 67.000 | 0.0215 |
| 543 | 3.500 | 15.500 | 0.042 |
| 544 | 3.500 | 20.500 | 0.017 |
| 545 | 4.000 | 17.000 | 0.0109 |
| 546 | 3.500 | 73.500 | 0.000225 |
| 547 | 11.000 | 70.000 | 0.00775 |
| 548 | 40.000 | 387.000 | 0.00975 |
| 549 | 724.000 | 4541 | 0.0265 |
| 550 | 47.000 | 374.000 | 0.0124 |
| 551 | 24.000 | 117.500 | 0.01 |
| 552 | 11.500 | 127.000 | 0.00355 |
| 553 | 12.500 | 72.000 | 0.0195 |
| 554 | 15.000 | 156.500 | 0.0119 |
| 555 | 87.500 | 378.500 | 0.405 |
| 556 | 8.500 | 54.000 | 0.0044 |
| 557 | 18.000 | 64.000 | 0.00855 |
| 558 | 17.000 | 41.000 | 0.0061 |
| 559 | 2.000 | 13.500 | 0.01005 |
| 560 | 269.000 | 504.500 | 0.1 |
| 561 | 11.5 | 59.0 | 0.006 |
| 562 | 1.0 | 10.5 | 0.004 |
| 563 | 2.5 | 33.5 | 0.003 |
| 564 | 0.6 | 16.5 | 0.001 |
| 565 | 4.1 | 38.0 | 0.001 |
| 566 | 2.6 | 18.0 | 0.002 |
| 567 | 14.5 | 90.0 | 0.002 |
| 568 | 3.5 | 18.0 | 0.010 |
| 569 | 74.5 | 375.0 | 0.008 |
| 570 | 5.5 | 48.0 | 0.013 |
| 571 | 21.0 | 108.0 | 0.000 |
| 572 | 0.9 | 15.0 | 0.000 |
| 573 | 6.5 | 64.0 | 0.004 |
| 574 | 1.0 | 12.5 | 0.006 |
| 575 | 3.0 | 19.0 | 0.015 |
| 576 | 761.0 | 2081.0 | 0.140 |
| 577 | 63.0 | 104.0 | 0.030 |
| 578 | 2406.0 | 2511.0 | 2.100 |
| 579 | 462.0 | 658.0 | 0.120 |
| 580 | 465.0 | 1315.0 | 0.100 |
| 581 | 113.5 | 461.0 | 0.037 |
| 582 | 513.0 | 1094.0 | 0.230 |
| 583 | 123.0 | 718.0 | 0.048 |
| 584 | | | |

TABLE 2-continued

| Example | IC$_{50}$ PI3Kα nM | IC$_{50}$ PI3Kγ nM | IC$_{50}$ mTOR M |
|---|---|---|---|
| 585 | 65.0 | 131.0 | 0.012 |
| 586 | 947.0 | 1246.0 | 0.365 |
| 587 | 350.0 | 675.0 | 0.100 |
| 588 | 524.5 | 2249.0 | 0.054 |
| 589 | 718.0 | 1615.0 | 0.057 |
| 590 | 343.0 | 403.5 | 0.049 |
| 591 | 250.0 | 726.0 | 0.033 |
| 592 | 25.5 | 122.0 | 0.009 |
| 593 | 40.0 | 143.0 | 0.012 |
| 594 | 349.5 | 744.0 | 0.022 |
| 595 | 6.5 | 58.5 | 0.010 |
| 596 | 5.0 | 40.5 | 0.013 |
| 597 | 5.0 | 58.0 | 0.011 |
| 598 | 5.5 | 40.0 | 0.010 |
| 599 | 64.5 | 190.0 | 0.013 |
| 600 | 45.5 | 161.5 | 0.008 |
| 601 | 3.5 | 57.5 | 0.003 |
| 602 | 7.0 | 46.5 | 0.011 |
| 603 | 8.5 | 50.5 | 0.017 |
| 604 | 3.5 | 55.5 | 0.010 |
| 605 | 2.2 | 46.0 | 0.003 |
| 606 | 12.0 | 87.0 | 0.026 |
| 607 | 12.0 | 94.0 | 0.019 |
| 608 | 9.0 | 107.0 | 0.005 |
| 609 | 11.5 | 93.5 | 0.003 |
| 610 | 3.5 | 50.5 | 0.005 |
| 611 | 18.5 | 151.5 | 0.013 |
| 612 | 5.5 | 67.0 | 0.061 |
| 613 | 3.8 | 53.5 | 0.001 |
| 614 | 2.7 | 32.5 | 0.001 |
| 615 | 26.5 | 115.5 | 0.001 |
| 616 | 4.0 | 58.5 | 0.001 |
| 617 | 2.5 | 27.0 | 0.001 |
| 618 | 2.0 | 18.5 | 0.001 |
| 619 | 33.0 | 137.0 | 0.001 |
| 620 | 4.0 | 32.5 | 0.003 |
| 621 | 3.5 | 43.5 | 0.001 |
| 622 | 3.0 | 50.5 | 0.000 |
| 623 | 12.5 | 104.0 | 0.001 |
| 624 | 17.5 | 58.5 | 0.001 |
| 625 | 16.5 | 102.5 | 0.003 |
| 626 | 59.0 | 207.5 | 0.001 |
| 627 | 18.5 | 101.5 | 0.002 |
| 628 | | | |
| 629 | 26.0 | 95.0 | 0.004 |
| 630 | 13.5 | 84.5 | 0.001 |
| 631 | 28.0 | 133.0 | 0.004 |
| 632 | 15.0 | 74.5 | 0.001 |
| 633 | 11.5 | 175.0 | 0.001 |
| 634 | 6.0 | 121.5 | 0.000 |
| 635 | 22.0 | 377.5 | 0.000 |
| 636 | 231.0 | 468.5 | 0.027 |
| 637 | 21.5 | 190.5 | 0.004 |
| 638 | 16.0 | 113.5 | 0.002 |
| 639 | 14.5 | 123.0 | 0.001 |
| 640 | 345.0 | 795.0 | 2.800 |
| 641 | 88.5 | 275.5 | 0.007 |
| 642 | 69.0 | 254.5 | 0.001 |
| 643 | 6.2 | 42.5 | 0.007 |
| 644 | 7.8 | 59.5 | 0.001 |
| 645 | 105.0 | 230.5 | 0.120 |
| 646 | 23.0 | 85.5 | 0.006 |
| 647 | 24.3 | 107.0 | 0.003 |
| 648 | 2.0 | 27.0 | 0.003 |
| 649 | 6.4 | 38.0 | 0.006 |
| 650 | 23.5 | 103.5 | 0.022 |
| 651 | 71.0 | 247.5 | 0.014 |
| 652 | 36.0 | 84.5 | 0.004 |
| 653 | 4.1 | 34.0 | 0.007 |
| 654 | 6.0 | 70.0 | 0.008 |
| 655 | 91.5 | 745.5 | 0.625 |
| 656 | 73.0 | 651.0 | 0.019 |
| 657 | 11.5 | 127.5 | 0.385 |
| 658 | 41.5 | 265.0 | 0.020 |
| 659 | 3621.0 | 10000.0 | 0.720 |
| 660 | 7.5 | 168.5 | 0.305 |
| 661 | 56.5 | 461.5 | 0.580 |
| 662 | 34.3 | 197.0 | 0.770 |
| 663 | 47.3 | 296.0 | 0.590 |
| 664 | NA | NA | NA |
| 665 | 71.0 | 283.5 | 0.445 |
| 666 | 11.5 | 662.5 | 0.000 |
| 667 | 102 | 1081 | 0.000405 |
| 668 | 122 | 625.000 | 0.00056 |
| 669 | 8.0 | 89.0 | 0.00048 |
| 670 | 5.0 | 53.0 | 0.000212 |
| 671 | 17.5 | 150.5 | 0.000505 |
| 672 | 39.5 | 154.5 | 0.00195 |
| 673 | 7.0 | 98.7 | 0.00043 |
| 674 | 14.0 | 74.5 | 0.000325 |
| 675 | 21.0 | 135.5 | 0.00066 |
| 676 | 69.5 | 122.0 | 0.0013 |
| 677 | 86.5 | 290.0 | 0.00335 |
| 678 | 21.3 | 45.3 | 0.001168 |
| 679 | 1575.0 | 9500.0 | 0.0135 |
| 680 | 504.0 | 2083.0 | 0.0036 |
| 681 | 2547 | >10,000 | 0.091 |
| 682 | 84.3 | 1282.5 | 0.0885 |
| 683 | 121.3 | 1329.0 | 0.025 |
| 684 | 154.3 | 2345.0 | 0.0235 |
| 685 | 7.0 | 26.5 | 0.000825 |
| 686 | 77.0 | 540.0 | 0.026 |
| 687 | 4.0 | 39.5 | 0.00485 |
| 688 | 3.0 | 35.5 | 0.008 |
| 689 | 217.4 | 2482 | 0.03902 |
| 690 | 5.0 | 83.5 | 0.000525 |
| 691 | 6.0 | 199.0 | 0.00135 |
| 692 | 3.2 | 29.0 | 0.00375 |
| 693 | 69.0 | 289.0 | 0.00135 |
| 694 | 2.0 | 40.0 | 0.000245 |
| 695 | 4.0 | 70.5 | 0.00028 |
| 696 | 4.5 | 73.5 | 0.000275 |
| 697 | 2.7 | 42.7 | 0.000459 |
| 698 | 2.7 | 44.7 | 0.000302 |
| 699 | 5.0 | 62.5 | 0.0003 |
| 700 | 2.5 | 41.5 | 0.00053 |
| 701 | 2.0 | 25.0 | 0.00036 |
| 702 | 6.5 | 125.5 | 0.000555 |
| 703 | 1.5 | 23.5 | 0.00051 |
| 704 | 7217 | >10,000 | 2.35 |
| 705 | 13.5 | 132.0 | 0.0124 |
| 706 | 25.5 | 336.0 | 0.0145 |
| 707 | 14.0 | 234.5 | 0.034 |
| 708 | 39.5 | 8890.5 | 0.043 |
| 709 | 20.0 | 182.5 | 0.0245 |
| 710 | 15.5 | 143.5 | 0.034 |
| 711 | 207.5 | 4919.5 | 0.02 |
| 712 | 9.5 | 117.0 | 0.00855 |
| 713 | 36.0 | 444.0 | 0.0009 |
| 714 | 15.5 | 69.0 | 0.00645 |
| 715 | 59.5 | 146.5 | 0.006 |
| 716 | NA | NA | NA |
| 717 | 444.0 | 5874.0 | 0.000395 |
| 718 | 40.5 | 210.5 | 0.055 |
| 719 | 17.5 | 96.0 | 0.00015 |
| 720 | 0.4 | 7.0 | 0.0077 |
| 721 | 0.6 | 10.5 | 0.00565 |
| 722 | 0.8 | 9.5 | 0.0145 |
| 723 | 1.3 | 13.5 | 0.0225 |
| 724 | 1.5 | 4.0 | 0.0185 |
| 725 | 2.0 | 20.5 | 0.0082 |
| 726 | 25.0 | 216.5 | 0.0025 |
| 727 | 21.0 | 189.5 | 0.000805 |
| 728 | 10.5 | 47.0 | 0.00038 |
| 729 | 14.5 | 100.0 | 0.00185 |
| 730 | 15.5 | 64.5 | 0.0043 |
| 731 | 33.0 | 413.0 | 0.059 |
| 732 | 44.0 | 478.0 | 0.069 |
| 733 | 31.5 | 412.0 | 0.0755 |
| 734 | 25.5 | 210.0 | 0.0595 |
| 735 | 26.5 | 289.5 | 0.1225 |
| 736 | 9.5 | 53.5 | 0.0036 |
| 737 | 7.0 | 30.0 | 0.00445 |
| 738 | NA | NA | NA |
| 739 | NA | NA | NA |
| 740 | 11.5 | 34.5 | 0.00405 |

TABLE 2-continued

| Example | IC$_{50}$ PI3Kα nM | IC$_{50}$ PI3Kγ nM | IC$_{50}$ mTOR M |
|---|---|---|---|
| 741 | 2188 | 4981 | 2.80 |
| 742 | 97.0 | 166.0 | 0.145 |
| 743 | 368.0 | 711.0 | 0.19 |
| 744 | 1501.0 | 3693.0 | 0.068 |
| 745 | 764.0 | 533.0 | 0.47 |
| 746 | 23.5 | 99.0 | 0.001265 |
| 747 | 40.0 | 44.0 | 0.00345 |
| 748 | NA | NA | NA |
| 749 | 59.0 | 163.5 | 0.002 |
| 750 | NA | NA | NA |
| 751 | 143.0 | 403.5 | 0.003 |
| 752 | 1.2 | 18.5 | 0.00029 |
| 753 | 2.0 | 31.0 | 0.000315 |
| 754 | 3.0 | 28.0 | 0.000327 |
| 755 | 2.0 | 26.5 | 0.00057 |
| 756 | 0.5 | 7.0 | 0.0002 |
| 757 | 5.5 | 37.5 | 0.00028 |
| 758 | 2.0 | 16.0 | 0.00017 |
| 759 | 2.0 | 38.0 | 0.00016 |
| 760 | 4.3 | 28.3 | 0.00021 |
| 761 | 2.0 | 19.0 | 0.00012 |
| 762 | 2.7 | 19.7 | 0.000428 |
| 763 | 3.0 | 24.0 | 0.000445 |
| 764 | 8.5 | 67.5 | 0.00021 |
| 765 | 8.5 | 78.5 | 0.000195 |
| 766 | 24.0 | 85.5 | 0.001315 |
| 767 | 2.1 | 17.0 | 0.0002 |
| 768 | 1.2 | 18.5 | 0.000115 |
| 769 | 2.1 | 17.5 | 0.00023 |
| 770 | 30.5 | 99.0 | 0.00027 |
| 771 | 19.5 | 66.0 | 0.000215 |
| 772 | 0.8 | 9.5 | 0.00029 |
| 773 | 3.0 | 36.5 | 0.000305 |
| 774 | 2.0 | 41.5 | 0.00023 |
| 775 | 2.5 | 46.5 | 0.00023 |
| 776 | 3.0 | 29.5 | 0.000345 |
| 777 | 4.0 | 39.0 | 0.000265 |
| 778 | 11.5 | 126.0 | 0.00028 |
| 779 | 4.2 | 49.7 | 0.00023 |
| 780 | NA | NA | NA |
| 781 | 136.0 | 374.5 | 0.0305 |
| 782 | 124.5 | 251.5 | 0.11 |
| 783 | 346.0 | 736.0 | 0.295 |
| 784 | 40.5 | 174.0 | 0.088 |
| 785 | 6.0 | 45.5 | 0.0555 |
| 786 | 30.5 | 129.0 | 0.089 |
| 787 | 10.5 | 145.5 | 0.0585 |
| 788 | 13.0 | 160.0 | 0.026 |
| 789 | 870.0 | 1163.0 | 0.059 |
| 790 | 244.0 | 593.0 | 0.065 |
| 791 | 12.5 | 64.5 | 0.00068 |
| 792 | 3.3 | 35.5 | 0.00081 |
| 793 | 1.0 | 15.0 | 0.00042 |
| 794 | 4.1 | 26.0 | 0.00063 |
| 795 | 2.7 | 26.5 | 0.000425 |
| 796 | 2.6 | 31.5 | 0.00039 |
| 797 | 11.5 | 76.0 | 0.0013 |
| 798 | 4.1 | 43.5 | 0.000445 |
| 799 | 5.0 | 71.5 | 0.0005 |
| 800 | 5.5 | 35.5 | 0.00072 |
| 801 | 5.0 | 38.0 | 0.000455 |
| 802 | 3.5 | 23.0 | 0.000675 |
| 803 | 3.0 | 29.0 | 0.00019 |
| 804 | 6.0 | 59.5 | 0.000425 |
| 805 | 6.5 | 64.0 | 0.000415 |
| 806 | 4.5 | 47.0 | 0.00024 |
| 807 | Na | NA | NA |
| 808 | 381.0 | 1261.0 | 0.26 |
| 809 | 395.0 | 2189.0 | 0.067 |
| 810 | 2.8 | 30.5 | 0.00205 |
| 811 | 3.2 | 33.5 | 0.0015 |
| 812 | 2.8 | 30.5 | 0.002 |
| 813 | 3.1 | 30.0 | 0.0019 |
| 814 | 0.8 | 10.0 | 0.00105 |
| 815 | 1.9 | 24.0 | 0.000765 |
| 816 | 2.4 | 26.0 | 0.001065 |
| 817 | NA | NA | NA |
| 818 | 37.7 | 185.0 | 0.002 |
| 819 | 44.0 | 357.5 | 0.017 |
| 820 | 6.1 | 67.0 | 0.000515 |
| 821 | 9.3 | 58.3 | 0.0034 |
| 822 | 3.0 | 31.5 | 0.000335 |
| 823 | 661.0 | 2788.0 | 0.0000015 |
| 824 | 2 | 17 | NA |
| 825 | 2 | 13 | NA |
| 826 | 15 | 96 | 1.200 |
| 827 | 71.000 | 283.500 | 445.000 |
| 828 | 47.333 | 296.000 | 590.000 |
| 829 | 34.333 | 197.000 | 770.000 |
| 830 | 2.125 | 10.800 | 0.393 |
| 831 | 0.950 | 7.500 | 0.635 |
| 832 | 1.350 | 10.500 | 1.250 |
| 833 | 2.575 | 8.250 | 0.430 |
| 834 | 0.750 | 10.000 | 0.255 |
| 835 | 4.150 | 18.500 | 8.550 |
| 836 | 5.000 | 17.500 | 4.050 |
| 837 | 11.900 | 75.000 | 1.450 |
| 838 | 4.950 | 24.500 | 0.965 |
| 839 | 6.650 | 29.000 | 2.500 |
| 840 | 5.150 | 15.000 | 1.700 |
| 841 | 6.500 | 107.500 | 0.990 |
| 842 | 3.550 | 54.500 | 0.325 |
| 843 | 28.500 | 291.000 | 1500.000 |
| 844 | 21.000 | 237.500 | 345.000 |
| 845 | 0.250 | 2.750 | 1.300 |
| 846 | 3.500 | 22.500 | 485.000 |
| 847 | 10.500 | 87.500 | 165.000 |
| 848 | 1.050 | 6.000 | 2.200 |
| 849 | 0.300 | 3.167 | 0.865 |
| 850 | 0.650 | 6.100 | 1.200 |
| 851 | 0.850 | 5.600 | 1.010 |
| 852 | 0.400 | 5.550 | 1.250 |
| 853 | 0.300 | 5.050 | 1.400 |
| 854 | 8.840 | 164.000 | 260.000 |
| 855 | 54.000 | 864.000 | 305.000 |
| 856 | 28.500 | 532.000 | 11.000 |
| 857 | 10.000 | 145.500 | 660.000 |
| 858 | 5.000 | 134.500 | 290.000 |
| 859 | 17.850 | 239.500 | 830.000 |
| 860 | 57.000 | 434.500 | 150.000 |
| 861 | 4.000 | 56.000 | 425.000 |
| 862 | 23.500 | 154.000 | 835.000 |
| 863 | 2.100 | 8.000 | 3.600 |
| 864 | 1.000 | 7.500 | 5.250 |
| 865 | 2.450 | 12.000 | 1.350 |
| 866 | 1.600 | 16.500 | 0.980 |
| 867 | 0.400 | 7.000 | 0.610 |
| 868 | 0.650 | 4.500 | |
| 869 | 0.600 | 6.500 | |

Table 3 shows the results of the described hSMG-1 kinase assay.

TABLE 3

| Example | hSMG-1 IC$_{50}$ (μM) |
|---|---|
| 462 | 0.001 |
| 463 | 0.510 |
| 464 | 0.003 |
| 465 | 0.005 |
| 466 | 0.000 |
| 467 | 0.000 |
| 468 | <0.000 |
| 469 | 0.130 |
| 470 | 0.195 |
| 471 | 0.005 |
| 472 | 0.200 |
| 473 | 3.650 |
| 474 | 5.650 |

TABLE 3-continued

| Example | hSMG-1 IC$_{50}$ (μM) |
|---|---|
| 475 | >20 |
| 476 | 0.019 |
| 477 | 9.250 |

Table 4 shows the results of the described MDA-MB-361, PC3-mm2, and LNCap assays.

TABLE 4

| Example | IC$_{50}$ MDA-MB-361 (nM) | IC$_{50}$ PC3-mm2 (nM) | IC$_{50}$ LNCap (nM) |
|---|---|---|---|
| 1 | 45.0 | 43.0 | |
| 2 | 45.0 | 43.0 | |
| 3 | 45.0 | 43.0 | |
| 4 | 45.0 | 43.0 | |
| 5 | 45.0 | 43.0 | |
| 6 | 45.0 | 43.0 | |
| 7 | ND | ND | |
| 8 | 407.0 | 293.0 | |
| 9 | 102.0 | 161.0 | |
| 10 | 2709.0 | 1782.0 | |
| 11 | 794.0 | 5630.5 | |
| 12 | ND | ND | |
| 13 | 603.0 | 845.0 | |
| 14 | 376.0 | 590.0 | |
| 15 | 255.0 | 328.0 | |
| 16 | ND | ND | |
| 17 | 501.0 | 994.0 | |
| 18 | 2656.0 | 7102.0 | |
| 19 | 1031.0 | 1596.0 | |
| 20 | >10000 | >10000 | |
| 21 | 129.0 | 246.0 | |
| 22 | 1424.0 | 2445.0 | |
| 23 | 104.0 | 147.0 | |
| 24 | 122.0 | 142.0 | |
| 25 | 264.0 | 258.0 | |
| 26 | ND | ND | 190.0 |
| 27 | ND | ND | 350.0 |
| 28 | ND | ND | 2.4 |
| 29 | ND | ND | 180.0 |
| 30 | ND | ND | 90.0 |
| 31 | ND | ND | 45.0 |
| 32 | ND | ND | 0.7 |
| 33 | ND | ND | |
| 34 | 28.0 | 41.0 | |
| 35 | 22.5 | 27.5 | |
| 36 | 73.0 | 98.0 | |
| 37 | 98.0 | 176.0 | |
| 38 | 15.0 | 28.0 | |
| 39 | 22.0 | 30.0 | |
| 40 | <30 | 62.0 | |
| 41 | 167.0 | 301.0 | |
| 42 | 345.0 | 3600.0 | |
| 43 | 35.8 | 40.0 | |
| 44 | ND | ND | |
| 45 | ND | ND | |
| 46 | ND | ND | |
| 47 | 116.0 | 95.0 | |
| 48 | 38.0 | 48.0 | |
| 49 | 84.0 | 79.0 | |
| 50 | 36.0 | 39.0 | |
| 51 | <30 | <30 | |
| 52 | <30 | 49.0 | |
| 53 | 662.0 | 987.0 | |
| 54 | 133.0 | 214.0 | |
| 55 | ND | ND | |
| 56 | ND | ND | |
| 57 | 119.0 | 187.0 | |
| 58 | 115.0 | 45.0 | |
| 59 | 14.0 | 16.0 | |
| 60 | 83.0 | 92.0 | |
| 61 | 48.0 | 23.0 | |
| 62 | 27.0 | 34.0 | |
| 63 | 69.0 | 62.0 | |
| 64 | ND | ND | |
| 65 | 151.0 | 267.0 | |
| 66 | 59.0 | 66.0 | |
| 67 | 816.0 | 28.0 | |
| 68 | <3 | 11.0 | |
| 69 | 10.0 | 13.0 | |
| 70 | 19.0 | 24.0 | |
| 71 | <9.8 | 18.3 | |
| 72 | 1.0 | 13.0 | |
| 73 | 30.0 | 107.0 | |
| 74 | <3 | 8.3 | |
| 75 | <3 | 7.0 | |
| 76 | 4.0 | 13.1 | |
| 77 | <30 | <30 | |
| 78 | 68.0 | 31.0 | |
| 79 | ND | 320.0 | |
| 80 | ND | 320.0 | |
| 81 | ND | ND | |
| 82 | ND | ND | |
| 83 | ND | ND | |
| 84 | ND | ND | |
| 85 | ND | ND | |
| 86 | ND | ND | |
| 87 | ND | ND | |
| 88 | ND | ND | |
| 89 | 30.0 | 47.0 | |
| 90 | 19.0 | 19.0 | |
| 91 | 25.0 | 1567.0 | |
| 92 | 140.0 | 87.0 | |
| 93 | 42.0 | 60.0 | |
| 94 | 54.0 | 82.0 | |
| 95 | 333.0 | 364.0 | |
| 96 | 5.0 | 33.0 | |
| 97 | <30 | 52.0 | |
| 98 | ND | ND | |
| 99 | ND | ND | |
| 100 | 56.0 | 56.0 | |
| 101 | 32.7 | 37.3 | 3.0 |
| 102 | 592.0 | 854.0 | |
| 103 | 2917.0 | 4453.0 | |
| 104 | 412.0 | 684.0 | |
| 105 | 3710.0 | >10000 | |
| 106 | ND | ND | 370.0 |
| 107 | ND | ND | 1000.0 |
| 108 | ND | ND | 320.0 |
| 109 | ND | ND | 1900.0 |
| 110 | ND | ND | 220.0 |
| 111 | ND | ND | 58.0 |
| 112 | ND | ND | 300.0 |
| 113 | ND | ND | 120.0 |
| 114 | ND | ND | 38.0 |
| 115 | ND | ND | 200.0 |
| 116 | ND | ND | 70.0 |
| 117 | ND | ND | 700.0 |
| 118 | ND | ND | 3000.0 |
| 119 | ND | ND | 2800.0 |
| 120 | ND | ND | 1200.0 |
| 121 | ND | ND | 1000.0 |
| 122 | ND | ND | 900.0 |
| 123 | ND | ND | 4100.0 |
| 124 | ND | ND | 1950.0 |
| 125 | ND | ND | 1000.0 |
| 126 | ND | ND | 1300.0 |
| 127 | ND | ND | 1350.0 |
| 128 | ND | ND | 30000.0 |
| 129 | ND | ND | |
| 130 | 191.0 | 416.0 | |
| 131 | 696.0 | 839.0 | |
| 132 | 586.0 | 1012.0 | |
| 133 | 795.0 | 1950.0 | |
| 134 | 805.0 | 857.0 | |
| 135 | 533.0 | 509.0 | |
| 136 | ND | ND | |
| 137 | 582.0 | 551.0 | |
| 138 | ND | ND | 680.0 |

TABLE 4-continued

| Example | IC$_{50}$ MDA-MB-361 (nM) | IC$_{50}$ PC3-mm2 (nM) | IC$_{50}$ LNCap (nM) |
|---|---|---|---|
| 139 | ND | ND | 180.0 |
| 140 | 225 | 279 | |
| 141 | ND | ND | |
| 142 | 5 | 33 | |
| 143 | ND | 52 | |
| 144 | ND | ND | 1500 |
| 145 | ND | ND | 120 |
| 146 | ND | ND | 5 |
| 147 | ND | ND | 1000 |
| 148 | ND | ND | 680 |
| 149 | ND | ND | 32000 |
| 150 | ND | ND | 290 |
| 151 | ND | 14 | |
| 152 | 9 | 14 | |
| 153 | ND | ND | 4200 |
| 154 | ND | ND | 22000 |
| 155 | ND | ND | 400 |
| 156 | ND | ND | 22000 |
| 157 | ND | ND | 2700 |
| 158 | ND | ND | 49 |
| 159 | ND | ND | 1.2 |
| 160 | ND | ND | 220 |
| 161 | 328 | 675 | |
| 162 | ND | ND | |
| 163 | 10.7 | 28.3 | |
| 164 | ND | ND | |
| 165 | 210 | 333 | |
| 166 | 134 | 249 | |
| 167 | ND | 10 | |
| 168 | ND | ND | |
| 169 | ND | ND | 5000 |
| 170 | ND | ND | 4500 |
| 171 | ND | ND | 5200 |
| 172 | ND | ND | 9500 |
| 173 | ND | ND | 2500 |
| 174 | ND | ND | 4.25 |
| 175 | ND | ND | 9.5 |
| 176 | ND | ND | 1000 |
| 177 | ND | ND | 600 |
| 178 | ND | ND | 850 |
| 179 | ND | 8.333 | |
| 180 | ND | ND | 5800 |
| 181 | ND | ND | 3400 |
| 182 | ND | ND | 3500 |
| 183 | ND | ND | 8500 |
| 184 | 1246 | 2094 | |
| 185 | 5 | 13 | |
| 186 | 473 | 703 | |
| 187 | 11 | 41 | |
| 188 | ND | ND | |
| 189 | 84 | 99 | |
| 190 | ND | ND | 950 |
| 191 | ND | ND | 220 |
| 192 | ND | ND | 620 |
| 193 | ND | ND | 105 |
| 194 | ND | ND | 600 |
| 195 | ND | ND | |
| 196 | 50 | 82 | |
| 197 | 17 | 49 | |
| 198 | ND | 43 | |
| 199 | 96 | 93 | |
| 200 | 162 | 248 | |
| 201 | 29 | 44 | |
| 202 | ND | ND | 700 |
| 203 | ND | ND | 78 |
| 204 | ND | ND | 6000 |
| 205 | ND | ND | 400 |
| 206 | ND | ND | 5100 |
| 207 | ND | ND | 33.333 |
| 208 | ND | ND | 50 |
| 209 | 174 | 278 | |
| 210 | ND | ND | |
| 211 | 254 | 389 | |
| 212 | ND | ND | 420 |
| 213 | ND | ND | 420 |
| 214 | ND | ND | 700 |
| 215 | ND | ND | 30 |
| 216 | 0 | ND | 50 |
| 217 | ND | ND | 13 |
| 218 | ND | ND | 12 |
| 219 | ND | ND | 40 |
| 220 | ND | ND | 40 |
| 221 | ND | ND | 120 |
| 222 | ND | ND | 10 |
| 223 | 187 | 229 | |
| 224 | ND | ND | |
| 225 | ND | ND | |
| 226 | ND | ND | |
| 227 | 1495 | 4026 | |
| 228 | 3924 | 7174 | |
| 229 | 35.75 | 40 | |
| 230 | ND | ND | |
| 231 | 20 | 121 | |
| 232 | 38 | 177 | |
| 233 | 1214 | 3337 | |
| 234 | ND | ND | 10000 |
| 235 | ND | ND | 7900 |
| 236 | 22.333 | 67 | |
| 237 | 28 | 69 | |
| 238 | 23 | 61 | |
| 239 | 184 | 317 | |
| 240 | ND | 12 | |
| 241 | 24 | 135 | |
| 242 | 11 | 49 | |
| 243 | 15 | 34 | |
| 244 | ND | 71 | |
| 245 | 110 | 374 | |
| 246 | 35 | 91 | |
| 247 | 30 | 111 | |
| 248 | ND | 69 | |
| 249 | 92 | 142 | |
| 250 | 14 | 31 | |
| 251 | ND | 65 | |
| 252 | 219 | 747 | |
| 253 | 12 | 574 | |
| 254 | ND | ND | |
| 255 | 174 | 328 | |
| 256 | ND | ND | |
| 257 | ND | ND | |
| 258 | ND | ND | 60 |
| 259 | ND | ND | 580 |
| 260 | ND | ND | 380 |
| 261 | ND | ND | 30 |
| 262 | ND | ND | 22 |
| 263 | 68 | 31 | |
| 264 | ND | ND | |
| 265 | ND | ND | 1.7 |
| 266 | ND | ND | |
| 267 | 94 | 200 | |
| 268 | 59 | 107 | 38 |
| 269 | ND | 144 | |
| 270 | 397 | 953 | |
| 271 | 68 | 129 | |
| 272 | 70 | 340 | |
| 273 | 32 | 80 | |
| 274 | 1000 | 1491 | |
| 275 | 3100 | 4309 | |
| 276 | 1347 | 1654 | |
| 277 | 530 | 572 | |
| 278 | 2297 | 3701 | |
| 279 | 176 | 247 | |
| 280 | 176 | 404 | |
| 281 | ND | ND | |
| 282 | 83 | 84 | |
| 283 | 12.333 | 33.333 | |
| 284 | 12 | 36.333 | |
| 285 | ND | ND | 4 |
| 286 | ND | ND | 32000 |
| 287 | ND | ND | |
| 288 | ND | ND | 3 |
| 289 | ND | ND | 3 |
| 290 | ND | ND | |

TABLE 4-continued

| Example | IC$_{50}$ MDA-MB-361 (nM) | IC$_{50}$ PC3-mm2 (nM) | IC$_{50}$ LNCap (nM) |
|---|---|---|---|
| 291 | ND | ND | |
| 292 | ND | ND | |
| 293 | ND | ND | |
| 294 | 69 | 154 | |
| 295 | 133 | 189 | |
| 296 | 83 | 133 | |
| 297 | 115 | 290 | |
| 298 | 38 | 165 | |
| 299 | 73 | 219 | |
| 300 | 297 | 340 | |
| 301 | 430 | 759 | |
| 302 | 299 | 539 | |
| 303 | ND | ND | 0.8 |
| 304 | 7 | 39.333 | |
| 305 | 4 | 46 | |
| 306 | 7 | 30 | |
| 307 | ND | 362 | |
| 308 | 4 | 53 | |
| 309 | 64 | 109 | |
| 310 | 44 | 117 | |
| 311 | 126 | 366 | |
| 312 | ND | ND | 80 |
| 313 | ND | ND | 100 |
| 314 | ND | ND | 550 |
| 315 | ND | ND | 300 |
| 316 | ND | ND | 320 |
| 317 | ND | ND | 120 |
| 318 | ND | ND | 1000 |
| 319 | ND | ND | 220 |
| 320 | 32.333 | 73.667 | |
| 321 | 106 | 325 | |
| 322 | 13 | 86 | |
| 323 | ND | 77 | |
| 324 | 4 | 35 | |
| 325 | ND | ND | 310 |
| 326 | ND | ND | 580 |
| 327 | ND | ND | 400 |
| 328 | ND | ND | 1500 |
| 329 | ND | ND | 5900 |
| 330 | ND | ND | 260 |
| 331 | 0 | 0 | 0 |
| 332 | 0 | 0 | 0 |
| 333 | 0 | 0 | 0 |
| 334 | 0 | 0 | 0 |
| 335 | 0 | 0 | 0 |
| 336 | 56 | 45 | 0 |
| 337 | 142 | 373 | |
| 338 | 122 | 266 | |
| 339 | ND | ND | |
| 340 | ND | ND | |
| 341 | 150 | 237 | |
| 342 | 1256 | 2429 | |
| 343 | ND | ND | |
| 344 | ND | ND | |
| 345 | 554 | 395 | |
| 346 | ND | ND | |
| 347 | ND | ND | 9 |
| 348 | ND | ND | |
| 349 | 87 | 81 | |
| 350 | ND | 8.5 | |
| 351 | 50 | 66 | |
| 352 | ND | ND | <0.8 |
| 353 | ND | ND | <0.8 |
| 354 | ND | ND | 310 |
| 355 | ND | ND | 580 |
| 356 | ND | ND | 400 |
| 357 | ND | ND | 1500 |
| 358 | ND | ND | 5900 |
| 359 | ND | ND | 260 |
| 360 | ND | ND | 10000 |
| 361 | ND | ND | 2.2 |
| 362 | ND | ND | 1 |
| 363 | ND | ND | 1.2 |
| 364 | ND | ND | 70 |
| 365 | ND | ND | 3 |
| 366 | ND | ND | 2.8 |
| 367 | ND | ND | 5 |
| 368 | ND | ND | 0.7 |
| 369 | ND | ND | 3 |
| 370 | ND | ND | 0.8 |
| 371 | ND | ND | 0.8 |
| 372 | ND | ND | 0.8 |
| 373 | ND | ND | 1 |
| 374 | ND | ND | <0.8 |
| 375 | ND | ND | <0.8 |
| 376 | ND | ND | 50 |
| 377 | ND | ND | 90 |
| 378 | ND | ND | 50 |
| 379 | ND | ND | 140 |
| 380 | ND | ND | 300 |
| 381 | ND | ND | 140 |
| 382 | ND | ND | 48 |
| 383 | ND | ND | 150 |
| 384 | ND | ND | 50 |
| 385 | ND | ND | 70 |
| 386 | ND | ND | 140 |
| 387 | ND | ND | 70 |
| 388 | ND | ND | 110 |
| 389 | ND | ND | 240 |
| 390 | ND | ND | 650 |
| 391 | ND | ND | 300 |
| 392 | ND | ND | 480 |
| 393 | ND | ND | 580 |
| 394 | ND | ND | 800 |
| 395 | ND | ND | 590 |
| 396 | ND | ND | 280 |
| 397 | ND | ND | 7 |
| 398 | ND | ND | 12 |
| 399 | ND | ND | 3 |
| 400 | ND | ND | 12 |
| 401 | ND | ND | 21 |
| 402 | ND | ND | 7 |
| 403 | ND | ND | 8 |
| 404 | ND | ND | 60 |
| 405 | ND | ND | 25 |
| 406 | ND | ND | 2.4 |
| 407 | ND | ND | 0.8 |
| 408 | ND | ND | 9 |
| 409 | ND | ND | 50 |
| 410 | ND | ND | 110 |
| 411 | ND | ND | 250 |
| 412 | ND | ND | 25 |
| 413 | ND | ND | 150 |
| 414 | ND | ND | 120 |
| 415 | ND | ND | 29 |
| 416 | ND | ND | 12 |
| 417 | ND | ND | 6 |
| 418 | ND | ND | 40 |
| 419 | ND | ND | 12 |
| 420 | ND | ND | 2 |
| 421 | ND | ND | 1 |
| 422 | ND | ND | 2 |
| 423 | ND | ND | 2.8 |
| 424 | ND | ND | 1 |
| 425 | ND | ND | 2.8 |
| 426 | ND | ND | 700 |
| 427 | ND | ND | 7 |
| 428 | ND | ND | 1 |
| 429 | ND | ND | 9 |
| 430 | ND | ND | 16 |
| 431 | ND | ND | <0.8 |
| 432 | ND | ND | <0.8 |
| 433 | ND | ND | 40 |
| 434 | ND | ND | <0.8 |
| 435 | ND | ND | 4 |
| 436 | ND | ND | 10 |
| 437 | ND | ND | 1 |
| 438 | ND | ND | <0.8 |
| 439 | ND | ND | 1 |
| 440 | ND | ND | 1 |
| 441 | ND | ND | 6 |
| 442 | ND | ND | 13 |

TABLE 4-continued

| Example | IC$_{50}$ MDA-MB-361 (nM) | IC$_{50}$ PC3-mm2 (nM) | IC$_{50}$ LNCap (nM) |
|---|---|---|---|
| 443 | ND | ND | 8 |
| 444 | ND | ND | <0.8 |
| 445 | ND | ND | <0.8 |
| 446 | ND | ND | 15 |
| 447 | ND | ND | 8 |
| 448 | ND | ND | 18 |
| 449 | ND | ND | 40 |
| 450 | ND | ND | <0.8 |
| 451 | ND | ND | <0.8 |
| 452 | ND | ND | <0.8 |
| 453 | ND | ND | 30 |
| 454 | ND | ND | <0.8 |
| 455 | ND | ND | <0.8 |
| 456 | ND | ND | <0.8 |
| 457 | ND | ND | <0.8 |
| 458 | ND | ND | 8 |
| 459 | ND | ND | <0.8 |
| 460 | ND | ND | <0.8 |
| 461 | ND | ND | 68 |
| 462 | ND | ND | ND |
| 463 | ND | ND | ND |
| 464 | ND | ND | ND |
| 465 | ND | ND | ND |
| 466 | ND | ND | 420 |
| 467 | ND | ND | 170 |
| 468 | ND | ND | 50 |
| 469 | ND | ND | 2800 |
| 470 | ND | ND | 1000 |
| 471 | ND | ND | 130 |
| 472 | ND | ND | 3800 |
| 473 | ND | ND | ND |
| 474 | ND | ND | ND |
| 475 | ND | ND | ND |
| 476 | ND | ND | ND |
| 477 | ND | ND | ND |
| 478 | <3.080 | 8.5 | |
| 479 | 6 | 21 | |
| 480 | ND | ND | |
| 481 | ND | ND | |
| 482 | ND | ND | |
| 483 | ND | ND | |
| 484 | ND | ND | |
| 485 | ND | ND | |
| 486 | 7.0 | 39.3 | |
| 487 | 175.0 | 339.0 | |
| 488 | ND | ND | |
| 489 | ND | ND | 4300 |
| 490 | ND | ND | |
| 491 | 8.0 | 35.0 | |
| 492 | 26.0 | 57.0 | |
| 493 | ND | ND | |
| 494 | 115.0 | 276.0 | |
| 495 | 4.0 | 13.1 | |
| 496 | ND | ND | |
| 497 | 50.0 | 66.0 | |
| 498 | 4.0 | 16.5 | |
| 499 | 21.0 | 31.0 | |
| 500 | 1.0 | 6.5 | |
| 501 | <31 | 41 | |
| 502 | 4.0 | 11.0 | |
| 503 | 7.5 | 12.5 | |
| 504 | 22.5 | 25.5 | |
| 505 | 12.3 | 33.3 | |
| 506 | <21.7 | 12 | |
| 507 | 10.7 | 28.3 | |
| 508 | 12.0 | 36.3 | |
| 509 | ND | ND | <0.8 |
| 510 | ND | ND | |
| 511 | 2.0 | 10.0 | |
| 512 | 1.0 | 8.0 | |
| 513 | 2.0 | 13.0 | |
| 514 | <3.2 | 12 | |
| 515 | 3 | 12 | |
| 516 | ND | ND | |
| 517 | 18.0 | 7.0 | |
| 518 | 4.0 | 24.0 | |
| 519 | 3.0 | 9.0 | |
| 520 | 5.0 | 18.0 | |
| 521 | 8.0 | 27.0 | |
| 522 | 3.0 | 11.0 | |
| 523 | ND | ND | |
| 524 | ND | ND | |
| 525 | ND | ND | |
| 526 | ND | ND | |
| 527 | 1256.0 | 2429.0 | |
| 528 | ND | ND | |
| 529 | 150.0 | 237.0 | |
| 530 | ND | ND | |
| 531 | ND | ND | |
| 532 | 122.0 | 266.0 | |
| 533 | 142.0 | 373.0 | |
| 534 | 32.3 | 73.7 | |
| 535 | 554.0 | 395.0 | |
| 536 | 22.3 | 67.0 | |
| 537 | <31 | <31 | |
| 538 | ND | ND | |
| 539 | 9.0 | 161.0 | |
| 540 | 165.0 | 309.0 | |
| 541 | 964.0 | 1764.0 | |
| 542 | 281.0 | 569.0 | |
| 543 | <31 | 262.0 | |
| 544 | 58.0 | 253.0 | |
| 545 | 30.0 | 219.0 | |
| 546 | 7.0 | 25.0 | |
| 547 | 68.0 | 197.0 | |
| 548 | 524.0 | 869.0 | |
| 549 | ND | ND | |
| 550 | 315.0 | 711.0 | |
| 551 | 106.0 | 270.0 | |
| 552 | 105.0 | 243.0 | |
| 553 | 113.0 | 522.0 | |
| 554 | 521.0 | >1000 | |
| 555 | ND | ND | |
| 556 | 128.0 | 379.0 | |
| 557 | 34.0 | 31.0 | |
| 558 | 751.0 | 939.0 | |
| 559 | 8.0 | 149.0 | |
| 560 | ND | ND | |
| 561 | 66.0 | 218.0 | |
| 562 | 3.0 | 93.0 | |
| 563 | 10.0 | 171.0 | |
| 564 | 1.0 | 7.0 | |
| 565 | 9.0 | 27.0 | |
| 566 | 28.0 | 55.0 | |
| 567 | 106.0 | 130.0 | |
| 568 | 18.0 | 107.0 | |
| 569 | ND | ND | |
| 570 | 28.0 | 344.0 | |
| 571 | 90.0 | 168.0 | |
| 572 | 13.0 | 56.0 | |
| 573 | 99.0 | 206.0 | |
| 574 | 6.0 | 25.0 | |
| 575 | 15.0 | 242.0 | |
| 576 | ND | ND | |
| 577 | ND | ND | |
| 578 | ND | ND | |
| 579 | ND | ND | |
| 580 | ND | ND | |
| 581 | ND | ND | |
| 582 | ND | ND | |
| 583 | ND | ND | |
| 584 | ND | ND | |
| 585 | ND | ND | |
| 586 | ND | ND | |
| 587 | ND | ND | |
| 588 | ND | ND | |
| 589 | ND | ND | |
| 590 | ND | ND | |
| 591 | ND | ND | |
| 592 | 239.0 | 718.0 | |
| 593 | >1000 | >1000 | |
| 594 | ND | ND | |

TABLE 4-continued

| Example | IC$_{50}$ MDA-MB-361 (nM) | IC$_{50}$ PC3-mm2 (nM) | IC$_{50}$ LNCap (nM) |
|---|---|---|---|
| 595 | 43.0 | 193.0 | |
| 596 | 26.0 | 155.0 | |
| 597 | 45.0 | 229.0 | |
| 598 | 22.0 | 214.0 | |
| 599 | ND | ND | |
| 600 | ND | ND | |
| 601 | 22.0 | 155.0 | |
| 602 | 17.0 | 122.0 | |
| 603 | 17.0 | 137.0 | |
| 604 | 4.0 | 73.0 | |
| 605 | 7.0 | 92.0 | |
| 606 | 28.0 | 173.0 | |
| 607 | 24.0 | 213.0 | |
| 608 | 52.0 | 298.0 | |
| 609 | 24.0 | 26.0 | |
| 610 | 28.0 | 297.0 | |
| 611 | 194.0 | 581.0 | |
| 612 | 38.0 | 227.0 | |
| 613 | 6.0 | 21.0 | |
| 614 | 4.0 | 15.0 | |
| 615 | 88.0 | 123.0 | |
| 616 | 4.0 | 21.0 | |
| 617 | 4.0 | 17.0 | |
| 618 | 2.0 | 13.0 | |
| 619 | ND | ND | |
| 620 | 4.0 | 16.0 | |
| 621 | 8.0 | 35.0 | |
| 622 | 5.0 | 25.0 | |
| 623 | 6.0 | 32.0 | |
| 624 | 4.0 | 19.0 | |
| 625 | 12.0 | 43.0 | |
| 626 | ND | ND | |
| 627 | 16.0 | 55.0 | |
| 628 | ND | ND | |
| 629 | 28.0 | 133.0 | |
| 630 | 5.0 | 23.0 | |
| 631 | 28.0 | 120.0 | |
| 632 | 9.0 | 38.0 | |
| 633 | 15.0 | 64.0 | |
| 634 | 5.0 | 16.0 | |
| 635 | 26.0 | 106.0 | |
| 636 | ND | ND | |
| 637 | 26.0 | 62.0 | |
| 638 | 9.0 | 44.0 | |
| 639 | 16.0 | 27.0 | |
| 640 | ND | ND | |
| 641 | ND | ND | |
| 642 | ND | ND | |
| 643 | 19.0 | 59.0 | |
| 644 | 51.0 | 185.0 | |
| 645 | ND | ND | |
| 646 | 32.0 | 223.0 | |
| 647 | 46.0 | 136.0 | |
| 648 | 12.0 | 34.0 | |
| 649 | 9.0 | 37.0 | |
| 650 | ND | ND | |
| 651 | ND | ND | |
| 652 | ND | ND | |
| 653 | ND | ND | |
| 654 | ND | ND | |
| 655 | ND | ND | |
| 656 | ND | ND | |
| 657 | ND | ND | |
| 658 | ND | ND | |
| 659 | ND | ND | |
| 660 | ND | ND | |
| 661 | ND | ND | |
| 662 | ND | ND | |
| 663 | ND | ND | |
| 664 | ND | ND | |
| 665 | ND | ND | |
| 666 | ND | ND | |
| 667 | ND | ND | 60.0 |
| 668 | ND | ND | 0.8 |
| 669 | 28.0 | 41.0 | |
| 670 | 22.5 | 27.5 | |
| 671 | 73.0 | 98.0 | |
| 672 | 98.0 | 176.0 | |
| 673 | 15.0 | 28.0 | |
| 674 | 22.0 | 30.0 | |
| 675 | <30 | 62.0 | |
| 676 | 167.0 | 301.0 | |
| 677 | 345.0 | 3600.0 | |
| 678 | 35.8 | 40.0 | |
| 679 | ND | ND | |
| 680 | ND | ND | |
| 681 | ND | ND | |
| 682 | 1044.0 | 766.0 | |
| 683 | 673.0 | 584.0 | |
| 684 | 806.0 | 1015.0 | |
| 685 | >10000 | >10000 | |
| 686 | 569.0 | 1105.0 | |
| 687 | 355.0 | 389.0 | |
| 688 | 1412.0 | 1950.0 | |
| 689 | 53.0 | 85.0 | |
| 690 | 112.0 | 405.0 | |
| 691 | 52.0 | 131.0 | |
| 692 | 97.0 | 326.0 | |
| 693 | ND | ND | |
| 694 | <3 | 11.0 | |
| 695 | 6.0 | 7.0 | |
| 696 | 13.0 | 13.0 | |
| 697 | <30 | <30 | |
| 698 | <3 | 6.0 | |
| 699 | 36.0 | 40.0 | |
| 700 | 5.0 | 20.0 | |
| 701 | <30 | <30 | |
| 702 | 4.0 | 14.0 | |
| 703 | <3 | 13.0 | |
| 704 | ND | ND | |
| 705 | 191.0 | 416.0 | |
| 706 | 696.0 | 839.0 | |
| 707 | 586.0 | 1012.0 | |
| 708 | 795.0 | 1950.0 | |
| 709 | 805.0 | 857.0 | |
| 710 | 533.0 | 509.0 | |
| 711 | ND | ND | |
| 712 | 582.0 | 551.0 | |
| 713 | 29.0 | 44.0 | |
| 714 | 162.0 | 248.0 | |
| 715 | 254.0 | 389.0 | |
| 716 | ND | ND | |
| 717 | ND | ND | <0.8 |
| 718 | 3924.0 | 7174.0 | |
| 719 | <31 | <31 | |
| 720 | 15.0 | 34.0 | |
| 721 | <31 | 71.0 | |
| 722 | 110.0 | 374.0 | |
| 723 | 35.0 | 91.0 | |
| 724 | 30.0 | 111.0 | |
| 725 | <31 | 69.0 | |
| 726 | 92.0 | 142.0 | |
| 727 | 14.0 | 31.0 | |
| 728 | 59.0 | 107.0 | 38.000 |
| 729 | <31 | <31 | |
| 730 | 94.0 | 200.0 | |
| 731 | 1000.0 | 1491.0 | |
| 732 | 3100.0 | 4309.0 | |
| 733 | 1347.0 | 1654.0 | |
| 734 | 530.0 | 572.0 | |
| 735 | 2297.0 | 3701.0 | |
| 736 | 176.0 | 247.0 | |
| 737 | 176.0 | 404.0 | |
| 738 | ND | ND | |
| 739 | ND | ND | |
| 740 | 83.0 | 84.0 | |
| 741 | ND | ND | |
| 742 | ND | ND | |
| 743 | ND | ND | |
| 744 | ND | ND | |
| 745 | ND | ND | |
| 746 | 93.0 | 118.0 | |

TABLE 4-continued

| Example | IC$_{50}$ MDA-MB-361 (nM) | IC$_{50}$ PC3-mm2 (nM) | IC$_{50}$ LNCap (nM) |
|---|---|---|---|
| 747 | 56.0 | 45.0 | |
| 748 | ND | ND | |
| 749 | 87.0 | 81.0 | |
| 750 | ND | ND | |
| 751 | 144.0 | 238.0 | |
| 752 | <3 | 6.0 | |
| 753 | 4.0 | 14.0 | |
| 754 | 31.3 | 70.8 | |
| 755 | 3.0 | 13.0 | |
| 756 | <3 | 12.000 | |
| 757 | <3 | 6.000 | |
| 758 | 3.0 | 14.0 | |
| 759 | 1.0 | 10.0 | |
| 760 | 0.0 | 4.0 | |
| 761 | <3 | 4.0 | |
| 762 | 8.0 | 7.0 | |
| 763 | 4.0 | 7.0 | |
| 764 | 628.0 | 678.0 | |
| 765 | 21.0 | 27.0 | |
| 766 | 26.0 | 50.0 | |
| 767 | 5.0 | 13.0 | |
| 768 | 7.0 | 8.0 | |
| 769 | 6.0 | 14.0 | |
| 770 | 40.0 | 25.0 | |
| 771 | >1000 | >1000 | |
| 772 | 5.0 | 15.0 | |
| 773 | 4.0 | 6.0 | |
| 774 | 14.0 | 19.0 | |
| 775 | 5.0 | 7.0 | |
| 776 | <3.2 | 6.0 | |
| 777 | 2.0 | 4.0 | |
| 778 | 17.0 | 29.0 | |
| 779 | 13.0 | 23.0 | |
| 780 | ND | ND | |
| 781 | ND | ND | |
| 782 | ND | ND | |
| 783 | ND | ND | |
| 784 | >1000 | >1000 | |
| 785 | >1000 | >1000 | |
| 786 | >1000 | >1000 | |
| 787 | >1000 | >1000 | |
| 788 | >1000 | >1000 | |
| 789 | ND | ND | |
| 790 | ND | ND | |
| 791 | 11.0 | 42.0 | |
| 792 | 2.0 | 16.0 | |
| 793 | 2.0 | 26.0 | |
| 794 | 2.0 | 20.0 | |
| 795 | <3.2 | 10.0 | |
| 796 | 2.0 | 18.0 | |
| 797 | 11.0 | 29.0 | |
| 798 | 3.0 | 24.0 | |
| 799 | <3.2 | 24.0 | |
| 800 | 1.0 | 11.0 | |
| 801 | 3.0 | 32.0 | |
| 802 | 3.0 | 50.0 | |
| 803 | 1.0 | 6.0 | |
| 804 | 3.0 | 11.0 | |
| 805 | 3.0 | 13.0 | |
| 806 | <3.2 | 9.0 | |
| 807 | 35.000 | 37.000 | |
| 808 | ND | ND | |
| 809 | ND | ND | |
| 810 | 2.0 | 26.0 | |
| 811 | 2.0 | 19.0 | |
| 812 | 3.0 | 23.0 | |
| 813 | <3.2 | 24.0 | |
| 814 | 4.0 | 37.0 | |
| 815 | 3.0 | 24.0 | |
| 816 | 2.0 | 11.0 | |
| 817 | ND | ND | |
| 818 | 129.0 | 237.0 | |
| 819 | 442.0 | 768.0 | |
| 820 | ND | ND | |
| 821 | ND | ND | |
| 822 | ND | ND | |
| 823 | ND | ND | 55.0 |
| 823 | ND | ND | |
| 825 | ND | ND | |
| 826 | >1000 | >1000 | |

While particular aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Throughout this application, various publications are referenced. The disclosures of these publications in their entireties are hereby incorporated by reference into this application in order to more fully describe the state of the art as known to those skilled therein as of the date of the invention described and claimed herein.

What is claimed is:

1. A pharmaceutically acceptable salt of a compound of the Formula I:

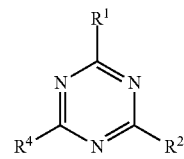

wherein:

$R^1$ is

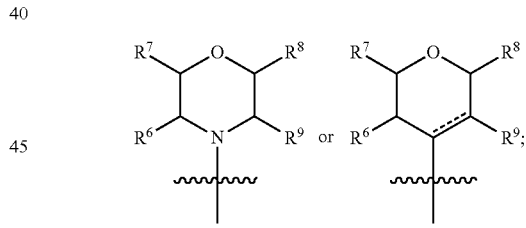

wherein:
$R^6$, $R^7$, $R^8$, $R^9$ are each independently selected from the group consisting of a hydrogen atom, and a $C_1$-$C_6$alkyl optionally substituted with $C_2$-$C_6$alkenyl, $C_4$-$C_6$alkadienyl, $C_2$-$C_6$alkynyl or $C_4$-$C_6$alkadiynyl;
or one of $R^6$ and $R^7$ or $R^8$ and $R^9$, together with the carbon atoms to which they are attached form an optionally substituted 5-8 membered saturated or unsaturated ring containing 0, 1 or 2 atoms independently selected from O, NH and S;
the dashed line - - - - - represents an optional second bond;
$R^2$ is optionally substituted $C_6$-$C_{14}$aryl-NH—COR$^3$, optionally substituted $C_1$-$C_9$heteroaryl-NH—COR$^3$, —CH=CH—$C_6$-$C_{10}$aryl-NH—COR$^3$ or —CH=CH—$C_1$-$C_9$heteroaryl-NH—COR$^3$;
$R^3$ is OR$^5$, NR$^5$R$^5$ or NHR$^5$;
$R^5$ is independently selected from the group consisting of $C_1$-$C_6$alkyl, $C_3$-$C_6$alkenyl, $C_3$-$C_6$alkynyl, optionally substituted $C_6$-$C_{10}$aryl, $C_1$-$C_6$haloalkyl, optionally substituted $C_1$-$C_9$heteroaryl, $C_1$-$C_6$hydroxylalkyl-, $C_3$-$C_{10}$saturated or unsaturated mono or bicyclic $C_3$-$C_{10}$cycloalkyl optionally substituted with OH, $NR^{11}R^{11}$ or 3-7 membered $C_1$-$C_6$heterocyclyl, and 3-10 membered saturated or unsaturated mono or bicyclic $C_1$-$C_9$heterocyclyl, with the proviso that three-membered cycloalkyl and heterocyclyl rings are saturated;

or two $R^5$ groups taken together with the nitrogen atom to which they are attached form a 3 to 8 membered ring system optionally substituted with $C_1$-$C_6$alkyl, which ring system is saturated or unsaturated and has, in addition to said nitrogen atom, 0 to 2 heteroatom ring members selected from O, S, S(O), S(O)$_2$ and $NR^{10}$;

$R^{10}$ is selected from the group consisting of H, $C_1$-$C_6$alkyl, —SO$_2$($C_1$-$C_6$alkyl), —COO($C_1$-$C_6$alkyl), —CONH($C_1$-$C_6$alkyl), —CON($C_1$-$C_6$alkyl)$_2$, —CO($C_1$-$C_6$alkyl), and —SO$_2$NHR$^{11}$;

$R^{11}$ is selected from the group consisting of H, $C_1$-$C_6$alkyl optionally substituted with OH, $NR^{11}R^{11}$ or a 3-7 membered $C_1$-$C_6$heterocyclyl, —CO($C_1$-$C_6$alkyl), optionally substituted $C_6$-$C_{10}$aryl, and optionally substituted $C_1$-$C_9$heteroaryl;

$R^4$ is selected from the group consisting of: a) $C_1$-$C_6$alkyl optionally substituted with: i) 3-10 membered $C_1$-$C_9$heterocyclyl optionally substituted with $C_1$-$C_6$alkyl-, ii) H$_2$N—, iii) ($C_1$-$C_6$alkyl)NH—, iv) ($C_1$-$C_6$alkyl)$_2$N—, v) NH(CH$_2$)$_a$N($C_1$-$C_6$alkyl)$_2$ wherein a is 2, 3 or 4, and vi) CHO, b) $C_3$-$C_6$alkenyl, c) $C_3$-$C_6$alkynyl, d) —O—$C_1$-$C_8$alkyl optionally substituted with —O—$C_1$-$C_8$alkyl, e) —O—$C_3$-$C_8$alkenyl, f) —O—$C_3$-$C_8$alkynyl, g) saturated or unsaturated mono or bicyclic $C_3$-$C_8$cycloalkyl, and h) saturated or unsaturated mono or bicyclic —O—$C_3$-$C_{12}$cycloalkyl, all the above optionally substituted with OH, $NR^{11}R^{11}$ or a 3-7 membered $C_1$-$C_6$heterocyclyl optionally substituted with $C_1$-$C_6$alkyl-, provided that an OH or $NR^{11}R^{11}$ is not directly bonded to a carbon atom that is double- or triple-bonded to another carbon atom; i) —CH═CH—$C_6$-$C_{10}$aryl; j) —CH═CH—$C_1$-$C_9$heteroaryl; k) optionally substituted $C_6$-$C_{10}$aryl; l) optionally substituted 5-10 membered $C_1$-$C_9$heteroaryl attached to the triazine moiety via a carbon atom; m) 3-10 membered saturated or unsaturated monocyclic $C_1$-$C_9$heterocyclyl attached to the triazine moiety through a carbon or nitrogen atom and optionally substituted with from 1 to 3 substituents independently selected from: OH, $NR^{11}R^{11}$, $C_1$-$C_6$alkyl, ($C_1$-$C_6$alkyl)amido-, ($C_1$-$C_6$alkyl)C(O)—, ($C_1$-$C_6$alkoxy)carbonyl-, adamantyl, $C_1$-$C_6$hydroxylalkyl-, ($C_1$-$C_6$alkyl)amido-; or a 3-7 membered $C_1$-$C_6$heterocyclyl, with the proviso that 3 membered heterocyclyl is saturated and attached to the triazine moiety through a nitrogen atom, and 5 membered bicyclic heterocyclyl is saturated; n) optionally substituted —O—$C_6$-$C_{10}$aryl; o) optionally substituted —O—$C_1$-$C_9$heteroaryl; p) —O-(3-12 membered saturated or unsaturated mono or bicyclic)$C_1$-$C_9$heterocyclyl optionally substituted with ($C_1$-$C_6$alkoxy)carbonyl-, H$_2$NS(O)$_2$—, or $C_1$-$C_6$alkyl further optionally substituted with OH, $NR^{11}R^{11}$ or a 3-7 membered $C_1$-$C_6$heterocyclyl, with the proviso that three membered heterocyclyl is saturated; q) —NHC$_6$-$C_{10}$aryl, r) —NHC$_1$-$C_6$heteroaryl, s) —NHNH$_2$, t) —NHNHC$_1$-$C_6$alkyl, u) —NHN($C_1$-$C_6$alkyl)$_2$, v) —NHOH, w) — aa) 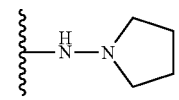

bb) 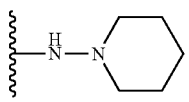

cc) 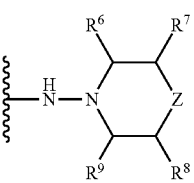

dd) 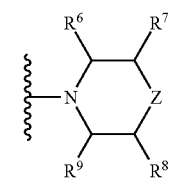

COOH, x) —COO—$C_1$-$C_6$alkyl, y) —CONR$^{12}$R$^{13}$, z) —NR$^{12}$R$^{13}$, wherein Z is CH$_2$, O, S(O)$_n$ or $NR^{10}$ and n is 0, 1 or 2;

ee) halogen, ff) $C_6$-$C_{14}$aryl-S(O)$_2$—NH—, gg) R$^{11}$NHC(O)NH—O—, and hh) optionally substituted 5-membered monocyclic $C_1$-$C_4$heteroaryl attached to the triazine moiety via a nitrogen atom;

$R^{12}$ and $R^{13}$ are each independently selected from H, optionally mono or disubstituted $C_1$-$C_6$alkyl, optionally substituted $C_3$-$C_6$alkenyl, and optionally substituted $C_3$-$C_6$alkynyl, the optional substituents being selected from $C_1$-$C_6$alkoxy, OH, $NR^{11}R^{11}$, and 3-7 membered $C_1$-$C_6$heterocyclyl, provided that an OH or $NR^{11}R^{11}$ is not directly bonded to a carbon atom that is double- or triple-bonded to another carbon atom;

or $R^{12}$ and $R^{13}$ taken together with the nitrogen atom to which they are attached form a 3 to 8 membered monocyclic ring system optionally substituted with $C_1$-$C_6$alkyl, which ring system is saturated or unsaturated and has, in addition to said nitrogen atom, 0 to 2 heteroatom ring members selected from O, S(O)$_n$ and $NR^{10}$;

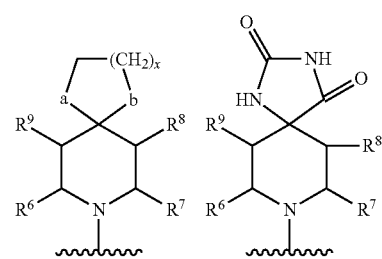

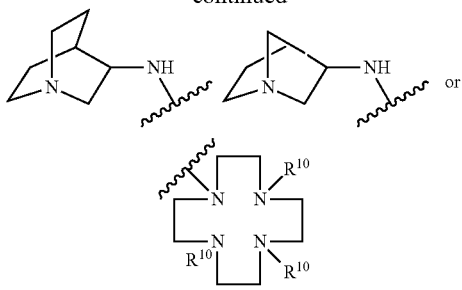

or $R^{12}$ and $R^{13}$ taken together with the nitrogen atom to which they are attached form wherein a and b are each independently —CH$_2$—, O, S, or NR$^{10}$, and x is 1-3;

$C_1$-$C_9$heteroaryl refers to a 5-10 membered aromatic ring system having one or more rings and 1, 2, 3 or 4 ring members independently selected from O, NR$^{10}$, and S(O)$_n$;

$C_1$-$C_9$heterocyclyl refers to a 3-10 membered ring system having one or more rings and 1, 2, 3 or 4 ring members independently selected from O, NR$^{10}$, and S(O)$_n$; and optionally substituted aryl and heteroaryl groups are unsubstituted or are substituted with 1 or 2 moieties selected from the group consisting of: a) $C_1$-$C_6$alkyl optionally substituted with OH, NH$_2$, NH($C_1$-$C_6$alkyl), N($C_1$-$C_6$alkyl)$_2$, —NH(CH$_2$)$_w$N($C_1$-$C_6$alkyl)$_2$ wherein w is 2, 3 or 4, or 3-10 membered $C_1$-$C_9$heterocyclyl optionally substituted with from 1 to 3 independently selected $C_1$-$C_6$alkyl- substituents; b) halogen; c) hydroxy; d) NH$_2$; e) NO$_2$; f) SO$_2$NH$_2$; g) COOH; h) COO($C_1$-$C_6$alkyl); i) NHCOO($C_1$-$C_6$alkyl); j) NH($C_1$-$C_6$alkyl); k) N($C_1$-$C_6$alkyl)$_2$; l) C(O)NR$^a$R$^b$, wherein R$^a$ is H or $C_1$-$C_6$alkyl, and R$^b$ is H, $C_1$-$C_6$alkyl, ($C_6$-$C_{14}$aryl)alkyl-, or ($C_1$-$C_9$heteroaryl)alkyl-; m) —Y-Q, wherein Y is: i) 0, ii) NH, iii) N($C_1$-$C_6$alkyl), iv) NHSO$_2$, v) SO$_2$NH, vi) NHCONH, vii) NHCON($C_1$-$C_6$alkyl), viii) S(O)$_q$, q is 0, 1 or 2, ix) —C(O)NH—, x) —NHC(O)— xi) —C(O)N(CH$_3$)—, xii) C(O), or xiii) absent, and Q is selected from: i) $C_6$-$C_{10}$aryl, optionally substituted with from 1 to 3 substituents independently selected from: A) $C_1$-$C_6$alkoxy-optionally substituted with 1) H$_2$N—, 2) ($C_1$-$C_6$alkyl)amino-, 3) di($C_1$-$C_6$alkyl)amino-, 4) $C_1$-$C_9$heterocyclyl- optionally substituted by $C_1$-$C_6$alkyl-, or 5) hydroxyl, B) ($C_1$-$C_6$alkoxy)carbonyl-, C) ($C_1$-$C_6$alkoxy)C(O)NH—, D) $C_1$-$C_6$alkyl- optionally substituted with 1) H$_2$N—, 2) ($C_1$-$C_6$alkyl)amino-, or 3) di($C_1$-$C_6$alkyl)amino-, E) ($C_1$-$C_6$alkyl)amino-, F) di($C_1$-$C_6$alkyl)amino-, G) ($C_1$-$C_6$alkyl)amido- optionally substituted with 1) H$_2$N—, 2) ($C_1$-$C_6$alkyl)amino-, or 3) di($C_1$-$C_6$alkyl)amino-, H) ($C_1$-$C_6$alkyl)carboxyamido-, I) $C_1$-$C_9$heterocyclyl-optionally substituted by $C_1$-$C_6$alkyl- or $C_1$-$C_6$hydroxylalkyl-, J) heterocyclyl($C_1$-$C_6$alkyl)- optionally substituted by $C_1$-$C_6$alkyl-, K) halogen, L) hydroxyl, M) $C_1$-$C_6$hydroxylalkyl-, N) perfluoro($C_1$-$C_6$)alkyl-, O) H$_2$N—, P) O$_2$N—, Q) H$_2$NSO$_2$—, R) HO$_2$C—, and S) NC—, ii) 5-10 membered $C_1$-$C_9$heteroaryl, optionally substituted with from 1 to 3 substituents independently selected from: A) $C_1$-$C_6$alkoxy- optionally substituted with 1) H$_2$N—, 2) ($C_1$-$C_6$alkyl)amino-, 3) di($C_1$-$C_6$alkyl)amino-, 4) $C_1$-$C_9$heterocyclyl- optionally substituted by $C_1$-$C_6$alkyl-, or 5) hydroxyl, B) ($C_1$-$C_6$alkoxy)carbonyl-, C) ($C_1$-$C_6$alkoxy)C(O)NH—, D) $C_1$-$C_6$alkyl-optionally substituted with 1) H$_2$N—, 2) ($C_1$-$C_6$alkyl)amino-, or 3) di($C_1$-$C_6$alkyl)amino-, E) ($C_1$-$C_6$alkyl)amino-, F) di($C_1$-$C_6$alkyl)amino-, G) ($C_1$-$C_6$alkyl)amido- optionally substituted with 1) H$_2$N—, 2) ($C_1$-$C_6$alkyl)amino-, or 3) di($C_1$-$C_6$alkyl)amino-, H) ($C_1$-$C_6$alkyl)carboxyamido-, I) $C_1$-$C_9$heterocyclyl-optionally substituted by $C_1$-$C_6$alkyl- or $C_1$-$C_6$hydroxylalkyl-, J) heterocyclyl($C_1$-$C_6$alkyl)- optionally substituted by $C_1$-$C_6$alkyl-, K) halogen, L) hydroxyl, M) $C_1$-$C_6$hydroxylalkyl-, N) perfluoro($C_1$-$C_6$)alkyl-, O) H$_2$N—, P) O$_2$N—, Q) H$_2$NSO$_2$—, R) HO$_2$C—, and S) NC—, iii) 3-10 membered $C_1$-$C_9$heterocyclyl, optionally substituted with from 1 to 3 substituents independently selected from: A) $C_1$-$C_6$alkyl-, B) heterocyclyl($C_1$-$C_6$alkyl)-, C) ($C_6$-$C_{14}$aryl)alkyl-, D) $C_1$-$C_6$acyl-, E) ($C_1$-$C_6$alkoxy)carbonyl-, F) ($C_1$-$C_6$alkyl)carboxyl-, G) halogen, H) $C_1$-$C_6$haloalkyl-, I) hydroxyl, J) $C_1$-$C_6$hydroxyalkyl-, K) H$_2$N—, L) ($C_1$-$C_6$alkyl)amino-, M) di($C_1$-$C_6$alkyl)amino-, N) HO$_2$C—, O) ($C_1$-$C_6$alkoxy)carbonyl-, P) ($C_1$-$C_6$alkyl)carboxyl-, Q) ($C_1$-$C_6$alkyl)amido-, R) H$_2$NC(O)—, S) ($C_1$-$C_6$alkyl)carboxyamido-, T) 5-10 membered $C_1$-$C_9$heteroaryl, U) $C_6$-$C_{14}$ary, V) $C_3$-$C_6$cycloalkyl W) 3-10 membered $C_1$-$C_9$heterocyclyl, X)NC—; and Y) —NO$_2$; iv) $C_3$-$C_{10}$cycloalkyl, v) $C_1$-$C_6$alkyl, vi) $C_2$-$C_6$alkenyl, vii) $C_2$-$C_6$alkynyl, viii) $C_1$-$C_6$hydroxyalkyl-, ix) (CH$_2$)$_v$O($C_1$-$C_6$alkyl), x) (CH$_2$)$_v$NH$_2$, xi) (CH$_2$)$_v$NH($C_1$-$C_6$alkyl), xii) (CH$_2$)$_v$N($C_1$-$C_6$alkyl)$_2$, xiii) O(CH$_2$)$_v$N($C_1$-$C_6$alkyl)$_2$, xiv) (CH$_2$)$_v$$C_6$-$C_{10}$aryl, xv) —CN, xvi) (CH$_2$)$_v$ 5-10 membered $C_1$-$C_9$heteroaryl, xvii) (CH$_2$)$_v$ 3-10 membered $C_1$-$C_9$heterocyclyl, optionally substituted by $C_1$-$C_6$alkyl-, wherein v is 1, 2, 3 or 4, and xviii) $C_1$-$C_6$perfluoroalkyl-; and n) C(O)R$^c$ wherein R$^c$ is: i) H, ii) $C_1$-$C_6$alkyl, or iii) $C_3$-$C_6$cycloalkyl, wherein said pharmaceutically acceptable salt is selected from the group consisting of: acetate, aluminum, amsonate (4,4-diaminostilbene-2,2-disulfonate), benzathine (N,N'-dibenzylethylenediamine), benzenesulfonate, benzoate, bicarbonate, bismuth, bisulfate, bitartrate, borate, bromide, butyrate, calcium, calcium edetate, camsylate (camphorsulfonate), carbonate, chloride, choline, citrate, clavulariate, diethanolamine, dihydrochloride, diphosphate, edetate, edisylate (camphorsulfonate), esylate (ethanesulfonate), ethylenediamine, fumarate, gluceptate (glucoheptonate), gluconate, glucuronate, glutamate, hexafluorophosphate, hexylresorcinate, hydrabamine (N,N'-bis(dehydroabietyl)ethylenediamine), hydrobromide, hydrochloride, hydroxynaphthoate, 1-hydroxy-2-naphthoate, 3-hydroxy-2-naphthoate, iodide, isothionate (2-hydroxyethanesulfonate), lactate, lactobionate, laurate, lauryl sulfate, lithium, magnesium, malate, maleate, mandelate, meglumine (1-deoxy-1-(methylamino)-D-glucitol), mesylate, methyl bromide, methylnitrate, methylsulfate, mucate, napsylate, nitrate, N-methylglucamine ammonium salt, oleate, oxalate, palmitate, pamoate (4,4'-methylenebis-3-hydroxy-2-naphthoate, or embonate), pantothenate, phosphate, picrate, polygalacturonate, potassium, propionate, p-toluenesulfonate, salicylate, sodium, stearate, subacetate, succinate, sulfate, sulfosaliculate, suramate, tannate, tartrate, teoclate (8-chloro-3,7-dihydro-1,3-dimethyl-1H-purine-2,6-dione), triethiodide, tromethamine (2-amino-2-(hydroxymethyl)-1,3-propanediol), valerate, and zinc salts.

2. A pharmaceutically acceptable salt of: 1-(4-{[4-(dimethylamino)piperidin-1-yl]carbonyl}phenyl)-3-[4-(4,6-dimorpholin-4-yl-1,3,5-triazin-2-yl)phenyl]urea:

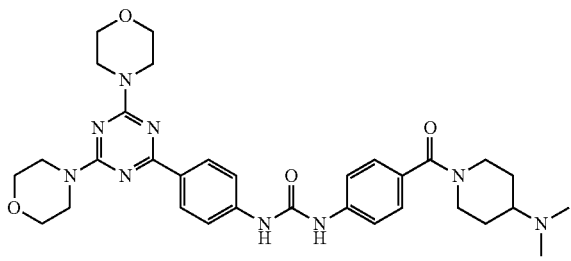 [SMILES: CN(C)C1CCN(C(=O)c2ccc(NC(=O)Nc3ccc(-c4nc(N5CCOCC5)nc(N5CCOCC5)n4)cc3)cc2)CC1]

wherein said pharmaceutically acceptable salt is selected from the group consisting of: acetate, aluminum, amsonate (4,4-diaminostilbene-2,2-disulfonate), benzathine (N,N'-dibenzylethylenediamine), benzenesulfonate, benzoate, bicarbonate, bismuth, bisulfate, bitartrate, borate, bromide, butyrate, calcium, calcium edetate, camsylate (camphorsulfonate), carbonate, chloride, choline, citrate, clavulariate, diethanolamine, dihydrochloride, diphosphate, edetate, edisylate (camphorsulfonate), esylate (ethanesulfonate), ethylenediamine, fumarate, gluceptate (glucoheptonate), gluconate, glucuronate, glutamate, hexafluorophosphate, hexylresorcinate, hydrabamine (N,N'-bis(dehydroabietyl)ethylenediamine), hydrobromide, hydrochloride, hydroxynaphthoate, 1-hydroxy-2-naphthoate, 3-hydroxy-2-naphthoate, iodide, isothionate (2-hydroxyethanesulfonate), lactate, lactobionate, laurate, lauryl sulfate, lithium, magnesium, malate, maleate, mandelate, meglumine (1-deoxy-1-(methylamino)-D-glucitol), mesylate, methyl bromide, methylnitrate, methylsulfate, mucate, napsylate, nitrate, N-methylglucamine ammonium salt, oleate, oxalate, palmitate, pamoate (4,4'-methylenebis-3-hydroxy-2-naphthoate, or embonate), pantothenate, phosphate, picrate, polygalacturonate, potassium, propionate, p-toluenesulfonate, salicylate, sodium, stearate, subacetate, succinate, sulfate, sulfosaliculate, suramate, tannate, tartrate, teoclate (8-chloro-3,7-dihydro-1,3-dimethyl-1H-purine-2,6-dione), triethiodide, tromethamine (2-amino-2-(hydroxymethyl)-1,3-propanediol), valerate, and zinc salts.

* * * * *